US011883030B2

United States Patent
Quadri et al.

(10) Patent No.: US 11,883,030 B2
(45) Date of Patent: Jan. 30, 2024

(54) SYSTEMS, DEVICES, AND METHODS FOR CONTROLLABLY AND SELECTIVELY OCCLUDING, RESTRICTING, AND DIVERTING FLOW WITHIN A PATIENT'S VASCULATURE

(71) Applicant: inQB8 Medical Technologies, LLC, Winchester, MA (US)

(72) Inventors: Arshad Quadri, West Hartford, CT (US); J. Brent Ratz, Winchester, MA (US); Alexander H. Cooper, Costa Mesa, CA (US); Juliet Laura Schwartz, Tustin, CA (US)

(73) Assignee: inQB8 Medical Technologies, LLC, Winchester, MA (US)

( * ) Notice: Subject to any disclaimer, the term of this patent is extended or adjusted under 35 U.S.C. 154(b) by 0 days.

(21) Appl. No.: 18/300,076

(22) Filed: Apr. 13, 2023

(65) Prior Publication Data
US 2023/0346381 A1 Nov. 2, 2023

Related U.S. Application Data

(60) Provisional application No. 63/336,924, filed on Apr. 29, 2022, provisional application No. 63/484,635, filed on Feb. 13, 2023.

(51) Int. Cl.
*A61B 17/12* (2006.01)
*A61F 2/48* (2006.01)
(Continued)

(52) U.S. Cl.
CPC .... *A61B 17/12109* (2013.01); *A61B 17/1204* (2013.01); *A61F 2/2475* (2013.01);
(Continued)

(58) Field of Classification Search
CPC ........ A61B 17/12036; A61B 17/12109; A61B 17/1204; A61B 17/12168;
(Continued)

(56) References Cited

U.S. PATENT DOCUMENTS 7,001,409 B2   2/2006  Amplatz
7,387,636 B2   6/2008  Cohn et al.
(Continued)

FOREIGN PATENT DOCUMENTS

CN   106264645 B   2/2019
CN   115884801 A   3/2023
(Continued)

OTHER PUBLICATIONS

"Revamp Medical" (website homepage), Revamp Medical Ltd., accessed Jan. 19, 2023, in 6 pages. URL: https://www.revampmedical.com/.
(Continued)

*Primary Examiner* — Sarah W Aleman
(74) *Attorney, Agent, or Firm* — Knobbe, Martens, Olson & Bear, LLP

(57) ABSTRACT

Various systems, devices, components and methods are disclosed for controllably and selectively occluding, restricting, and/or diverting flow within a patient's vasculature. The flow restriction systems can include an implant having a flow restrictor and an implantable controller having an actuator for actuating the flow restrictor. The flow restriction systems can also include an external device for controlling operation of the implant via the implantable controller.

11 Claims, 70 Drawing Sheets

(51) Int. Cl.
*A61F 2/24* (2006.01)
*A61B 90/00* (2016.01)

(52) U.S. Cl.
CPC ........ *A61F 2/482* (2021.08); *A61B 2090/064* (2016.02); *A61F 2/2403* (2013.01); *A61F 2250/0001* (2013.01)

(58) Field of Classification Search
CPC ........ A61B 17/12022; A61B 17/12145; A61B 5/026; A61M 60/122; A61M 60/135; A61M 60/139; A61M 60/157; A61M 2039/2413; A61M 2039/242; A61M 2039/244; A61F 2/2475; A61F 2/2403; A61F 2002/068; A61F 2/01; A61F 2/0105; A61F 2/04; A61F 2/06; A61F 2/48
See application file for complete search history.

(56) References Cited

U.S. PATENT DOCUMENTS

| | | | |
|---|---|---|---|
| 7,445,623 B2 | 11/2008 | Mialhe | |
| 7,476,200 B2 | 1/2009 | Tal | |
| 7,967,769 B2 | 6/2011 | Faul et al. | |
| 8,016,782 B2 | 9/2011 | Brenneman et al. | |
| 8,048,016 B2 | 11/2011 | Faul et al. | |
| 9,056,171 B2 | 6/2015 | Ward et al. | |
| 9,393,384 B1 | 7/2016 | Kapur et al. | |
| 9,504,781 B2 | 11/2016 | Kassab et al. | |
| 9,561,035 B2 | 2/2017 | Carrison | |
| 9,597,205 B2 | 3/2017 | Tuval | |
| 9,681,948 B2 * | 6/2017 | Levi .................. | A61B 17/0057 |
| 9,789,294 B2 | 10/2017 | Taft et al. | |
| 10,279,094 B2 | 5/2019 | Williams et al. | |
| 10,279,152 B2 | 5/2019 | Kapur et al. | |
| 10,363,044 B2 * | 7/2019 | Tal .................. | A61B 17/12168 |
| 10,376,680 B2 | 8/2019 | McNamara et al. | |
| 10,413,284 B2 | 9/2019 | McNamara et al. | |
| 10,568,634 B2 | 2/2020 | Goldie et al. | |
| 10,583,231 B2 | 3/2020 | Schwammenthal et al. | |
| 10,667,931 B2 | 6/2020 | Bruckheimer et al. | |
| 10,709,832 B2 | 7/2020 | Criado et al. | |
| 10,758,715 B2 | 9/2020 | Kapur et al. | |
| 10,842,974 B2 | 11/2020 | Kapur et al. | |
| 10,842,975 B2 | 11/2020 | Kapur et al. | |
| 10,912,645 B2 | 2/2021 | Rottenberg et al. | |
| 11,033,727 B2 | 6/2021 | Tuval et al. | |
| 11,039,915 B2 | 6/2021 | Tuval et al. | |
| 11,058,862 B2 | 7/2021 | Kaiser et al. | |
| 11,096,692 B2 | 8/2021 | Rowe et al. | |
| 11,160,691 B2 | 11/2021 | Fahey et al. | |
| 11,160,961 B2 | 11/2021 | Fahey et al. | |
| 11,234,702 B1 | 2/2022 | Eigler et al. | |
| 11,278,289 B2 | 3/2022 | Goldie et al. | |
| 11,364,132 B2 | 6/2022 | Bellomo et al. | |
| 11,484,701 B2 | 11/2022 | Schwammenthal et al. | |
| 11,564,596 B2 | 1/2023 | Gifford, III et al. | |
| 11,612,725 B2 | 3/2023 | Kapur et al. | |
| 11,701,018 B2 | 7/2023 | Sweeney et al. | |
| 11,717,425 B2 | 8/2023 | Bruckheimer et al. | |
| 11,717,429 B2 | 8/2023 | Schwartz et al. | |
| 2002/0115982 A1 | 8/2002 | Barbut et al. | |
| 2003/0171771 A1 | 9/2003 | Anderson et al. | |
| 2004/0111006 A1 | 6/2004 | Alferness et al. | |
| 2004/0147803 A1 | 7/2004 | Hegde et al. | |
| 2004/0163655 A1 | 8/2004 | Gelfand et al. | |
| 2004/0167415 A1 | 8/2004 | Gelfand et al. | |
| 2006/0064059 A1 | 3/2006 | Gelfand et al. | |
| 2006/0106449 A1 | 5/2006 | Ben Muvhar | |
| 2006/0111704 A1 | 5/2006 | Brenneman et al. | |
| 2007/0293808 A1 | 12/2007 | Williams et al. | |
| 2009/0105631 A1 | 4/2009 | Kieval | |
| 2009/0117334 A1 * | 5/2009 | Sogard .................. | B32B 27/302 |
| | | | 428/156 |
| 2009/0131785 A1 | 5/2009 | Lee et al. | |
| 2010/0125288 A1 | 5/2010 | Gelfand et al. | |
| 2010/0331876 A1 | 12/2010 | Cedeno | |
| 2011/0257462 A1 | 10/2011 | Rodefeld et al. | |
| 2013/0178750 A1 * | 7/2013 | Sheehan ............... | A61B 5/0215 |
| | | | 604/9 |
| 2014/0371778 A1 | 12/2014 | Rudakov et al. | |
| 2015/0057687 A1 | 2/2015 | Gittard et al. | |
| 2017/0100527 A1 | 4/2017 | Schwammenthal et al. | |
| 2017/0164949 A1 | 6/2017 | Carrison | |
| 2018/0085128 A1 | 3/2018 | Bellomo et al. | |
| 2018/0116522 A1 | 5/2018 | Brenneman et al. | |
| 2018/0206974 A1 * | 7/2018 | Goodman ................. | A61F 2/07 |
| 2019/0224396 A1 | 7/2019 | Williams et al. | |
| 2019/0343531 A1 | 11/2019 | Tal et al. | |
| 2020/0038566 A1 | 2/2020 | Johnson et al. | |
| 2020/0085600 A1 | 3/2020 | Schwartz et al. | |
| 2020/0101270 A1 | 4/2020 | Sutherland | |
| 2020/0197178 A1 | 6/2020 | Vecchio | |
| 2020/0222187 A1 * | 7/2020 | Thornton .................. | A61F 2/95 |
| 2020/0254228 A1 | 8/2020 | Taft et al. | |
| 2020/0289299 A1 | 9/2020 | Bruckheimer et al. | |
| 2020/0360024 A1 | 11/2020 | Bellomo et al. | |
| 2021/0007747 A1 | 1/2021 | Carrison | |
| 2021/0040194 A1 | 2/2021 | Leow et al. | |
| 2021/0077792 A1 | 3/2021 | Kapur et al. | |
| 2021/0085934 A1 | 3/2021 | Kapur et al. | |
| 2021/0085935 A1 * | 3/2021 | Fahey .................... | A61B 17/11 |
| 2021/0177425 A1 * | 6/2021 | Kapur ................. | A61M 60/289 |
| 2021/0177426 A1 * | 6/2021 | Tal .................... | A61B 17/12186 |
| 2021/0186517 A1 | 6/2021 | Tal et al. | |
| 2021/0244381 A1 | 8/2021 | Sweeney et al. | |
| 2021/0338465 A1 | 11/2021 | Bruckheimer et al. | |
| 2021/0370032 A1 * | 12/2021 | Fahey ................ | A61B 5/02158 |
| 2021/0401494 A1 | 12/2021 | Passman et al. | |
| 2022/0001163 A1 | 1/2022 | Kaiser et al. | |
| 2022/0031235 A1 | 2/2022 | Sweeney et al. | |
| 2022/0061852 A1 * | 3/2022 | Shohat ............... | A61B 5/02152 |
| 2022/0151774 A1 | 5/2022 | Tuval | |
| 2022/0183696 A1 | 6/2022 | Goldie et al. | |
| 2022/0202557 A1 * | 6/2022 | Coffman ............... | A61B 5/4836 |
| 2022/0218976 A1 | 7/2022 | Friedland et al. | |
| 2022/0287831 A1 * | 9/2022 | Thornton .................. | A61F 2/07 |
| 2022/0323214 A1 | 10/2022 | Thornton | |
| 2022/0370074 A1 | 11/2022 | Goldie et al. | |
| 2022/0401718 A1 | 12/2022 | Kapur et al. | |
| 2023/0068326 A1 | 3/2023 | DeBeer et al. | |

FOREIGN PATENT DOCUMENTS

| | | | |
|---|---|---|---|
| EP | 2858711 B1 | 3/2018 | |
| EP | 3300672 A1 | 4/2018 | |
| EP | 2879751 B1 | 9/2019 | |
| EP | 3518825 B1 | 5/2020 | |
| EP | 3145559 B1 | 8/2020 | |
| EP | 3337386 B1 | 12/2020 | |
| EP | 3700604 B1 | 7/2021 | |
| EP | 3909524 A1 | 11/2021 | |
| EP | 3573577 B1 | 10/2022 | |
| EP | 4171675 A2 | 5/2023 | |
| RU | 2700127 C2 | 9/2019 | |
| WO | WO-0238085 A1 * | 5/2002 | ............... A61F 2/90 |
| WO | WO 2004/075776 A2 | 9/2004 | |
| WO | WO 2004/075948 A2 | 9/2004 | |
| WO | WO 2015/109028 A1 | 7/2015 | |
| WO | WO 2017/136341 A1 | 8/2017 | |
| WO | WO 2018/096531 A1 | 5/2018 | |
| WO | WO 2018/132623 A1 | 7/2018 | |
| WO | WO 2020/163820 A1 | 8/2020 | |
| WO | WO 2020/198694 A1 | 10/2020 | |
| WO | WO 2020/214819 A1 | 10/2020 | |
| WO | WO 2020/229636 A1 | 11/2020 | |
| WO | WO 2020/232384 A1 | 11/2020 | |
| WO | WO 2020/234785 A1 | 11/2020 | |
| WO | WO 2021/022090 A1 | 2/2021 | |
| WO | WO 2021/102203 A1 | 5/2021 | |
| WO | WO 2021/117021 A1 | 6/2021 | |
| WO | WO 2021/126699 A1 | 6/2021 | |
| WO | WO 2021/150765 A1 | 7/2021 | |

(56) References Cited

FOREIGN PATENT DOCUMENTS

| WO | WO 2021/162888 A1 | 8/2021 |
| WO | WO 2021/226014 A2 | 11/2021 |
| WO | WO 2022/005909 A2 | 1/2022 |
| WO | WO 2022/187187 A1 | 9/2022 |
| WO | WO 2022/192483 A1 | 9/2022 |

OTHER PUBLICATIONS

"Restore Medical" (website homepage), Restore Medical Ltd., accessed Jan. 19, 2023, in 7 pages. URL: https://restoremedical.co/.

Dierckx, Dr. R. et al., "Doraya: First-in-man clinical study—Concept and initial results", 2019 Euro PCR (OLV, Aalst, Belgium), in 14 pages.

Kaiser, D. W. et al., "First-in-Human Experience of Mechanical Preload Control in Patients with HFpEF During Exercise", JACC: Basic to Translational Science, vol. 6, No. 3, pp. 189-198. URL: https://doi.org/10.1016/j.jacbts.2020.12.007.

International Search Report and Written Opinion in PCT Application No. PCT/US2023/020471, dated Aug. 25, 2023, in 16 pages.

\* cited by examiner

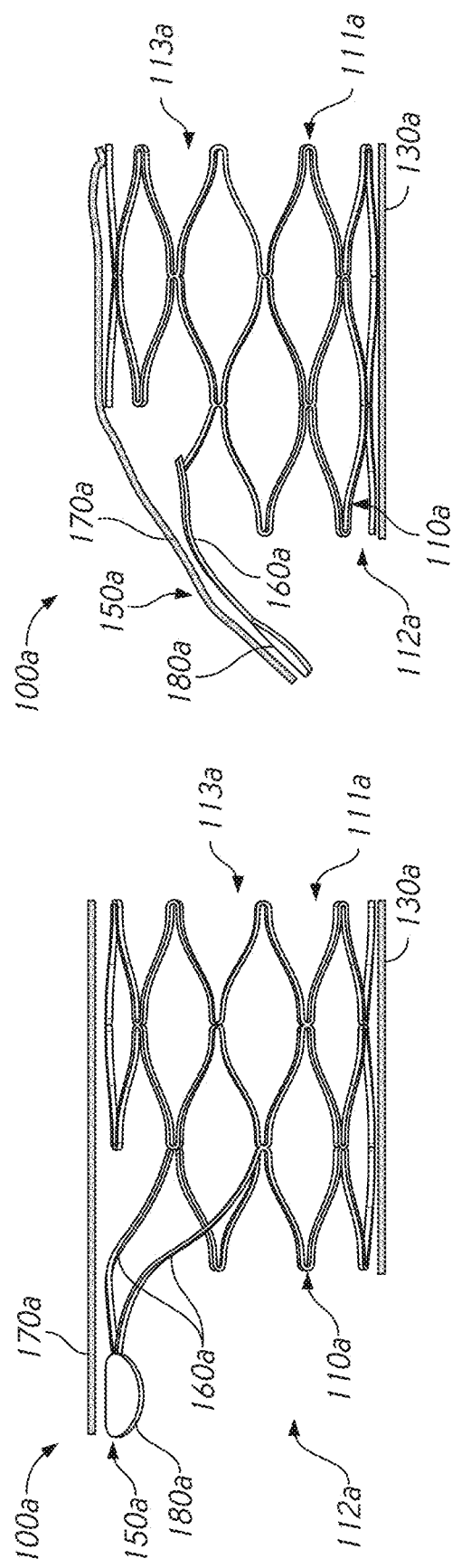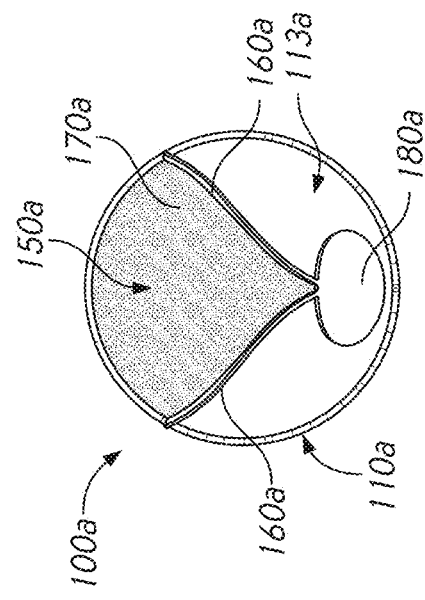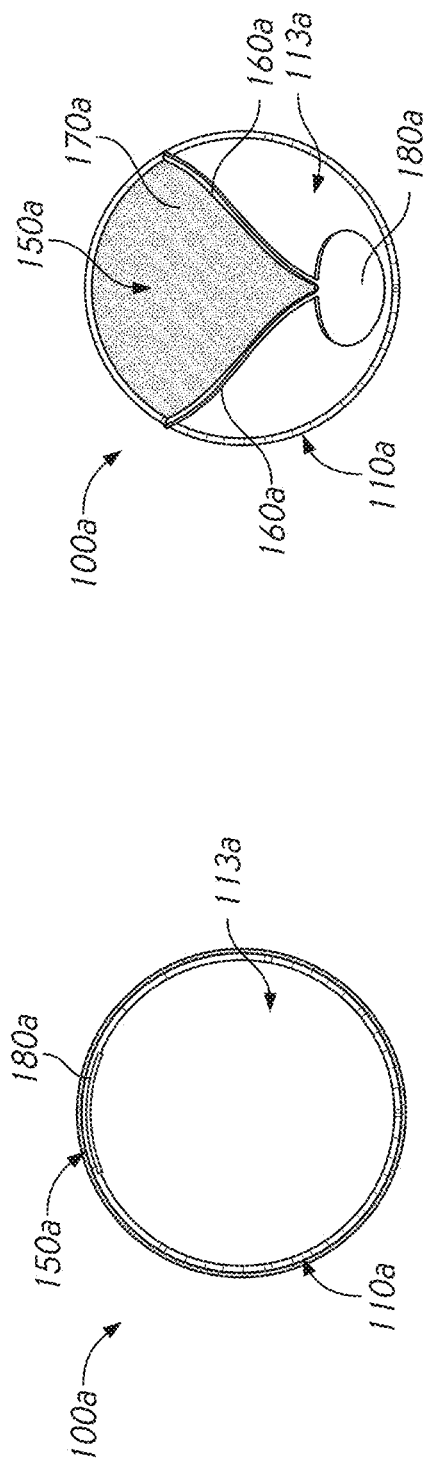

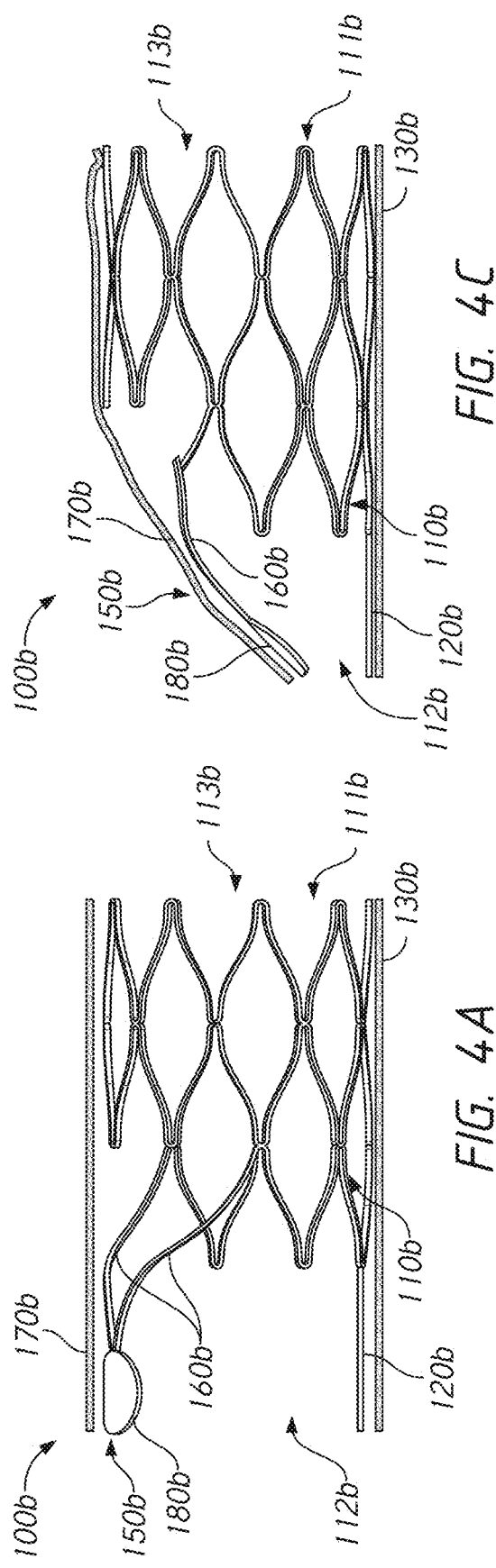
FIG. 4C
FIG. 4A
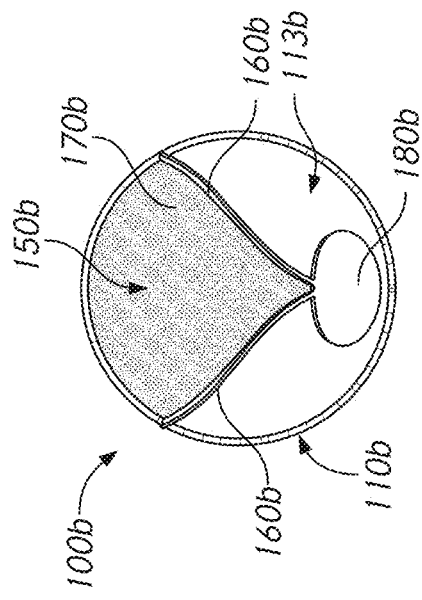
FIG. 4D
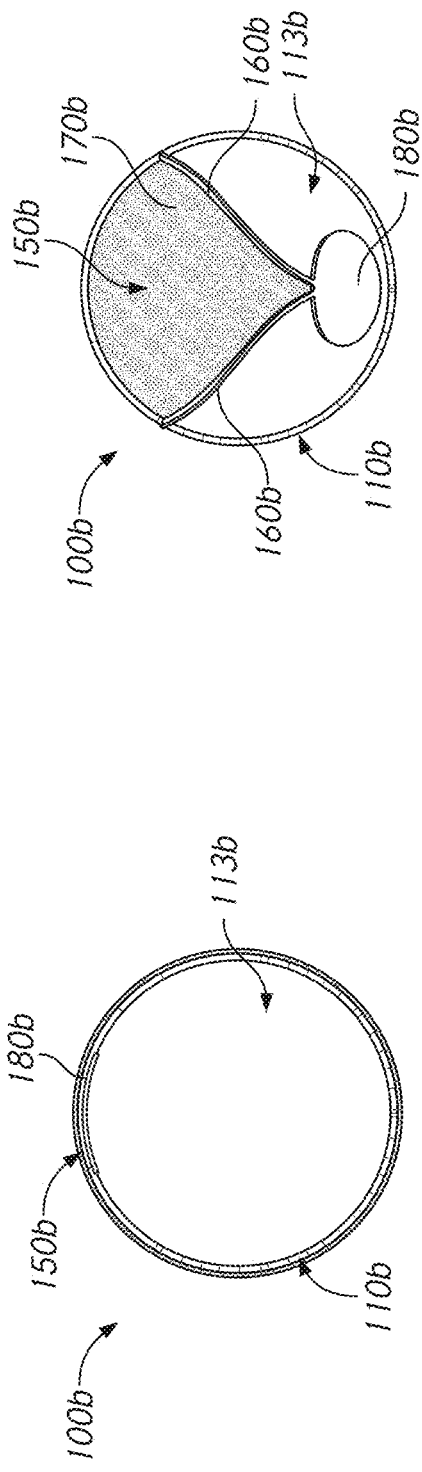
FIG. 4B

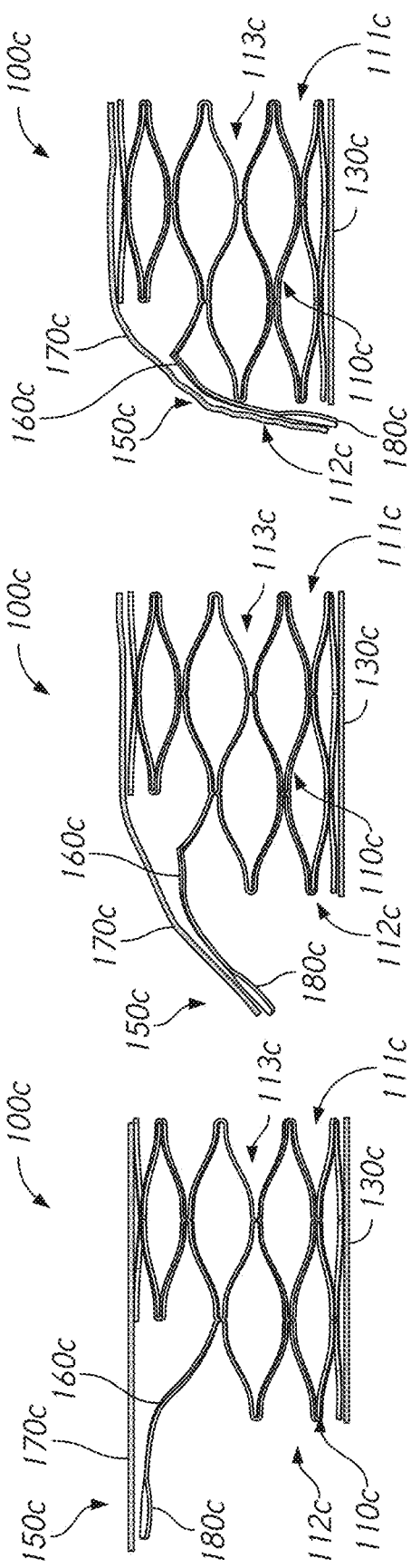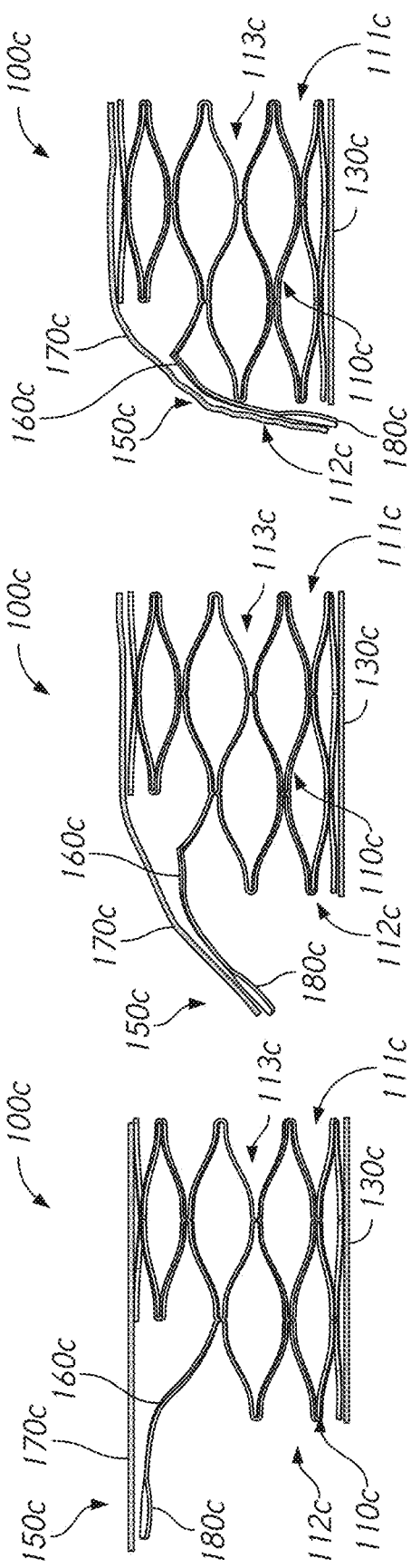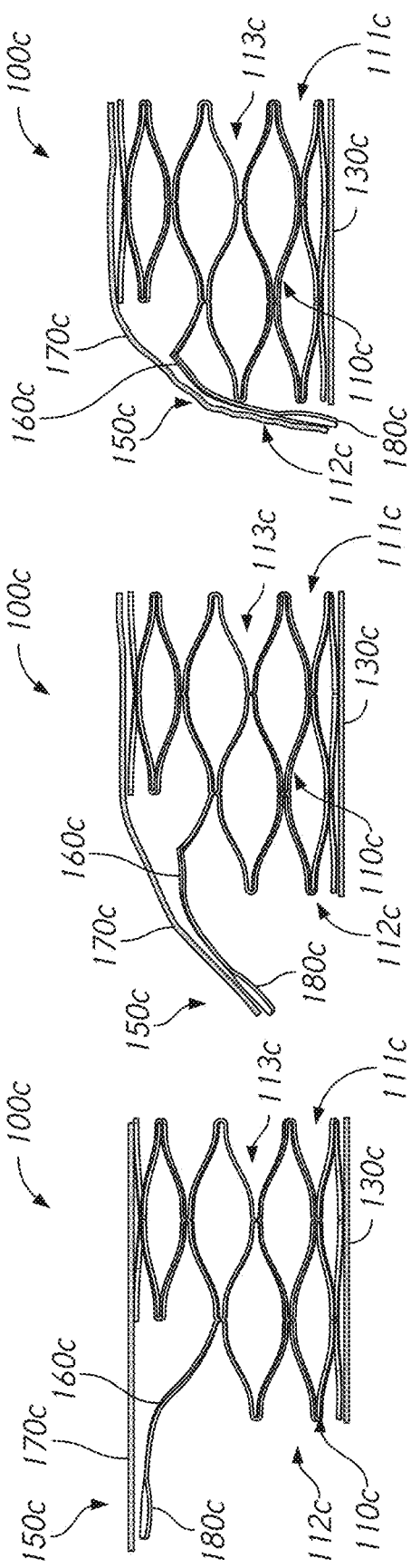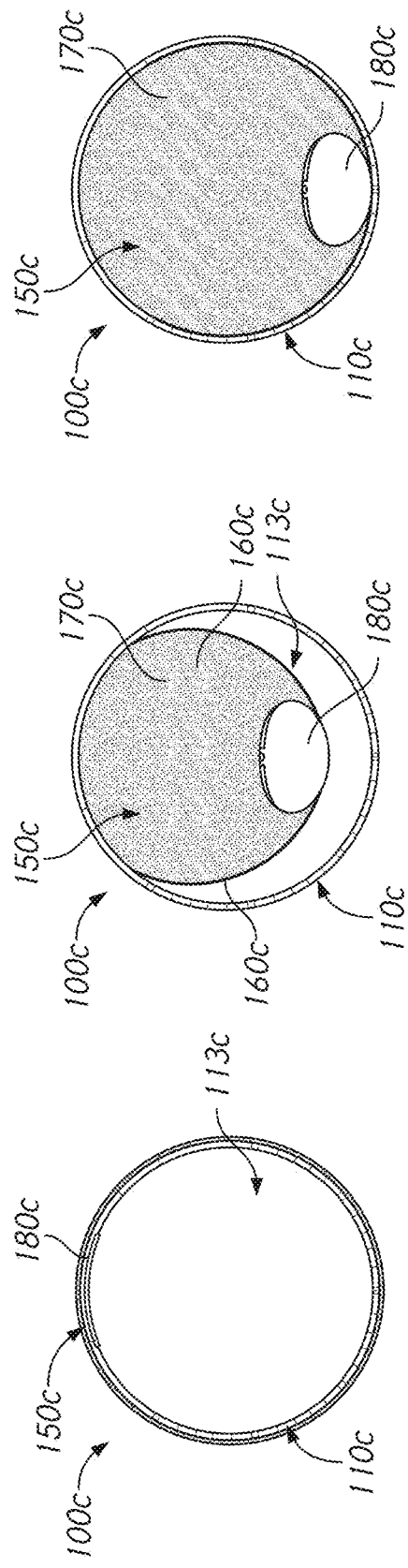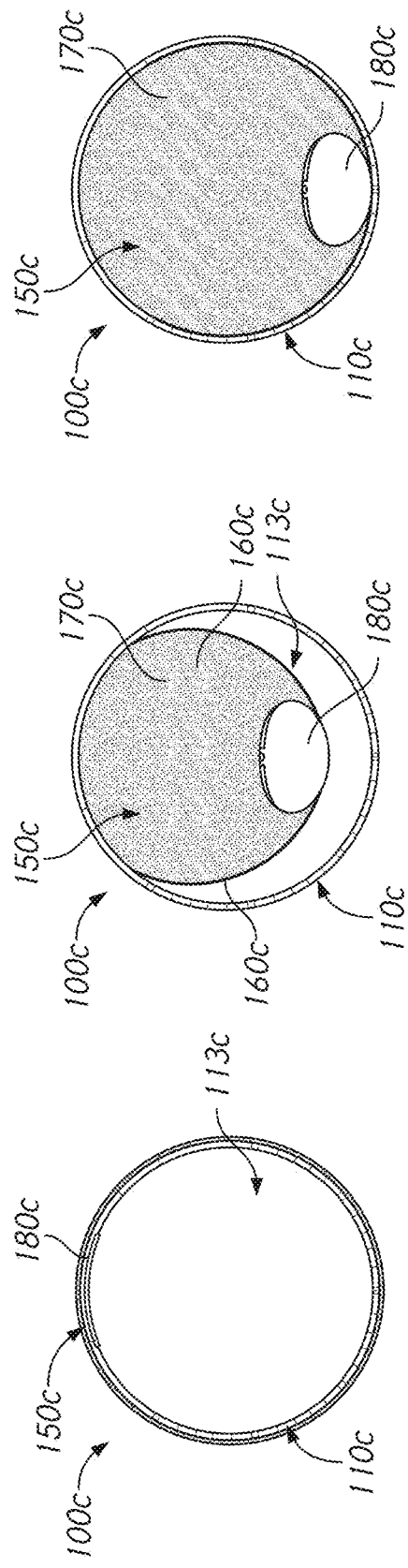

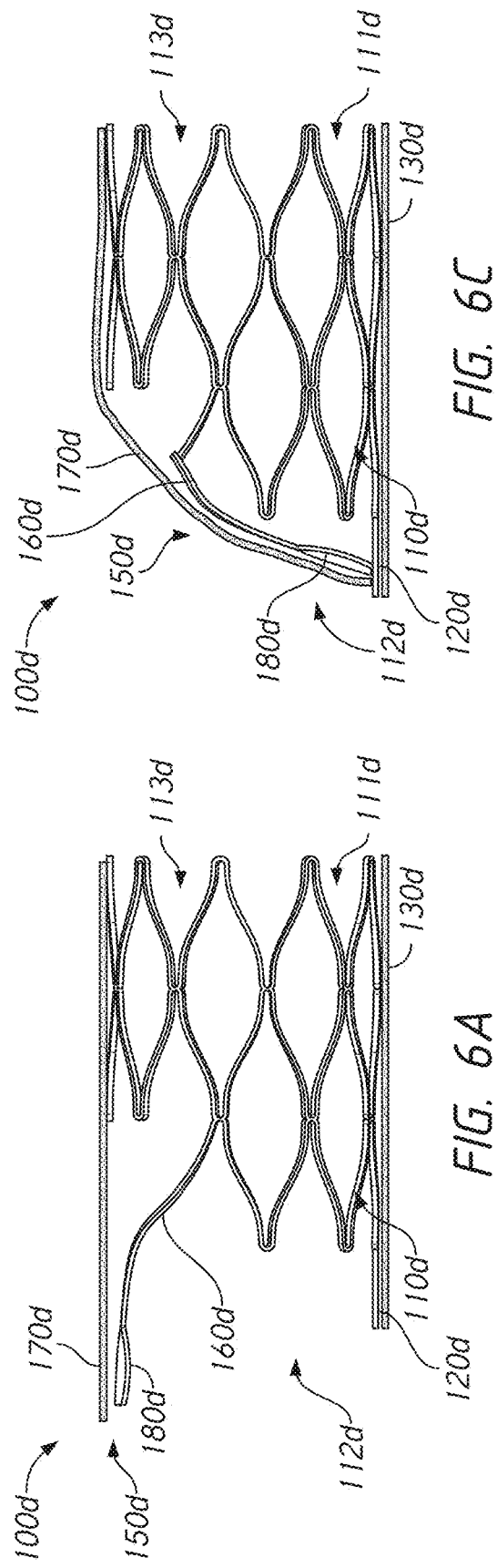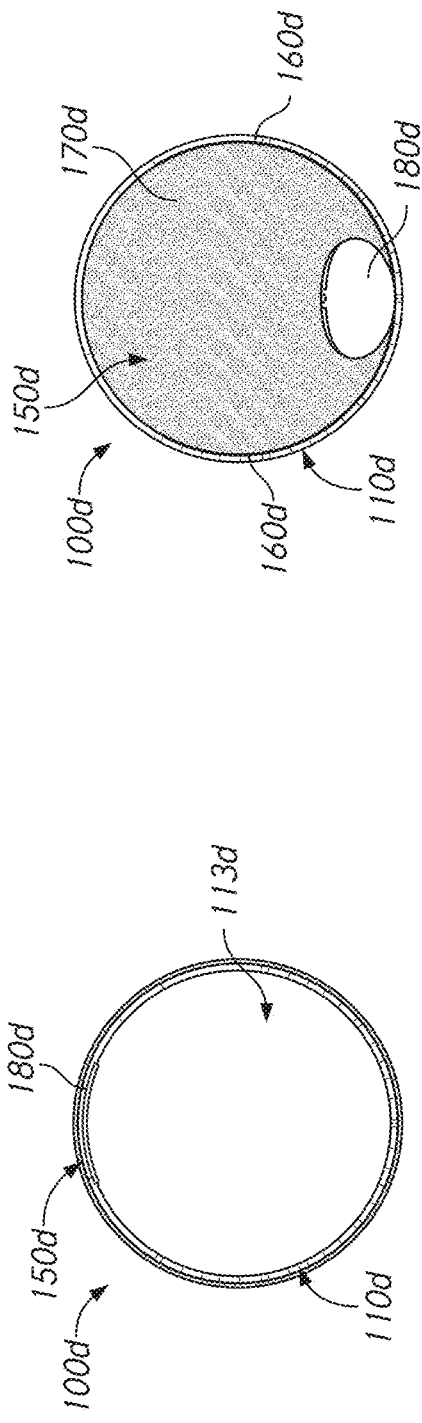
FIG. 6A
FIG. 6B
FIG. 6C
FIG. 6D

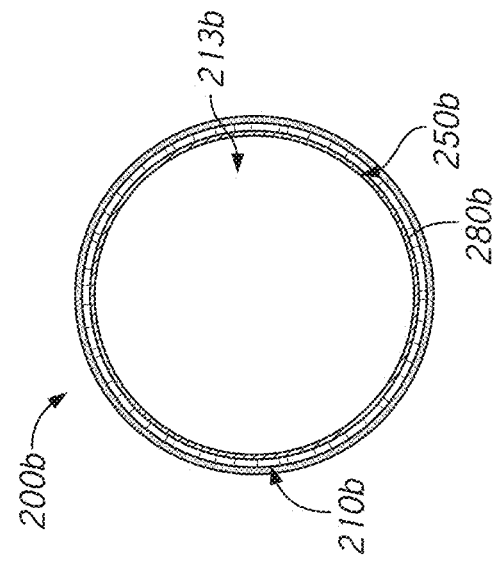
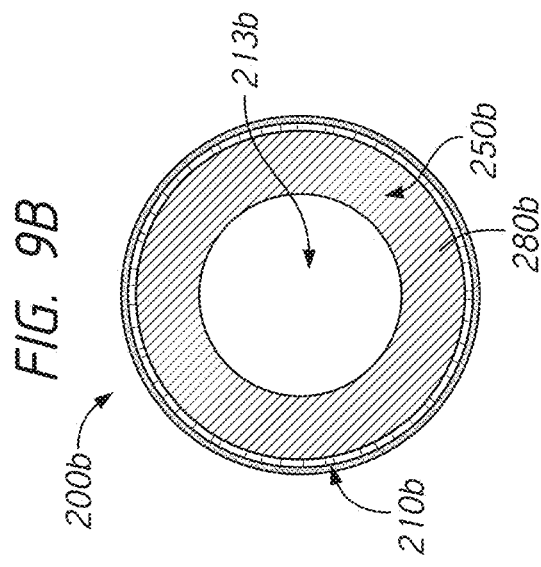
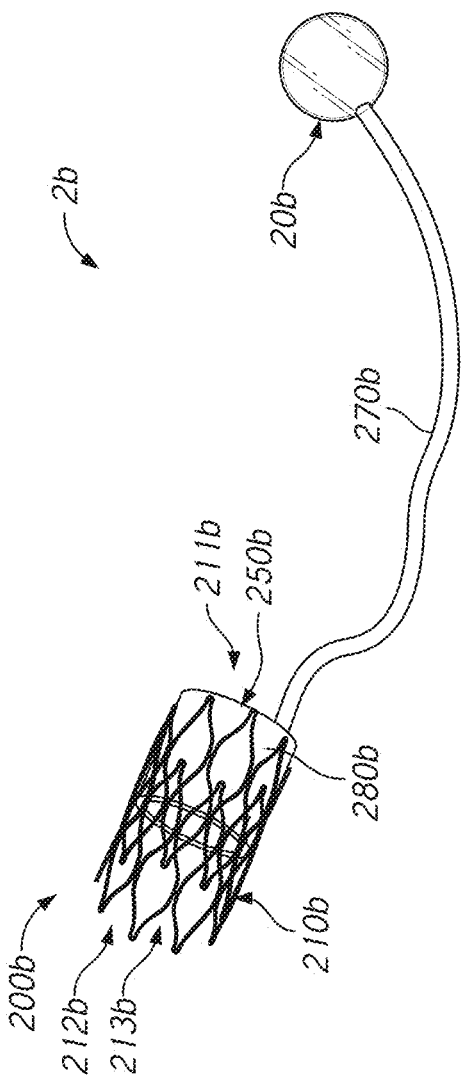
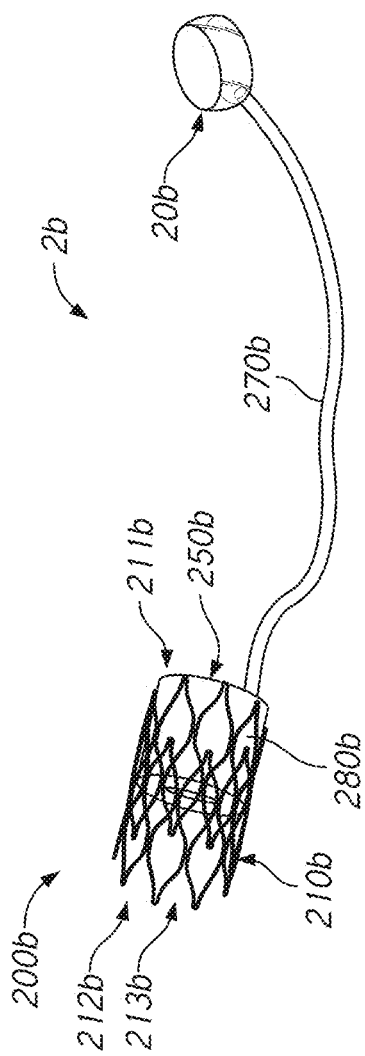
FIG. 9A
FIG. 9B
FIG. 9C
FIG. 9D

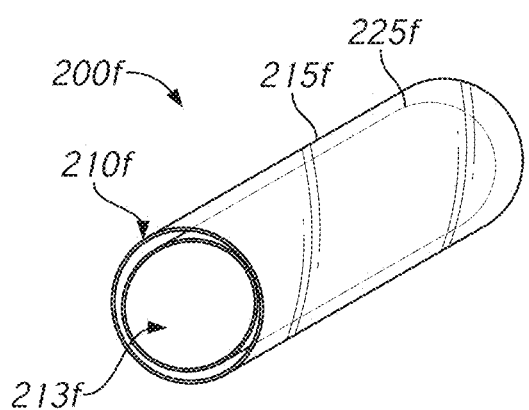
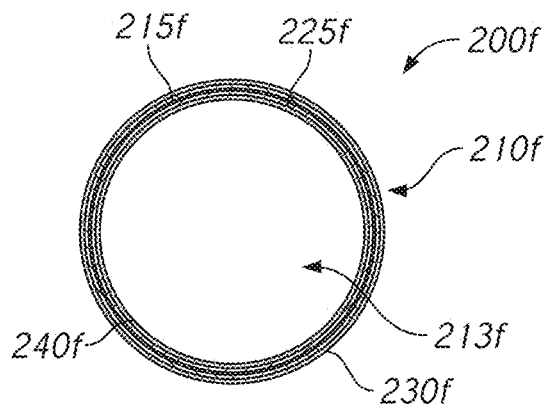
FIG. 13A   FIG. 13B
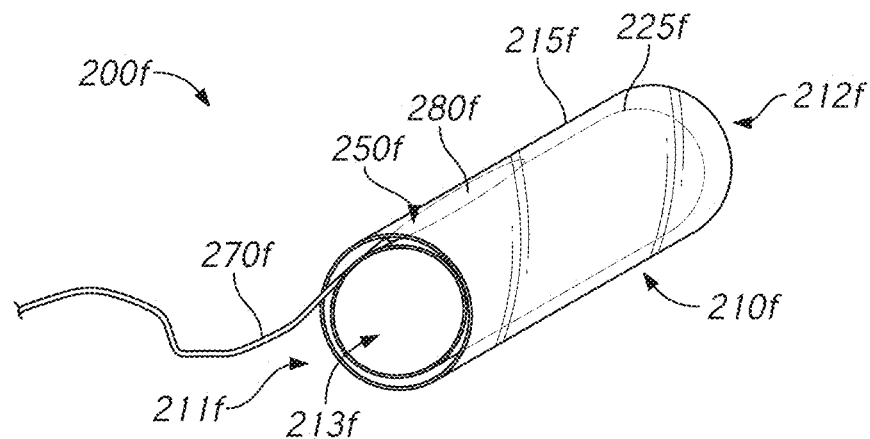
FIG. 13C
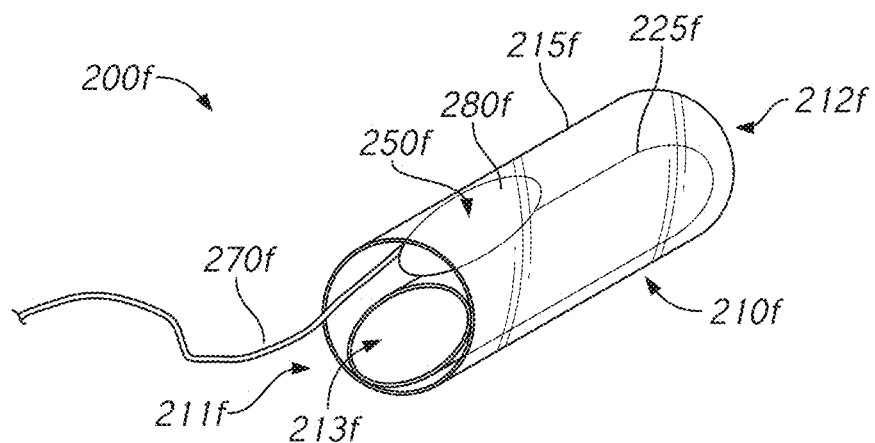
FIG. 13D

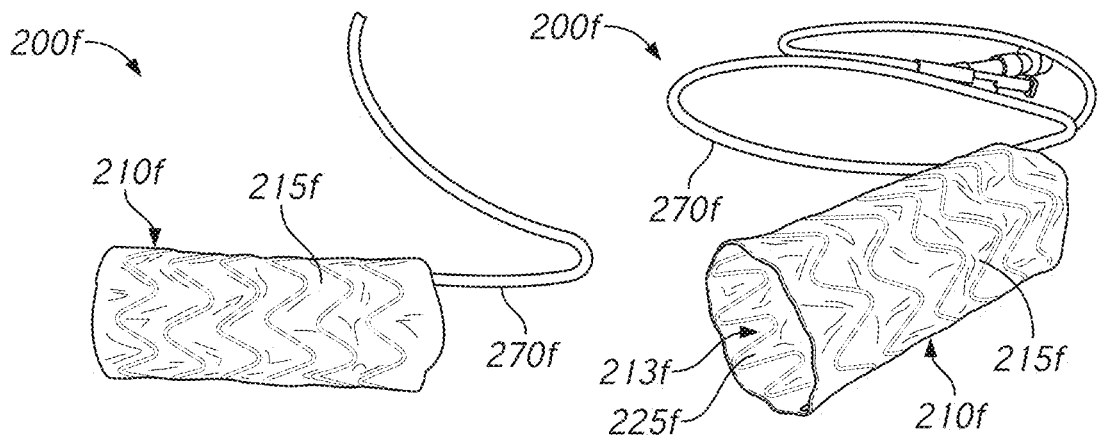
FIG. 14A
FIG. 14B
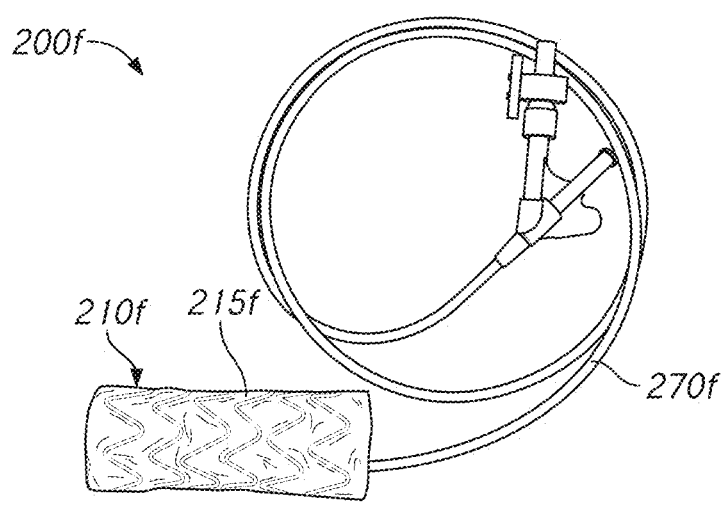
FIG. 14C
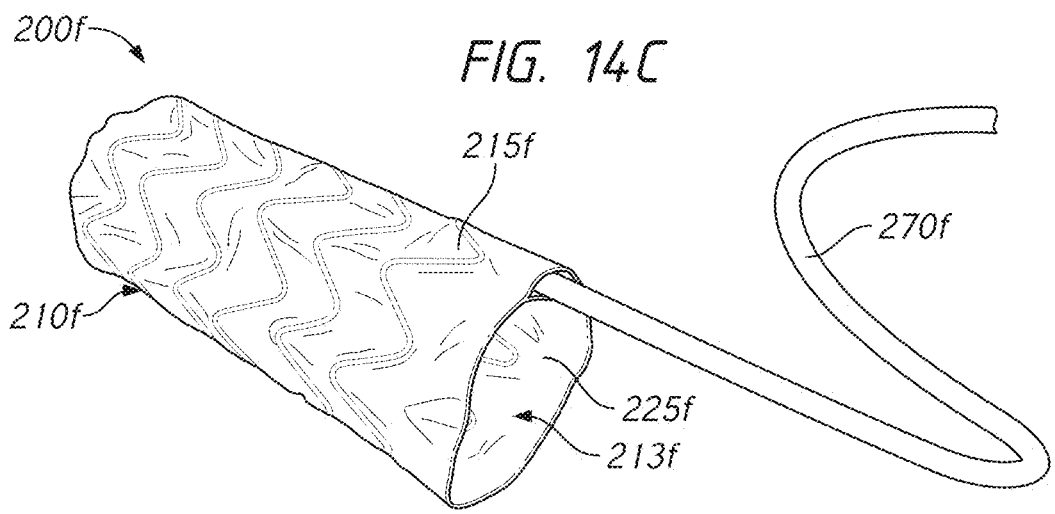
FIG. 14D

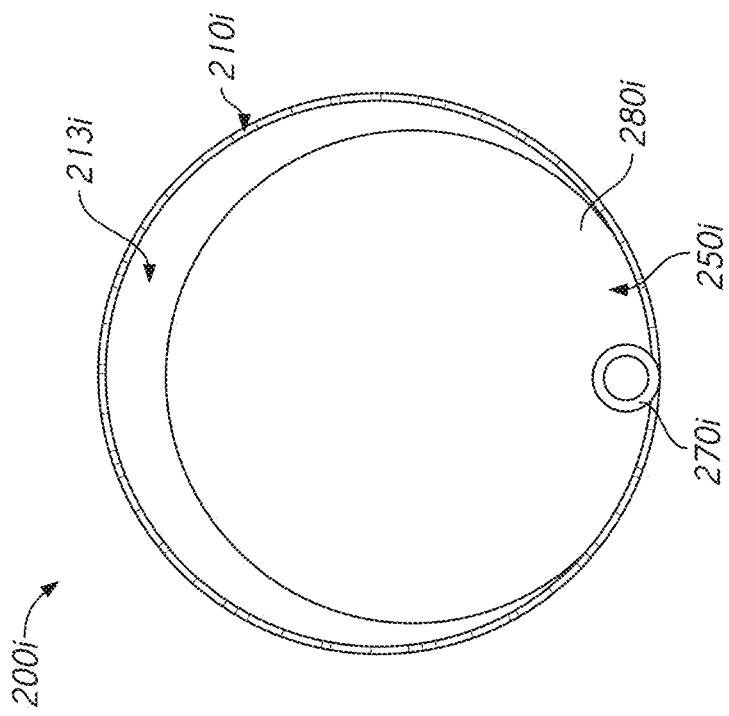
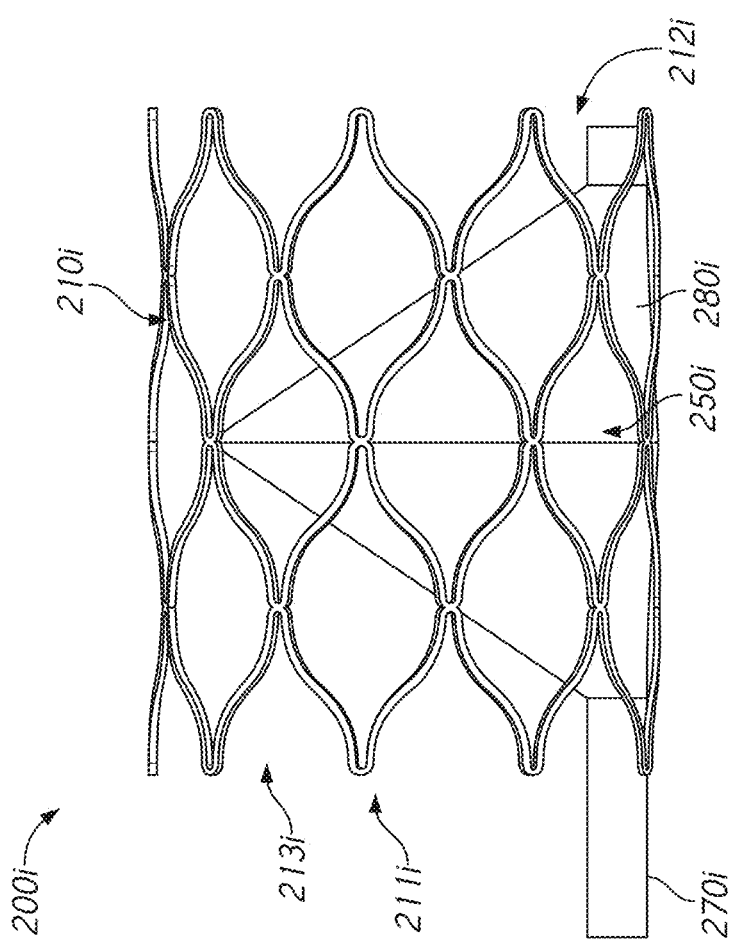
FIG. 17B
FIG. 17A

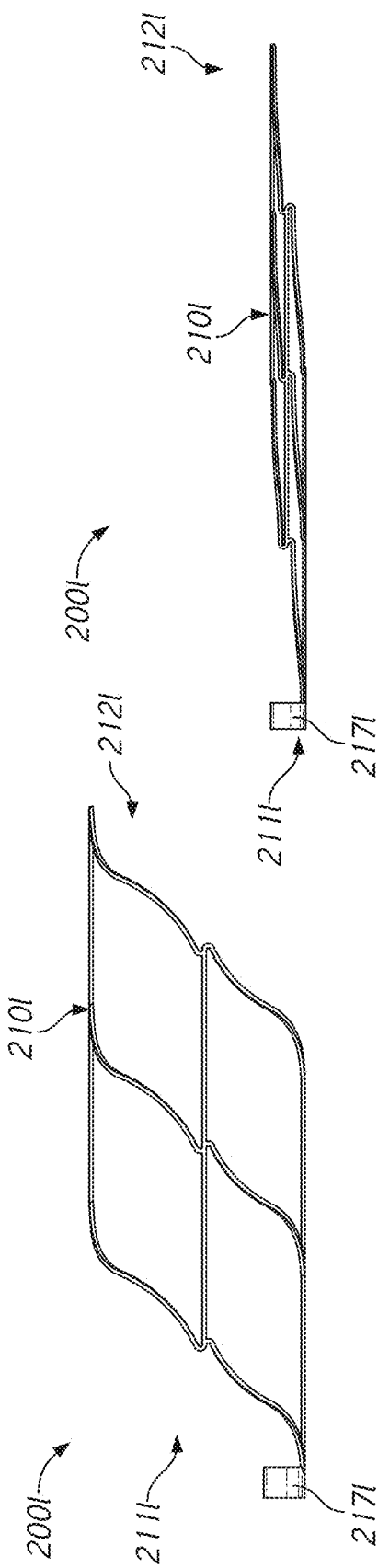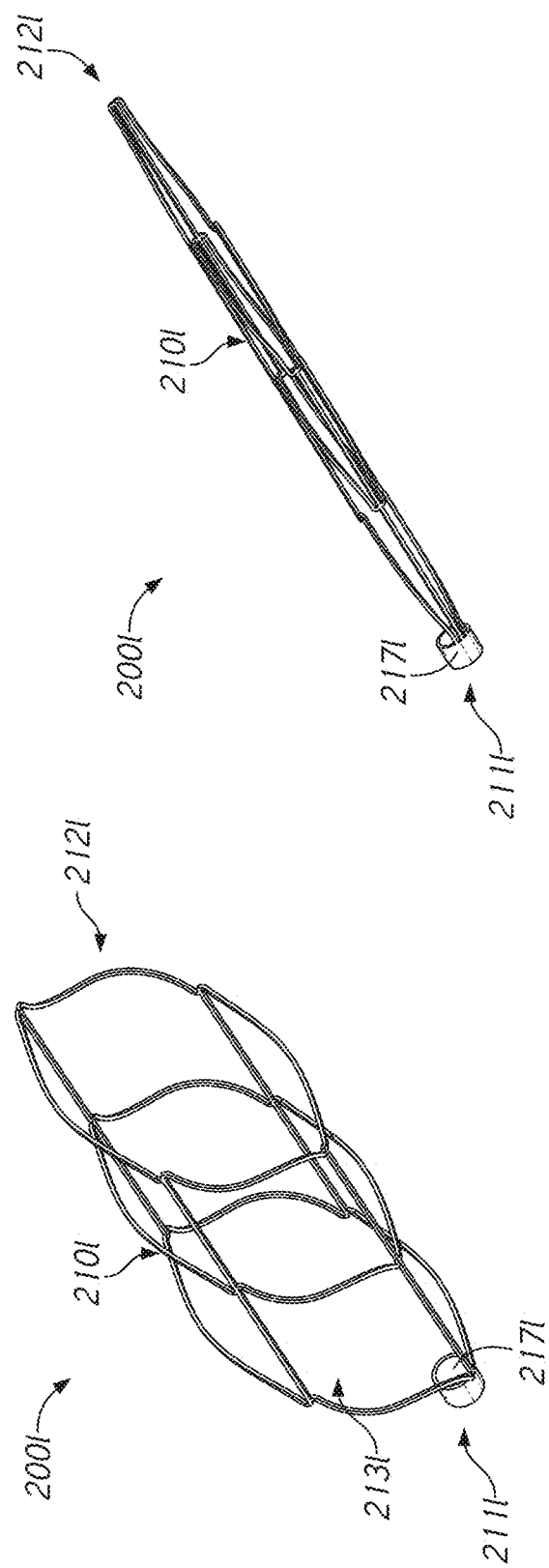

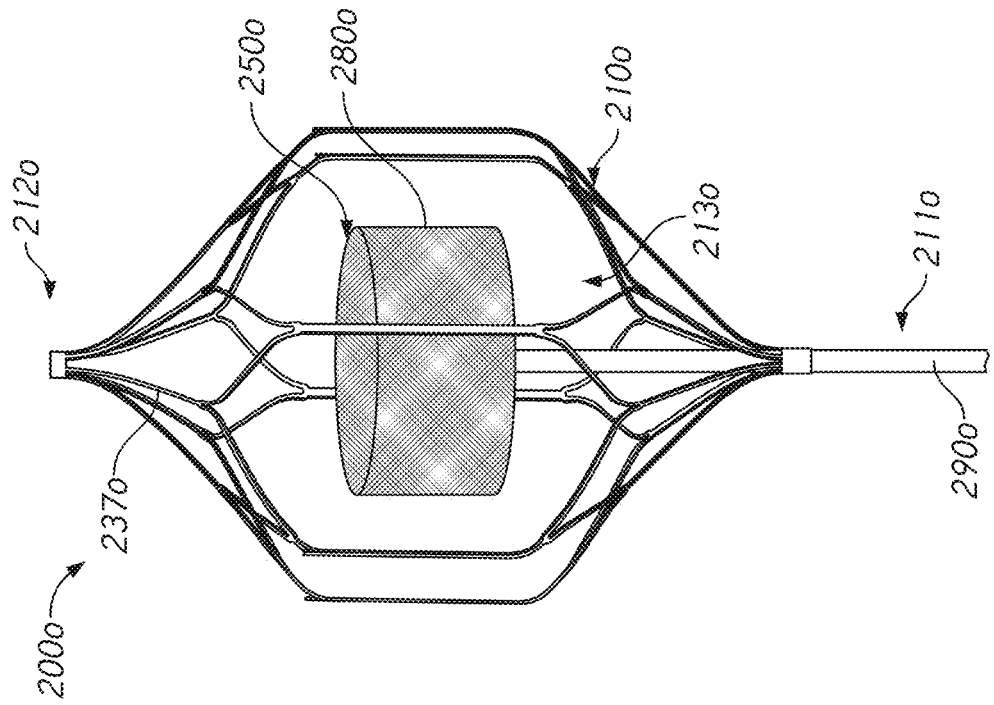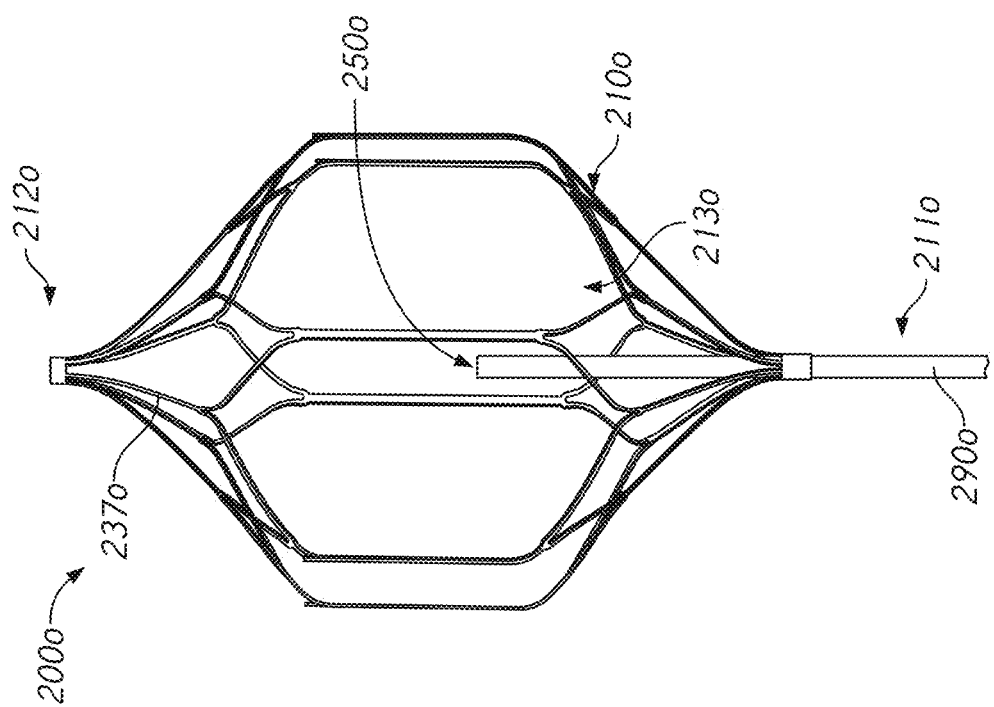
FIG. 21C

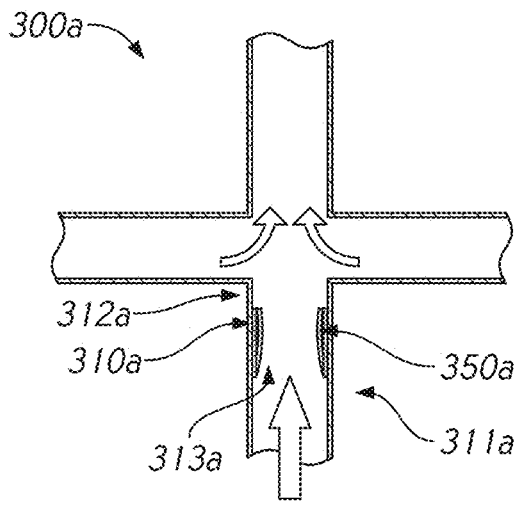
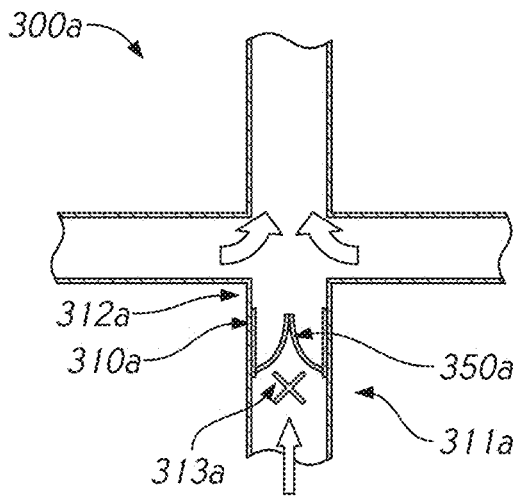
FIG. 23A  FIG. 23B
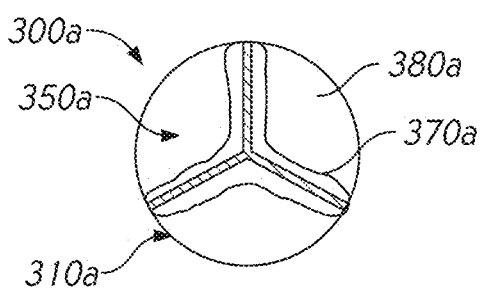
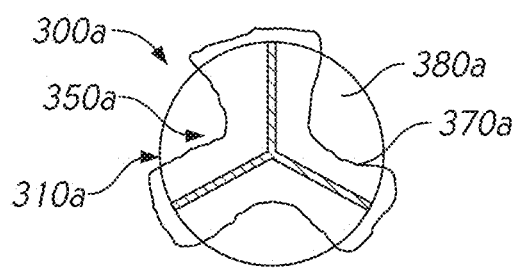
FIG. 24A  FIG. 24B
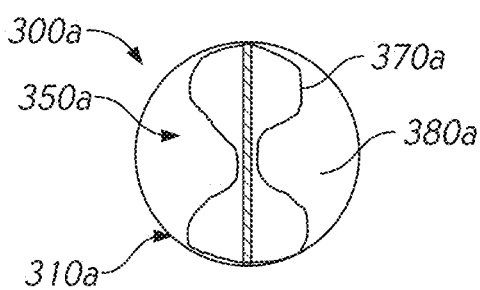
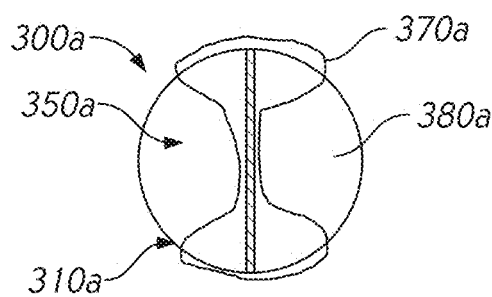
FIG. 25A  FIG. 25B
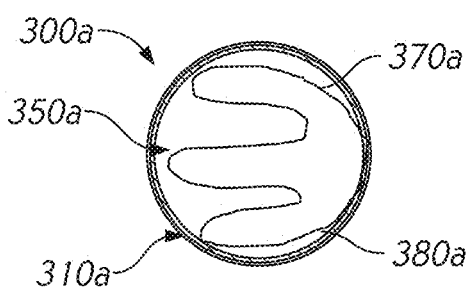
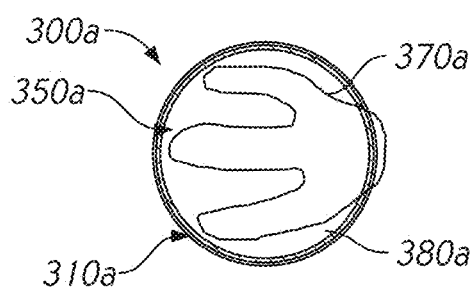
FIG. 26A  FIG. 26B

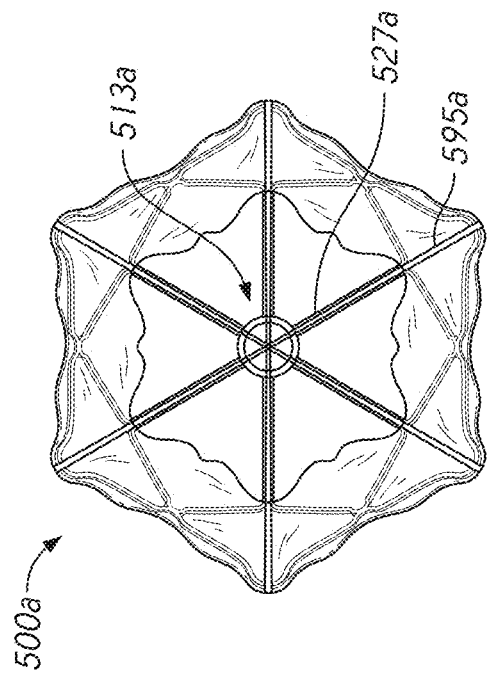
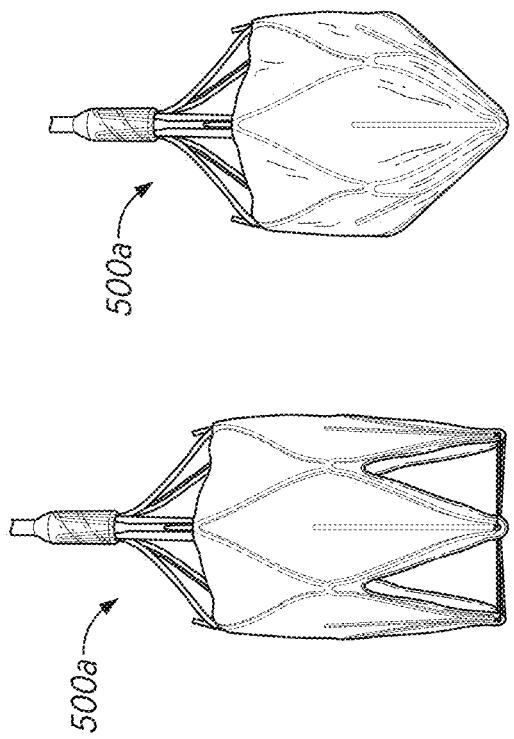
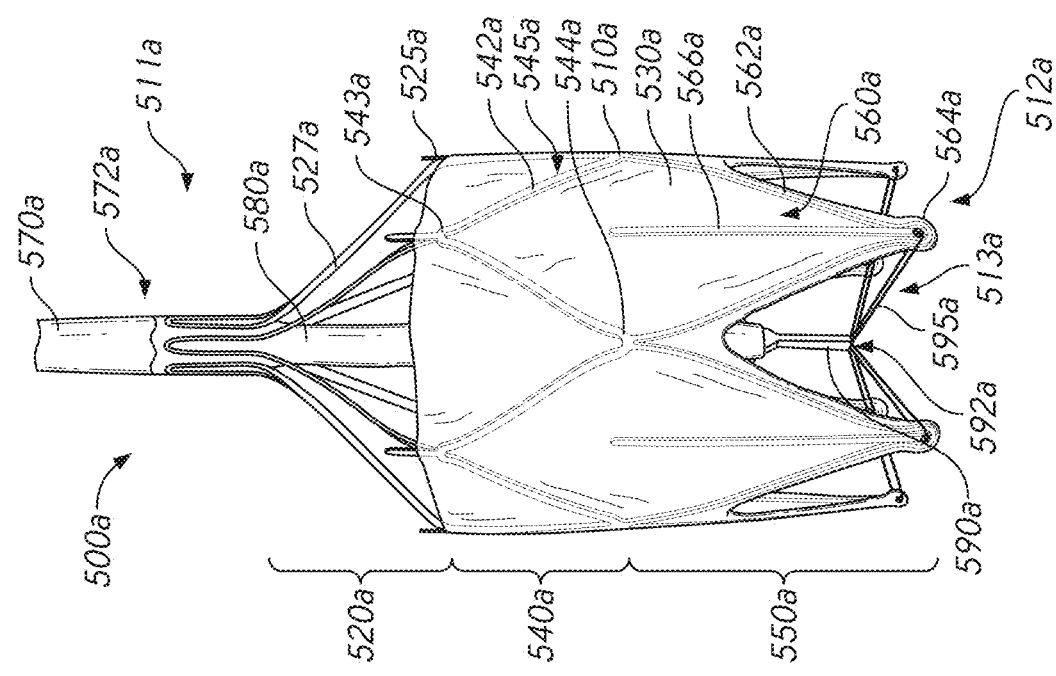
FIG. 43B
FIG. 43D
FIG. 43C
FIG. 43A

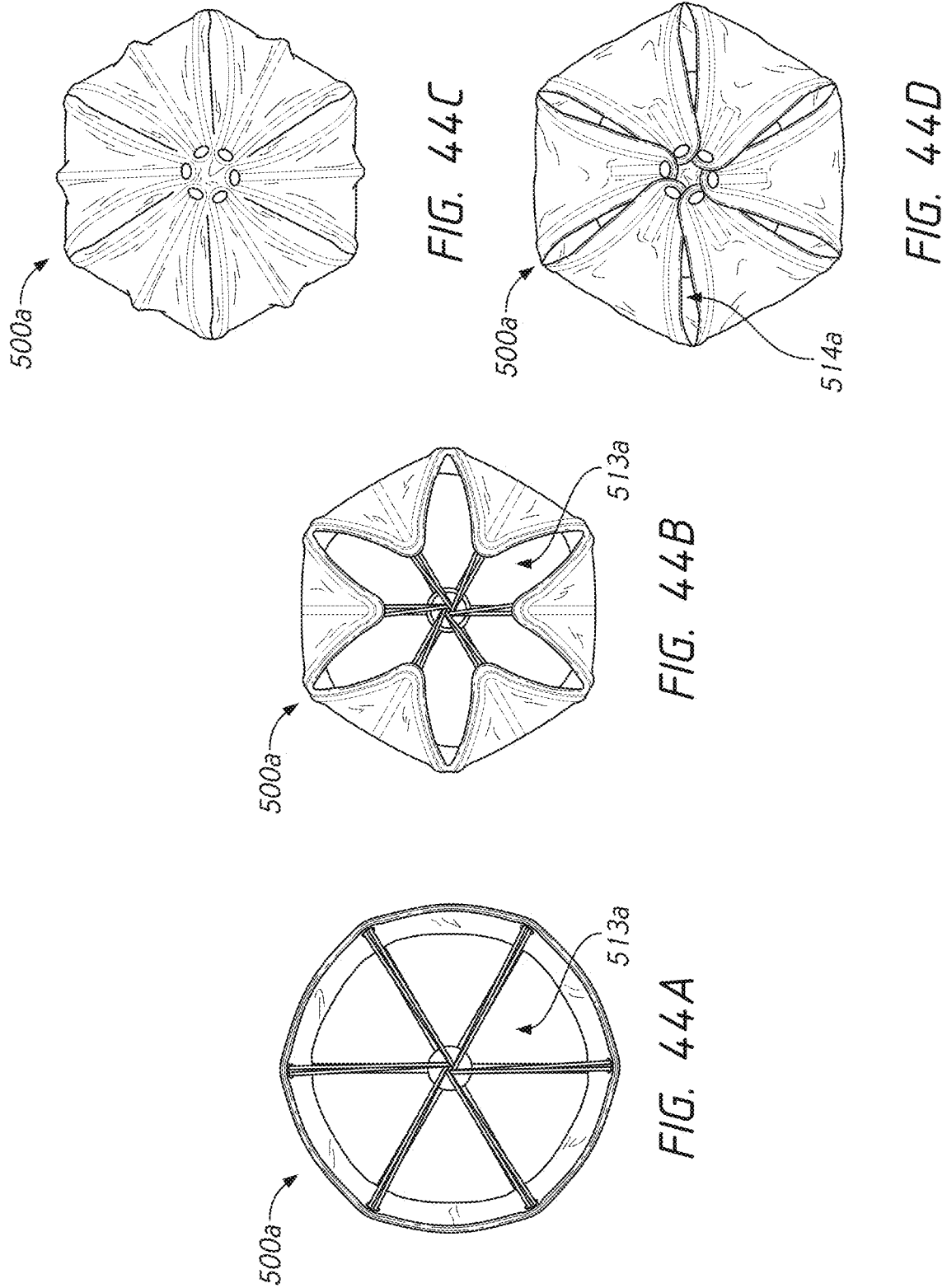

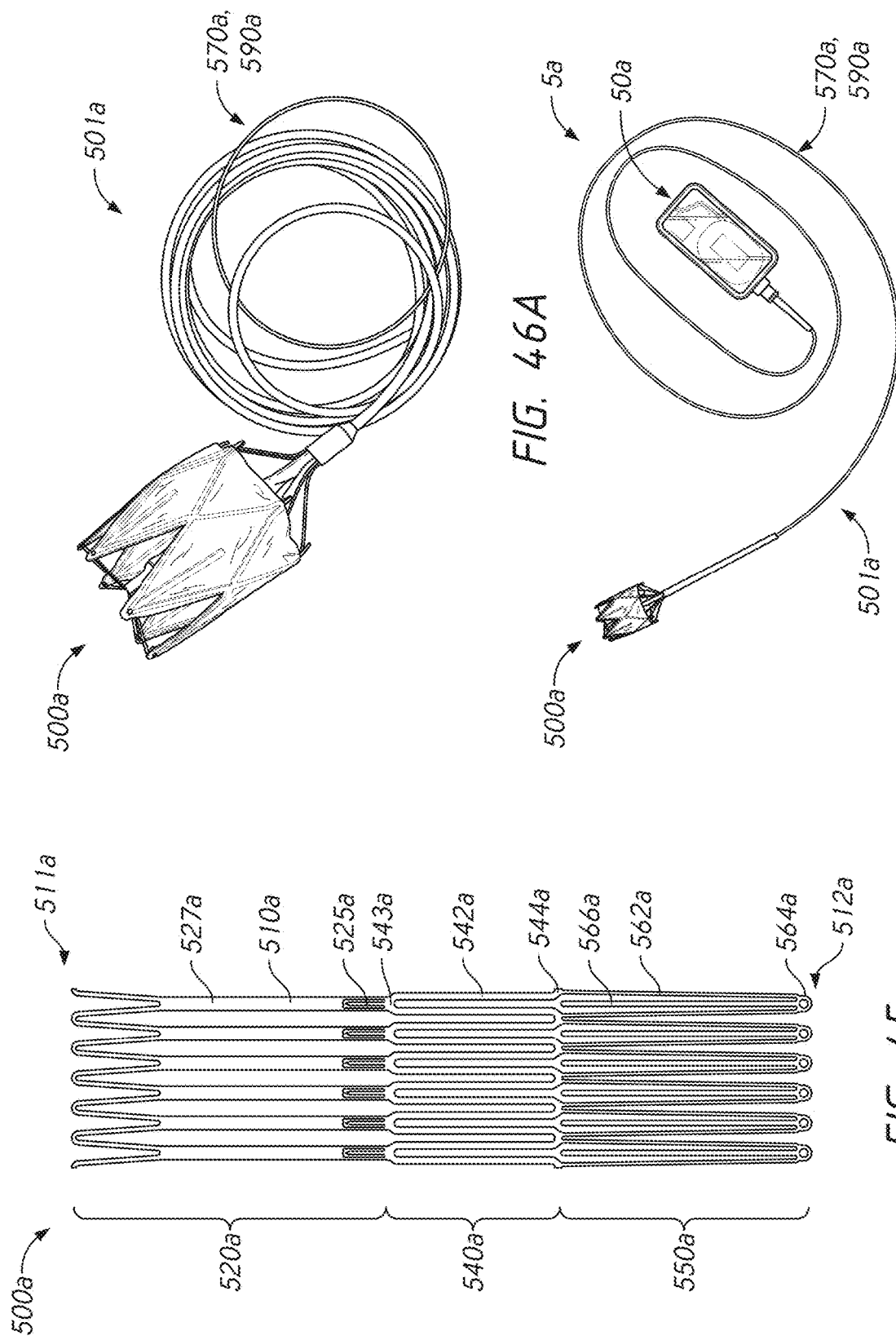

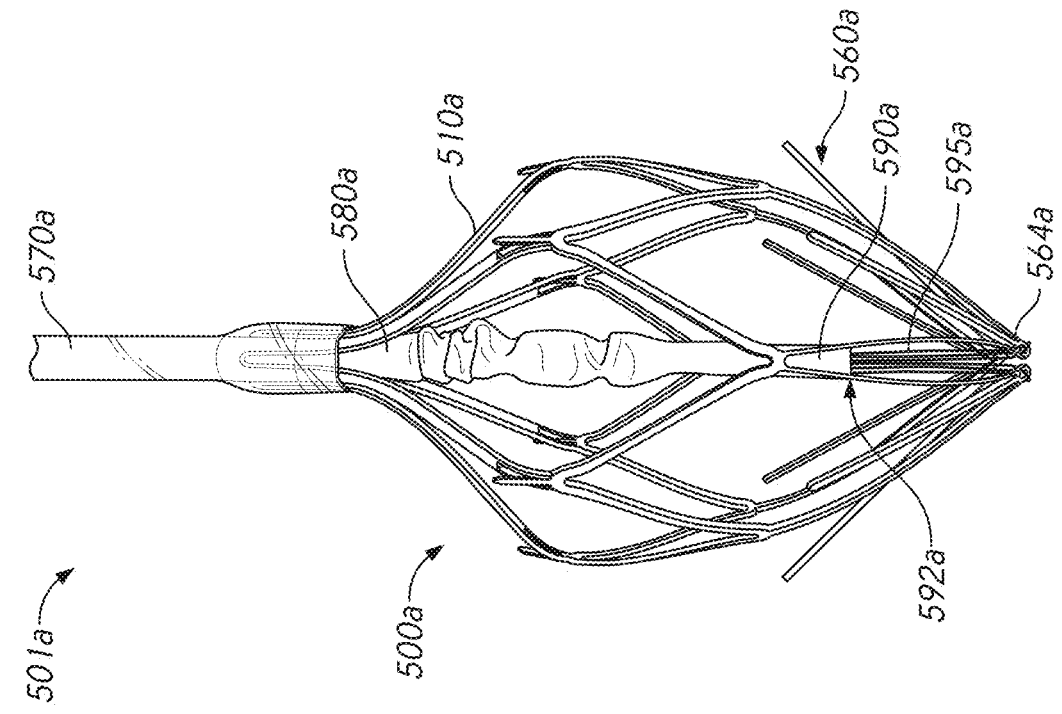
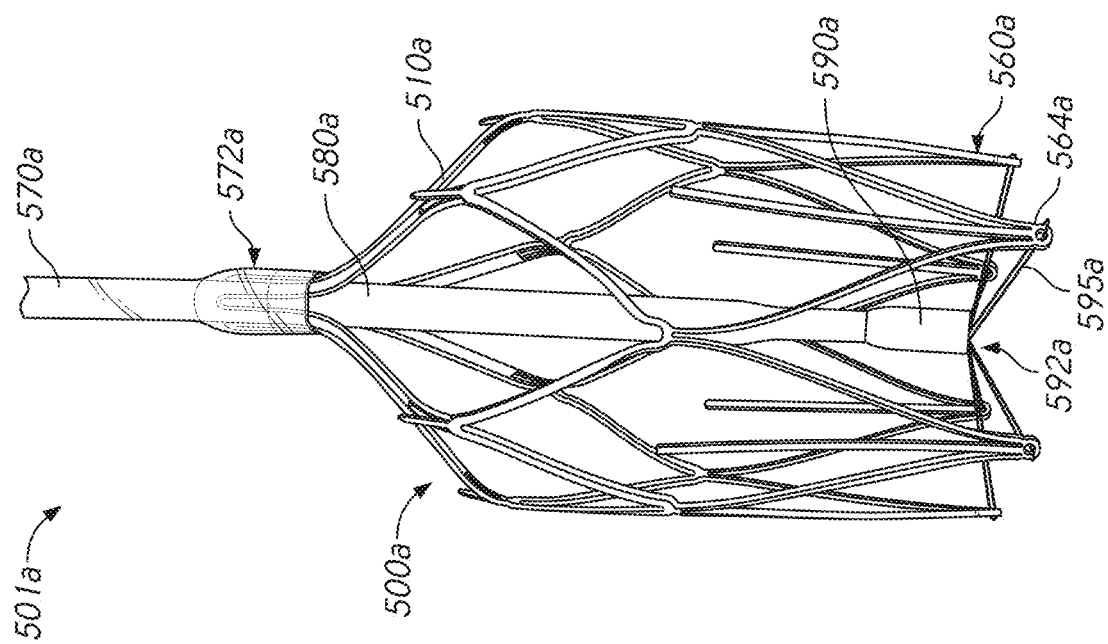

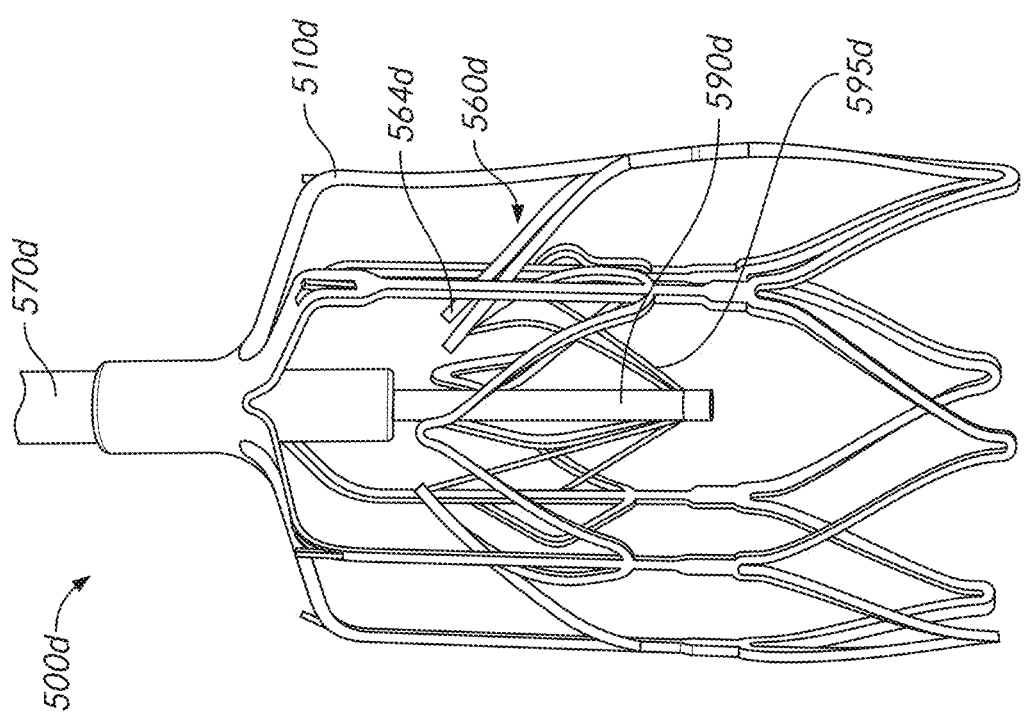
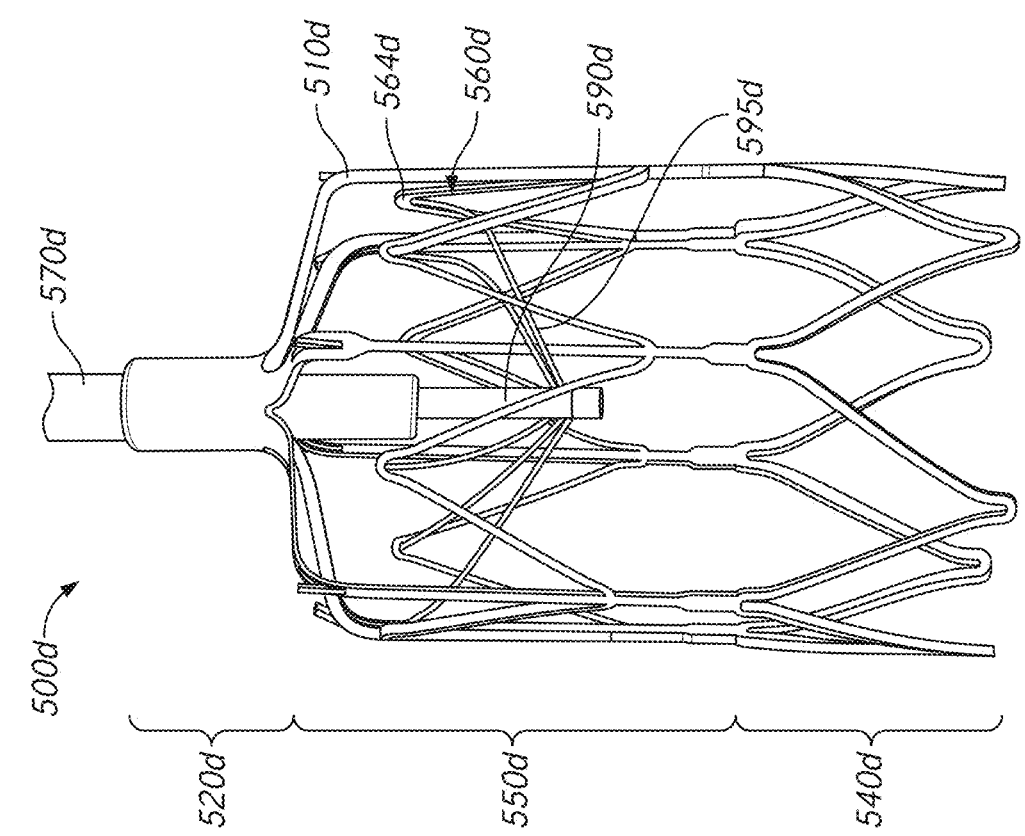
FIG. 51A
FIG. 51B

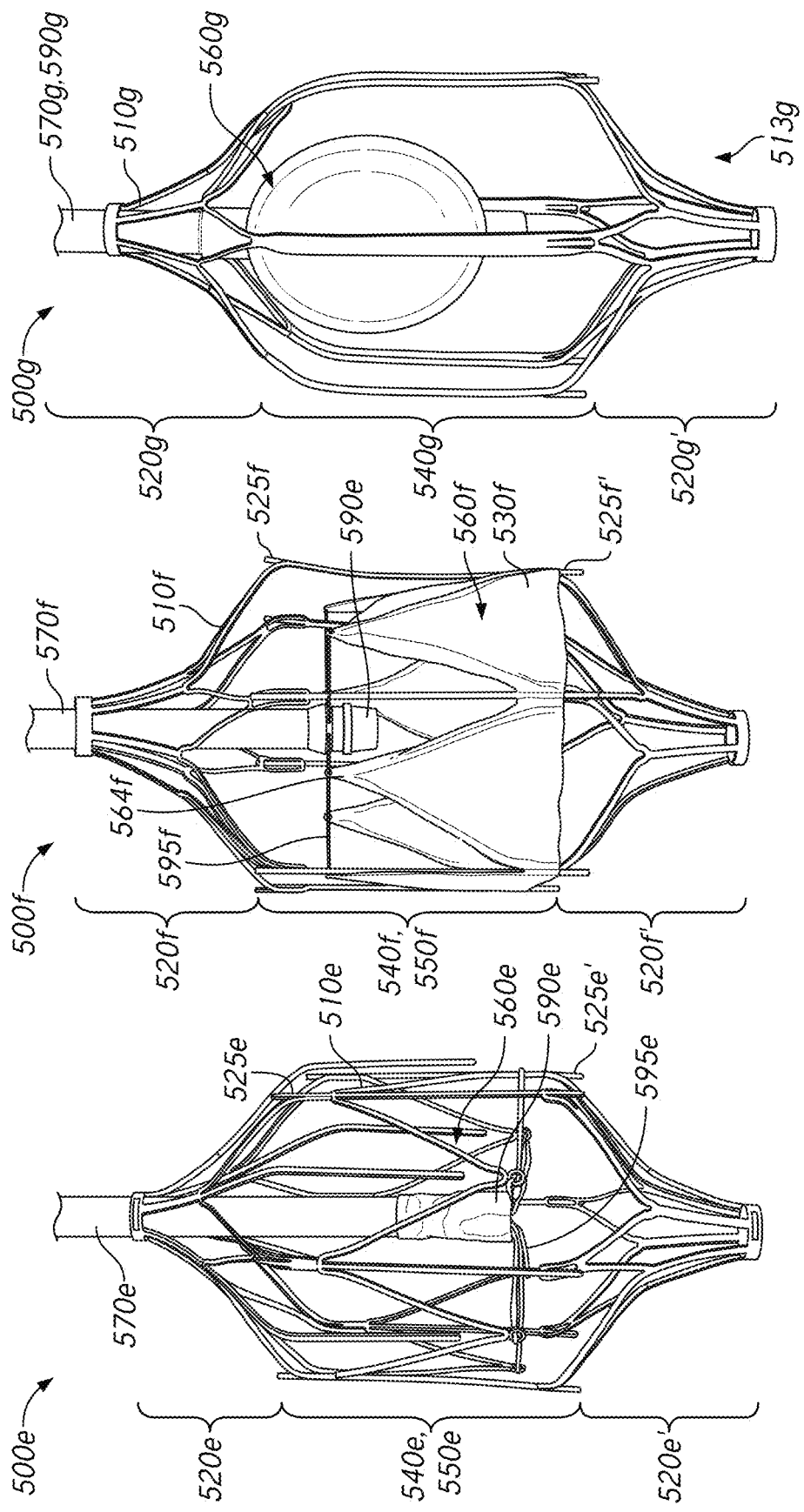

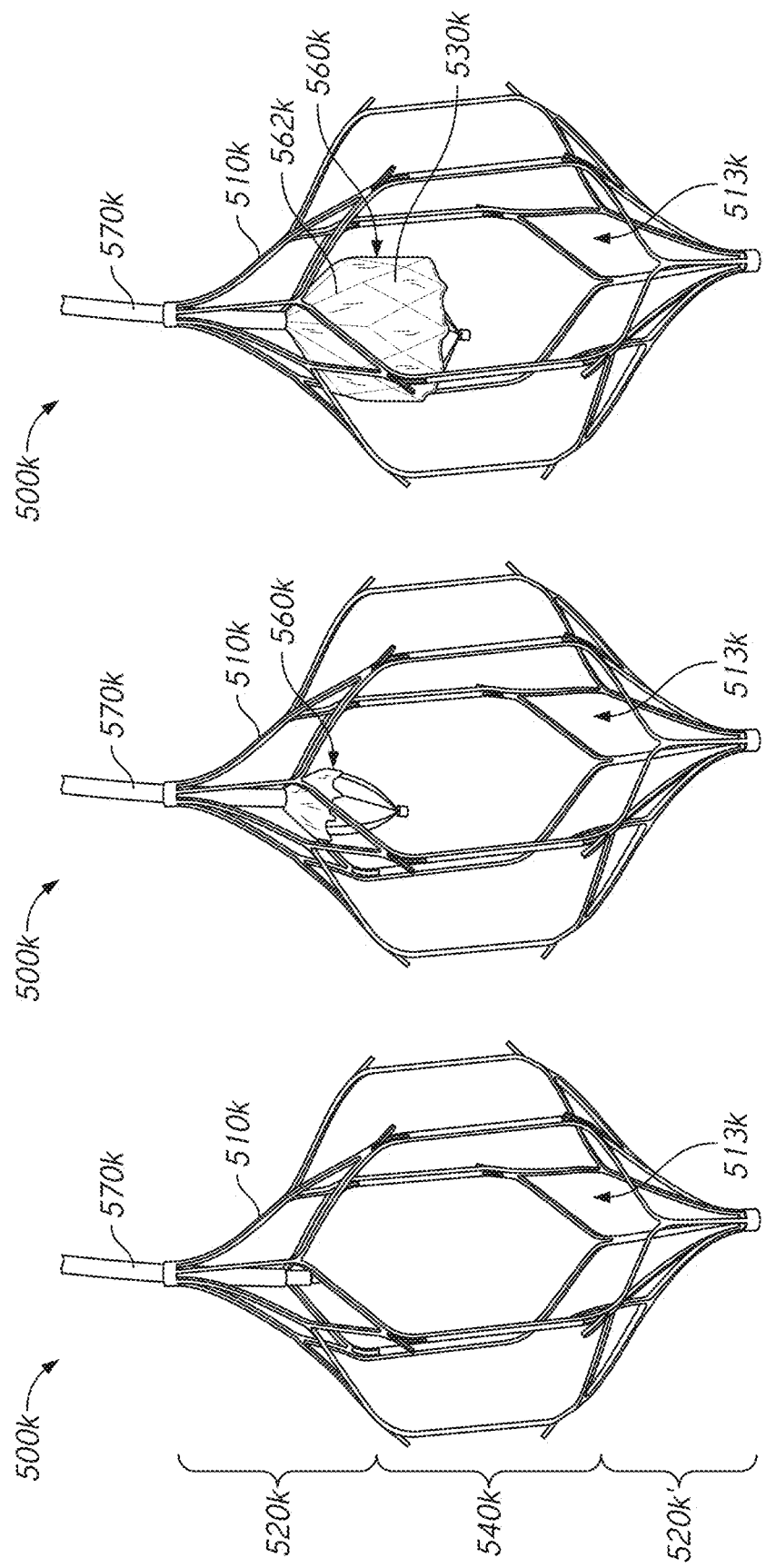

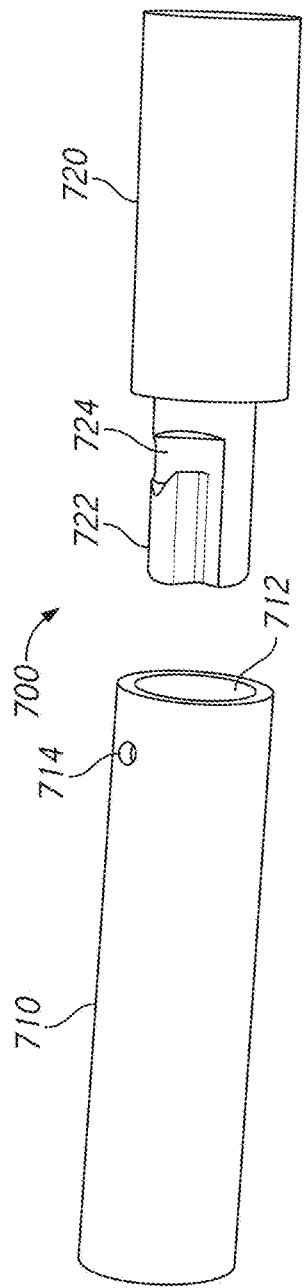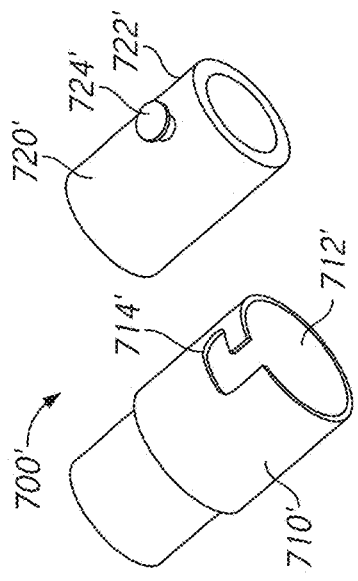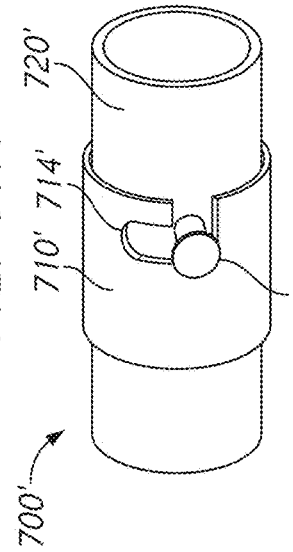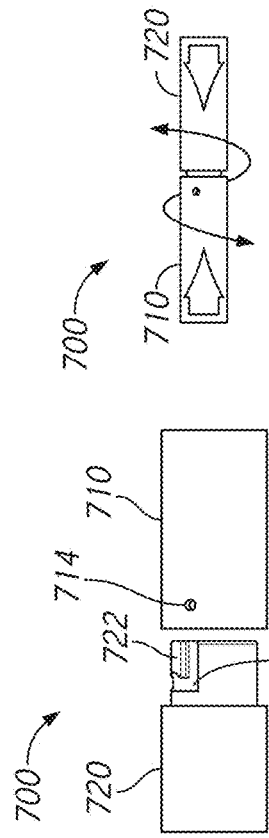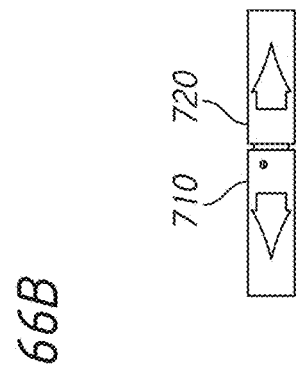
FIG. 66A
FIG. 66B
FIG. 66C
FIG. 67A
FIG. 67B

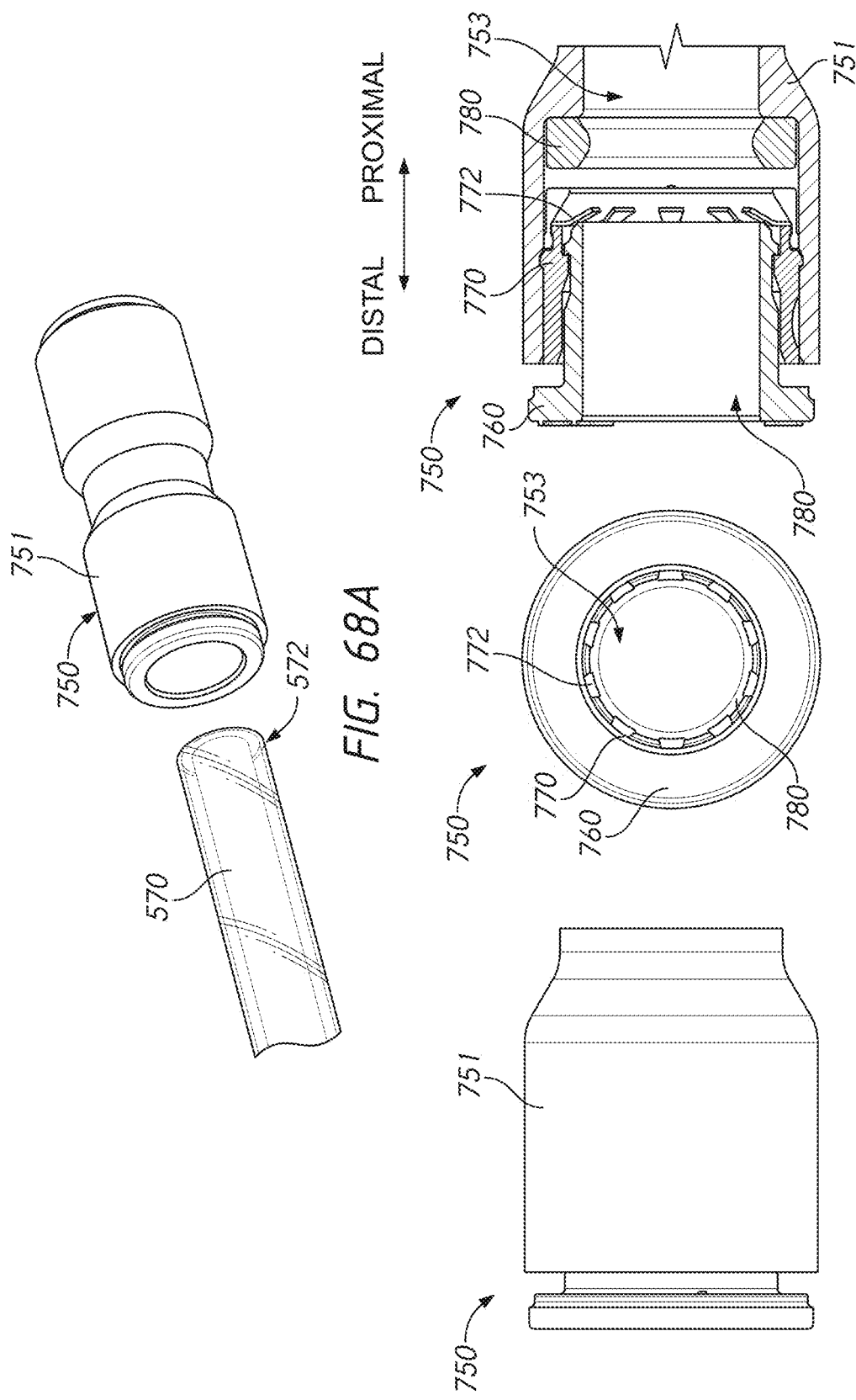

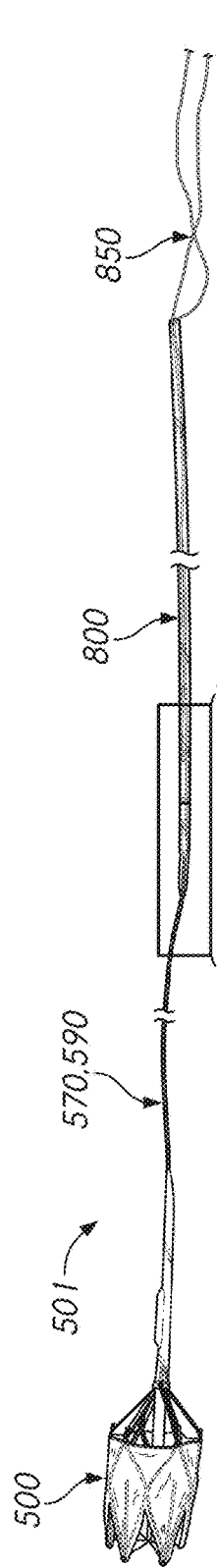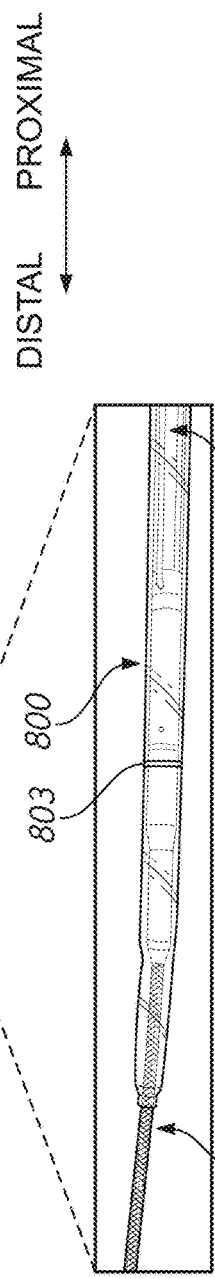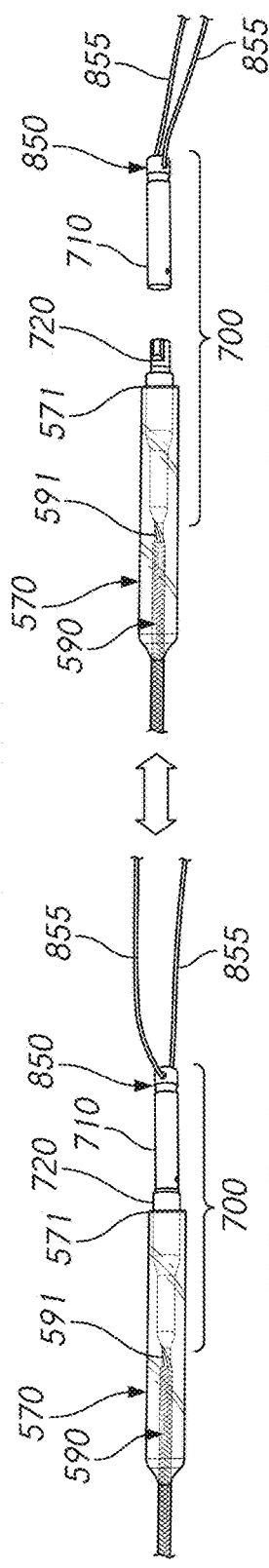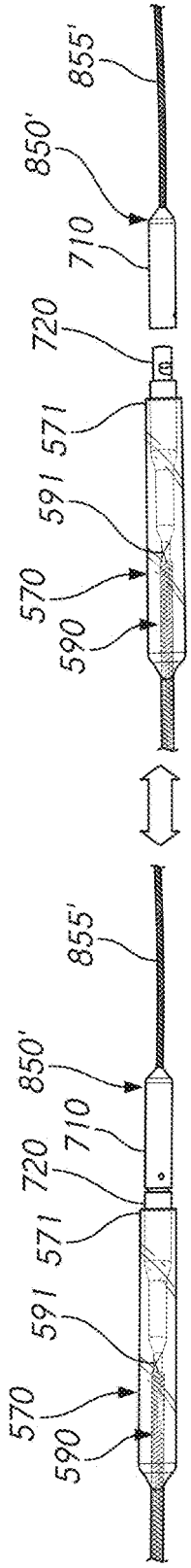

```
                        Manual Method of Use
1200 ─┐
     1205 ─┐
          ┌─────────────────────────────────────────┐
          │  Patient requests pressure measurement  │
          └─────────────────────────────────────────┘
     1210 ─┐           │
          ┌─────────────────────────────────────────┐
          │         System measures pressure        │
          └─────────────────────────────────────────┘
     1215 ─┐           │
          ┌─────────────────────────────────────────┐
          │      System detects pressure increase   │
          └─────────────────────────────────────────┘
     1220 ─┐           │
          ┌─────────────────────────────────────────┐
          │  System notifies patient of pressure increase │
          └─────────────────────────────────────────┘
     1225 ─┐           │
          ┌─────────────────────────────────────────┐
          │           Patient activates system      │
          └─────────────────────────────────────────┘
     1230 ─┐           │
          ┌─────────────────────────────────────────┐
          │             System deactivates          │
          └─────────────────────────────────────────┘
```

Semi-Automatic Method of Use

1305 — System measures pressure

1310 — System detects pressure increase

1315 — System notifies patient of pressure increase

1320 — Patient activates system

1325 — System deactivates

FIG. 76

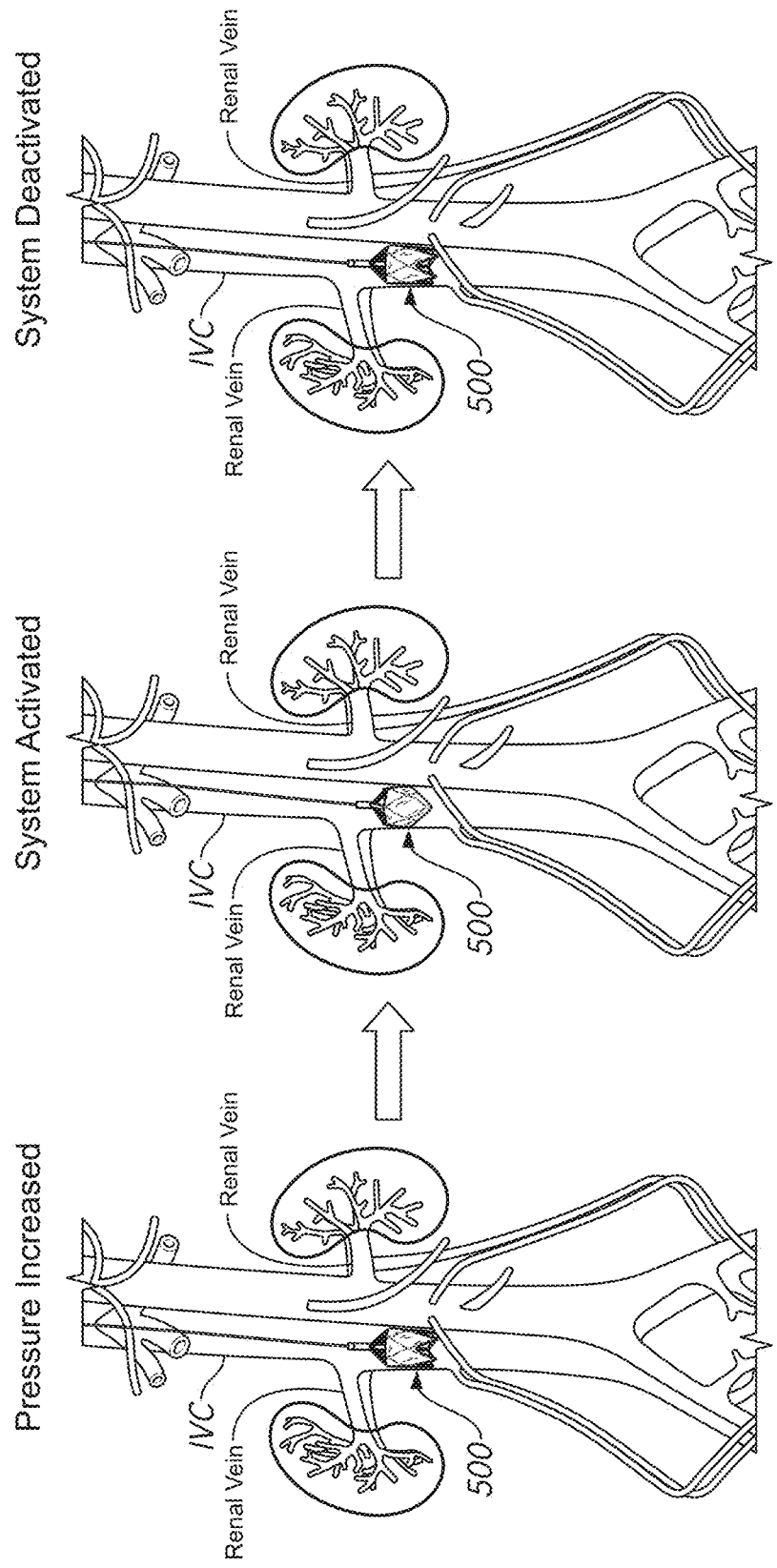

SYSTEMS, DEVICES, AND METHODS FOR CONTROLLABLY AND SELECTIVELY OCCLUDING, RESTRICTING, AND DIVERTING FLOW WITHIN A PATIENT'S VASCULATURE

INCORPORATION BY REFERENCE TO ANY PRIORITY APPLICATIONS

This application claims the benefit of priority under 35 U.S.C. § 119(e) to U.S. Provisional Patent Application No. 63/336,924, filed Apr. 29, 2022, and U.S. Provisional Patent Application No. 63/484,635, filed Feb. 13, 2023. All of the above-mentioned applications are hereby incorporated by reference herein in their entireties. Any and all applications for which a foreign or domestic priority claim is identified in the Application Data Sheet as filed with the present application are hereby incorporated by reference under 37 CFR 1.57.

TECHNICAL FIELD

The present disclosure relates to systems, devices, and methods for treating heart failure, including systems, devices, and methods for controllably and selectively occluding, restricting, and/or diverting flow within a patient's vasculature.

BACKGROUND

An identified issue in heart failure is volume overload, wherein there is an excess of pressure built up in the venous system which can cause the heart to not work as well as a pump. Reducing the total volume of fluid in the body, such as by the administration of diuretics, is one method to reduce volume overload and improve heart function. Another way to improve heart function in heart failure is to shift the distribution of blood in the vascular system. Such a shift in the distribution of blood can affect the preload on the heart and thus the heart's ability to pump effectively. Additionally, shifting venous blood volume away from the renal system and/or lymphatic ducts can enhance diuresis, further reducing volume overload and improving heart function.

SUMMARY

Current nonpharmacological therapies aimed at reducing volume overload and/or reducing preload lack chronic controllability and/or adjustability. Additionally, current methods to improve and/or control diuresis include systemic application of diuretics, which can significantly affect patient quality of life. A more controllable method of controlling diuresis is desired. To address these and other unmet needs, the present disclosure describes various implementations of chronic, implantable flow restriction systems, devices, and methods for controllably and selectively occluding, restricting, and/or diverting flow within a patient's vasculature. The chronic, implantable flow restriction systems and devices described herein can be actuated in a variety of ways, including magnetically, fluidically including pneumatically, mechanically, via heat (e.g., induction heating), and/or via another energy source. Furthermore, the chronic, implantable flow restriction systems and devices described herein can be configured to provide partial and/or full occlusion of a vessel from within the vessel and/or external to the vessel. Such ability to chronically control the occlusion of a patient's vessel(s) can allow, for example, the control of diuresis without systemic drugs/medication.

Disclosed herein is a chronic, implantable flow restriction system for controllably and selectively occluding, restricting and/or diverting flow within a patient's vasculature to reduce renal congestion and/or to reduce cardiac preload.

In the above chronic, implantable flow restriction system or in other implementations as described herein, one or more of the following features can also be provided. In some implementations, the system is adapted to controllably and selectively reduce central venous pressure and/or other venous pressure, which can include inferior vena cava pressure, renal venous pressure, and/or pressure of other veins disclosed herein. In some implementations the system is adapted to enhance renal circulation. In some implementations, the system is adapted to enhance or to control diuresis. In some implementations, the system is adapted to improve cardiac output. In some implementations, the system is adapted to controllably and selectively occlude or divert flow from the superior vena cava. In some implementations, the system is adapted to controllably and selectively occlude or divert flow from the inferior vena cava. In some implementations, the system comprises a magnetically actuated implantable device. In some implementations, the system comprises a fluidically actuated implantable device. In some implementations, the system comprises a heat actuated implantable device. In some implementations, the system comprises a mechanically actuated implantable device. In some implementations, the system comprises an implantable device configured to be delivered extravenously to at least partially surround or be positioned adjacent to a patient's vein. In some implementations, the system comprises a mechanical cinching mechanism on an implantable stent. In some implementations, the system further comprises a control unit configured to control occluding, restricting and/or diverting flow within the patient's vasculature. In some implementations, the control unit is configured to receive readings from one or more pressure sensors positioned within the patient, and the control unit is configured to control occluding, restricting and/or diverting flow within the patient's vasculature based on the readings. In some implementations, therapy delivered by the system is digitally actuated. In some implementations, therapy delivered by the system is scheduled based on a time of a day and/or on an amount of time per day.

Disclosed herein is a chronic, implantable flow restriction system for controllably and selectively occluding, restricting and/or diverting flow of a patient's vasculature, the system comprising an implant. The implant can comprise an expandable body and a flow restrictor. The expandable body can comprise a proximal end and a distal end and a lumen extending from the proximal end to the distal end, wherein the expandable body is configured to collapse to a collapsed configuration for delivery into a patient and to expand from the collapsed configuration to an expanded configuration for implantation within the patient. The flow restrictor can be connected to the expandable body, the flow restrictor configured to adjustably occlude the lumen when the expandable body is in the expanded configuration.

In the above chronic, implantable flow restriction system or in other implementations as described herein, one or more of the following features can also be provided. In some implementations, the expandable body comprises an expandable metallic frame comprising a plurality of struts and defining a plurality of collapsible cells. In some implementations, one or more of the plurality of struts of the expandable body are aligned diagonally relative to a longitudinal axis of the implant. In some implementations, the expandable body is configured to collapse sideways and/or via elongation. In some implementations, the expandable body is configured to collapse radially. In some implementations, one or more of the plurality of struts of the expandable body coalesce at an end of the implant that is offset relative to a central longitudinal axis of the implant. In some implementations, the flow restrictor comprises a magnet and the implant is magnetically actuated. In some implementations, the flow restrictor is configured to move between a first, non-occluding position and a second, at least partially occluding position that at least partially blocks the lumen. In some implementations, the flow restrictor comprises one or more struts connecting the magnet to the expandable body and a material spanning the one or more struts. In some implementations, the system further comprises a magnetic field source configured to actuate the implant. In some implementations, the magnetic field source is configured to be implanted within an interstitial space and/or a vessel adjacent the implant. In some implementations, the magnetic field source is configured to be positioned outside the patient's body. In some implementations, the flow restrictor comprises a balloon and the implant is fluidically actuated. In some implementations, the balloon is configured to expand from a non-actuated state to an actuated state that at least partially blocks the lumen. In some implementations, the balloon is configured as a prolate or oblate spheroid. In some implementations, the balloon is configured as an elongate partial circle that is adhered to an interior of the expandable body and/or to a mounting portion of the expandable body. In some implementations, the balloon is configured as a cylinder with a through opening that is adhered to an interior of the expandable body and/or to a mounting portion of the expandable body. In some implementations, the expandable body comprises an inner body and an outer body, and the balloon is disposed in between the inner body and the outer body. In some implementations, the inner body is configured to be more compliant than the outer body. In some implementations, the inner body is configured to encapsulate the balloon and hide it from flow going through the lumen. In some implementations, the inner body is configured to have a smooth inner surface. In some implementations, the inner body is configured to deflect inwards and at least partially occlude the lumen when the balloon is actuated. In some implementations, the system further comprises tubing and a fluid reservoir fluidically connected to the balloon. In some implementations, the fluid reservoir is configured to be implanted subcutaneously. In some implementations, the tubing is connected coaxial with the balloon. In some implementations, the tubing is connected off-center and/or tangent to the balloon. In some implementations, the expandable body further comprises a plurality of struts and/or a membrane positioned downstream of the balloon in relation to a direction of flow within the implant and located within a flow path of the lumen, the plurality of struts and/or membrane configured to filter and/or capture thrombus. In some implementations, the flow restrictor further comprises a shaft configured to cover the balloon when the balloon is in its non-actuated state. In some implementations, the shaft is configured to hide the balloon from flow through the lumen when the balloon is in its non-actuated state. In some implementations, the flow restrictor comprises a material, a balloon, and/or a wire configured to change shape upon heating and the implant is heat actuated. In some implementations, the flow restrictor comprises a material, a balloon, and/or a wire configured to change shape upon movement and the implant is mechanically actuated. In some implementations, the flow restrictor comprises a shape memory material configured to at least partially occlude the lumen when mechanically actuated.

Disclosed herein is a chronic, implantable flow restriction system. The system can comprise: an implantable control unit comprising a housing and an actuator disposed within the housing, an implant comprising an expandable body having a proximal end and a distal end and a lumen extending longitudinally therethrough, and a flow restrictor configured to adjustably occlude the lumen when the expandable body is in an expanded configuration, tubing connecting the proximal end of the expandable body of the implant to the housing of the control unit, and a shaft movingly disposed within the tubing configured to connect the actuator of the implantable control unit to the flow restrictor of the implant; wherein actuation of the actuator of the implantable control unit slides the shaft within the tubing to cause the flow restrictor of the implant to adjustably occlude the lumen.

In the above chronic, implantable flow restriction system or in other implementations as described herein, one or more of the following features can also be provided. In some implementations, the expandable body of the implant further comprises: a filter portion disposed adjacent the proximal end configured to capture thrombus, the filter portion comprising a plurality of struts that extend radially outward and distally from the connection between the proximal end of the expandable body and the tubing, and a radial support portion connected to and disposed distal of the filter portion configured to fluidically seal against an inner wall of the patient's vasculature, the radial support portion comprising a ring that extends along a circumference of the expandable body in a chevron pattern. In some implementations, the flow restrictor is connected to and extends distally from the radial support portion. In some implementations, the flow restrictor is integrally formed with the expandable body. In some implementations, the flow restrictor comprises: a plurality of petals each formed by a pair of struts that extend distally from adjacent distal apexes of the chevron patterned ring of the radial support portion and that join at a distal apex, and a material spanning each of the plurality of petals. In some implementations, the flow restrictor comprises three petals or more. In some implementations, the material further spans the radial support portion. In some implementations, a distal end of each of the petals of the flow restrictor connect to a distal end of the shaft via a suture or a wire, and wherein proximal sliding of the shaft within the tubing causes the suture or the wire to pull the distal end of each of the petals of the flow restrictor towards one another to at least partially occlude the lumen. In some implementations, a distal end of the tubing is fluidically sealed with the shaft by a collapsible and extendible flexible coupling. In some implementations, the implant is configured to be implanted in an inferior vena cava of the patient below renal veins of the patient and a distal end of the flow restrictor positioned to receive blood flow therethrough. In some implementations, the system further comprises one or more pressure sensors configured to measure a pressure of the patient's vasculature and output at least one signal responsive to the measured pressure. In some implementations, the one or more pressure sensors comprise a pressure sensor configured to measure a renal pressure of the patient. In some implementations, the pressure sensor configured to measure the renal pressure of the patient is disposed proximal of the flow restrictor. In some implementations, the pressure sensor configured to measure the renal pressure of the patient is disposed adjacent the proximal end of the expandable body or the distal end of the tubing. In some implementations, the one or more pressure sensors comprise a pressure sensor configured to measure an inferior vena cava pressure of the patient. In some implementations, the pressure sensor configured to measure the inferior vena cava pressure of the patient is disposed proximal or distal of the flow restrictor. In some implementations, the pressure sensor configured to measure the inferior vena cava pressure of the patient is disposed adjacent the distal end of the expandable body. In some implementations, the implantable control unit further comprises a processor, wherein the processor is operably connected to the one or more pressure sensors and configured to receive and process the at least one signal to determine the pressure of the patient's vasculature. In some implementations, the implantable control unit further comprises a communication module operably connected to the processor and configured to wirelessly communicate with an external device. In some implementations, the communication module transmits the determined pressure of the patient's vasculature to the external device. In some implementations, the processor is operably connected to the actuator of the implantable control unit, and based on the determined pressure, the patient or a user can digitally actuate via the external device the actuator and thereby cause the flow restrictor of the implant to adjustably occlude the lumen. In some implementations, the expandable body further comprises one or more anchors configured to anchor the implant within the patient's vasculature. In some implementations, the implantable control unit is configured to be powered by a battery disposed within the housing. In some implementations, the battery of the implantable control unit is configured to be charged by induction charging. In some implementations, the implantable control unit is configured to be powered by induction.

Disclosed herein is an implant for controllably and selectively occluding, restricting and/or diverting flow of a patient's vasculature. The implant can be configured to be implanted in an inferior vena cava of the patient. The implant can comprise: an expandable body having a proximal end and a distal end and a lumen extending longitudinally therethrough; and a flow restrictor extending from the expandable body, the flow restrictor configured to adjustably occlude the lumen when the expandable body is in an expanded configuration. When implanted, the flow restrictor can be configured to be positioned upstream of the expandable body with respect to blood flow.

In the above implant or in other implementations as described herein, one or more of the following features can also be provided. In some implementations, the expandable body of the implant further comprises a filter portion disposed adjacent the proximal and/or distal end configured to capture thrombus. In some implementations, the flow restrictor comprises a plurality of petals configured to fold radially inward to adjustable occlude the lumen, wherein when folded radially inward, an exterior surface of the plurality of petals is configured to occlude blood flow. In some implementations, each of the plurality of petals is formed by a pair of struts that extend from the expandable body and join at a distal apex. In some implementations, the flow restrictor carries an occlusive material, and wherein regions between the plurality of petals are free of the occlusive material. In some implementations, the occlusive material further spans at least a portion of the expandable body. In some implementations, the flow restrictor has a non-circular opening when at least partially occluding the lumen. In some implementations, the flow restrictor has a stellate shaped opening when at least partially occluding the lumen.

Disclosed herein is a method of controllably and selectively occluding, restricting and/or diverting flow of a patient's vasculature. The method can comprise: measuring a renal pressure from an implant; detecting an increase in the renal pressure; transmitting, to an external device, an indication the renal pressure has increased; receiving, from the external device, an instruction to activate the implant; wherein activating the implant causes the implant to at least partially occlude blood through a vessel in the patient's vasculature.

Disclosed herein is a chronic, implantable flow restriction system. The system can comprise: an implant configured to be implanted in an inferior vena cava of the patient and adjustably occlude the inferior vena cava, the implant comprising a pressure sensor; and an implantable control unit comprising: an actuator, wherein actuation of the actuator causes the implant to adjustably occlude the inferior vena cava; a processor operably connected to the pressure sensor and configured to receive and process a signal from the pressure sensor to determine the pressure of the inferior vena cava; and a communication module operably connected to the processor and configured to wirelessly communicate with an external device, wherein the processor is further configured to receive, from the external device, an instruction to actuate the actuator and cause the implant to adjustably occlude the inferior vena cava.

In the above chronic, implantable flow restriction system or in other implementations as described herein, one or more of the following features can also be provided. In some implementations, the pressure sensor is further configured to measure a renal pressure of the patient. In some implementations, the system does not include an assist device or a pump. In some implementations, the implantable control unit further comprises a housing, and the actuator is disposed within the housing. In some implementations, the implant is configured to be implanted in the inferior vena cava upstream of renal veins of the patient.

Disclosed herein is a chronic, implantable flow restriction system. The system can comprise: an implant configured to be implanted in an inferior vena cava of a patient and adjustably occlude the inferior vena cava; and an implantable control unit removably connected to the implant, the implantable control unit comprising: an actuator, wherein actuation of the actuator causes the implant to adjustably occlude the inferior vena cava; a processor configured to receive an instruction to actuate the actuator; and a communication module operably connected to the processor and configured to wirelessly communicate with an external device. In some implementations, the implantable control unit further comprises a housing, and the actuator is disposed within the housing. In some implementations, the implant is configured to be implanted in the inferior vena cava upstream of renal veins of the patient.

Disclosed herein is a chronic, implantable flow restriction system. The system can comprise: an implant configured to be implanted in an inferior vena cava of the patient upstream of renal veins of the patient and adjustably occlude the inferior vena cava; an implantable control unit operably connected to the implant via tubing, the implantable control unit comprising: an actuator, wherein actuation of the actuator causes the implant to adjustably occlude the inferior vena cava; a processor configured to receive an instruction to actuate the actuator; and a communication module operably connected to the processor and configured to wirelessly communicate with an external device.

Disclosed herein is a method for implanting a chronic, implantable flow restriction system in a patient. The method can comprise: accessing a subclavian vein of the patient; implanting an implant in an inferior vena cava of the patient below renal veins of the patient, the implant configured to at least partially occlude the inferior vena cava upon actuation; testing actuation of the implant; creating an infraclavicular subcutaneous pocket for an implantable controller, the implantable controller configured to actuate the implant for at least partially occluding the inferior vena cava; operably connecting the implant to the implantable controller; and implanting the implantable controller in the infraclavicular subcutaneous pocket.

In the above method or in other implementations as described herein, one or more of the following features can also be provided. In some implementations, the method further comprises identifying the renal veins of the patient. In some implementations, the method further comprises testing function of the system once the implantable controller is operably connected to the implant. In some implementations, testing function of the system comprises digitally actuating the system via an external device.

Disclosed herein is a method of controllably and selectively occluding, restricting and/or diverting flow of a patient's vasculature. The method can comprise: measuring an inferior vena cava pressure from an implant implanted in the inferior vena cava of the patient upstream of renal veins of the patient; detecting an increase in the inferior vena cava pressure; transmitting, to an external device, an indication the inferior vena cava pressure has increased; and receiving, from the external device, an instruction to activate the implant; wherein activating the implant causes the implant to at least partially occlude blood flow through the inferior vena cava.

In the above method or in other implementations as described herein, one or more of the following features can also be provided. In some implementations, activating the implant to at least partially occlude blood flow through the inferior vena cava enhances renal circulation. In some implementations, activating the implant to at least partially occlude blood flow through the inferior vena cava enhances diuresis. In some implementations, activating the implant to at least partially occlude blood flow through the inferior vena cava reduces renal venous pressure. In some implementations, the method further comprises measuring a renal venous pressure from the implant when blood flow through the inferior vena cava is at least partially occluded by the implant. In some implementations, the implant is chronically implanted.

Disclosed herein is a method of controllably and selectively occluding, restricting and/or diverting flow of a patient's vasculature. The method can comprise: measuring an inferior vena cava pressure from an implant implanted in the inferior vena cava of the patient upstream of renal veins of the patient; detecting the inferior vena cava pressure has reached a threshold value; transmitting, to an external device, an indication the inferior vena cava pressure has reached the threshold value; and receiving, from the external device, an instruction to activate the implant; wherein activating the implant causes the implant to at least partially occlude blood flow through the inferior vena cava. In some implementations, the implant is chronically implanted.

Disclosed herein is a flow restriction system. The flow restriction system can be a chronic, implantable flow restriction system. The flow restriction system can comprise: an implant configured to be implanted in an inferior vena cava of a patient upstream of renal veins of the patient and adjustably occlude the inferior vena cava; and an implantable control unit operably connectable to the implant via a tubing, the implantable control unit comprising: an actuator, wherein actuation of the actuator causes the implant to adjustably occlude the inferior vena cava; a processor configured to receive an instruction to actuate the actuator; and a communication module operably connected to the processor and configured to wirelessly communicate with an external device.

In the above system or in other implementations as described herein, one or more of the following features can also be provided. In some implementations, the implant comprises: an expandable body having a proximal end and a distal end and a lumen extending longitudinally therethrough; and a flow restrictor configured to hinge relative to the expandable body to at least partially restrict flow through the lumen. In some implementations, the flow restrictor comprises struts and a material spanning the struts, the material configured to block blood flow. In some implementations, the flow restrictor is positioned adjacent the distal end of the expandable body such that, when implanted in the inferior vena cava, the flow restrictor is upstream of the expandable body with respect to blood flow. In some implementations, the implant further comprises a filter portion disposed adjacent the proximal end of the expandable body, the filter portion configured to capture thrombus. In some implementations, the implant comprises a pressure sensor operably connectable to the processor of the implantable control unit. In some implementations, the implantable control unit is configured to wirelessly transmit pressure readings from the pressure sensor to the external device. In some implementations, the system further comprises the external device. In some implementations, the external device comprises a handheld or mobile device. In some implementations, actuation of the actuator to cause the implant to adjustably occlude the inferior vena cava is controlled via the external device. In some implementations, said actuation via the external device is controlled by the patient or a user. In some implementations, the flow restrictor has a non-circular opening when at least partially restricting flow through the lumen. In some implementations, the system does not include an assist device or a pump. In some implementations, the implantable control unit is configured to be removably connectable to the implant. In some implementations, the implant is configured to be actuated mechanically by a wire.

Disclosed herein is a flow restriction system. The flow restriction system can be a chronic, implantable flow restriction system. The flow restriction system can comprise: an implantable control unit comprising a housing and an actuator disposed within the housing; an implant comprising an expandable body having a proximal end and a distal end and a lumen extending longitudinally therethrough, and a flow restrictor configured to adjustably occlude the lumen when the expandable body is in an expanded configuration; a tubing configured to connect the proximal end of the expandable body of the implant to the housing of the implantable control unit; and a shaft movingly disposed within the tubing configured to connect the actuator of the implantable control unit to the flow restrictor of the implant; wherein actuation of the actuator of the implantable control unit moves the shaft within the tubing to cause the flow restrictor of the implant to adjustably occlude the lumen.

In the above system or in other implementations as described herein, one or more of the following features can also be provided. In some implementations, the expandable body of the implant further comprises: a filter portion disposed adjacent the proximal end configured to capture thrombus, the filter portion comprising a plurality of struts that extend radially outward and distally from the connection between the proximal end of the expandable body and the tubing; and a radial support portion connected to and disposed distal of the filter portion, the radial support portion configured to fluidically seal against an inner wall of the patient's vasculature. In some implementations, the flow restrictor is connected to and extends distally from the radial support portion. In some implementations, the flow restrictor is integrally formed with the expandable body. In some implementations, the flow restrictor comprises: a plurality of petals each formed by a pair of struts that extend distally from the radial support portion and that join at a distal apex; and a material spanning each of the plurality of petals. In some implementations, the flow restrictor comprises three petals or more. In some implementations, the material further spans at least a portion of the radial support portion. In some implementations, a distal end of each of the petals of the flow restrictor connect to a distal end of the shaft via a suture or a wire, and wherein proximal sliding or rotation of the shaft within the tubing causes the suture or the wire to pull the distal end of each of the petals of the flow restrictor towards one another to at least partially occlude the lumen. In some implementations, a distal end of the tubing is fluidically sealed with the shaft by a collapsible and extendible flexible coupling. In some implementations, the implant is configured to be implanted in an inferior vena cava of the patient below renal veins of the patient and a distal end of the flow restrictor positioned to first receive blood flow therethrough. In some implementations, the system further comprises one or more pressure sensors configured to measure a pressure of the patient's vasculature and output at least one signal responsive to the measured pressure. In some implementations, the one or more pressure sensors comprise a pressure sensor configured to measure a renal pressure of the patient. In some implementations, the pressure sensor configured to measure the renal pressure of the patient is disposed proximal of the flow restrictor. In some implementations, the pressure sensor configured to measure the renal pressure of the patient is disposed adjacent the proximal end of the expandable body or the distal end of the tubing. In some implementations, the one or more pressure sensors comprise a pressure sensor configured to measure an inferior vena cava pressure of the patient. In some implementations, the pressure sensor configured to measure the inferior vena cava pressure of the patient is disposed proximal or distal of the flow restrictor. In some implementations, the pressure sensor configured to measure the inferior vena cava pressure of the patient is disposed adjacent the distal end of the expandable body. In some implementations, the implantable control unit further comprises a processor, wherein the processor is operably connectable to the one or more pressure sensors and configured to receive and process the at least one signal to determine the pressure of the patient's vasculature. In some implementations, the implantable control unit further comprises a communication module operably connected to the processor and configured to wirelessly communicate with an external device. In some implementations, the communication module transmits the determined pressure of the patient's vasculature to the external device. In some implementations, the processor is operably connected to the actuator of the implantable control unit, and based on the determined pressure, the patient or a user can digitally actuate the actuator via the external device and thereby cause the flow restrictor of the implant to adjustably occlude the lumen. In some implementations, the system further comprises the external device. In some implementations, the expandable body further comprises one or more anchors configured to anchor the implant within the patient's vasculature. In some implementations, the implantable control unit is configured to be powered by a battery disposed within the housing. In some implementations, the battery is configured to be charged by induction charging. In some implementations, the implantable control unit is configured to be powered by induction.

Disclosed herein is an implantable flow restriction system. The system can comprise: an implant comprising: an expandable body comprising a metallic frame having a proximal end and a distal end and a lumen extending longitudinally therethrough; and a flow restrictor comprising: a plurality of petals each formed by struts; and a material spanning each of the plurality of petals; wherein the flow restrictor is configured to hinge relative to the expandable body to at least partially restrict flow through the lumen; and an implantable control unit comprising: an actuator configured to operably connect with the flow restrictor of the implant; a processor configured to receive an instruction to actuate the actuator; and a communication module operably connected to the processor and configured to wirelessly communicate with an external device; wherein actuation of the actuator causes the flow restrictor to at least partially restrict flow through the lumen.

In the above system or in other implementations as described herein, one or more of the following features can also be provided. In some implementations, the system further comprises: a tubing configured to connect the proximal end of the expandable body of the implant to the implantable control unit; and a shaft movingly disposed within the tubing configured to connect the actuator of the implantable control unit to the flow restrictor of the implant; wherein actuation of the actuator of the implantable control unit moves the shaft within the tubing to cause the flow restrictor of the implant to at least partially restrict flow through the lumen. In some implementations, the implant further comprises a filter portion disposed adjacent the proximal end of the expandable body, the filter portion configured to capture thrombus. In some implementations, the struts that form each of the plurality of petals comprise a pair of struts that extend distally from the expandable body and join at a distal apex. In some implementations, the implant comprises a pressure sensor operably connectable to the processor of the implantable control unit. In some implementations, the implantable control unit is configured to wirelessly transmit pressure readings from the pressure sensor to the external device. In some implementations, the system further comprises the external device. In some implementations, the external device comprises a handheld or mobile device. In some implementations, actuation of the actuator to cause the flow restrictor to at least partially restrict flow through the lumen is controlled via the external device. In some implementations, the implant is configured to be implanted in an inferior vena cava of a patient upstream of renal veins of the patient and adjustably occlude blood flow in the inferior vena cava when the flow restrictor at least partially restricts flow through the lumen of the implant. In some implementations, when implanted in a patient, the flow restrictor of the implant is configured to be positioned upstream of the expandable body with respect to flow through the lumen. In some implementations, when hinged relative to the expandable body, an exterior surface of the plurality of petals is configured to occlude blood flow.

Disclosed herein is an implantable flow restriction system. The system can comprise: an implant comprising: an expandable body having a proximal end and a distal end and a lumen extending longitudinally therethrough; and a flow restrictor configured to be secured within a vessel of a patient's vasculature; and an implantable control unit comprising: an actuator configured to operably connect with the flow restrictor of the implant; a processor configured to receive an instruction to actuate the actuator; and a communication module operably connected to the processor and configured to wirelessly communicate with an external device; wherein actuation of the actuator causes the flow restrictor to pull in a wall of the vessel to at least partially restrict flow through the lumen.

In the above system or in other implementations as described herein, one or more of the following features can also be provided. In some implementations, the system further comprises: a tubing configured to connect the proximal end of the expandable body of the implant to the implantable control unit; and a shaft movingly disposed within the tubing configured to connect the actuator of the implantable control unit to the flow restrictor of the implant; wherein actuation of the actuator of the implantable control unit moves the shaft within the tubing to cause the flow restrictor of the implant to pull in the wall of the vessel to at least partially restrict flow through the lumen. In some implementations, the flow restrictor comprises a plurality of petals each formed by struts and configured to hinge relative to the expandable body. In some implementations, the struts that form each of the plurality of petals comprise a pair of struts that extend distally from the expandable body and join at a distal apex. In some implementations, the flow restrictor further comprises a material spanning each of the plurality of petals. In some implementations, the flow restrictor is configured to ingrow at least partially into the vessel wall. In some implementations, the flow restrictor further comprises one or more anchors configured to secure the flow restrictor to the vessel wall. In some implementations, the implant comprises a pressure sensor operably connectable to the processor of the implantable control unit. In some implementations, the implantable control unit is configured to wirelessly transmit pressure readings from the pressure sensor to the external device. In some implementations, the system further comprises the external device. In some implementations, the external device comprises a handheld or mobile device. In some implementations, actuation of the actuator to cause the flow restrictor to pull in the wall of the vessel to at least partially restrict flow through the lumen is controlled via the external device. In some implementations, the implant is configured to be implanted in an inferior vena cava of the patient upstream of renal veins of the patient and adjustably occlude blood flow in the inferior vena cava when the flow restrictor pulls in a wall of the inferior vena cava to at least partially restrict flow through the lumen of the implant. In some implementations, when implanted in the patient, the flow restrictor of the implant is configured to be positioned upstream of the expandable body with respect to flow through the lumen. In some implementations, the system does not include an assist device or a pump.

Disclosed herein is a method for implanting a chronic, implantable flow restriction system in a patient. The method can comprise: implanting an implant in an inferior vena cava of the patient below renal veins of the patient, the implant configured to at least partially occlude the inferior vena cava upon actuation; implanting an implantable controller subcutaneously; and operably connecting the implant to the implantable controller, the implantable controller comprising an actuator configured to actuate the implant for at least partially occluding the inferior vena cava and a processor configured to receive an instruction to actuate the actuator.

In the above method or in other implementations as described herein, one or more of the following features can also be provided. In some implementations, the implant is operably connected to the implantable controller prior to implanting the implantable controller. In some implementations, the method further comprises accessing a subclavian vein of the patient. In some implementations, the method further comprises testing actuation of the implant after its implantation in the inferior vena cava and before operably connecting the implant to the implantable controller. In some implementations, implanting the implantable controller comprises implanting the implantable controller subcutaneously adjacent a collarbone of the patient. In some implementations, the implantable controller further comprises a communication module operably connected to the processor and configured to wirelessly communicate with an external device. In some implementations, the method further comprises actuating the implant to at least partially occlude the inferior vena cava. In some implementations, actuating the implant comprises receiving an instruction from an external device. In some implementations, the implant comprises: an expandable body having a proximal end and a distal end and a lumen extending longitudinally therethrough; and a flow restrictor configured to hinge relative to the expandable body to at least partially restrict flow through the lumen. In some implementations, the flow restrictor is positioned adjacent the distal end of the expandable body, and wherein implanting the implant in the inferior vena cava includes positioning the distal end to first receive blood flow therethrough. In some implementations, the implantable flow restriction system further comprises: a tubing extending from the implant configured to releasably connect with the implantable controller; and a shaft movingly disposed within the tubing configured to releasably connect the actuator of the implantable controller with the flow restrictor of the implant; wherein operably connecting the implant to the implantable controller comprises: connecting the tubing to the implantable controller; and connecting the shaft to the actuator of the implantable controller. In some implementations, the method further comprises implanting the tubing and the shaft such that they extend from the implant through the inferior vena cava, through a right atrium, through at least a portion of a superior vena cava, and through at least a portion of the subclavian vein of the patient. In some implementations, the implant further comprises a pressure sensor disposed downstream of the flow restrictor in regard to a direction of blood flow in the inferior vena cava, the pressure sensor configured to measure pressure. In some implementations, the pressure sensor is positioned adjacent the renal veins of the patient when the implant is implanted in the inferior vena cava below the renal veins. In some implementations, the method further comprises removing the implant and the implantable controller from the patient.

Disclosed herein is a method of controllably and selectively occluding, restricting and/or diverting flow of a patient's vasculature. The method can comprise: measuring an inferior vena cava pressure from an implant implanted in the inferior vena cava of the patient upstream of renal veins of the patient; transmitting the inferior vena cava pressure from an implantable controller positioned within the patient to an external device; receiving, by the implantable controller from the external device, an instruction to activate the implant; and activating the implant; wherein activating the implant causes the implant to at least partially occlude blood flow through the inferior vena cava.

In the above method or in other implementations as described herein, one or more of the following features can also be provided. In some implementations, activating the implant to at least partially occlude blood flow through the inferior vena cava enhances renal circulation. In some implementations, activating the implant to at least partially occlude blood flow through the inferior vena cava enhances diuresis. In some implementations, activating the implant to at least partially occlude blood flow through the inferior vena cava reduces renal venous pressure. In some implementations, activating the implant to at least partially occlude blood flow through the inferior vena cava reduces cardiac preload. In some implementations, the method further comprises measuring a renal venous pressure from the implant when blood flow through the inferior vena cava is at least partially occluded by the implant. In some implementations, the method further comprises: detecting an increase in the inferior vena cava pressure; and transmitting, to the external device, an indication the inferior vena cava pressure has increased. In some implementations, the method further comprises: detecting the inferior vena cava pressure has reached a threshold value; and transmitting, to the external device, an indication the inferior vena cava pressure has reached the threshold value. In some implementations, the implant comprises: a flow restrictor configured to at least partially occlude blood flow through the inferior vena cava when the implant is activated; and a pressure sensor disposed downstream of the flow restrictor in regard to a direction of blood flow in the inferior vena cava, the pressure sensor configured to measure said pressure. In some implementations, activation of the implant is controlled via the external device. In some implementations, activation of the implant is patient controlled via the external device. In some implementations, the instruction to activate the implant is wirelessly received from the external device. In some implementations, the method further comprises receiving, from the external device, an instruction to deactivate the implant, wherein deactivating the implant causes the implant to not occlude blood flow through the inferior vena cava. In some implementations, the method further comprises deactivating the implant after a duration of time. In some implementations, the method further comprises deactivating the implant after the pressure measured from the implant reaches a threshold value. In some implementations, the method further comprises deactivating the implant after a duration of time after the pressure measured from the implant reaches a threshold value. In some implementations, the implantable controller comprises: a communication module configured to wirelessly communicate with the external device; a processor operably connected to the communication module, the processor configured to receive the instruction to activate the implant; and an actuator operably connected to the processor, the actuator configured to activate the implant. In some implementations, activating the implant comprises causing the flow restrictor to hinge relative to an expandable body of the implant to at least partially occlude blood flow through the inferior vena cava. In some implementations, activating the implant comprises mechanically activating the implant by a wire.

Disclosed herein is a method of controllably and selectively occluding, restricting and/or diverting flow of a patient's vasculature. The method can comprise: activating a flow restrictor implanted in a vessel of the patient's vasculature, wherein activating the flow restrictor causes the flow restrictor to pull in a wall of the vessel to at least partially restrict flow through the vessel.

In the above method or in other implementations as described herein, one or more of the following features can also be provided. In some implementations, the flow restrictor is implanted in an inferior vena cava of the patient upstream of renal veins of the patient, and wherein activating the flow restrictor causes the flow restrictor to pull in a wall of the inferior vena cava to at least partially restrict flow through the inferior vena cava. In some implementations, activating the flow restrictor to cause the flow restrictor to pull in the wall of the inferior vena cava to at least partially restrict flow through the inferior vena cava enhances renal circulation. In some implementations, activating the flow restrictor to cause the flow restrictor to pull in the wall of the inferior vena cava to at least partially restrict flow through the inferior vena cava enhances diuresis. In some implementations, activating the flow restrictor to cause the flow restrictor to pull in the wall of the inferior vena cava to at least partially restrict flow through the inferior vena cava reduces renal venous pressure. In some implementations, activating the flow restrictor to cause the flow restrictor to pull in the wall of the inferior vena cava to at least partially restrict flow through the inferior vena cava reduces cardiac preload. In some implementations, the method further comprises measuring an inferior venous pressure from an implant comprising the flow restrictor. In some implementations, the method further comprises transmitting the inferior venous pressure from an implantable controller positioned within the patient to an external device. In some implementations, the method further comprises receiving, by the implantable controller from the external device, an instruction to activate the flow restrictor. In some implementations, the method further comprises measuring a renal venous pressure from the implant comprising the flow restrictor when flow through the inferior vena cava is at least partially restricted. In some implementations, the method further comprises: detecting an increase in the inferior vena cava pressure; and transmitting, to the external device, an indication the inferior vena cava pressure has increased. In some implementations, the method further comprises: detecting the inferior vena cava pressure has reached a threshold value; and transmitting, to the external device, an indication the inferior vena cava pressure has reached the threshold value. In some implementations, activation of the flow restrictor is controlled via the external device. In some implementations, the instruction to activate the flow restrictor is wirelessly received from the external device. In some implementations, the method further comprises receiving, from the external device, an instruction to deactivate the flow restrictor, wherein deactivating the flow restrictor causes the wall of the inferior vena cava to not occlude flow through the inferior vena cava. In some implementations, the method further comprises deactivating the flow restrictor after a duration of time. In some implementations, the method further comprises deactivating the flow restrictor after the pressure measured from the implant reaches a threshold value. In some implementations, the method further comprises deactivating the implant after a duration of time after the pressure measured from the implant reaches a threshold value. In some implementations, the implantable controller comprises: a communication module configured to wirelessly communicate with the external device; a processor operably connected to the communication module, the processor configured to receive the instruction to activate the flow restrictor; and an actuator operably connected to the processor, the actuator configured to activate the flow restrictor. In some implementations, activating the flow restrictor comprises causing the flow restrictor to hinge relative to an expandable body of an implant comprising the flow restrictor. In some implementations, activating the flow restrictor comprises mechanically activating the flow restrictor by a wire.

Disclosed herein is an implant configured to be implanted in a patient for controllably and selectively occluding, restricting and/or diverting flow of the patient's vasculature. The implant can comprise: an expandable body having a proximal end and a distal end and a lumen extending longitudinally therethrough, and a filter portion disposed adjacent the proximal end configured to capture thrombus; and a flow restrictor extending from the distal end of the expandable body, the flow restrictor configured to adjustably occlude the lumen when the expandable body is in an expanded configuration; wherein when implanted, the flow restrictor is configured to be positioned upstream of the expandable body with respect to blood flow.

In the above implant or in other implementations as described herein, one or more of the following features can also be provided. In some implementations, the filter portion comprises a plurality of struts that extend proximally and radially inward. In some implementations, the expandable body of the implant further comprises a radial support portion connected to and disposed distal of the filter portion, the radial support portion configured to fluidically seal against an inner wall of the patient's vasculature. In some implementations, the flow restrictor is connected to and extends distally from the radial support portion. In some implementations, the flow restrictor is integrally formed with the expandable body. In some implementations, the flow restrictor comprises a plurality of petals configured to fold radially inward to adjustable occlude the lumen, wherein when folded radially inward, an exterior surface of the plurality of petals is configured to occlude blood flow. In some implementations, each of the plurality of petals is formed by a pair of struts that extend from the expandable body and join at a distal apex. In some implementations, the flow restrictor comprises three petals or more. In some implementations, the flow restrictor carries an occlusive material, and wherein regions between the plurality of petals are free of the occlusive material. In some implementations, the flow restrictor carries an occlusive material, and wherein the occlusive material spans the plurality of petals and regions between the plurality of petals. In some implementations, the occlusive material further spans at least a portion of the expandable body. In some implementations, the flow restrictor has a non-circular opening when at least partially occluding the lumen. In some implementations, the flow restrictor has a stellate shaped opening when at least partially occluding the lumen. In some implementations, the implant further comprises a pressure sensor. In some implementations, the pressure sensor is disposed proximal of the flow restrictor. In some implementations, the implant further comprises an anchor that extends proximally from the radial support portion, the anchor configured to anchor the implant within the patient's vasculature. In some implementations, the implant is configured to be implanted in an inferior vena cava of the patient. In some implementations, a system is provided comprising the implant as described herein and a delivery sheath configured to implant the implant. In some implementations, in the above system the implant is configured to remain in a collapsed configuration when extending out of the delivery sheath while at least a portion of the radial support portion remains inside the delivery sheath.

Disclosed herein is an implant configured to be implanted in a patient for occluding, restricting and/or diverting flow of the patient's vasculature. The implant can comprise: an expandable body comprising a metallic frame having a proximal end and a distal end and a lumen extending longitudinally therethrough; and a flow restrictor comprising: a plurality of petals each formed by a pair of struts that extend distally from the expandable body and join at a distal apex; and a material spanning each of the plurality of petals; wherein the flow restrictor is configured to fold radially inward to at least partially restrict flow through the lumen.

In the above implant or in other implementations as described herein, one or more of the following features can also be provided. In some implementations, the expandable body of the implant further comprises a filter portion disposed adjacent the proximal end configured to capture thrombus. In some implementations, the expandable body of the implant further comprises a radial support portion connected to and disposed distal of the filter portion, the radial support portion configured to fluidically seal against an inner wall of the patient's vasculature. In some implementations, the flow restrictor is integrally formed with the expandable body. In some implementations, when folded radially inward, an exterior surface of the plurality of petals of the flow restrictor is configured to occlude blood flow. In some implementations, the flow restrictor comprises three petals or more. In some implementations, regions between the plurality of petals are free of the material. In some implementations, the material further spans regions between the plurality of petals. In some implementations, the material further spans at least a portion of the expandable body. In some implementations, the flow restrictor has a non-circular opening when at least partially occluding the lumen. In some implementations, the flow restrictor has a stellate shaped opening when at least partially occluding the lumen. In some implementations, the implant further comprises a pressure sensor. In some implementations, the pressure sensor is disposed proximal of the flow restrictor. In some implementations, the implant further comprises an anchor that extends proximally from the radial support portion, the anchor configured to anchor the implant within the patient's vasculature. In some implementations, the implant is configured to be implanted in an inferior vena cava of the patient. In some implementations, when implanted, the flow restrictor is configured to be positioned upstream of the expandable body with respect to blood flow. In some implementations, a system is provided comprising the implant as described herein and a delivery sheath configured to implant the implant. In some implementations, in the above system the implant is configured to remain in a collapsed configuration when extending out of the delivery sheath while at least a portion of the radial support portion remains inside the delivery sheath.

Disclosed herein is an implant configured to be implanted in a patient for occluding, restricting and/or diverting flow of the patient's vasculature. The implant can comprise: an expandable body having a proximal end and a distal end and a lumen extending longitudinally therethrough; and a flow restrictor configured to be secured within a vessel of the patient's vasculature; wherein activation of the flow restrictor causes the flow restrictor to pull in a wall of the vessel to at least partially restrict flow through the lumen.

In the above implant or in other implementations as described herein, one or more of the following features can also be provided. In some implementations, the flow restrictor comprises a plurality of petals each formed by struts and configured to hinge relative to the expandable body. In some implementations, the struts that form each of the plurality of petals comprise a pair of struts that extend distally from the expandable body and join at a distal apex. In some implementations, the flow restrictor further comprises a material spanning each of the plurality of petals. In some implementations, the flow restrictor is configured to ingrow at least partially into the vessel wall. In some implementations, the flow restrictor further comprises one or more anchors configured to secure the flow restrictor to the vessel wall. In some implementations, the flow restrictor is integrally formed with the expandable body. In some implementations, the implant comprises a pressure sensor configured to measure pressure. In some implementations, the pressure sensor is disposed proximal of the flow restrictor. In some implementations, the expandable body of the implant further comprises a filter portion disposed adjacent the proximal end of the expandable body, the filter portion configured to capture thrombus. In some implementations, the filter portion comprises a plurality of struts that extend proximally and radially inward. In some implementations, the implant is configured to be implanted in an inferior vena cava of the patient. In some implementations, when implanted, the flow restrictor is configured to be positioned upstream of the expandable body with respect to flow through the lumen of the implant.

For purposes of summarizing the disclosure, certain aspects, advantages and novel features of several implementations have been described herein. It is to be understood that not necessarily all such advantages are achieved in accordance with any particular implementation of the technology disclosed herein. Thus, the implementations disclosed herein can be implemented or carried out in a manner that achieves or optimizes one advantage or group of advantages as taught herein without necessarily achieving other advantages that can be taught or suggested herein.

BRIEF DESCRIPTION OF THE DRAWINGS

Certain features of this disclosure are described below with reference to the drawings. The illustrated implementations are intended to illustrate, but not to limit, the implementations. Various features of the different disclosed implementations can be combined to form further implementations, which are part of this disclosure.

FIGS. 3A-3D illustrate various views of an implementation of a magnetically actuated, chronic, implantable flow restriction system in accordance with some aspects of this disclosure.

FIGS. 4A-4D illustrate various views of another implementation of a magnetically actuated, chronic, implantable flow restriction system in accordance with some aspects of this disclosure.

FIGS. 5A-5F illustrate various views of another implementation of a magnetically actuated, chronic, implantable flow restriction system in accordance with some aspects of this disclosure.

FIGS. 6A-6D illustrate various views of another implementation of a magnetically actuated, chronic, implantable flow restriction system in accordance with some aspects of this disclosure.

FIGS. 9A-9D illustrate various views of another implementation of a fluidically actuated, chronic, implantable flow restriction system in accordance with some aspects of this disclosure.

FIGS. 13A-13D illustrate another implementation of a fluidically actuated, chronic, implantable flow restriction system in accordance with some aspects of this disclosure.

FIGS. 14A-D illustrate various views of an implementation of a fluidically actuated, chronic, implantable flow restriction system according to FIGS. 13A-13C and in accordance with some aspects of this disclosure.

FIGS. 17A-17B illustrate various views of another implementation of a fluidically actuated, chronic, implantable flow restriction system in accordance with some aspects of this disclosure.

FIGS. 20A-20D illustrate various views of a frame of another implementation of a fluidically actuated, chronic, implantable flow restriction system in collapsed and expanded configurations in accordance with some aspects of this disclosure.

FIG. 21C illustrates an implementation of a mechanically actuated, chronic, implantable flow restriction system in accordance with some aspects of this disclosure.

FIGS. 23A-23B illustrate an implementation of a heat-actuated, chronic, implantable flow restriction system in accordance with some aspects of this disclosure.

FIGS. 24A-26B illustrate various implementations of heat-actuated, chronic, implantable flow restriction systems in accordance with some aspects of this disclosure.

FIGS. 43A-43D illustrate an implementation of an implant of a chronic, implantable flow restriction system in accordance with some aspects of this disclosure.

FIGS. 44A-44C illustrate various end views of the implant of FIGS. 43A-43D in accordance with some aspects of this disclosure.

FIG. 44D illustrates an end view of another implementation of the implant of FIGS. 43A-43D in accordance with some aspects of this disclosure.

FIG. 45 illustrates a flat pattern of view of the expandable body of the implant of FIGS. 43A-43D in accordance with some aspects of this disclosure.

FIGS. 46A-46B illustrate various views of components of a chronic, implantable flow restriction system in accordance with some aspects of this disclosure.

FIGS. 47A-47D illustrate interaction of various components of a flow restriction system to actuate the implant of FIGS. 43A-43D in accordance with some aspects of this disclosure.

FIGS. 51A-51B illustrate an implementation of an implant of an implantable flow restriction system in accordance with some aspects of this disclosure.

FIG. 52 illustrates an implementation of an implant of an implantable flow restriction system in accordance with some aspects of this disclosure.

FIG. 53 illustrates an implementation of an implant of an implantable flow restriction system in accordance with some aspects of this disclosure.

FIG. 54 illustrates an implementation of an implant of an implantable flow restriction system in accordance with some aspects of this disclosure.

FIGS. 58A-58C illustrate an implementation of an implant of an implantable flow restriction system in accordance with some aspects of this disclosure.

FIGS. 66A-66C illustrate an implementation of a connector between components of a flow restriction system in accordance with some aspects of this disclosure.

FIGS. 67A-67B illustrate an implementation of a connector between components of a flow restriction system in accordance with some aspects of this disclosure.

FIGS. 68A-68D illustrate an implementation of a connector between components of a flow restriction system in accordance with some aspects of this disclosure.

FIGS. 69A-69B illustrate an implementation of an implant assembly having an extender for implantation in accordance with some aspects of this disclosure.

FIGS. 70A-70B illustrate an implementation of a device for testing function of an implant during implantation thereof in accordance with some aspects of this disclosure.

FIGS. 71A-71B illustrate an implementation of a device for testing function of an implant during implantation thereof in accordance with some aspects of this disclosure.

FIG. 75 illustrates a manual method of using an implantable flow restriction system in accordance with some aspects of this disclosure.

FIG. 76 illustrates a semi-automatic method of using an implantable flow restriction system in accordance with some aspects of this disclosure.

FIGS. 78A-78C illustrate an implementation of delivering therapy using an implantable flow restriction system in accordance with some aspects of this disclosure.

DETAILED DESCRIPTION

Figure 1A:
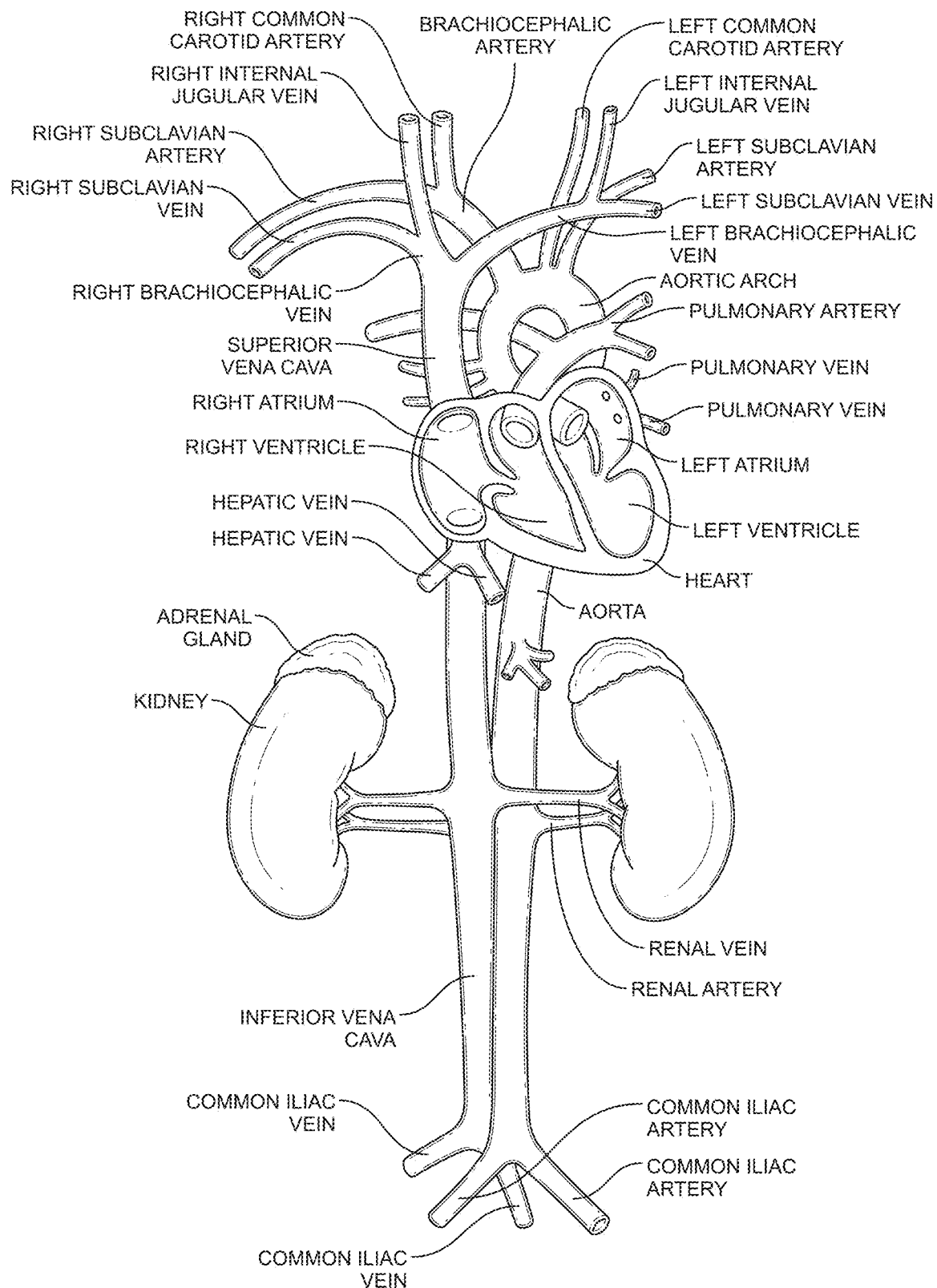
FIG. 1A illustrates a patient's anatomy including a heart with a right atrium, a right ventricle, a left atrium, and a left ventricle, a superior vena cava connected to the right atrium, an inferior vena cava connected to the right atrium as well as to the patient's renal veins, and other vessels and organs of the patient.

Various features and advantages of this disclosure will now be described with reference to the accompanying figures. The following description is merely illustrative in nature and is in no way intended to limit the disclosure, its application, or uses. This disclosure extends beyond the specifically disclosed implementations and/or uses and obvious modifications and equivalents thereof. Thus, it is intended that the scope of this disclosure should not be limited by any particular implementations described below. The features of the illustrated implementations can be modified, combined, removed, and/or substituted as will be apparent to those of ordinary skill in the art upon consideration of the principles disclosed herein. Furthermore, implementations disclosed herein can include several novel features, no single one of which is solely responsible for its desirable attributes or which is essential to practicing the systems, devices, and/or methods disclosed herein.

Parts, components, features, and/or elements of the chronic, implantable flow restriction systems and devices described herein that can function the same or similarly across various implementations are identified using the same reference numerals with a different letter added after the reference numerals. Differences between the various implementations are discussed herein.

The present disclosure describes various implementations of chronic, implantable flow restriction systems, devices, and methods for controllably and selectively occluding, restricting, and/or diverting flow within a patient's vasculature. Such systems, devices, and methods can be used to redirect flow and/or enhance perfusion within the patient's vasculature and/or one or more of the patient's organs. In some circumstances, it can be advantageous to controllably and selectively occlude, restrict, and/or divert flow within a patient's vasculature to reduce renal congestion (or promote renal decongestion), to reduce hepatic congestion (or promote hepatic decongestion), to reduce cardiac preload, and/or to reduce lymphatic/interstitial congestion. For example, a chronically implantable flow restriction system adapted to controllably and selectively occlude and/or restrict a patient's superior vena cava upstream of where the superior vena cava enters the patient's right atrium can be used to reduce cardiac preload. Such a chronically implantable flow restriction system can also be adapted to controllably and selectively reduce central venous pressure and/or pressure of other veins disclosed herein and/or improve cardiac output. As another example, a chronically implantable flow restriction system adapted to controllably and selectively occlude and/or restrict a patient's inferior vena cava upstream of where the patient's renal veins connect with the inferior vena cava (e.g., below where the renal veins connect with the inferior vena cava) can be used to reduce renal congestion. Such a chronically implanted system can also be adapted to controllably and selectively enhance renal circulation, enhance and/or control diuresis, and/or reduce volume overload. The various implementations of chronic, implantable flow restriction systems and devices described herein can be configured to be implanted within a patient for months, a year, or years. Furthermore, the various implementations of chronic, implantable flow restriction systems and devices can be configured to controllably and selectively occlude, restrict, and/or divert flow within a patient's vasculature without an assist device or a pump.

The chronic, implantable flow restriction systems, devices, and methods described herein can be adapted for percutaneous delivery. As such, the systems and devices described herein can be configured to be delivered via a catheter or a similar delivery device and can have a collapsed configuration for delivery into a patient and can expand from the collapsed configuration to an expanded configuration for implantation within the patient. Additionally, the systems and devices or components thereof described herein can be adapted to be retrievable after deployment, such as for repositioning and/or for removal from the body (e.g., by including a hook or other feature for retrieval). In some implementations, the systems and devices described herein can be configured to be delivered and implanted within the patient's vasculature. For example, a chronic, implantable flow restriction system as described herein can be percutaneously implanted within a superior vena cava of a patient upstream of a right atrium of the patient. Such an implantable flow restriction system can be controlled to selectively occlude, restrict, and/or divert flow within the patient's superior vena cava (e.g., to reduce cardiac preload). As another example, a chronic, implantable flow restriction system as described herein can be percutaneously implanted within an inferior vena cava of a patient upstream of where renal veins of the patient connect with the inferior vena cava. Such an implantable flow restriction system can be controlled to selectively occlude, restrict, and/or divert flow within the patient's inferior vena cava (e.g., to reduce renal congestion). In some implementations, the systems and devices described herein can be configured to be delivered extravenously to at least partially surround or be positioned adjacent to the patient's vasculature. For example, a chronic, implantable flow restriction system as described herein can be percutaneously implanted external of an inferior vena cava of a patient and at least partially surround or be positioned adjacent to the patient's superior vena cava. Such an implantable flow restriction system can be controlled to selectively occlude, restrict, and/or divert flow within the patient's inferior vena cava (e.g., to reduce renal congestion).

The chronic, implantable flow restriction systems, devices, and methods described herein can be actuated in a variety of ways. Without limitation, the systems and devices of the present disclosure can be actuated magnetically including electromagnetically, fluidically including pneumatically, mechanically, via heat (e.g., induction heating), and/or via another energy source. Furthermore, the systems and devices described herein can be actuated by direct connection (e.g., a wire, a tube in fluid communication) and/or advantageously remotely. For example, a magnetically actuated flow restriction device as described herein implanted in a patient's superior vena cava can be actuated by a magnet on the patient's back. As another example, a fluidically actuated flow restriction device as described herein implanted within or external and adjacent to a patient's inferior vena cava can be actuated by pressing into a subcutaneously implanted fluid reservoir fluidically connected to the flow restriction device. In another example, a heat actuated flow restriction device as described herein implanted in a patient's superior vena cava can be actuated by heat due to induction heating via a separate device implanted within the patient and/or a separate device external to the patient. Remote actuation can provide for a safer and more pleasant patient experience, including in regard to infection risk versus other ways that may include a direct connection into/out of the body.

The chronic, implantable flow restriction systems and devices described herein can be configured to partially occlude and/or fully occlude a target vessel. Additionally, the systems and devices described herein can be configured to not occlude or substantially not occlude a target vessel until actuated. In other words, the systems and devices of the present disclosure can be controlled to substantially occlude all flow through a vessel, occlude partial flow through the vessel, and/or allow substantially all flow through the vessel unimpeded. For example, a flow restriction system and/or device can be configured to adjustably occlude blood flow in a vessel in a range of 0 to 100 percent. In some implementations of the systems and devices described herein, an implantable flow restriction system and/or device can be configured to not substantially occlude flow through a vessel unless actuated to close partially and/or fully. In some cases, the systems and devices described herein can be configured to substantially occlude all and/or partial flow through a vessel unless actuated to open. Furthermore, in some implementations, the systems and devices described herein can have a bias to be partially closed, however once implanted they can open fully due to the flow of blood in the target vessel. It should be understood that the chronic, implantable flow restriction systems and devices of the present disclosure can be configured to be controllable so as provide between and including substantially no occlusion of flow to substantially full occlusion to flow within a vessel. In some cases, such control can be binary (e.g., open or closed) or graded (e.g., open, various degrees of partially closed, or closed).

The chronic, implantable flow restriction systems and devices described herein can be sized and configured for implantation within a target vessel of interest of a patient, such as a superior vena cava (SVC), an inferior vena cava (IVC), and others. A flow restriction device, which can also be referred to herein as an implant, an occluder, and/or a prosthetic, can have an expanded (e.g., implanted) diameter in the range of about 5 mm to about 50 mm, about 10 mm to about 40 mm, about 15 mm to about 30 mm, or it can have a diameter greater than about 50 mm or less than about 5 mm depending on the application. In some implementations, an implant as described herein can be oversized for the vessel of interest and thus impart an outward force on the vessel in which it is implanted (e.g., to improve anchoring within the vessel). A flow restriction device can have an expanded (e.g., implanted) length in the range of about 0.5 cm to about 5 cm, about 0.75 cm to about 4 cm, about 1 cm to about 3 cm, or it can have a length greater than about 5 cm or less than about 0.5 cm depending on the application.

The chronic, implantable flow restriction devices described herein configured for implantation within a vessel of a patient can generally include an expandable body (configured for percutaneous delivery as described herein) and a flow restrictor configured to controllably and selectively occlude, restrict, and/or divert flow within the patient's vasculature. The expandable body can have a proximal end, a distal end, and a lumen extending from the proximal end to the distal end. The expandable body can generally comprise a frame (which can also be referred to as a stent) having an open cell and/or a closed cell structure. Furthermore, the expandable body can include features to aid in anchoring and/or maintaining its placement within the body, such as free apices, barbs, and/or anchors, which can extend in any direction relative to the implant. In some cases, such barbs and/or anchors can comprise a partial hook, hook, and/or straight configuration. The expandable body can be made of a material configured to expand upon delivery, and as such can comprise a shape memory material such as nitinol. In some implementations, the expandable body can be configured to radially collapse/crimp. Alternatively, or in addition, the expandable body can be configured to collapse/crimp sideways upon being pushed or pulled. In some variations, the expandable body can comprise a material without or with little shape memory, and a balloon can be used to expand the expandable body for implantation. The expandable body can include one or more material layers, such as an inner material layer (e.g., within its lumen) and/or an outer material layer (e.g., external to its lumen). Such inner and/or outer material layers can comprise ePTFE, PTFE, PET cloth, polyurethane, and/or the like. Additionally, any of such layers can include an anti-thrombotic coating, a drug-eluting coating, or the like. In some implementations, it is desirable to utilize a material and/or coating to prevent ingrowth within the implant to aid in later implant retrieval and/or removal. Conversely, in some cases it is desirable to utilize a material and/or coating to allow and/or promote ingrowth within the implant. Expandable bodies as described herein for one implementation with a particular type of flow restrictor are not limited to only being utilized with that particular flow restrictor, and may be used in other implementations with other types of flow restrictors. In some implementations, a flow restrictor can be integrally formed with an expandable body.

A flow restrictor of an implant as described herein can be sized and/or oriented in a number of ways relative to the expandable body it connects to or is formed with. For example, a flow restrictor can be sized to fully or partially occlude the lumen of the expandable body it connects to or is formed with upon full actuation. Regarding orientation, a flow restrictor can be configured to span the entire length of the expandable body it connects to or is formed with or configured to span a part of the length of the expandable body. In the latter scenario, the flow restrictor can be oriented at the proximal end, the distal end, or anywhere in between (e.g., the middle or near the middle) of the expandable body. In some instances, the flow restrictor can be positioned adjacent the distal or proximal end of the expandable body, extend beyond the distal or proximal end of the expandable body, or the like.

The implants described herein or portions thereof (e.g., a flow restrictor of an implant) can be configured to secure within a vessel of the patient's vasculature. In some implementations, activating a flow restrictor implanted in a vessel of the patient's vasculature causes the flow restrictor to pull in a wall of the vessel to at least partially restrict flow through the vessel and/or a lumen of the implant comprising the flow restrictor. To pull in a wall of the vessel, a flow restrictor or portions thereof can attach or secure to the wall of the vessel (e.g., an inner wall of the vessel). Such attachment/securement can include a mechanical attachment. For example, a flow restrictor can include one or more anchors configured to attach/secure at least a portion of the flow restrictor with at least a portion of a wall of a vessel (e.g., an inner wall of the vessel). As another example, a flow restrictor or a portion thereof can be configured to ingrow at least partially into the wall of the vessel. In such an example, the flow restrictor or a portion thereof can have a structure, material, and/or coating that promotes ingrowth. Further to this example, such flow restrictor can include a structure having struts, a structure having struts with a mesh spanning the struts, or a structure having struts with a material (e.g., a porous or a non-porous material) spanning the struts.

Vascular access for the delivery of a chronic, implantable flow restriction device as described herein can include an internal jugular vein, a subclavian vein, a femoral vein, and/or others. From such access points, a flow restriction device can be advanced within the patient's vasculature by a delivery device (e.g., a delivery catheter) until the desired location of implantation is reached, thereupon the flow restriction device can be delivered and expanded for chronic implantation. A guidewire, introducers, etc. can be utilized for delivery, as well as standard imaging methods. Furthermore, the flow restriction devices herein can include radiopaque features to aid in delivery and implantation. Additionally, the flow restriction devices can include features for indexing to its delivery device to help enable precise orientation of the flow restriction device within the patient. For example, an implant can be indexed to a feature of its delivery device that remains external to the patient (e.g., a logo or other marking). A chronic, implantable flow restriction system can comprise a flow restriction device, a source for actuating the flow restriction device, and a delivery device.

The chronic, implantable flow restriction systems and devices described herein can be configured for open-loop and/or closed-loop control. For example, the flow restriction systems and devices described herein can be actuated manually, semi-automatically, and/or fully automatically. In some cases, therapy provided by the flow restriction systems and devices described herein can be digitally actuated, such as by interaction with a smart phone, an external terminal/device, or the like. For example, if a patient desires to enhance diuresis, they can activate such therapy via a press of a button or touchscreen of their smart phone (e.g., therapy can be digitally actuated). In some implementations, the flow restriction devices described herein can comprise and/or work with sensors attached to or located remote from the flow restriction device that can provide physiological parameters of interest useful for control of the flow restriction device. Such physiological parameters of interest can include pressure, flow rate, etc. As an example, a flow restriction device can have a MEMS pressure sensor attached to its proximal end, its distal end, or both of its ends, the pressure sensor configured to measure the pressure at such location relative to the flow restriction device (e.g., upstream, downstream, both upstream and downstream, etc.). As another example, MEMS pressure sensors can be located within vessels and/or organs remote from the flow restriction device and provide a measure of the pressure at such locations for the control of the flow restriction device. Sensors can be utilized to allow for fully-automatic, real-time control of the flow restriction devices described herein. Furthermore, absolute values of sensor data and/or differentials of sensor data can be utilized.

Utilization of the chronic, implantable flow restriction systems and devices described herein can be standardized across patients or preferably customized to an individual patient, such as via a prescription provided by a care provider. Treatment protocols can vary depending on the type of flow restriction device implanted, its type of actuation, and/or the location in which it is implanted. The flow restriction systems and devices described herein can be utilized continuously, hourly, multiple times a day, once a day, overnight, once every other day, once every few days, once a week, once a month, or with any frequency as needed or prescribed. Additionally, therapy provided by the flow restriction systems and devices described herein can be based on an amount of time per day, the time of day, a number of days per week, specific days of the week, and the like. Furthermore, instances of treatment can have a duration of seconds, minutes, hours, days, etc. For example, treatment using a flow restriction device described herein can have a duration of 15 minutes, 30 minutes, 1 hour, 1 hour and 30 minutes, 2 hours, 5 hours, 12 hours, or any duration of time necessary or required for the intended use and desired outcome. Additionally, treatment times can vary in their duration or they can be standardized. In some cases, treatment can be determined via an algorithm, with such algorithm providing a duration and amount of flow restriction to be utilized. Such output from an algorithm can be implemented manually, semi-automatically, or fully-automatically. In some implementations, therapy provided by the flow restriction systems and devices described herein can be based on venous pressure, such as inferior vena cava pressure, renal venous pressure, femoral venous pressure, and/or pressure of other veins disclosed herein. For example, treatment using a flow restriction device described herein can be applied until a pressure threshold is met (e.g., treatment can be applied until a pressure of interest reaches or falls below a pressure threshold). Such threshold can be, for example, about 8 mmHg for the inferior vena cava. In some implementations, therapy provided by the flow restriction systems and devices described herein can be based on a combination of a duration and a venous pressure. For example, treatment using a flow restriction device described herein can be applied for a duration of time after a pressure threshold is met (e.g., once inferior vena cava pressure gets below 8 mmHg, turn off after 4 hours).

One or more chronic, implantable flow restriction devices as described herein can be implanted within a patient. In some cases, it can be beneficial to have only one flow restriction device implanted within a patient, or it can be beneficial to have multiple flow restriction devices implanted within a patient. If multiple flow restriction devices are implanted within a patient, such devices can work together as needed to achieve the treatment outcome desired. Furthermore, flow restriction devices that utilize the same or different forms of actuation can be implanted within the same patient.

Although the chronic, implantable flow restriction systems, devices, and methods disclosed herein are described in a particular manner which can provide certain advantages, such description is not intended to be limiting. The chronic, implantable flow restriction systems and devices can be implanted in various vessels and/or passageways of a patient, including vessels (e.g., veins, arteries) of the patient's vascular system, the patient's lymphatic system, the patient's reproductive system, etc.

Any and/or all of the implementations and/or features of the chronic, implantable flow restriction systems, devices, and methods described and/or illustrated herein can be applied to the various systems, devices, and methods described and/or illustrated in U.S. Provisional Patent Application No. U.S. 63/331,496, filed Apr. 15, 2022, titled "SYSTEMS AND METHODS FOR TREATING HEART FAILURE BY DIRECTING BLOOD FLOW THROUGH A SHUNT BETWEEN THE PULMONARY ARTERY AND THE AZYGOS VEIN" and in U.S. patent application Ser. No. 18/300,293, filed Apr. 13, 2023, titled "SYSTEMS AND METHODS FOR TREATING HEART FAILURE BY REDIRECTING BLOOD FLOW IN THE AZYGOS VEIN," the entire contents of both of which are hereby incorporated by reference in its entirety, and vice versa. For example, any and/or all of the implementations and/or features of the chronic, implantable flow restriction systems, devices, and methods described and/or illustrated herein, such as a flow restrictor actuated magnetically, fluidically, mechanically, and/or via heat, can be applied in a pulmonary artery to azygos vein shunt as described in the above-referenced applications. As another example, any and/or all of the implementations and/or features of a shunt between a pulmonary artery and an azygos vein as described and/or illustrated in the above-referenced applications, such as an adjustable shunt including a rotatable disk that can rotate relative to a stationary frame to control the size of an opening through the shunt, can be applied to the chronic, implantable flow restriction systems, devices, and methods described and/or illustrated herein. Additionally, any and/or all of the implementations and/or features of the chronic, implantable flow restriction systems, devices, and methods described and/or illustrated herein can be applied to and/or used in atrial-septal shunts and/or pulmonary artery-to-superior vena cava shunts.

FIG. 1A illustrates a simplified representation of a patient's anatomy including a heart with a right atrium, a right ventricle, a left atrium, and a left ventricle, a superior vena cava connected to the right atrium, an inferior vena cava connected to the right atrium as well as to the patient's renal veins and hepatic veins, and other vessels and organs of the patient.

Figure 1B:
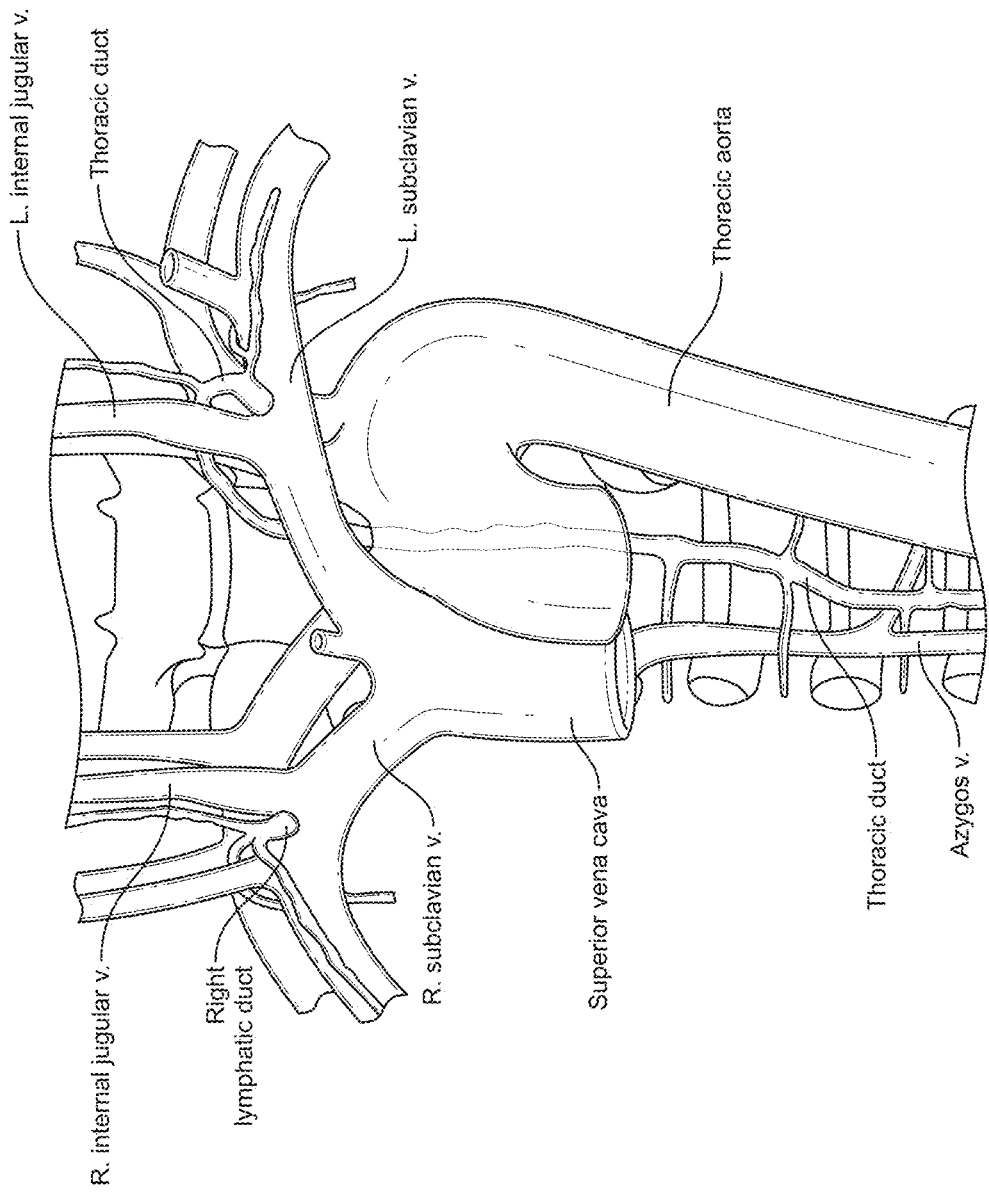
FIG. 1B illustrates a patient's anatomy including the connections between ducts of the patient's lymphatic system, such as the thoracic duct and right lymphatic duct, and veins of the patient.

FIG. 1B illustrates a simplified representation of a patient's anatomy including the connections between ducts of the patient's lymphatic system, such as the thoracic duct and right lymphatic duct, and veins of the patient. As shown, the thoracic duct connects and empties into the left subclavian vein near its confluence with the left internal jugular vein. Also shown, the right lymphatic duct connects and drains into the right subclavian vein.

Figure 2A:
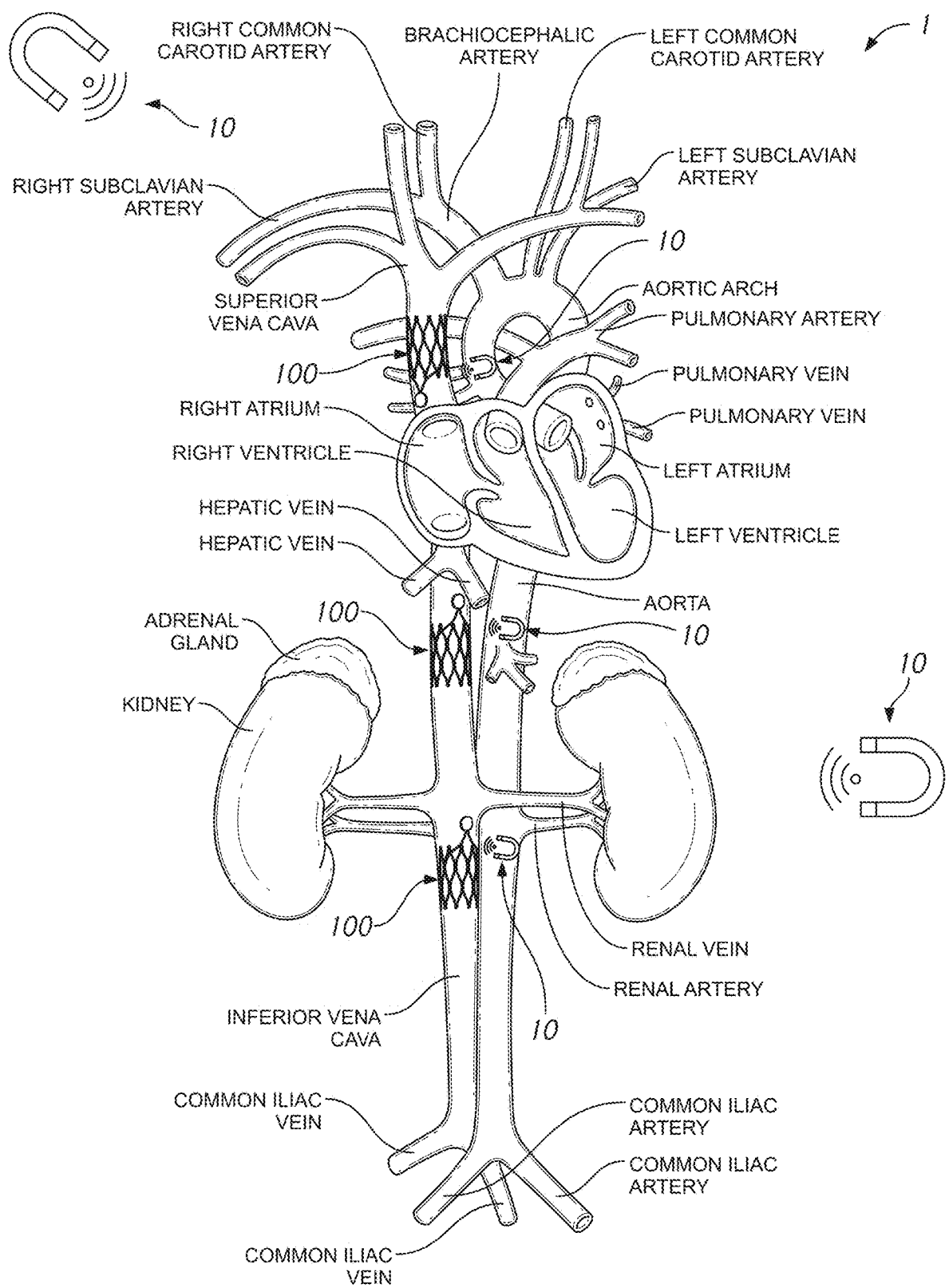
FIGS. 2A-2B illustrate chronic, implantable flow restriction systems that are magnetically actuated implanted within the patient in accordance with some aspects of this disclosure.

FIG. 2A illustrates potential locations for implantation and placement of a magnetically actuated, chronic, implantable flow restriction system 1. A magnetically actuated, chronic, implantable flow restriction system 1 can include a magnetically actuated implant 100, a magnetic field source 10 configured to actuate (e.g., open/close) the implant 100, and a delivery device (not shown). Shown are multiple implants 100 implanted within the patient along with multiple potential locations for magnetic field sources 10. Specifically, FIG. 2A shows an implant 100 implanted within the patient's SVC upstream of its connection to the right atrium, with options for the location of its accompanying magnetic field source 10 being external to the patient, such as proximal to the patient's back, and/or internal to the patient, such as in the aortic arch or an interstitial space adjacent the SVC. An implant 100 placed at this location can controllably and selectively occlude, restrict and/or divert flow within the patient's SVC and connected vasculature and/or organs, such as to reduce cardiac preload, reduce central venous pressure and/or pressure of other veins disclosed herein, and/or improve cardiac output. Also shown is an implant 100 implanted within the patient's IVC upstream of its connection to the hepatic veins, and an implant 100 implanted within the patient's IVC upstream of its connection to the renal veins. The location of a magnetic field source 10 for actuation of the implants 100 placed within the IVC can include the aorta as shown, an interstitial space adjacent the IVC, and/or the magnetic field source 10 can be located external to the patient, such as proximal to the patient's back. An implant 100 placed in the IVC upstream of the hepatic veins can controllably and selectively occlude, restrict and/or divert flow within the patient's IVC and connected vasculature and/or organs, such as to reduce hepatic congestion (or promote hepatic decongestion). Furthermore, an implant 100 placed in the IVC upstream of the renal veins can controllably and selectively occlude, restrict and/or divert flow within the patient's IVC and connected vasculature and/or organs, such as to reduce renal congestion (or promote renal decongestion), enhance renal circulation, and/or to control diuresis (e.g., to increase diuresis). While multiple implants 100 and multiple magnetic field sources 10 are shown, only one implant 100 can be implanted, or multiple implants 100 can be implanted in the locations as shown and/or in others, each having a corresponding magnetic field source 10. In some implementations with multiple implants 100 implanted, a magnetic field source 10 can be configured to actuate more than one implant 100.

Figure 2B:
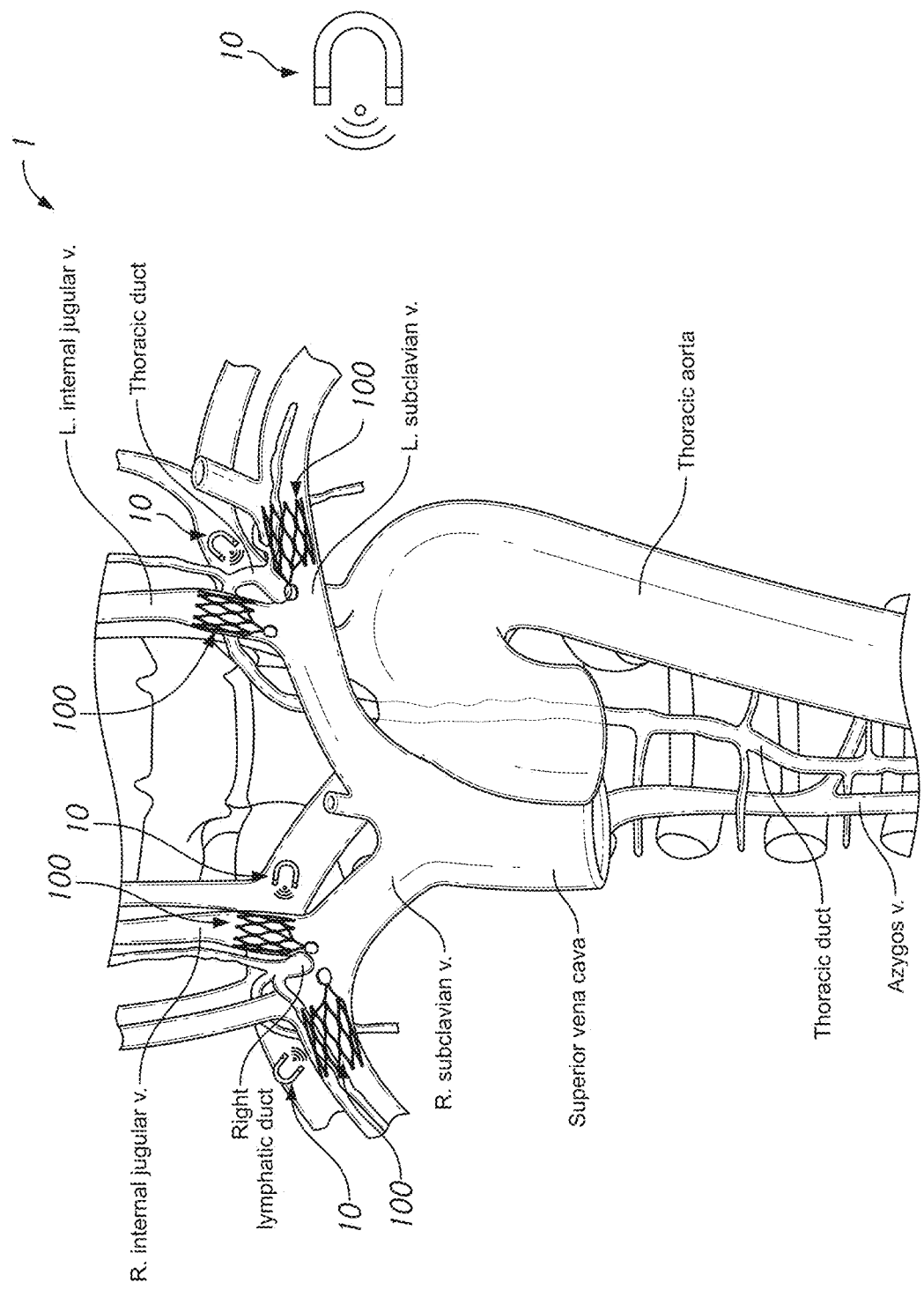

FIG. 2B illustrates additional potential locations for implantation and placement of a magnetically actuated, chronic, implantable flow restriction system 1. Shown are multiple implants 100 implanted within the patient along with multiple potential locations for magnetic field sources 10. Specifically, FIG. 2B shows an implant 100 implanted within the patient's right subclavian vein upstream of where the right lymphatic duct connects to the right subclavian vein as well as an implant 100 implanted within the patient's right internal jugular vein upstream of where the right internal jugular vein connects with the right subclavian vein. Implants 100 in such locations can controllably and selectively occlude, restrict and/or divert flow within the veins they are implanted within to decrease pressure at the right lymphatic duct, increase lymphatic drainage, and/or reduce interstitial pressure (which can each improve cardiac and renal function), as well as to reduce cardiac preload and/or increase cardiac output. Also shown is an implant 100 implanted within the patient's left internal jugular vein upstream of where it connects to the left subclavian vein as well as an implant 100 implanted within the patient's left subclavian vein upstream of where the thoracic duct connects and empties into the left subclavian vein. Implants 100 in such locations can controllably and selectively occlude, restrict and/or divert flow within the veins they are implanted within to decrease pressure at the thoracic duct, increase lymphatic drainage, and/or reduce interstitial pressure (which can each improve cardiac and renal function), as well as to reduce cardiac preload and/or increase cardiac output. A magnetic field source 10 for actuation of the implants 100 shown in FIG. 2B can be located external to the patient, such as proximal to the patient's back, and/or in an artery or interstitial space adjacent the implant 100. While multiple implants 100 and multiple magnetic field sources 10 are shown, only one implant 100 can be implanted, or multiple implants 100 can be implanted in the locations as shown and/or in others, each having a corresponding magnetic field source 10. In some implementations with multiple implants 100 implanted, a magnetic field source 10 can be configured to actuate more than one implant 100.

The magnetic field source 10 for actuating a magnetically actuated implant 100 can be a permanent magnet, an electromagnet, or the like. The magnetic field source 10 can be worn and/or place proximate to the patient when it is desired to actuate the implant 100. For example, the magnetic field source 10 can be placed in a belt worn by the patient, placed in the patient's clothes, and/or placed or mounted in furniture used by the patient (e.g., a patient's bed, a patient's chair, etc.). In some implementations, the magnetic field source 10 can include a safety mechanism that can be actuated to expose and/or turn on the magnetic field source 10 and allow its magnetic field to actuate the implant 100. The actuation of the implant 100 by the magnetic field source 10 can be controlled and/or adjusted by selecting a magnet of a particular strength and/or displacement, and/or by selecting a particular voltage for an electromagnet. Thus, the magnetic actuation of implant 100 can be tuned and/or modulated during use so that the implant 100 provides substantially no occlusion to flow, grades of partial occlusion to flow, and/or substantially full occlusion to flow. In some implementations, magnetic actuation can actuate the implant 100 such that the implant 100 provides substantially no occlusion to flow or substantially full occlusion to flow (e.g., binary on/off). In some cases, binary on/off control of an implant 100 can include providing substantially no occlusion to flow (binary off) and partial occlusion to flow (binary on), or vice versa. In other words, even when fully actuated and "closed", an implant 100 can be configured to still allow at least partial flow therethrough.

FIGS. 3A-3D illustrate various views of an implementation of a magnetically actuated implant 100a, with FIG. 3A showing a side view and FIG. 3B showing an end view of the implant 100a in a non-occluding (e.g., open) state, and FIG. 3C showing a side view and FIG. 3D showing an end view of the implant 100a in an occluding (e.g., at least partially closed) state. The implant 100a can include an expandable body 110a having a proximal end 111a, a distal end 112a, and a lumen 113a extending from the proximal end 111a to the distal end 112a. As described above, the expandable body 110a can be configured to collapse for delivery into the patient and expand into engagement with an inner wall of a vessel of the patient once implanted, with the expanded configuration shown. The expandable body 110a as illustrated in this implementation or that may be used in other implementations may comprise a plurality of struts defining a plurality of cells. The cells may form a symmetrical or asymmetrical pattern around a central longitudinal axis of the expandable body. In an asymmetrical pattern as illustrated, the expandable body 110a may include a first row of cells at the proximal end 111a circumferentially arranged around a central longitudinal axis. The expandable body 110a may comprise a second row of cells distal to the first row of cells, for example at the distal end 112a, wherein the second row of cells are circumferentially arranged around the central longitudinal axis but may be missing one or more cells so that only a partial circumference of cells is formed. Once implanted, blood flowing through the vessel in which the implant 100a is implanted can flow through the lumen 113a. The implant 100a can also have a flow restrictor 150a connected to the expandable body 110a. The flow restrictor 150a may be offset from the central longitudinal axis of the expandable body 110a. The flow restrictor 150a can include a magnet 180a, struts 160a connecting the magnet 180a to the expandable body 110a, and material 170a spanning between the struts 160a and/or magnet 180a and the expandable body 110a for occluding flow through the lumen 113a. When the implant 100a is in an expanded configuration, the struts 160a may extend distally from the second row of cells and toward one side of the expandable body 110a. The magnet 180a may be positioned to one side of the expandable body 110a, and may be aligned with a side wall of the expandable body 110a. The material 170a can be continuous with a material 130a of the expandable body 110a, which as described above can be ePTFE, PTFE, PET cloth, polyurethane, and/or the like placed internal and/or external to the expandable body 110a, coated with an anti-thrombotic or other functional coating or uncoated, or the material 170a can be separate of or discontinuous with the material 130a.

In use, the magnetic field source 10 can actuate the implant 100a by interacting with the magnet 180a. The magnet 180a may move from a non-actuated (e.g., resting state) that is offset from the central longitudinal axis, and that may be aligned with a side wall of the expandable body 110a, to an actuated state toward an opposite side of the expandable body 110a. In the actuated state, the magnet 180a may move toward or past the central longitudinal axis. In the actuated state, the magnet 180a may extend the material 170a at least partially across the lumen to at least partially occlude or block the lumen. Depending upon the desired non-actuated (e.g., resting) state of the implant 100a, the implant 100a can be oriented with its distal end 112a receiving blood flow of the vessel in which the implant 100a is implanted and its proximal end 111a expelling the blood flow, or it can implanted in a reverse orientation. For example, if it is desired to have the implant 100a not occlude flow in its non-actuated state, the implant can be oriented with its proximal end 111a receiving flow and its distal end 112a expelling flow. In such orientation, when actuated by the magnetic field source 10, the magnet 180a of the flow restrictor 150a can be attracted to or repelled by the magnetic field source 10 (depending upon how oriented relative to the magnetic field source 10) and hinge relative to the expandable body 110*a* via struts 160*a* to occlude the lumen 113*a* (as shown in FIGS. 3C-3D). As another example, if it is desired to have the implant 100*a* occlude flow in its non-actuated state, the implant can be oriented with its distal end 112*a* receiving flow and its proximal end 111*a* expelling flow. In such orientation, blood flow can cause the flow restrictor 150*a* to occlude the lumen 113*a* until the magnetic field source 10 actuates the flow restrictor 150*a* via attraction or repulsion, upon which the flow restrictor 150*a* can hinge open to not occlude flow (as shown in FIGS. 3A-3B).

With continued reference to FIGS. 3A-3D, the implant 100*a* can be configured to partially occlude flow of the lumen 113*a* even when the flow restrictor 150*a* is in a closed position, such as shown in FIG. 3D. Such a configuration can be advantageous when actuation of the implant 100*a* is binary and it is desired to not fully occlude flow through lumen 113*a* when actuated.

In some implementations, the level of occlusion provided by the magnetically actuated implant 100*a* based on a given strength of the magnetic field source 10 can be modulated by the design of the implant, such as by the number and/or thickness of the struts 160*a* connecting the magnet 180*a* to the expandable body 110*a*. As shown in FIGS. 3A-3D, two struts 160*a* are utilized, however one strut, three struts, four struts, or any number of struts can be utilized to tune the force required to actuate the flow restrictor 150*a*.

In addition to anti-thrombotic coatings and the like, the implant 100*a* can be actuated periodically to help prevent the occurrence of thromboses and/or clogging between the flow restrictor 150*a* and the internal vessel wall when utilizing implant 100*a*, particularly if the distal end 112*a* is receiving flow. In the circumstance that a patient with an implant 100*a* needs to undergo an MRI, the magnet 180*a* can be configured to be removable from the implant 100*a*, such as via a catheter-based procedure that removes the magnet 180*a* but leaves the implant 100*a*. In some implementations and as described above, the implant 100*a* can be configured to be retrievable, thus the implant 100*a* can be removed from the patient before any imaging in which the magnet 180*a* could interfere or pose an issue.

FIGS. 4A-4D illustrate various views of another implementation of a magnetically actuated implant 100*b*, with FIG. 4A showing a side view and FIG. 4B showing an end view of the implant 100*b* in a non-occluding (e.g., open) state, and FIG. 4C showing a side view and FIG. 4D showing an end view of the implant 100*b* in an occluding (e.g., at least partially closed) state. The implant 100*b* can be the same or similar to and/or incorporate any of the features described with respect to the implant 100*a*. For instance, the implant 100*b* can have an expandable body 110*b* and a flow restrictor 150*b* the same or similar to the expandable body 110*a* and the flow restrictor 150*a* of implant 100*a*. The expandable body 110*b* of the implant 100*b*, or that may be used in other implementations, however, can have an extension 120*b* as shown in FIG. 4A and FIG. 4C. The extension 120*b* can extend from the distal end 112*b* of the expandable body 110*b* such that it can provide a landing area for the flow restrictor 150*b* to touch upon when closed to occlude flow. The extension 120*b* can comprise one or more struts extending distally from the second row of cells of the expandable body 110*b*, and may comprise one or more cells extending only partially circumferentially around the central longitudinal axis. The extension 120*b* can thus advantageously provide a surface for receiving an end of the flow restrictor 150*b* instead of such end potentially touching upon the inner wall of the vessel in which the implant 100*b* is implanted.

Also shown, the material 130*b* of the expandable body 110*b* can extend to the extension 120*b* in a continuous fashion.

FIGS. 5A-5F illustrate various views of another implementation of a magnetically actuated implant 100*c*, with FIG. 5A showing a side view and FIG. 5B showing an end view of the implant 100*b* in a non-occluding (e.g., open) state, FIG. 5C showing a side view and FIG. 5D showing an end view of the implant 100*b* in a partially occluding (e.g., partially closed) state, and FIG. 5E showing a side view and FIG. 5F showing an end view of the implant 100*b* in a fully occluding (e.g., fully closed) state. The implant 100*c* can be the same or similar to and/or incorporate any of the features described with respect to the implant 100*a*. For instance, the implant 100*c* can have an expandable body 110*c* and a flow restrictor 150*c* the same or similar to the expandable body 110*a* and the flow restrictor 150*a* of implant 100*a*. The flow restrictor 150*c* of the implant 100*c*, however, can be configured to provide full or substantially full occlusion of the lumen 113*c* when fully closed, such as shown in FIG. 5F.

FIGS. 6A-6D illustrate various views of another implementation of a magnetically actuated implant 100*d*, with FIG. 6A showing a side view and FIG. 6B showing an end view of the implant 100*b* in a non-occluding (e.g., open) state, and FIG. 6C showing a side view and FIG. 6D showing an end view of the implant 100*d* in a fully or substantially full occluding (e.g., fully closed) state. The implant 100*d* can be the same or similar to and/or incorporate any of the features described with respect to the implants 100*a*, 100*b*, and/or 100*c*. For instance and as shown, the implant 100*d* can have an expandable body 110*d* with an extension 120*d* the same or similar to the extension 120*b* of implant 100*b*, and a flow restrictor 150*d* the same or similar to the flow restrictor 150*c* of implant 100*c*.

Figure 7A:
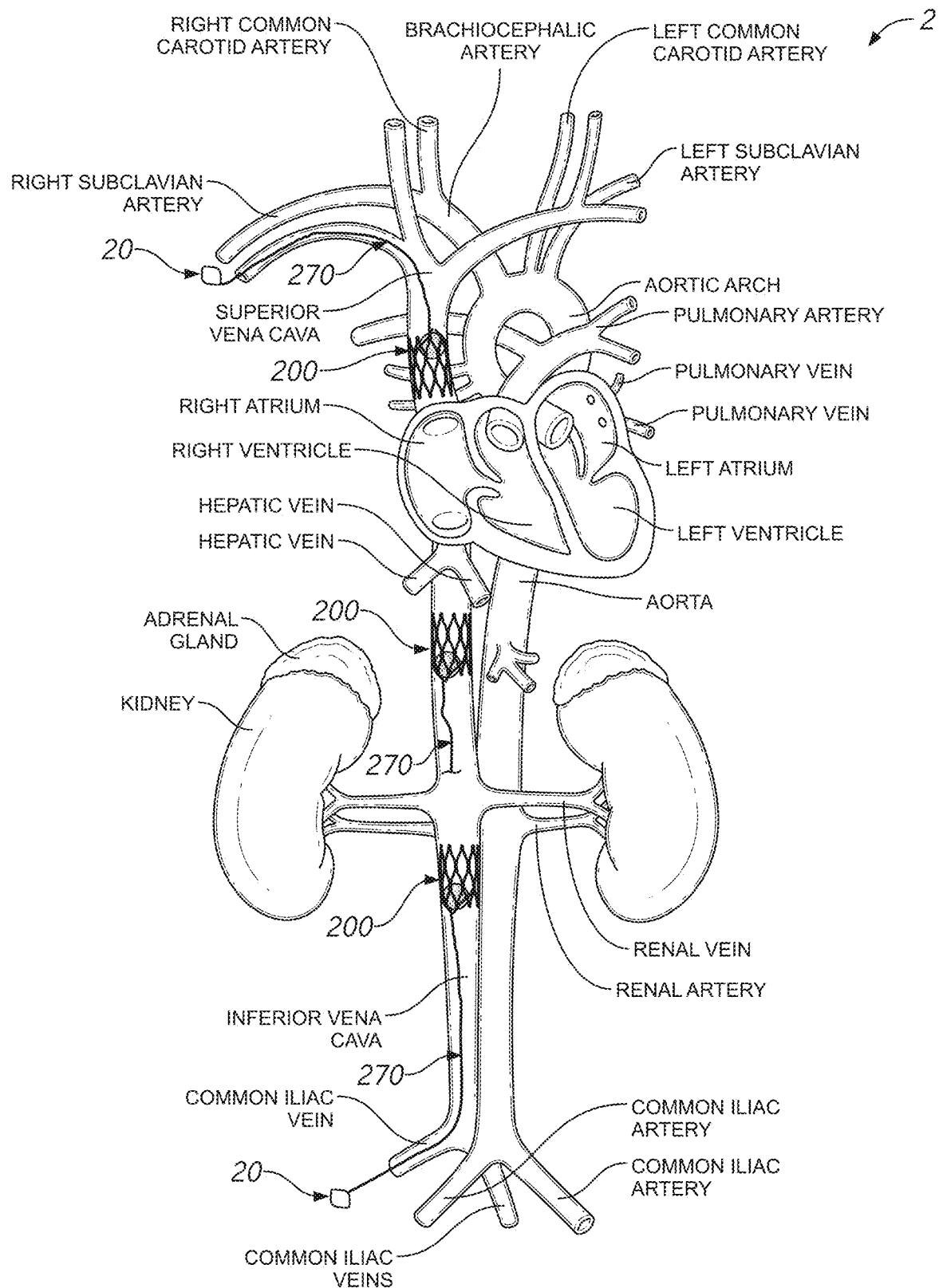
FIGS. 7A-7B illustrate chronic, implantable flow restriction systems that are fluidically actuated implanted within the patient in accordance with some aspects of this disclosure.

FIG. 7A illustrates potential locations for implantation and placement of a fluidically actuated, chronic, implantable flow restriction system 2. A fluidically actuated, chronic, implantable flow restriction system 2 can include a fluidically actuated implant 200 with a fluid reservoir 20 configured to actuate (e.g., open/close) the implant 200 and tubing 270 configured to fluidically connect the implant 200 and the fluid reservoir 20, and a delivery device (not shown). Shown are multiple implants 200 implanted within the patient along with multiple potential routing options for the tubing 270. Specifically, FIG. 7A shows an implant 200 implanted within the patient's SVC upstream of its connection to the right atrium. An implant 200 placed at this location can controllably and selectively occlude, restrict and/or divert flow within the patient's SVC and connected vasculature and/or organs, such as to reduce cardiac preload, reduce central venous pressure and/or pressure of other veins disclosed herein, and/or improve cardiac output. Also shown is an implant 200 implanted within the patient's IVC upstream of its connection to the hepatic veins, and an implant 200 implanted within the patient's IVC upstream of its connection to the renal veins. An implant 200 placed in the IVC upstream of the hepatic veins can controllably and selectively occlude, restrict and/or divert flow within the patient's IVC and connected vasculature and/or organs, such as to reduce hepatic congestion (or promote hepatic decongestion). Furthermore, an implant 200 placed in the IVC upstream of the renal veins can controllably and selectively occlude, restrict and/or divert flow within the patient's IVC and connected vasculature and/or organs, such as to reduce renal congestion (or promote renal decongestion), enhance renal circulation, and/or to control diuresis (e.g., to increase diuresis). While multiple implants 200 are shown, only one implant 200 can be implanted, or multiple implants 200 can be implanted in the locations as shown and/or in others, each having a corresponding fluid reservoir 20. In some implementations with multiple implants 200 implanted, a fluid reservoir 20 can be configured to actuate more than one implant 200.

Figure 7B:
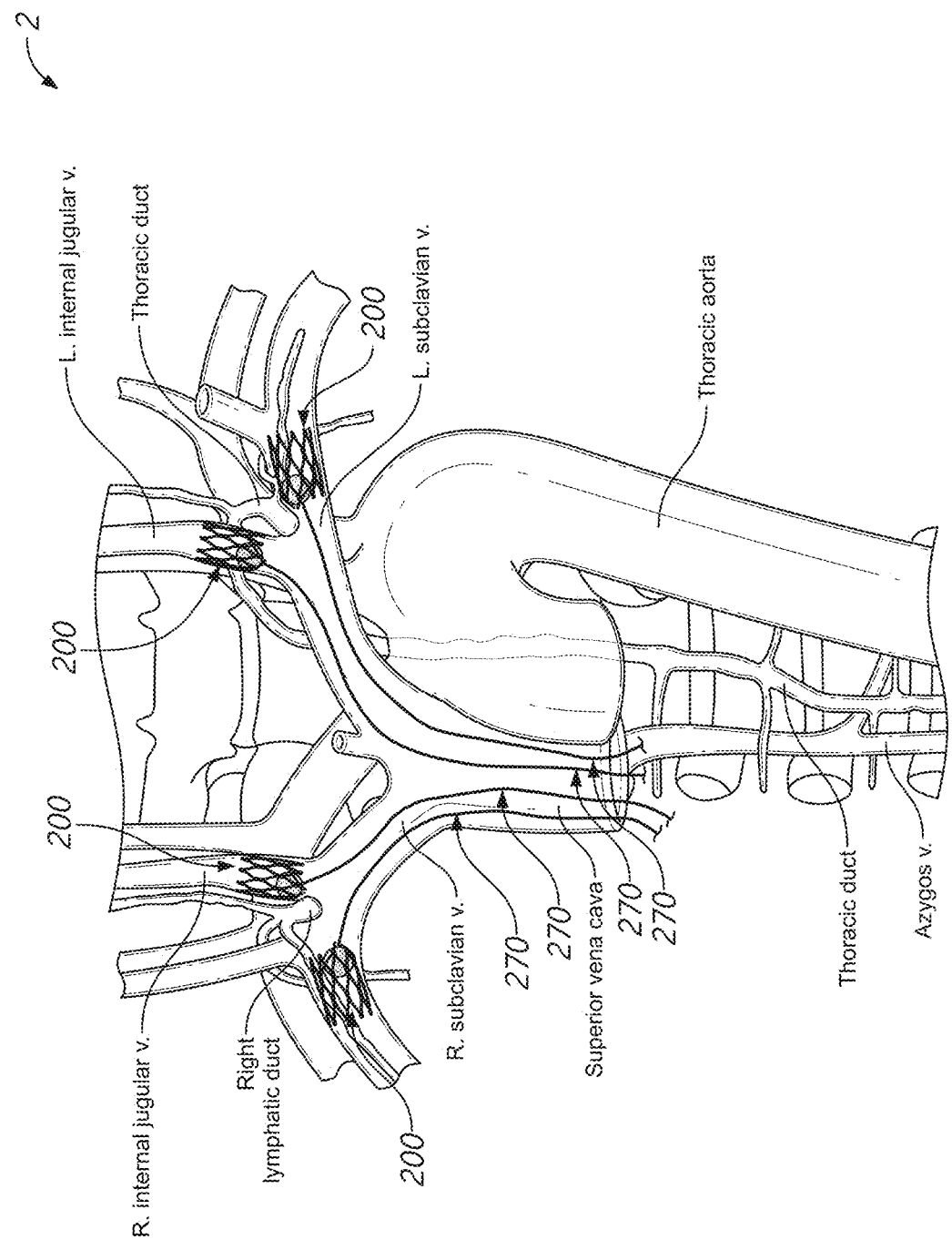

FIG. 7B illustrates additional potential locations for implantation and placement of a fluidically actuated, chronic, implantable flow restriction system 2. Shown are multiple implants 200 implanted within the patient along with multiple potential routings of associated tubing 270. Specifically, FIG. 7B shows an implant 200 implanted within the patient's right subclavian vein upstream of where the right lymphatic duct connects to the right subclavian vein as well as an implant 200 implanted within the patient's right internal jugular vein upstream of where the right internal jugular vein connects with the right subclavian vein. Implants 200 in such locations can controllably and selectively occlude, restrict and/or divert flow within the veins they are implanted within to decrease pressure at the right lymphatic duct, increase lymphatic drainage, and/or reduce interstitial pressure (which can each improve cardiac and renal function), as well as to reduce cardiac preload and/or increase cardiac output. Also shown is an implant 200 implanted within the patient's left internal jugular vein upstream of where it connects to the left subclavian vein as well as an implant 200 implanted within the patient's left subclavian vein upstream of where the thoracic duct connects and empties into the left subclavian vein. Implants 200 in such locations can controllably and selectively occlude, restrict and/or divert flow within the veins they are implanted within to decrease pressure at the thoracic duct, increase lymphatic drainage, and/or reduce interstitial pressure (which can each improve cardiac and renal function), as well as to reduce cardiac preload and/or increase cardiac output. While multiple implants 200 are shown, only one implant 200 can be implanted, or multiple implants 200 can be implanted in the locations as shown and/or in others, each having a corresponding tubing 270 and fluid reservoir 20. In some implementations with multiple implants 200 implanted, a fluid reservoir 20 can be configured to actuate more than one implant 200.

A fluid reservoir 20 can be implanted subcutaneously and located in or adjacent to a thigh, a pelvis, and/or a collarbone of the patient, for example, similar to a how and where a pacemaker is implanted. External pressure can be applied to the fluid reservoir 20 (e.g., such as over the subcutaneous location where the fluid reservoir is implanted subcutaneously) to actuate the implant 200 fluidically connected to the reservoir 20 via tubing 270.

Figure 8A:
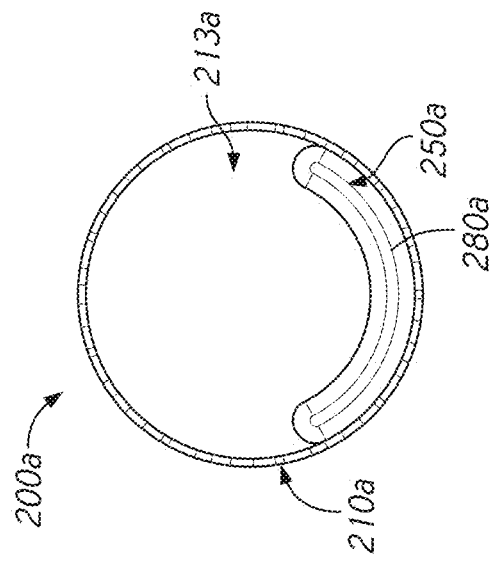
FIGS. 8A-8D illustrate various views of an implementation of a fluidically actuated, chronic, implantable flow restriction system in accordance with some aspects of this disclosure.
Figure 8B:
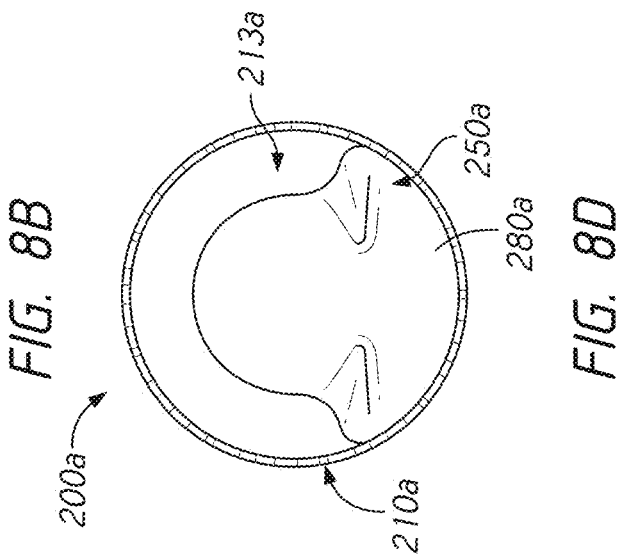
Figure 8C:
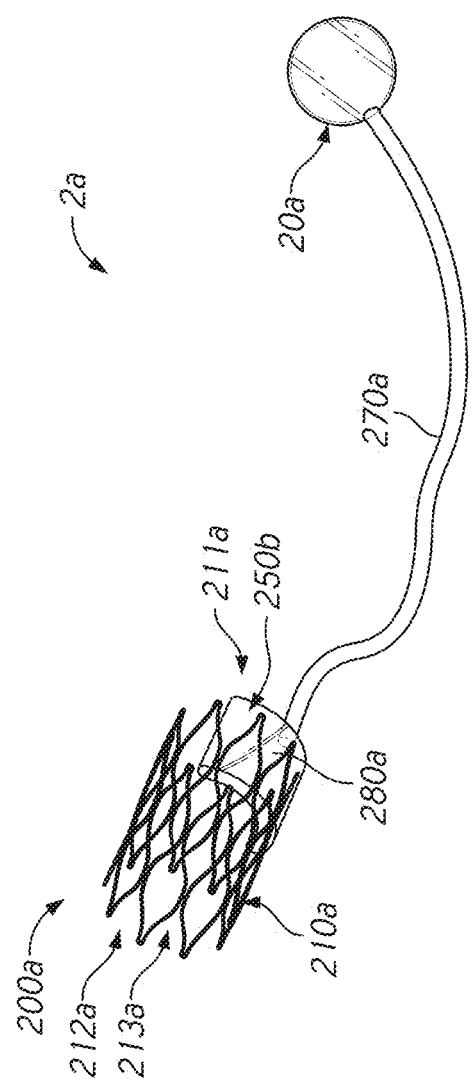
Figure 8D:
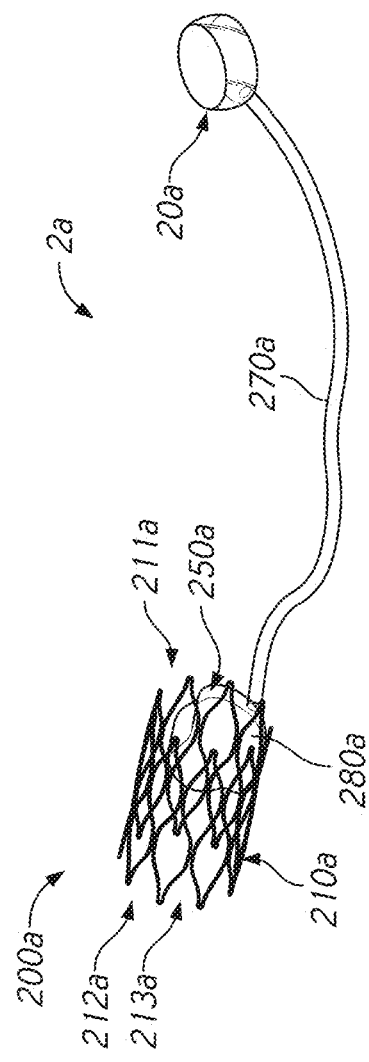

FIGS. 8A-8D illustrate various views of an implementation of a fluidically actuated implant 200a, with FIG. 8A showing a perspective view and FIG. 8B showing an end view of the implant 200a in a non-actuated (e.g., non-occluding) state, and FIG. 8C showing a perspective view and FIG. 8D showing an end view of the implant 200a in an actuated (e.g., occluding) state. The implant 200a can include an expandable body 210a having a proximal end 211a, a distal end 212a, and a lumen 213a extending from the proximal end 211a to the distal end 212a. As described above, the expandable body 210a can be configured to collapse for delivery into the patient and expand into engagement with an inner wall of a vessel of the patient once implanted, with the expanded configuration shown. Once implanted, blood flowing through the vessel in which the implant 200a is implanted can flow through the lumen 213a. The implant 200a can also have a flow restrictor 250a connected to the expandable body 210a. The flow restrictor 250a can include a balloon 280a, a fluid reservoir 20a, and tubing 270a fluidically connecting the balloon 280a with the fluid reservoir 20a. As shown, in some implementations the balloon 280a can be configured as an elongate partial circle that is adhered to an interior of the expandable body 210a (and/or to a mounting portion of the expandable body as described herein), however other balloon shapes can be utilized. The implant 200a can be oriented within a vessel of the patient with either its proximal end 211a or its distal end 212a receiving flow, with the orientation dictated by the location of the implant 200a and the location of the fluid reservoir 20a.

The balloon 280a can be made of polyurethane, polysiloxane, or the like, and can have a hydrophilic and anti-thrombotic coating. In some cases, the balloon 280a and/or tubing 270a can be made of an anti-thrombotic hydrogel. While not shown, as described above the expandable body 210a can have an ePTFE, PTFE, PET cloth, polyurethane, and/or the like material placed internal and/or external to the expandable body 210a, coated with an anti-thrombotic or other functional coating or uncoated.

The fluid reservoir 20a can be configured to maintain an expanded (e.g., full) state when at rest. For example, the fluid reservoir 20a can include a braided nitinol ball configured to maintain the fluid reservoir in an expanded state when at rest. As discussed above, external pressure can be applied to collapse the fluid reservoir 20a, causing fluid within the fluid reservoir 20a to flow out of the fluid reservoir 20a, through the tubing 270a, and into the balloon 280a, causing the balloon 280a to expand/inflate. The expansion/inflation of the balloon 280a can provide partial occlusion of the lumen 213a (as shown in FIG. 8D) and/or full occlusion of the lumen 213a as described in other implementations herein. Upon cessation of external pressure to the fluid reservoir 20a, the fluid reservoir 20a can return to its expanded state, pulling a vacuum on the balloon 280a and causing both the fluid reservoir 20a to fill with fluid and the balloon 280a to return to its collapsed/uninflated state. The fluid used to actuate the flow restrictor 250a can include saline, another biologically safe and compatible fluid, or air or another gas.

With continued reference to FIGS. 8A-8D, the implant 200a can be configured to partially occlude flow of the lumen 213a even when the balloon 280a of the flow restrictor 250a is fully expanded, such as shown in FIG. 8D. Such a configuration can be advantageous when actuation of the implant 200a is binary and it is desired to not fully occlude flow through lumen 213a when actuated.

In some implementations, the level of occlusion provided by the fluidically actuated implant 200a is based on the level of external pressure applied to the fluid reservoir 20a. Alternatively, or in addition, the level of occlusion provided by the fluidically actuated implant 200a can be based on the design of the balloon 280a and whether or not it fully occludes the lumen 213a when fully expanded/inflated.

In some variants, the balloon 280a of flow restrictor 250a can be fluidically connected to a port configured to extend from inside the patient's body to outside the patient's body and allow fluidic activation of the balloon 280a external to the patient. Such a port can be connected directly to the tubing 270a (in which case no fluid reservoir 20a may be required), or it can be connected to the fluid reservoir 20a.

FIGS. 9A-9D illustrate various views of another implementation of a fluidically actuated implant 200b, with FIG. 9A showing a perspective view and FIG. 9B showing an end view of the implant 200b in a non-occluding state, and FIG. 9C showing a perspective view and FIG. 9D showing an end view of the implant 200*b* in an occluding state. The implant 200*b* can be the same or similar to and/or incorporate any of the features described with respect to the implant 200*a*. For instance, the implant 200*b* can have an expandable body 210*b* and a flow restrictor 250*b* the same or similar to the expandable body 210*a* and the flow restrictor 250*a* of implant 200*a*. The balloon 280*b* of the flow restrictor 250*b*, however, can have a different shape. As shown, the balloon 280*b* of implant 200*b* can have a cylindrical shape with a through opening with its exterior longitudinal surface adhered to the interior of the expandable body 210*b* (and/or to a mounting portion of the expandable body as described herein). Upon actuation, the balloon 280*a* can expand/inflate to effectively narrow the lumen 213*b* and thus occlude flow of the lumen 213*b*.

Figure 10A:
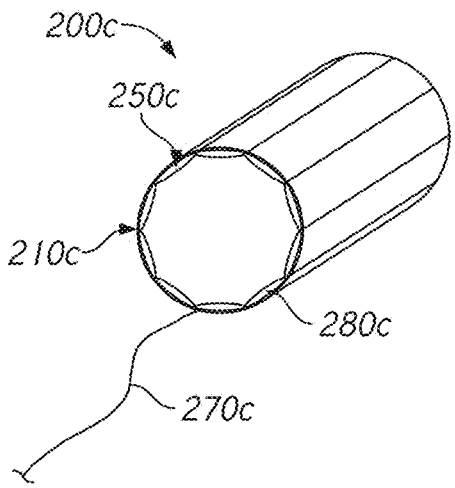
FIGS. 10A-12C illustrate various implementations of fluidically actuated, chronic, implantable flow restriction systems in accordance with some aspects of this disclosure.
Figure 10B:
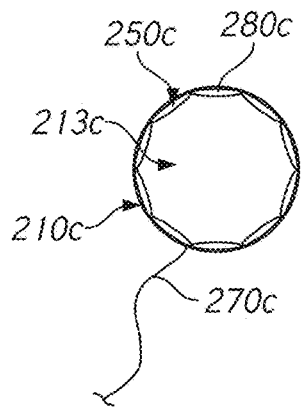
Figure 10C:
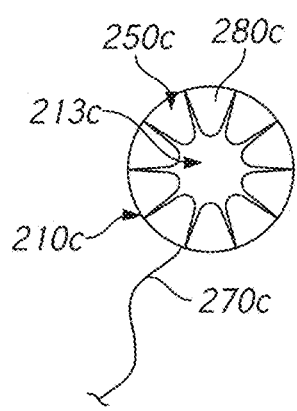
Figure 11A:
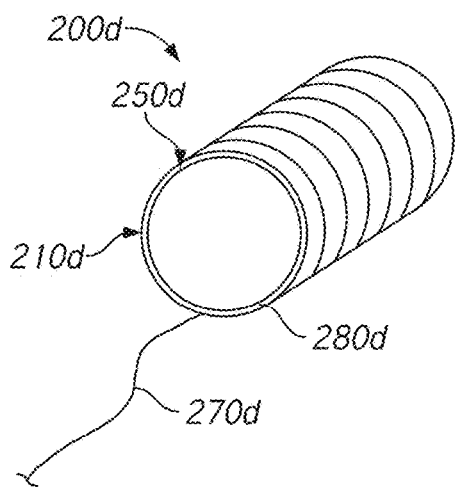
Figure 11B:
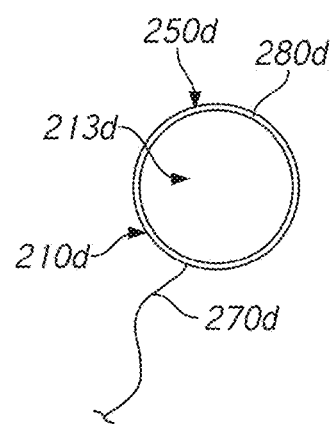
Figure 11C:
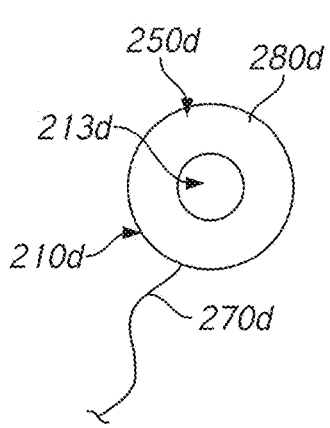
Figure 12A:
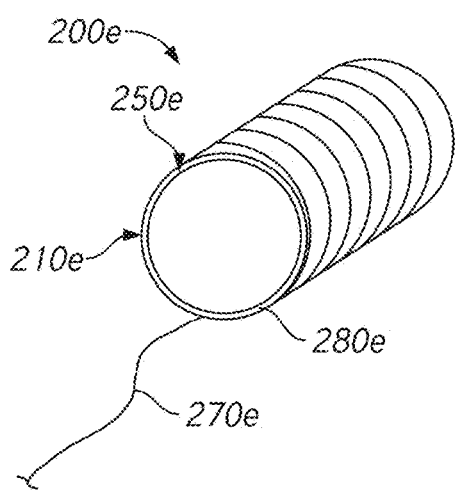
Figure 12B:
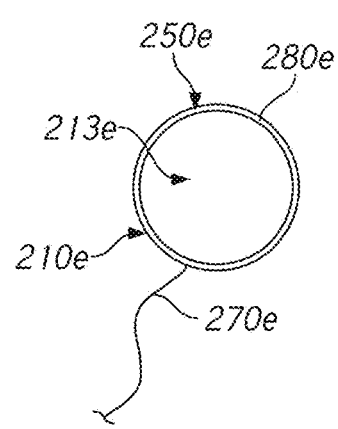
Figure 12C:
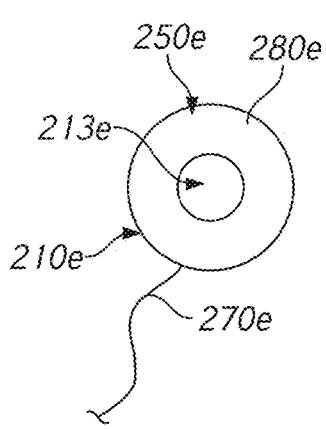

FIGS. 10A-12C illustrate various implementations of balloon(s) of a flow restrictor of a fluidically actuated implant. FIGS. 10A-10C illustrate an implant 200*c* with a flow restrictor 250*c* comprising multiple balloons 280*c* arranged longitudinally along the length of expandable body 210*c*. FIG. 10A shows a perspective view of the implant 200*c* in a non-actuated (e.g., non-occluding) state, FIG. 10B shows an end view of the implant 200*c* in a non-actuated state, and FIG. 10C shows an end view of the implant 200*c* in an actuated (e.g., occluding) state. FIGS. 11A-11C illustrate an implant 200*d* with a flow restrictor 250*d* comprising multiple balloons 280*d* arranged transverse to the length of expandable body 210*d*. FIG. 11A shows a perspective view of the implant 200*d* in a non-actuated (e.g., non-occluding) state, FIG. 11B shows an end view of the implant 200*d* in a non-actuated state, and FIG. 11C shows an end view of the implant 200*d* in an actuated (e.g., occluding) state. FIGS. 12A-12C illustrate an implant 200*e* with a flow restrictor 250*e* comprising a balloon 280*e* arranged such that it coils along the length of expandable body 210*e*. FIG. 12A shows a perspective view of the implant 200*e* in a non-actuated (e.g., non-occluding) state, FIG. 12B shows an end view of the implant 200*e* in a non-actuated state, and FIG. 12C shows an end view of the implant 200*e* in an actuated (e.g., occluding) state.

FIGS. 13A-13D illustrate another implementation of a fluidically actuated implant 200*f*. FIG. 13A shows a perspective view the implant 200*f*, FIG. 13B shows an end view of the implant 200*f*, FIG. 13C shows a perspective view of the implant 200*f* in a non-actuated state, and FIG. 13D shows a perspective view of the implant 200*f* in an actuated state. The implant 200*f* can be the same or similar to and/or incorporate any of the features described with respect to the implants 200*a*, 200*b*, 200*c*, 200*d*, and/or 200*e*. Different than the fluidically actuated implants discussed so far, the expandable body 210*f* of the implant 200*f* can include an outer body 215*f* and an inner body 225*f*. Each of the outer body 215*f* and the inner body 225*f* can comprise frames comprising a plurality of struts and/or a plurality of cells as described herein. Furthermore, both the outer body 215*f* and the inner body 225*f* can be configured to collapse and expand as described herein. Additionally, the outer body 215*f* and the inner body 225*f* can be configured to collapse and expand together. In other words, the expandable body 210*f* can be configured as a double-walled stent, with the outer body 215*f* comprising the outer wall, and the inner body 225*f* comprising the inner wall. The outer body 215*f* can have material 230*f* layered external and/or internal as described herein. Similarly, the inner body 225*f* can have material 240*f* layered external and/or internal as described herein. As shown in FIGS. 13C-13D, a balloon 280*f* of flow restrictor 250*f* can be disposed in between the outer body 215*f* and the inner body 225*f*. The balloon 280*f* can comprise any shape and/or configuration as described herein, including a prolate spheroid or an oblate spheroid shape. Additionally, although not shown, the inner body 225*f* can seal with the outer body 215*f* along their respective distal and proximal ends. Such a seal can be completely circumferential except for where tubing 270*f* extends out from the expandable body 210*f*. The outer body 215*f* can be stiffer than the more compliant inner body 225*f*, which can allow for the inner body 225*f* to deflect inwards (e.g., buckle inwards) and occlude (e.g., at least partially occlude and/or fully occlude) the lumen 213*f* upon actuation of the flow restrictor 250*f* and expansion/inflation of the balloon 2280*f* as shown in FIG. 13D. The difference in stiffness and/or compliance between the outer body 215*f* and inner body 225*f* can be accomplished via a different strut design, a different strut thickness, or the like. Having the inner body 225*f*, which can effectively encapsulate the balloon 280*f* and hide it from flow going through lumen 213*f*, can advantageously reduce the risk of thrombus formation. Additionally, the inner body 225*f* can provide a smooth surface for the lumen 213*f* (which can thus create an implant 200*f* in which all blood-contact surfaces are smooth), which can also advantageously reduce the risk of thrombus formation.

FIGS. 14A-14D show various views of an implementation of the fluidically actuated implant 200*f* according to FIGS. 13A-13D. FIG. 14A shows a side view, FIG. 14B shows a perspective view, FIG. 14C shows a top view, and FIG. 14D shows another perspective view of the implant 200*f*. As shown, the inner body 225*f* is located within the outer body 215*f*, with a balloon 280*f* (not visible) disposed in between the two. Visible in these views is the tubing 270*f* fluidically connected to balloon 280*f*. Further as shown, the implant 200*f* includes a port connected to tubing 270*f* opposite where tubing 270*f* connects to balloon 280*f*, the port configured for fluidically activating the balloon 280*f* instead of a fluid reservoir.

Figure 15A:
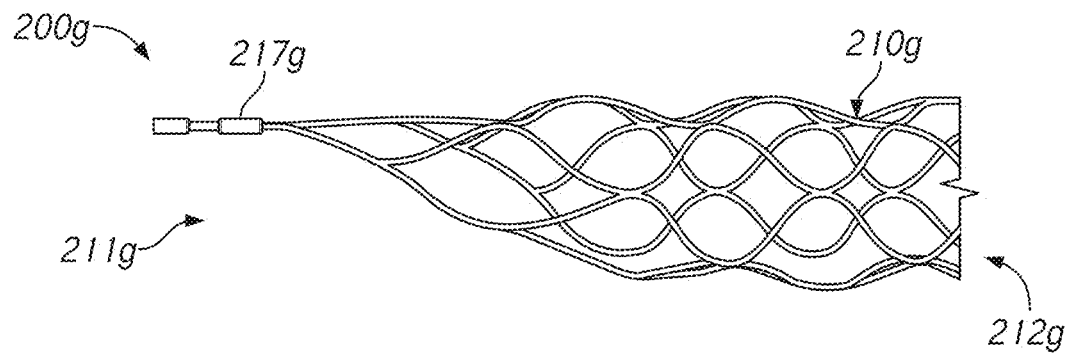
FIGS. 15A-15C illustrate another implementation of a fluidically actuated, chronic, implantable flow restriction system and a method of fabricating a fluidically actuated, chronic, implantable flow restriction system in accordance with some aspects of this disclosure.
Figure 15B:
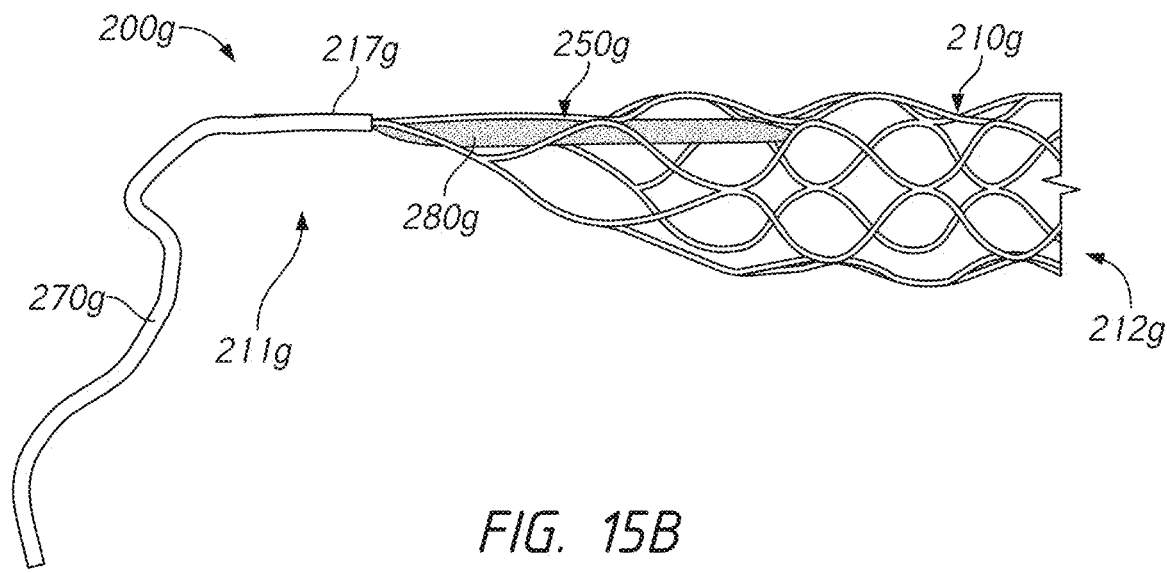
Figure 15C:
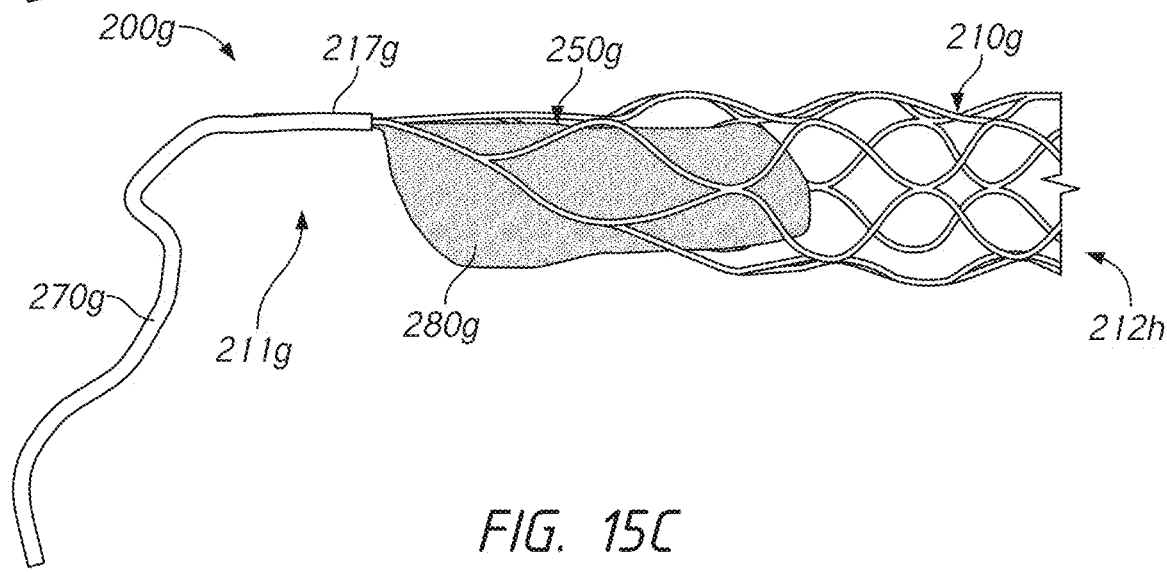

FIGS. 15A-15C illustrate another implementation of a fluidically actuated implant 200*g*, and a method of fabricating a fluidically actuated implant 200*g*. The implant 200*g* can be the same or similar to and/or incorporate any of the features described with respect to implants 200*a* through 200*f*. Although the implant 200*g* is shown without a material layer or membrane covering the expandable body 210*g*, such a material layer or membrane as described herein can optionally be present. The expandable body 210*g* as illustrated or that may be used in other implementations may comprise a metallic frame that may be laser cut or formed from one or more wires. FIG. 15A shows a side view of expandable body 210*g* with a mounting portion 217*g* configured to connect a balloon 280*g* of flow restrictor 250*g* to the expandable body 210*g*. As shown, the mounting portion 217*g* can have a tubular shape. Additionally, the mounting portion 217*g* can be located off center and along a side of the expandable body 210*g* of the implant 200*g*. As shown, struts of the expandable body 210*g* can extend distally from the mounting portion 217*g* to form a tapered or inclined opening at the proximal end 211*g*. As part of the manufacturing process, the balloon 280*g* and/or its associated tubing 270*g* can be connected (e.g., reflowed) to at least the mounting portion 217*g* of the expandable body 210*g* as shown in the side view of FIG. 15B. The balloon 280*g* and/or its associated tubing 270*g* can be connected to a side of the mounting portion 217*g*, or it can pass through the mounting portion 270*g*. The balloon 280*g* can also be connected to the interior of the expandable body 210*g*. After being connected/adhered to the mounting portion 217*g* and/or the interior of the expandable body 210g, the balloon 280f of flow restrictor 250f can be actuated to occlude the lumen of the expandable body 210g as shown in the side view of FIG. 15C. In some implementations and as shown, when actuated the balloon 280g of flow restrictor 250g can expand at least partially within the expandable body 210g as well as at least partially outside or proximal to the opening of the expandable body 210g. In some cases, when actuated the balloon 280g of flow restrictor 250g can expand fully within the expandable body 210g. The balloon 280g can comprise any shape and/or configuration as described herein, including a prolate spheroid or an oblate spheroid shape.

Figure 16A:
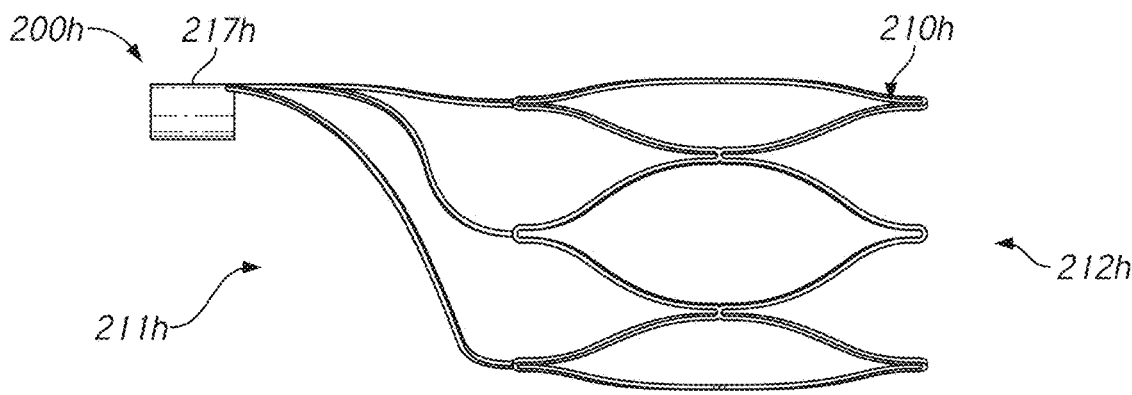
FIGS. 16A-16C illustrate another implementation of a fluidically actuated, chronic, implantable flow restriction system and another method of fabricating a fluidically actuated, chronic, implantable flow restriction system in accordance with some aspects of this disclosure.
Figure 16B:
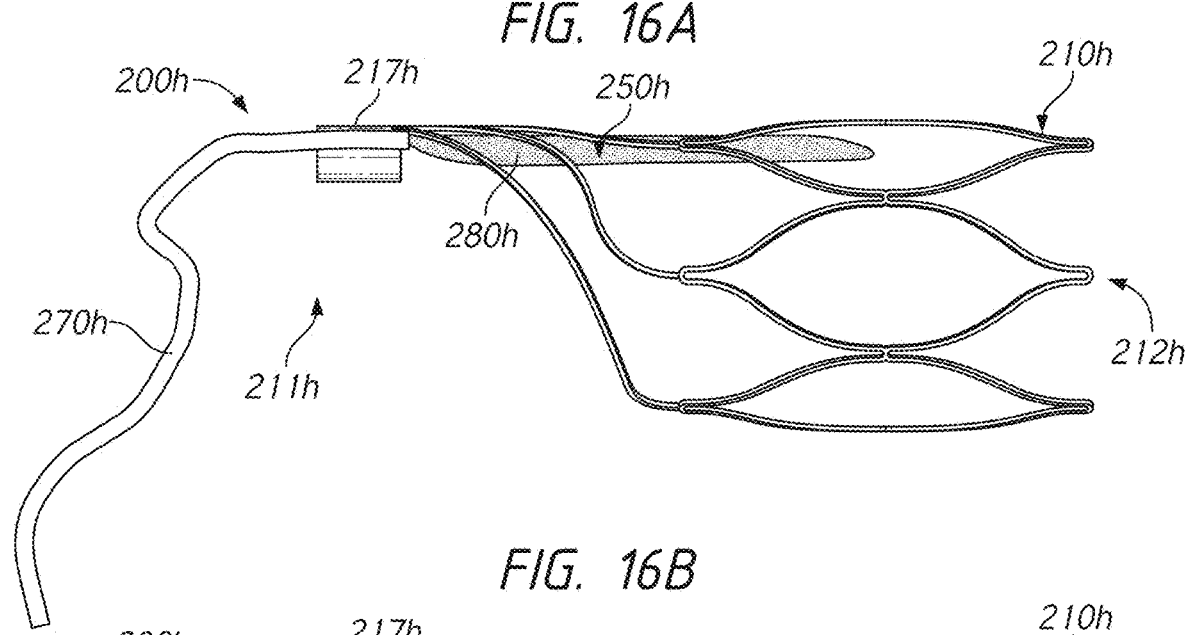
Figure 16C:
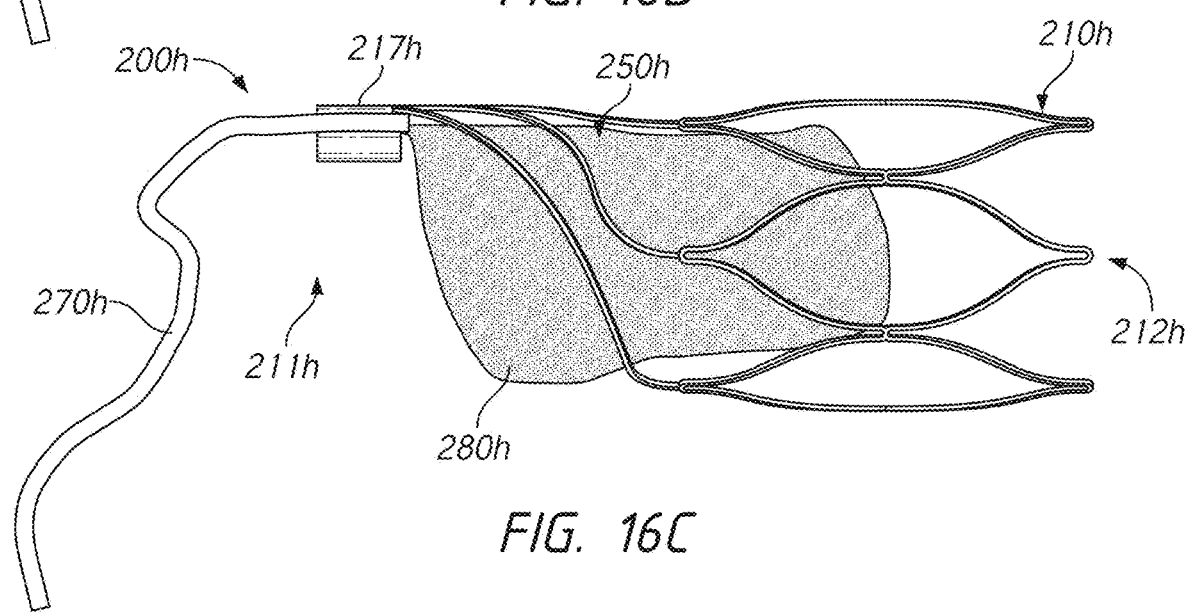

FIGS. 16A-16C illustrate another implementation of a fluidically actuated implant 200h, and another method of fabricating a fluidically actuated implant 200h. The implant 200h can be the same or similar to and/or incorporate any of the features described with respect to implants 200a through 200f. Although the implant 200h is shown without a material layer or membrane covering the expandable body 210h, such a material layer or membrane as described herein can optionally be present. The expandable body 210h as illustrated or that may be used in other implementations may comprise a metallic frame that may be laser cut or formed from one or more wires. FIG. 16A shows a side view of expandable body 210h with a mounting portion 217g configured to connect a balloon 280h of flow restrictor 250h to the expandable body 210h. The mounting portion 217g can have a cylindrical shape with a longitudinal through opening. Additionally, the mounting portion 217h can be located off center and along a side of the expandable body 210h of the implant 200h. As shown, struts of the expandable body 210h can extend distally from the mounting portion 217h to form a tapered or inclined opening at the proximal end 211h. Distal to the tapered or proximal opening, the expandable body 210h may have a circumferential portion comprising at least one row of collapsible cells. As part of the manufacturing process, the balloon 280h and/or its associated tubing 270h can be connected (e.g., reflowed) to at least the mounting portion 217h of the expandable body 210h as shown in the side view of FIG. 16B. The balloon 280h and/or its associated tubing 270h can be connected to a side of the mounting portion 217h, or it can pass through the mounting portion 270h. The balloon 280h can also be connected to the interior of the expandable body 210h. After being connected/adhered to the mounting portion 217h and/or the interior of the expandable body 210h, the balloon 280h of flow restrictor 250h can be actuated to occlude the lumen of the expandable body 210h as shown in the side view of FIG. 16C. In some implementations and as shown, when actuated the balloon 280h of flow restrictor 250h can expand at least partially within the expandable body 210h as well as at least partially outside or proximal to the opening of the expandable body 210h. In some cases, when actuated the balloon 280h of flow restrictor 250h can expand fully within the expandable body 210h. The balloon 280h can comprise any shape and/or configuration as described herein, including a prolate spheroid or an oblate spheroid shape.

FIGS. 17A-17B illustrate various views of another implementation of a fluidically actuated implant 200i. The implant 200i can be the same or similar to and/or incorporate any of the features described with respect to implants 200a through 200h. FIG. 17A illustrates a side view and FIG. 17B illustrates an end view of the implant 200i in an actuated configuration. The expandable body 210i as illustrated or that may be used in other implementations may be symmetrical about its central longitudinal axis, and may comprise a plurality of rows of collapsible cells. As shown, the flow restrictor 250i can include a balloon 280i with tubing 270i located off-center/tangent to the balloon 280i instead of coaxial with the balloon. Such an off-center/tangent configuration can advantageously prevent the balloon from pushing off from the inner wall of the expandable body 210i upon expansion/inflation, which is a phenomenon that can occur with a coaxial configuration. Furthermore, an off-center/tangent configuration can advantageously allow for the tubing 270i to be connected to the inner wall of the expandable body 210i both proximal and distal to the balloon 280i (e.g., for better securement of the balloon 280i). This configuration of a flow restrictor 250i can be utilized with any of the fluidically actuated implants described herein, including with implants having an expandable body comprising an outer body and an inner body (e.g., such as shown in FIGS. 13A-13D and FIGS. 14A-14D). Furthermore, the balloon 280i can comprise any shape and/or configuration as described and/or illustrated herein, including a prolate spheroid or an oblate spheroid shape.

Figure 18A:
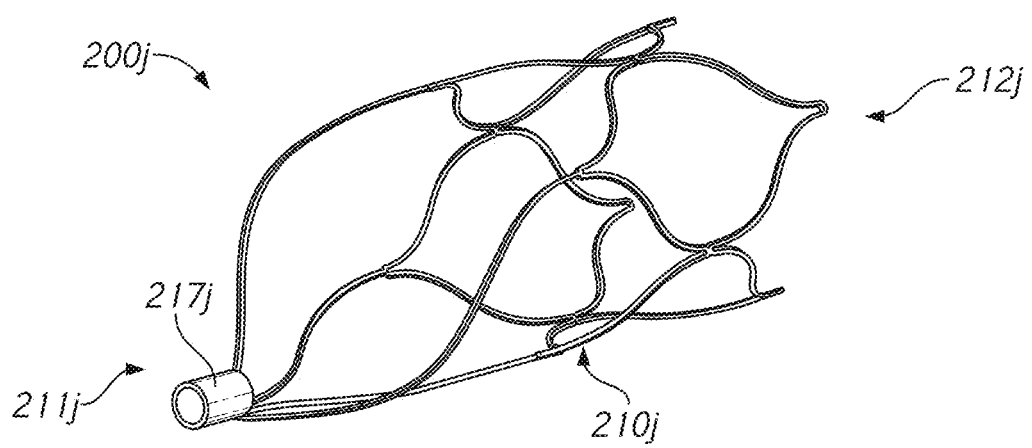
FIGS. 18A-18C illustrate various views of a frame of another implementation of a fluidically actuated, chronic, implantable flow restriction system in accordance with some aspects of this disclosure.
Figure 18B:
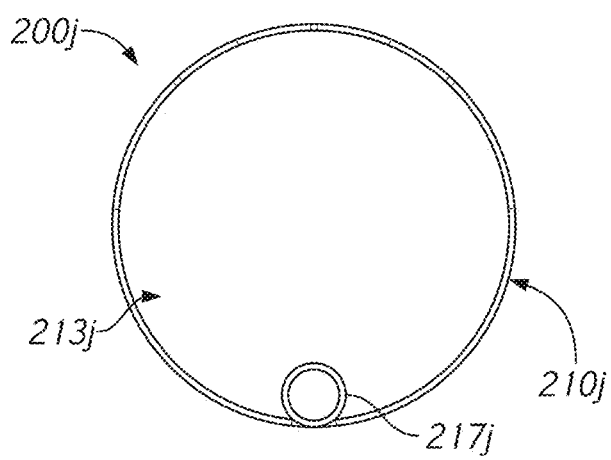
Figure 18C:
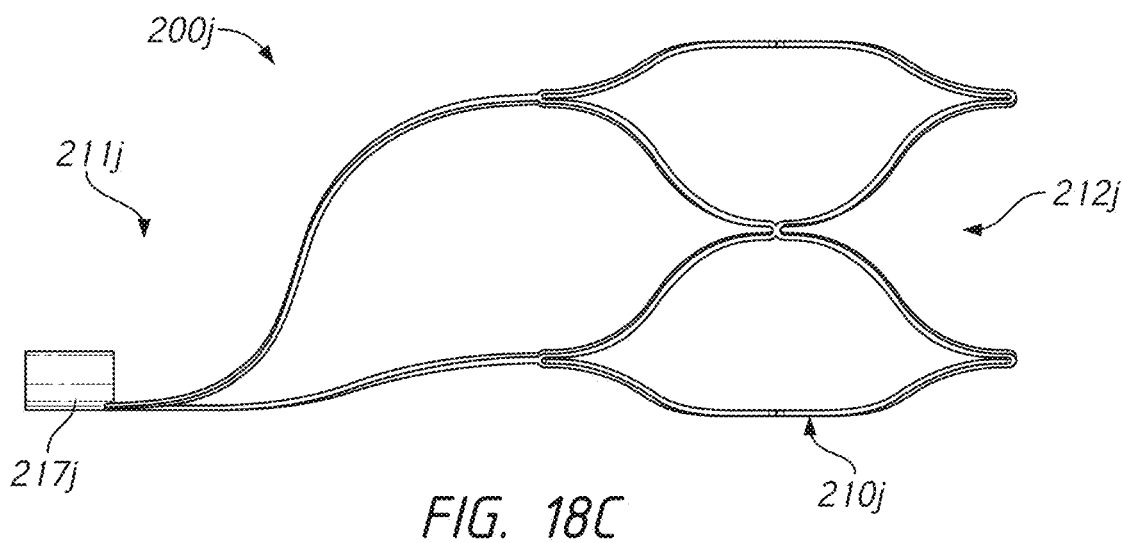

FIGS. 18A-18C illustrate various views of an implementation of an expandable body 210j of a fluidically actuated implant 200j. FIG. 18A shows a perspective view, FIG. 18B shows an end view, and FIG. 18C shows a side view of the expandable body 210j. As shown, the expandable body 210j or that may be used in other implementations comprises a 4-cell configuration, comprising 4 collapsible cells at the distal end 212j extending circumferentially around the central longitudinal axis. Also shown, the expandable body 210j includes a mounting portion 217j similar to or the same as the mounting portion 217g of implant 200g that may be offset relative to a central longitudinal axis of the expandable body. As shown, struts at the proximal end 211j of the expandable body 210j can extend away from the mounting portion 217j and/or an end of the implant that is offset relative to a central longitudinal axis of the implant to advantageously facilitate implant 200j collapse and/or retrieval. In other words, the design of the expandable body 210j, in which struts at the proximal end 211j of the expandable body 210j coalesce in the proximal direction at the mounting portion 217j and/or at an end of the implant that is offset relative to a central longitudinal axis of the implant, can facilitate the collapse of the implant 200j. The 4-cell expandable body 210j can be utilized with any of the fluidically actuated implants described herein.

Figure 19A:
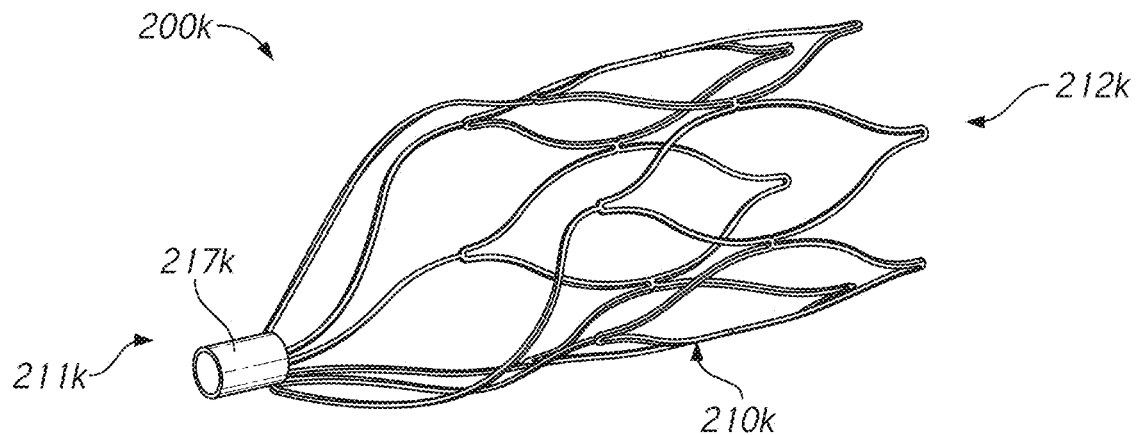
FIGS. 19A-19C illustrate various views of a frame of another implementation of a fluidically actuated, chronic, implantable flow restriction system in accordance with some aspects of this disclosure.
Figure 19B:
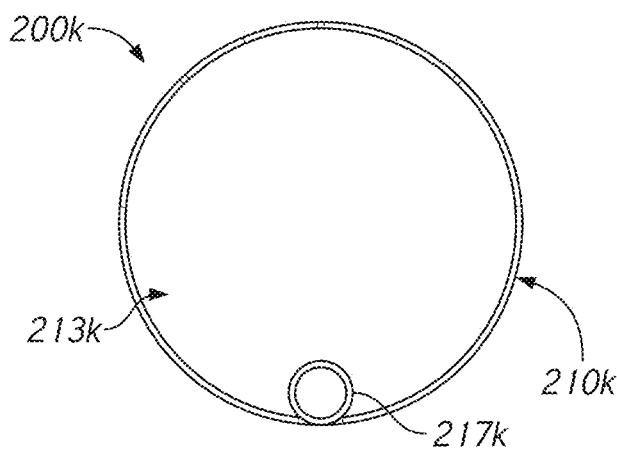
Figure 19C:
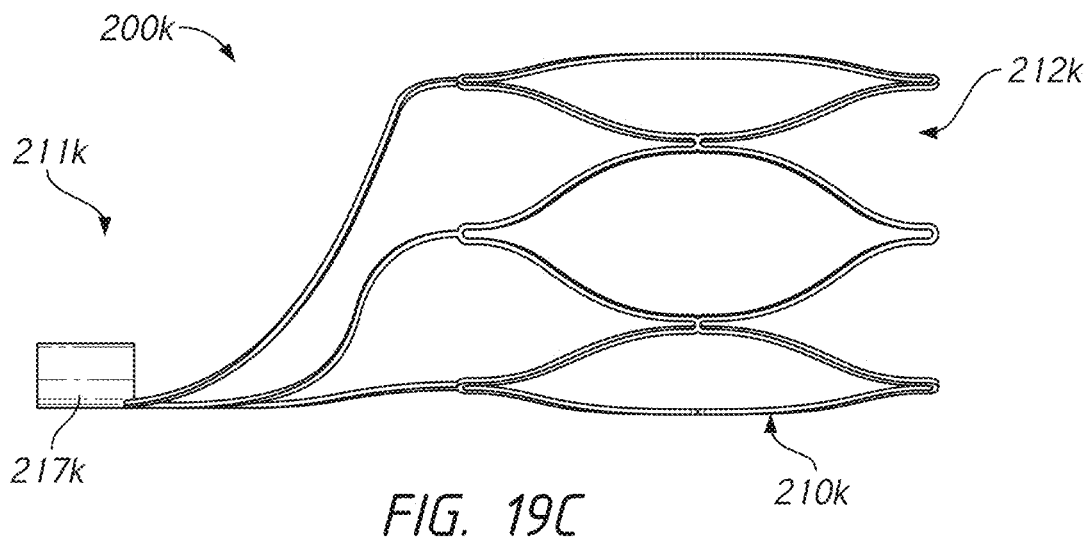

FIGS. 19A-19C illustrate various views of an implementation of an expandable body 210k of a fluidically actuated implant 200k. FIG. 19A shows a perspective view, FIG. 19B shows an end view, and FIG. 19C shows a side view of the expandable body 210k. As shown, the expandable body 210k comprises a 6-cell configuration, comprising 6 collapsible cells at the distal end 212j extending circumferentially around the central longitudinal axis of the expandable body. Also shown, the expandable body 210k includes a mounting portion 217k similar to or the same as the mounting portion 217g of implant 200g that may be offset relative to a central longitudinal axis of the expandable body. As shown, struts at the proximal end 211k of the expandable body 210k can extend away from the mounting portion 217k and/or an end of the implant that is offset relative to a central longitudinal axis of the implant to advantageously facilitate implant 200k collapse and/or retrieval. In other words, the design of the expandable body 210k, in which struts at the proximal end 211k of the expandable body 210k coalesce in the proximal direction at the mounting portion 217k and/or an at end of the implant that is offset relative to a central longitudinal axis of the implant, can facilitate the collapse of the implant

200*k*. The 6-cell expandable body 210*k* can be utilized with any of the fluidically actuated implants described herein.

FIGS. 20A-20D illustrate various views of an implementation of an expandable body 210*l* of a fluidically actuated implant 200*l*. FIG. 20A shows a side view of the expandable body 210*l* in an expanded configuration, FIG. 20B shows a side view of the expandable body 210*l* in a collapsed configuration, FIG. 20C shows a perspective view of the expandable body 210*l* in an expanded configuration, and FIG. 20D shows a perspective view of the expandable body 210*l* in a collapsed configuration. Also shown, the expandable body 210*l* can include a mounting portion 217*l* similar to or the same as the mounting portion 217*g* of implant 200*g* that may be offset relative to a central longitudinal axis of the expandable body. The expandable body 210*l* as illustrated or that may be used in other implementations can have an angled or inclined proximal opening at its proximal end 211*l*, with struts of the expandable body 210*l* extending distally away from the mounting portion 217*l* such that a portion of the expandable body 210*l* opposite the side of the body where the mounting portion 217*l* is located (e.g., about 180 degrees from the location of the mounting portion 217*l* when viewed on end) is further distal than the portion of the expandable body 210*l* that connects with the mounting portion 217*l*. The expandable body 210*l* can similarly have an angled or inclined distal opening at its distal end 212*l* as shown, with a side of the expandable body 210*l* longitudinally aligned with the mounting portion 217*l* being located more proximal than the side opposite. In some cases and as shown, the distal opening can have a similar (or the same) angle or incline as the proximal opening. Furthermore, the expandable body 210*l* may comprise longitudinally extending struts (e.g., extending parallel or substantially parallel with the central longitudinal axis of the expandable body 210*l*) and diagonal struts. The diagonal struts of the expandable body 210*l*, when expanded, can be aligned diagonally relative to the longitudinally extending struts and oriented in the same or in generally the same direction (best shown in the side view of FIG. 20A). Struts of the expandable body 210*l* can coalesce at its proximal end 211*j* in the proximal direction at the mounting portion 217*l* (e.g., at an end of the implant that is offset relative to a central longitudinal axis of the implant). By such arrangement, the expandable body 210*l* is advantageously configured to collapse/crimp by being pulled/pushed (e.g., via elongation for a sideways collapse/crimp versus a radial collapse/crimp), which can allow for easier retrieval after deployment. For example, the expandable body 210*l* can be collapsed from its expanded configuration by pulling on the mounting portion 217*l* or any tubing that would be connected to the implant 200*l*. As another example, the expandable body 210*l* can be collapsed from its expanded configuration by applying longitudinal force towards the expandable body 210*l* (e.g. pushing) above where the mounting portion 217*l* is located. The expandable body 210*l* can be utilized with any of the fluidically actuated implants described herein.

Figure 21A:
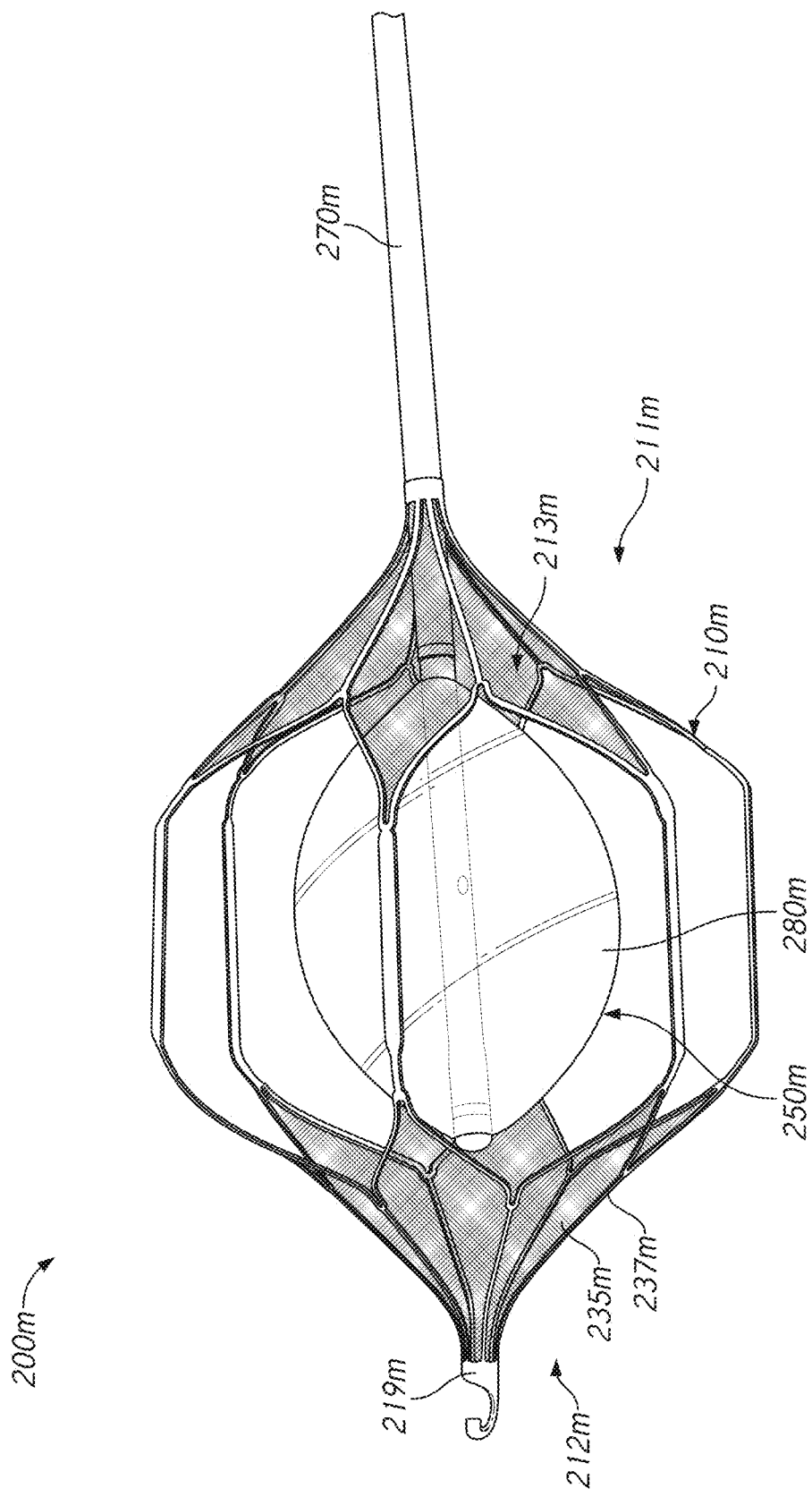
FIG. 21A illustrates another implementation of a fluidically actuated, chronic, implantable flow restriction system in accordance with some aspects of this disclosure.

FIG. 21A illustrates a side view of another implementation of a fluidically actuated implant 200*m*. The implant 200*m* can be the same or similar to and/or incorporate any of the features described with respect to any of the fluidically actuated implants described herein. As shown, the implant 200*m* can be configured to have flow restrictor 250*m*, which includes balloon 280*m* and tubing 270*m*, substantially aligned coaxial with expandable body 210*m* such that the balloon 280*m* is substantially centered in the lumen 213*m*. The balloon 280*m* can comprise any shape and/or configuration as described and/or illustrated herein, including a prolate spheroid or an oblate spheroid shape. In some implementations, a portion of tubing 270*m* can extend through an interior of the balloon 280*m*, either part-way or fully through the balloon 280*m* as shown (e.g., from a proximal end of the balloon 280*m* to a distal end of the balloon 280*m*). Furthermore, in some cases the portion of tubing 270*m* that extends through the interior of the balloon 280*m* can have a diameter (e.g., overall diameter) than is less than a diameter of the tubing 270*m* that does not extend through the interior of the balloon 280*m* (e.g., tubing 270*m* proximal to the balloon 280*m* as shown). In some implementations, the portion of tubing 270*m* extending through the interior of the balloon 280*m* may have a smaller wall thickness than other portions of the tubing 270*m*. When the balloon 280*m* is not actuated (e.g., when the balloon 280*m* is collapsed against the portion of tubing 270*m* that extends through its interior), such a configuration of a variable diameter and/or variable wall thickness tubing can advantageously create a smooth transition between the tubing 270*m* proximal to the balloon 280*m* and the balloon 280*m* with internal tubing 270*m* such that the flow restrictor 250*m* has a substantially uniform overall diameter (e.g., an outer diameter of the balloon 280*m*, when collapsed, is not greater than the outer diameter of tubing 270*m* proximal to the balloon 280*m*). The flow restrictor 250*m* having a substantially uniform overall diameter can advantageously reduce a risk of thrombus formation, particularly in a chronic implant 200*m*.

Different than other implementations described, the expandable body 210*m* as illustrated or that may be used in other implementations can include struts 237*m* and/or a membrane 235*m* disposed at a distal end 212*m* of the implant 200*m* (e.g., distal to the flow restrictor 250*m* in relation to the direction of flow through the implant 200*m*) and located within the flow path of the lumen 213*m*. The expandable body 210*m* when expanded may comprise a proximal portion that increases in radial dimension in a proximal-to-distal direction, a central portion that may have a constant outer dimension configured to engage an inner wall of a vessel, and a distal portion that decreases in radial dimension in a proximal-to-distal direction. The distal portion may comprise the membrane 235*m*. The tubing 270*m* may terminate proximal to the distal portion, or the distal portion may be connected to the tubing 270*m*. Such struts 237*m* and/or membrane 235*m* can act as a filter to catch thrombus that may pass through or be generated by the implant 200*m* (e.g., to prevent pulmonary-embolism). For example, about 4 to about 12 or more struts 237*m* can be disposed at the distal end of the implant 200*m*, the struts 237*m* configured to capture thrombus. Alternatively, or in addition, membrane 235*m* can be disposed at the distal end of the implant 200*m* in the flow path of the lumen 213*m*, the membrane configured to capture thrombus. The membrane 235*m* can be configured to allow flow therethrough but still capture thrombus, and as such can have perforations throughout. Perforations throughout the membrane 235*m* can range in size from about 0.5 mm to about 7 mm, about 1 mm to about 5 mm, or any size above or under such ranges. In some implementations and as shown, the implant 200*m* can include a retrieving portion 219*m* configured to aid in retrieving the implant 200*m* after implantation. For example and as shown, the retrieving portion 219*m* can be configured as a hook, although the retrieving portion 219*m* can be configured as a loop or other shape to aid in retrieval. The retrieving portion 219*m* can be positioned adjacent the distal end 212*m* of the implant 200*m* (as shown), or it can be positioned adjacent the proximal end 211*m* of the implant. In some cases, tubing 270m can be used to aid in retrieval and/or positioning of the implant 200m.

Figure 21B:
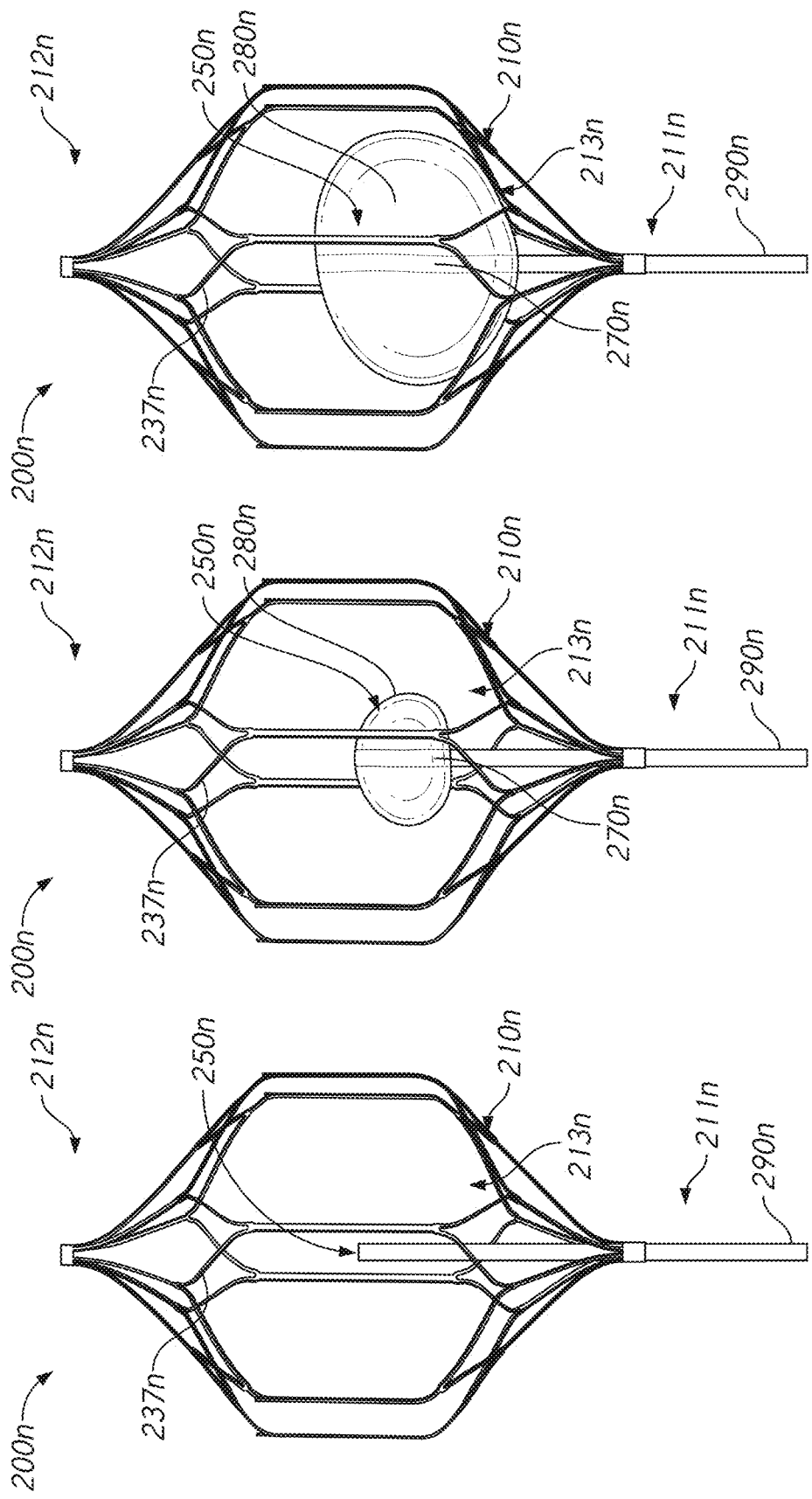
FIG. 21B illustrates another implementation of a fluidically actuated, chronic, implantable flow restriction system in accordance with some aspects of this disclosure.

FIG. 21B illustrates side views of another implementation of a fluidically actuated implant 200n, with the side view at left showing the flow restrictor 250n of the implant 200n in a non-actuated state, the side view at middle showing the flow restrictor 250n in a partially actuated state, and the side view at right showing the flow restrictor 250n in a substantially fully actuated state. The implant 200n can be the same or similar to and/or incorporate any of the features described with respect to any of the fluidically actuated implants described herein, such as implant 200m. As shown, the implant 200n can be configured to have flow restrictor 250n, which can include balloon 280n, tubing 270n, and a shaft 290n substantially aligned coaxial with expandable body 210n such that the balloon 280n is substantially centered in the lumen 213n. The balloon 280m can comprise any shape and/or configuration as described and/or illustrated herein, including a prolate spheroid or an oblate spheroid shape. Different than implant 200m, the flow restrictor 250n of implant 200m can be configured to hide the balloon 280n when in its non-actuated state (e.g., shown at left in FIG. 21B). For example, shaft 290n can be configured to cover the balloon and/or tubing 270n when the balloon 280n is in its non-actuated state. Furthermore, shaft 290n can be configured to hide the balloon 280n and/or tubing 270n from flow through the lumen when the balloon 280n is in its non-actuated state. Such a configuration can advantageously reduce a risk of thrombus formation, particularly in a chronic implant 200n.

In some implementations, the flow restrictor 250n can be configured such that the balloon 280n, when non-actuated, collapses internally within shaft 290n. In some cases and as shown in FIG. 21B, the flow restrictor 250n can be configured such that shaft 290n can advance in the distal direction to cover the balloon 280n when the balloon 280n is in its non-actuated state. In such configuration, the shaft 290n can be biased to advance forward to cover the balloon 280n when the balloon 280n is in its non-actuated state, for example, by a spring force and/or the shaft 290n can be spring-loaded. Furthermore, in such configuration, when the balloon 280n is actuated, the expansion of the balloon 280n can cause the shaft 290n to retract in the proximal direction. In other words, the shaft 290n can advance in the distal direction over the balloon 290n when the balloon deflates/collapses; when the balloon 280n inflates/expands, the force generated by the balloon inflation/expansion can cause the shaft 290n to retract in the proximal direction and allow the balloon 280n to at least partially occlude the lumen 213n (e.g., the biasing force of the shaft in the distal direction can be strong enough to swallow the balloon 280n when it is deflated/collapsed, but weak enough to retract in the proximal direction to allow the balloon 280n to inflate/expand upon actuation).

FIG. 21C illustrates side views of an implementation of a mechanically actuated implant 200o, with the side view at left showing the flow restrictor 250o of the implant 200o in a non-actuated state, and the side view at right showing the flow restrictor 250o in a substantially fully actuated state. The implant 200o can be the same or similar to and/or incorporate any of the features described with respect to any of the implants described herein, such as implants 200m and 200n. As shown, the implant 200o can be configured to have flow restrictor 250o, which can include an expandable occluder 280o and a shaft 290o substantially aligned coaxial with expandable body 210o such that the expandable occluder 280o is substantially centered in the lumen 213o.

The expandable occluder 280o can comprise any shape and/or configuration as described and/or illustrated herein, including a prolate spheroid, an oblate spheroid, a spherical shape, and/or a cylindrical shape as shown when in its actuated state. Different than implants 200m and 200n, the expandable occluder 280o of flow restrictor 250n can comprise a shape memory material (e.g., Nitinol) that can be moved between a non-actuated state and an actuated state. For example and as shown at left in FIG. 21C, the expandable occluder 280o can be retracted in a proximal direction relative to the shaft 290o to cause the expandable occluder 280o to collapse within the shaft 290o, effectively hiding it from flow through the lumen 213o. Upon mechanical actuation, such as distal movement of the expandable occluder 280o relative to the shaft 290o, the expandable occluder can expand within the lumen 213o to at least partially occlude the lumen 213o. To vary the degree of occlusion of the lumen 213o, the expandable occluder 280o can be either fully extended distally from within shaft 290o, partially extended distally from within shaft 290o, and or not extended and hid within the shaft 290o. The ability to hide the expandable body 280o within shaft 290o can advantageously reduce a risk of thrombus formation, particularly in a chronic implant 200o. The expandable body 280o can be configured as a mesh, a knit, and/or any other configuration to provide at least partial occlusion to flow. Furthermore, the flow restrictor 250o comprising an expandable body 280o and shaft 290o can be implemented in any of the implants described and/or illustrated herein.

Figure 22A:
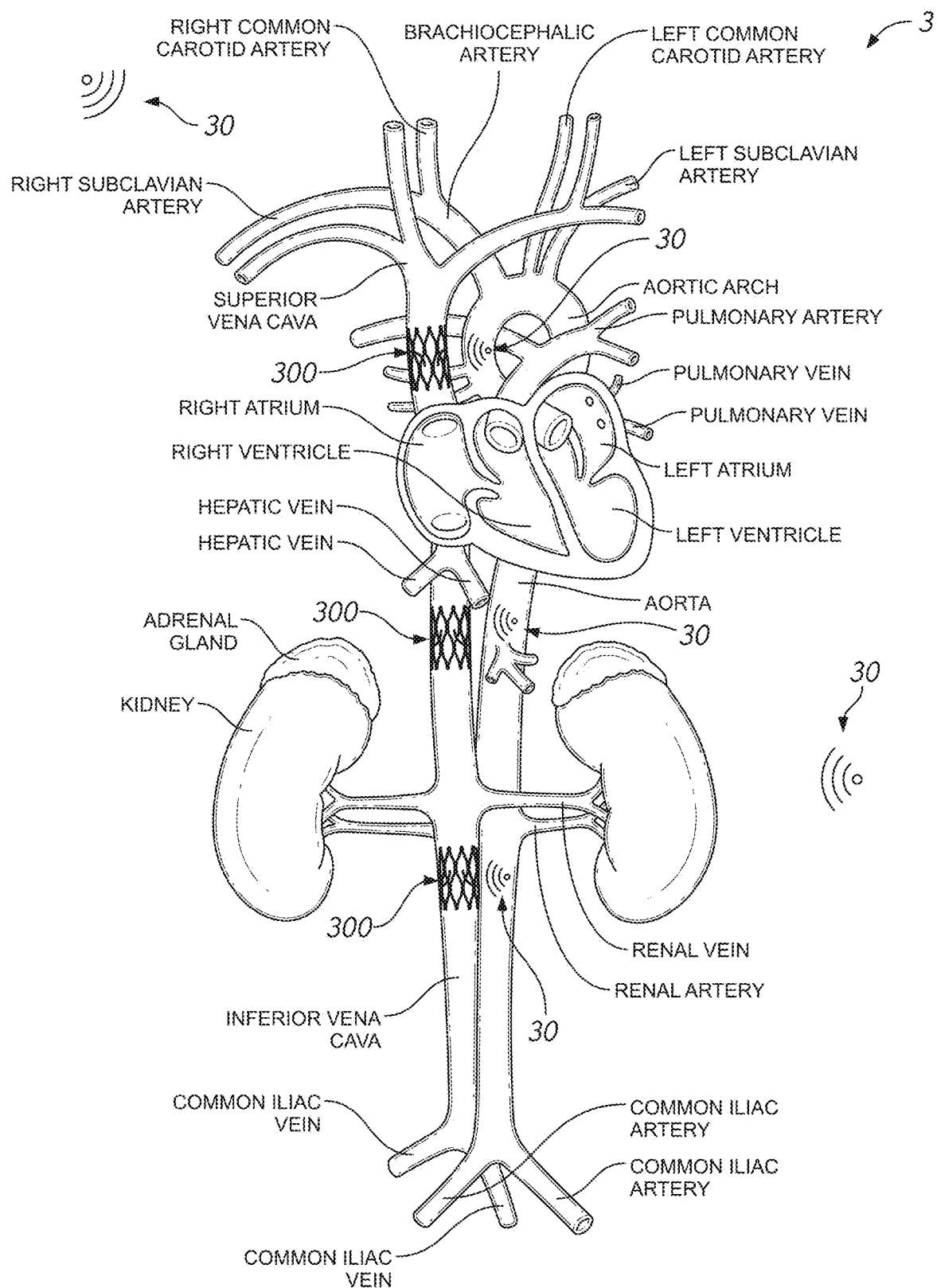
FIG. 22A-22B illustrate chronic, implantable flow restriction systems that are actuated via heat implanted within the patient in accordance with some aspects of this disclosure.

FIG. 22A illustrates potential locations for implantation and placement of a heat actuated, chronic, implantable flow restriction system 3. A heat actuated, chronic, implantable flow restriction system 3 can include a heat actuated implant 300, an energy source 30 configured to actuate (e.g., open/close) the implant 300, and a delivery device (not shown). Shown are multiple implants 300 implanted within the patient along with multiple potential locations for energy sources 30. Specifically, FIG. 22A shows an implant 300 implanted within the patient's SVC upstream of its connection to the right atrium, with options for the location of its accompanying energy source 30 being external to the patient, such as proximal to the patient's back, chest, and/or abdomen, and/or internal to the patient, such as in the aortic arch or an interstitial space adjacent the SVC. An implant 300 placed at this location can controllably and selectively occlude, restrict and/or divert flow within the patient's SVC and connected vasculature and/or organs, such as to reduce cardiac preload, reduce central venous pressure and/or pressure of other veins disclosed herein, and/or improve cardiac output. Also shown is an implant 300 implanted within the patient's IVC upstream of its connection to the hepatic veins, and an implant 300 implanted within the patient's IVC upstream of its connection to the renal veins. The location of an energy source 30 for actuation of the implants 300 placed within the IVC can include the aorta as shown, an interstitial space adjacent the IVC, and/or the energy source 30 can be located external to the patient, such as proximal to the patient's back, chest, and/or abdomen. An implant 300 placed in the IVC upstream of the hepatic veins can controllably and selectively occlude, restrict and/or divert flow within the patient's IVC and connected vasculature and/or organs, such as to reduce hepatic congestion (or promote hepatic decongestion). Furthermore, an implant 300 placed in the IVC upstream of the renal veins can controllably and selectively occlude, restrict and/or divert flow within the patient's IVC and connected vasculature and/or organs, such as to reduce renal congestion (or promote renal decongestion), enhance renal circulation, and/or to control diuresis (e.g., to increase diuresis). While multiple implants 300 and energy sources 30 are shown, only one implant 300 can be implanted, or multiple implants 300 can be implanted in the locations as shown and/or in others, each having a corresponding energy source 30. In some implementations with multiple implants 300 implanted, an energy source 30 can be configured to actuate more than one implant 300.

Figure 22B:
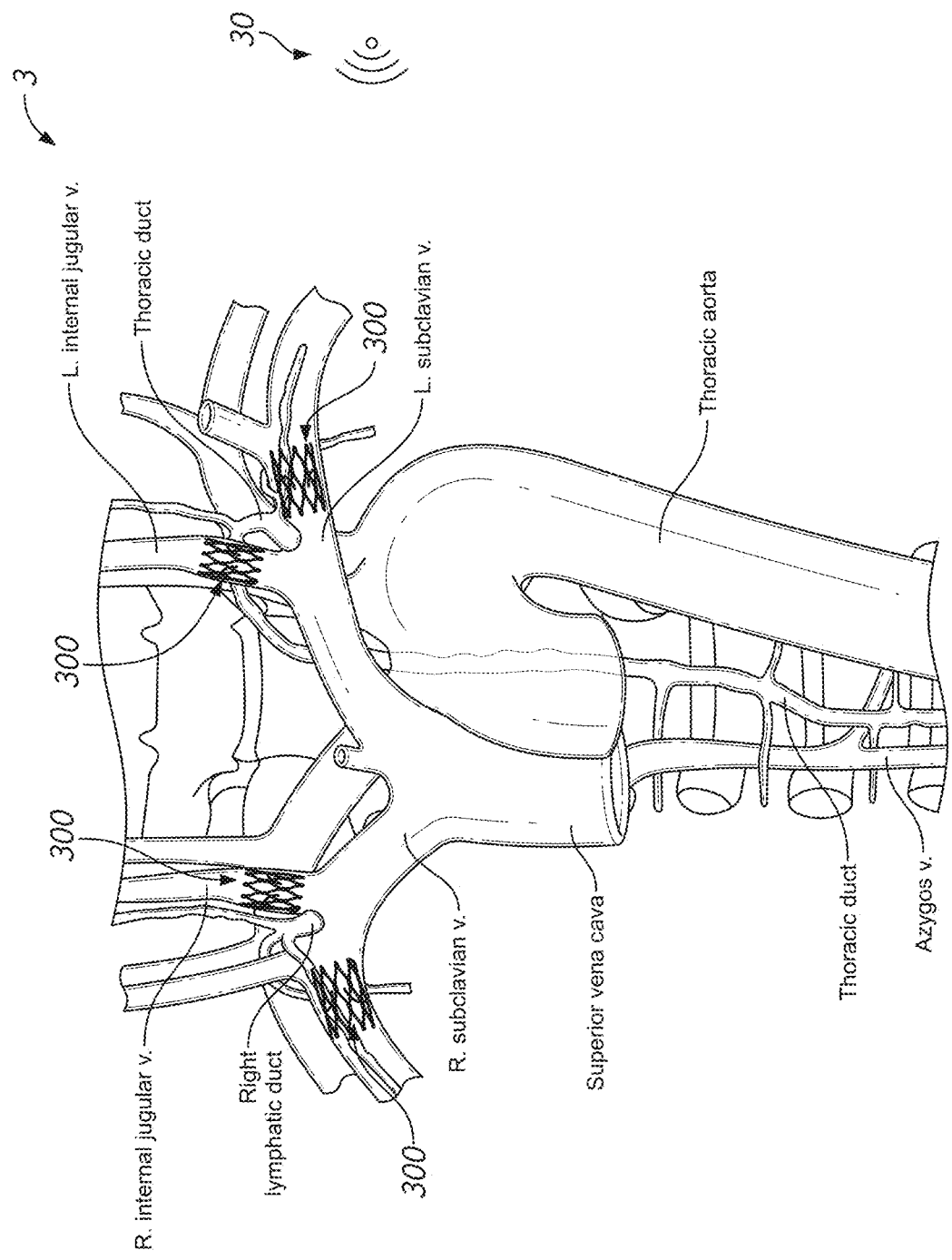

FIG. 22B illustrates additional potential locations for implantation and placement of a heat actuated, chronic, implantable flow restriction system 3. Shown are multiple implants 300 implanted within the patient as well as corresponding energy source 30. Specifically, FIG. 22B shows an implant 300 implanted within the patient's right subclavian vein upstream of where the right lymphatic duct connects to the right subclavian vein as well as an implant 300 implanted within the patient's right internal jugular vein upstream of where the right internal jugular vein connects with the right subclavian vein. Implants 300 in such locations can controllably and selectively occlude, restrict and/or divert flow within the veins they are implanted within to decrease pressure at the right lymphatic duct, increase lymphatic drainage, and/or reduce interstitial pressure (which can each improve cardiac and renal function), as well as to reduce cardiac preload and/or increase cardiac output. Also shown is an implant 300 implanted within the patient's left internal jugular vein upstream of where it connects to the left subclavian vein as well as an implant 300 implanted within the patient's left subclavian vein upstream of where the thoracic duct connects and empties into the left subclavian vein. Implants 300 in such locations can controllably and selectively occlude, restrict and/or divert flow within the veins they are implanted within to decrease pressure at the thoracic duct, increase lymphatic drainage, and/or reduce interstitial pressure (which can each improve cardiac and renal function), as well as to reduce cardiac preload and/or increase cardiac output. An energy source 30 for actuation of the implants 300 shown in FIG. 22B can be located external to the patient, such as proximal to the patient's back, chest, or neck, and/or in an artery or interstitial space adjacent the implant 300. While multiple implants 300 are shown, only one implant 300 can be implanted, or multiple implants 300 can be implanted in the locations as shown and/or in others, each having a corresponding energy source 30. In some implementations with multiple implants 300 implanted, an energy source 30 can be configured to actuate more than one implant 300.

The energy source 30 for actuating a heat actuated implant 300 can include ultrasound, microwaves, an electromagnet, and/or any form of induction heating. For example, a heat actuated implant 300 can generally include an inductive coil, such as a copper coil, that can generate a current via induction. Such a coil can be connected to a shape changing material, such as a nitinol wire, that can undergo a temperature change (e.g., heat up) due to the current from the connected coil and a corresponding change in shape and/or stiffness. The energy source 30 can be worn and/or place proximate to the patient when it is desired to actuate the implant 300. For example, the energy source 30 can be placed in a belt worn by the patient, placed in the patient's clothes, and/or placed or mounted in furniture used by the patient (e.g., a patient's bed, a patient's chair, etc.). The actuation of the implant 300 by the energy source 30 can be controlled and/or adjusted by changing the power of the energy source 30. Thus, the heat actuation of implant 300 can be tuned and/or modulated during use so that the implant 300 provides substantially no occlusion to flow, grades of partial occlusion to flow, and/or substantially full occlusion to flow. In some implementations, heat actuation can actuate the implant 300 such that the implant 300 provides substantially no occlusion to flow or substantially full occlusion to flow (e.g., binary on/off). In some cases, binary on/off control of an implant 300 can include providing substantially no occlusion to flow (binary off) and partial occlusion to flow (binary on), or vice versa. In other words, even when fully actuated and "closed", an implant 300 can be configured to still allow at least partial flow therethrough.

FIG. 23A-26B illustrate implementations of a heat actuated implant 300a, with FIG. 23A showing a side cross-sectional view of the implant 300a in a non-occluding (e.g., open) state within a vessel, and FIG. 23B showing a side cross-sectional view of the implant 300a in an occluding (e.g., closed) state. The implant 300a can include an expandable body 310a having a proximal end 311a, a distal end 312a, and a lumen 313a extending from the proximal end 311a to the distal end 312a. As described above, the expandable body 310a can be configured to collapse for delivery into the patient and expand into engagement with an inner wall of a vessel of the patient once implanted, with the expanded configuration shown. Once implanted, blood flowing through the vessel in which the implant 300a is implanted can flow through the lumen 313a. The implant 300a can also have a flow restrictor 350a connected to the expandable body 310a. The flow restrictor 350a can include a material 380a, such as a graft material used in artificial valves, for occluding flow through the lumen 313a with a wire 370a embedded within the material 380a. The wire 370a can comprise a shape changing material as described above, such as nitinol, that when heated can change shape. While not shown, the expandable body 310a can include an inductive coil, such as a copper coil, or be connected to an inductive coil. In some implementations, the expandable body 310a itself is an induction coil. Also not shown, the expandable body 310a can have material such as ePTFE, PTFE, PET cloth, polyurethane, and/or the like placed internal and/or external to the expandable body 310a, coated with an anti-thrombotic or other functional coating or uncoated, as described above.

In use, the energy source 30 can actuate the implant 300a by interacting with an inductive coil of the implant 300a. Depending upon the desired non-actuated (e.g., resting) state of the implant 300a, the implant 300a can be oriented with its distal end 312a receiving blood flow of the vessel in which the implant 300a is implanted and its proximal end 311a expelling the blood flow, or it can implanted in a reverse orientation. For example, if it is desired to have the implant 300a not occlude flow in its non-actuated state, the implant can be oriented with its proximal end 311a receiving flow and its distal end 312a expelling flow. In such orientation, when actuated by the energy source 30, the induction coil of the implant 300a can generate a current that travels through the connected wire 370a and causes the wire 370a to undergo a shape and/or stiffness change, which can cause the material 380a to move and close together so that the lumen 313a is occluded (as shown in FIG. 23B). As another example, if it is desired to have the implant 300a occlude flow in its non-actuated state, the implant can be oriented with its distal end 312a receiving flow and its proximal end 311a expelling flow. In such orientation, blood flow can cause the flow restrictor 350a to occlude the lumen 313a until the energy source 30 actuates the flow restrictor 350a, upon which the flow restrictor 150a can open to not occlude flow.

In some implementations, the level of occlusion provided by the heat actuated implant 300a can be based on a given power level of the energy source 30, can be modulated by the design of the implant 300a, such as by the thickness and/or shape of the wire 370a connected to the material 380a, and/or the by the shape and/or characteristics of the material 380a. Shown in FIGS. 24A-26B are various implementations of the material 380a with connected/embedded wire 370a. FIGS. 24A-24B show a tricuspid-like flow restrictor 350a comprising three sections of material 380a that can come together as shown to occlude the lumen 313a. FIGS. 25A-25B show a bicuspid-like flow restrictor 350a comprising two sections of material 380a that can come together as shown to occlude the lumen 313a. FIGS. 26A-26B show a unicuspid-like flow restrictor 350a comprising one section of material 380a that can occlude the lumen 313a as shown.

Figure 27A:
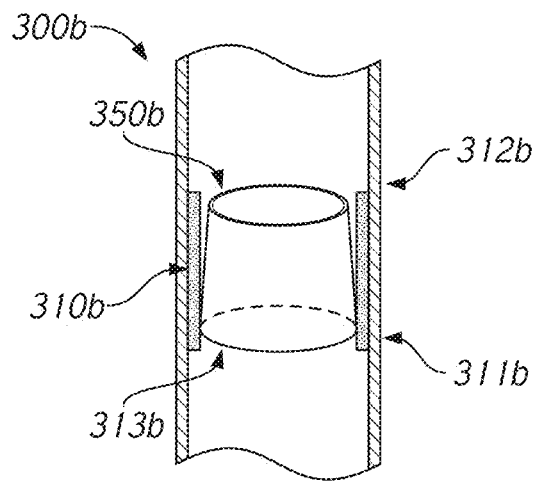
FIGS. 27A-27D illustrate various views of another implementation of a heat-actuated, chronic, implantable flow restriction system in accordance with some aspects of this disclosure.
Figure 27C:
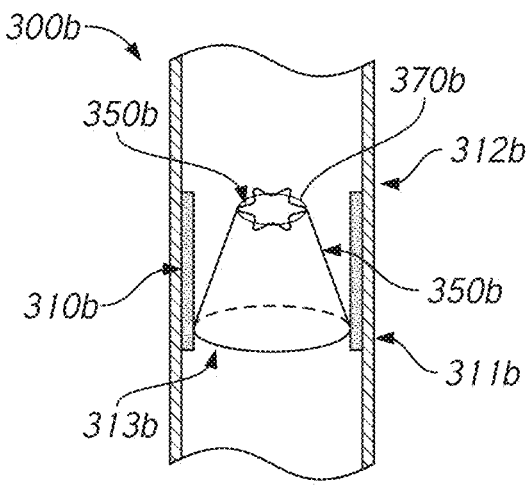
Figure 27B:
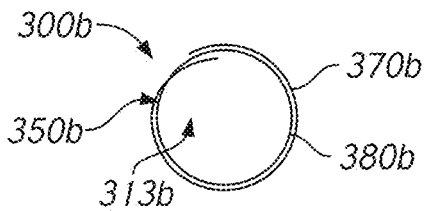
Figure 27D:
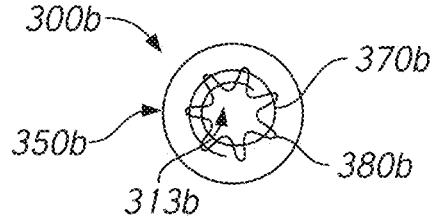

FIGS. 27A-27D show another implementation of a heat actuated implant 300b. FIG. 27A shows a side view and FIG. 27B shows a corresponding end view of the implant 300b in a non-actuated (e.g., open) state, while FIG. 27C shows a side view and 27D shows a corresponding end view of the implant 300b in an actuated (e.g., closed) state. The implant 300b can be the same or similar to and/or incorporate any of the features described with respect to the implant 300a. For instance, the implant 300b can have an induction coil, an expandable body 310b, and a flow restrictor 350b the same or similar to the induction coil, expandable body 310a and the flow restrictor 350a of implant 300a. The flow restrictor 350b, however, can have a different configuration. As shown, the flow restrictor 350b of implant 300b can have a funnel-like shape with material 380b forming the funnel and wire 370b slidingly embedded within an end of the funnel-like shape formed by the material 380b. Upon actuation, the wire 370b can coil upon itself or otherwise change shape to effectively close the end of the funnel-like flow restrictor 350b similar to a purse-string suture, thus occluding flow of the lumen 313b.

Figure 28A:
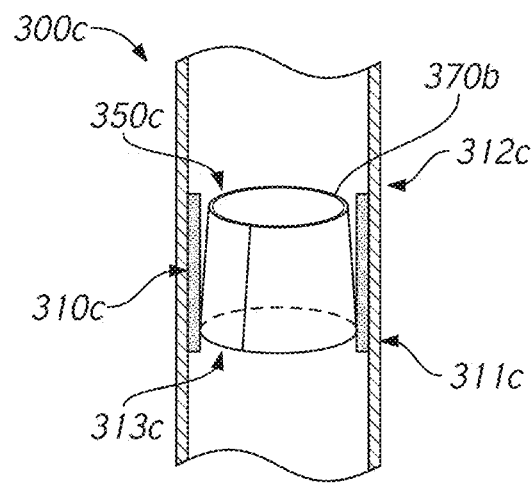
FIGS. 28A-28D illustrate various views of another implementation of a heat-actuated, chronic, implantable flow restriction system in accordance with some aspects of this disclosure.
Figure 28C:
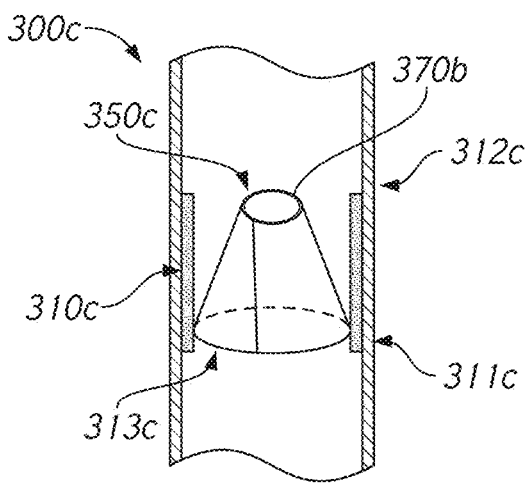
Figure 28B:
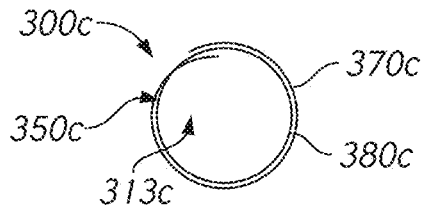
Figure 28D:
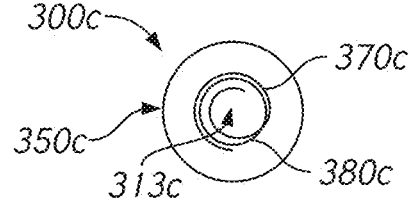

FIGS. 28A-28D show another implementation of a heat actuated implant 300c. FIG. 28A shows a side view and 28B shows a corresponding end view of the implant 300c in a non-actuated (e.g., open) state, while FIG. 28C shows a side view and 28D shows a corresponding end view of the implant 300c in an actuated (e.g., closed) state. The implant 300c can be the same or similar to and/or incorporate any of the features described with respect to the implants 300a and 300b. For instance, the implant 300c can have an induction coil, an expandable body 310c, and a flow restrictor 350c the same or similar to the induction coil, expandable body 310a/310b and the flow restrictor 350a/350b of implants 300a and 300b. The flow restrictor 350c, however, can have a different configuration. As shown, the flow restrictor 350c of implant 300c can have a funnel-like shape with material 380c forming the funnel and wire 370c slidingly embedded within an end of the funnel-like shape formed by the material 380c. Upon actuation, the wire 380c can coil upon itself or otherwise change shape to effectively close the end of the funnel-like flow restrictor 350c by causing a longitudinal end of the material to slide along itself, thus occluding flow of the lumen 313c.

Figure 29A:
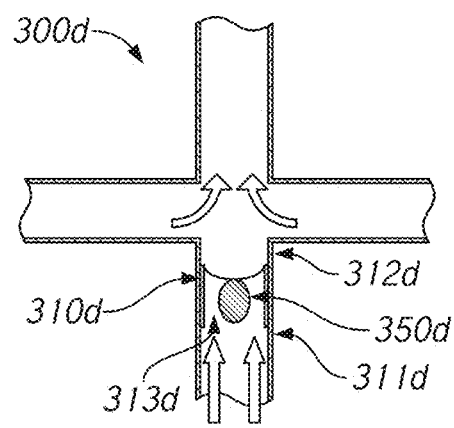
FIGS. 29A-29D illustrate various views of another implementation of a heat-actuated, chronic, implantable flow restriction system in accordance with some aspects of this disclosure.
Figure 29C:
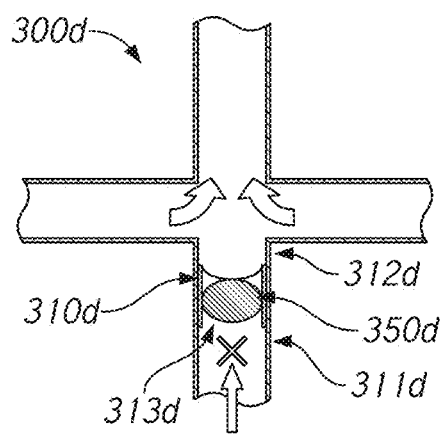
Figure 29B:
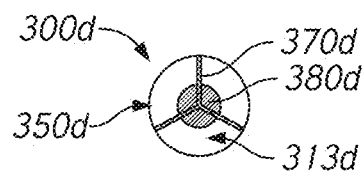
Figure 29D:
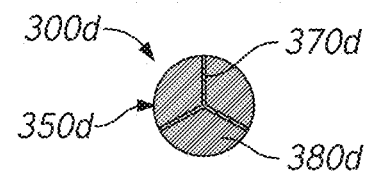

FIGS. 29A-29D show another implementation of a heat actuated implant 300d. FIG. 29A shows a side view and 29B shows a corresponding end view of the implant 300d in a non-actuated (e.g., open) state, while FIG. 29C shows a side view and 29D shows a corresponding end view of the implant 300d in an actuated (e.g., closed) state. The implant 300d can the same or similar to and/or incorporate any of the features described with respect to the implant 300a. For instance, the implant 300d can have an induction coil, an expandable body 310d, and a flow restrictor 350d the same or similar to the induction coil, expandable body 310a and the flow restrictor 350a of implant 300a. The flow restrictor 350d, however, can have a different configuration. As shown, the flow restrictor 350d of implant 300d can comprise a balloon 380d connected to and supported within the lumen 313d of the implant 300d by a wire 370d. As shown, the wire 370d can connect to the distal end 312d of the expandable body 310d of the implant 300d. Upon actuation, the wire 370d can transfer heat to the balloon 380d (e.g., the wire 370d can extend within the balloon 380d), causing the balloon 380d to expand and thus occlude flow of the lumen 313d.

Figure 30A:
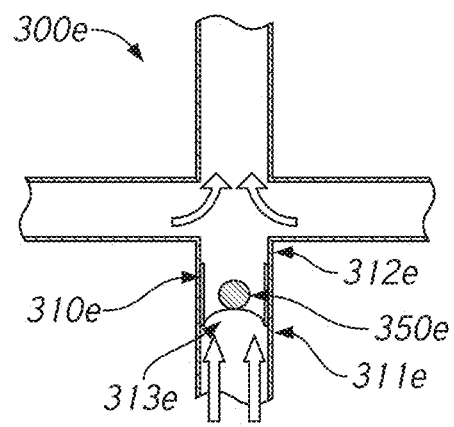
FIGS. 30A-30B illustrate various views of another implementation of a heat-actuated, chronic, implantable flow restriction system in accordance with some aspects of this disclosure.
Figure 30B:
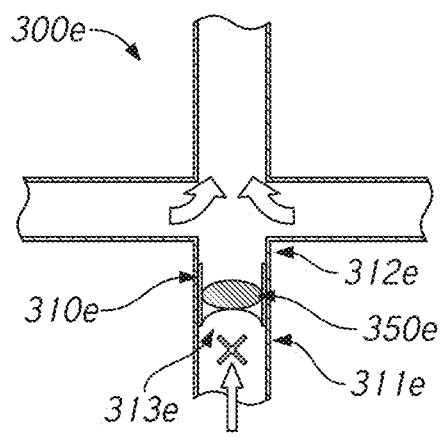

FIGS. 30A-30B show another implementation of a heat actuated implant 300e. FIG. 30A shows a side view of the implant 300e in a non-actuated (e.g., open) state, while FIG. 30B shows a side view of the implant 300e in an actuated (e.g., closed) state. The implant 300e can be the same or similar to and/or incorporate any of the features described with respect to the implant 300d. The wire 370e of the flow restrictor 350e, however, can connect to the proximal end 311d of the expandable body 310e of the implant 300e.

Figure 31A:
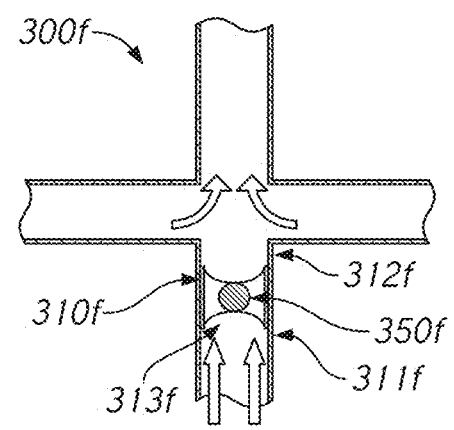
FIGS. 31A-31B illustrate various views of another implementation of a heat-actuated, chronic, implantable flow restriction system in accordance with some aspects of this disclosure.
Figure 31B:
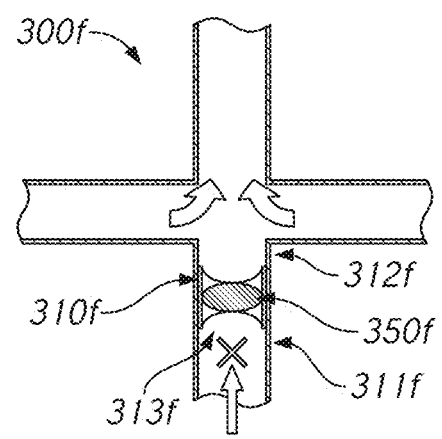

FIGS. 31A-31B show another implementation of a heat actuated implant 300f. FIG. 31A shows a side view of the implant 300f in a non-actuated (e.g., open) state, while FIG. 31B shows a side view of the implant 300f in an actuated (e.g., closed) state. The implant 300f can be the same or similar to and/or incorporate any of the features described with respect to the implants 300d and 300e. The flow restrictor 350f, however, can include multiple wires 370f that connect to both the proximal end 311f and the distal end 312f of the expandable body 310f of the implant 300f.

Figure 32A:
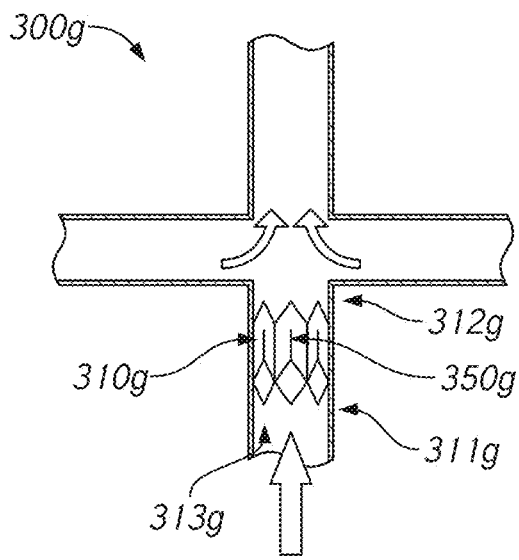
FIGS. 32A-32D illustrate various views of another implementation of a heat-actuated, chronic, implantable flow restriction system in accordance with some aspects of this disclosure.
Figure 32C:
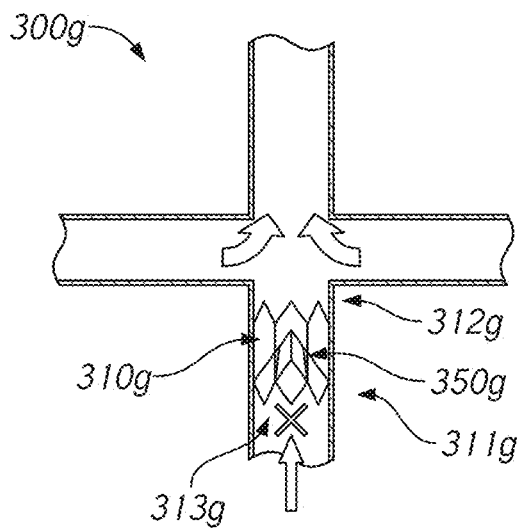
Figure 32B:
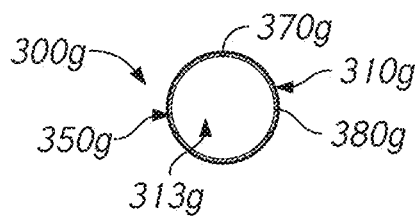
Figure 32D:
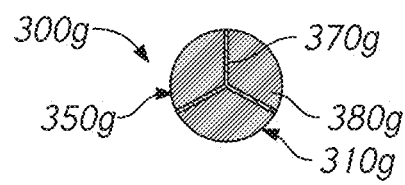

FIGS. 32A-32D show another implementation of a heat actuated implant 300g. FIG. 32A shows a side view and 32B shows a corresponding end view of the implant 300g in a non-actuated (e.g., open) state, while FIG. 32C shows a side view and 32D shows a corresponding end view of the implant 300g in an actuated (e.g., closed) state. The implant 300g can be the same or similar to and/or incorporate any of the features described with respect to the implant 300a. For instance, the implant 300g can have an induction coil, an expandable body 310g, and a flow restrictor 350g the same or similar to the induction coil, expandable body 310a and the flow restrictor 350a of implant 300a. The flow restrictor 350g, however, can have a different configuration. As shown, the flow restrictor 350g of implant 300g can comprise wires 370g with material 380g spanning between the wires. Upon actuation, the wires 370g can change shape, causing their free ends to come together and effectively occlude flow of the lumen 313g via the material 380g spanning the wires 370g.

Figure 33A:
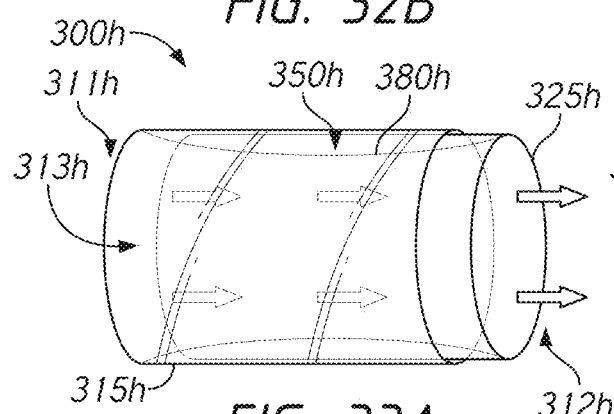
FIGS. 33A-33D illustrate various views of another implementation of a heat-actuated, chronic, implantable flow restriction system in accordance with some aspects of this disclosure.
Figure 33C:
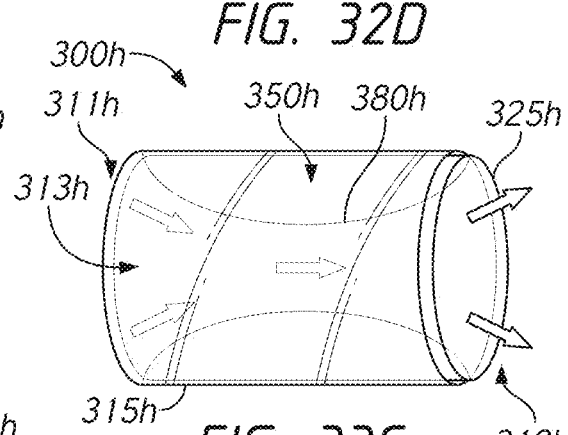
Figure 33B:
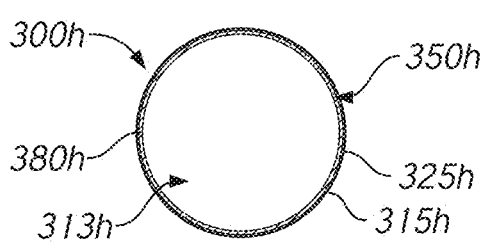
Figure 33D:
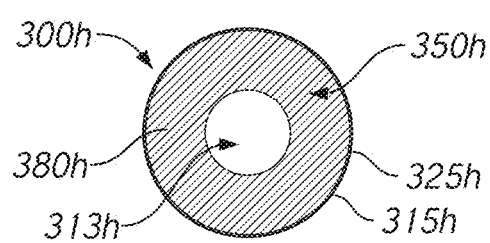

FIGS. 33A-33D show another implementation of a heat actuated implant 300h. FIG. 33A shows a side view and FIG. 33B shows a corresponding end view of the implant 300h in a non-actuated (e.g., open) state, while FIG. 33C shows a side view and FIG. 33D shows a corresponding end view of the implant 300h in an actuated (e.g., closed) state. The implant 300h can be the same or similar to and/or incorporate any of the features described with respect to the implant 300a. For instance, the implant 300h can have an induction coil, an expandable body 310h, and a flow restrictor 350h the same or similar to the induction coil, expandable body 310a and the flow restrictor 350a of implant 300a. The expandable body 310h and flow restrictor 350h, however, can have a different configuration. As shown, the expandable body 310*h* can comprise an outer body 315*h* and an inner body 325*h*. The inner body 325*h* can be configured to slidably move within the outer body 315*h*. Furthermore, an expandable membrane 380*h* (which can alternatively be a balloon) can connect one end of the outer body 315*h* to an opposite end of the inner body 325*h* and create a generally closed/sealed space underneath the membrane 380*h*. In the non-actuated state shown in FIGS. 33A-33B, the implant 300*h* can be configured such that the inner body 325*h* can be biased to extend out of the outer body 315*h*, collapsing the membrane 380*h* against an inner wall of the inner body 325*h*. Upon actuation, the closed/sealed space underneath the membrane 380*h* can be heated, causing the membrane 380*h* to expand and pull the inner body 325*h* inwards into the outer body 315*h*. In some implementations, the inner body 325*h* can be configured to move within the outer body 315*h* in a screw-like fashion. Additionally, in some implementations, the implant 300*h* can be actuated mechanically, such as by a pull wire, instead of via heat.

Figure 34:
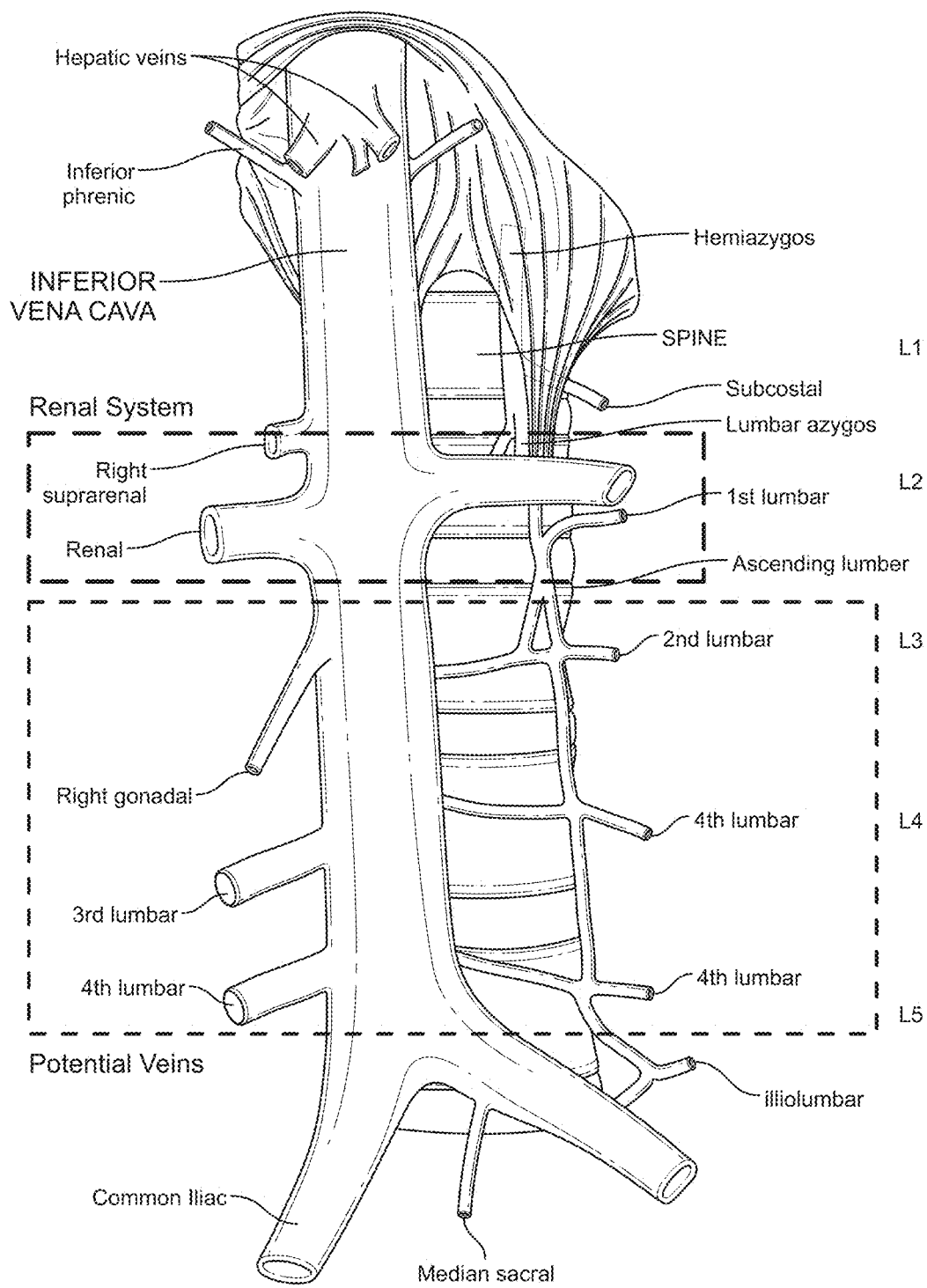
FIG. 34 illustrates a patient's anatomy including an inferior vena cava connected to the patient's renal system via renal veins as well as to other veins of the patient along with their location relative to the patient's spine.

FIG. 34 illustrates a patient's anatomy including the IVC and its approximation to the patient's spine. Further shown are the various veins that connect to the IVC, such as the renal veins and various lumbar veins. The extravascular space in this region is not open, it is sandwiched between membranes and muscles. Thus, there is limited-to-no free space. Furthermore, the IVC is more compliant relative to other surrounding tissues and/or structures.

Figure 35A:
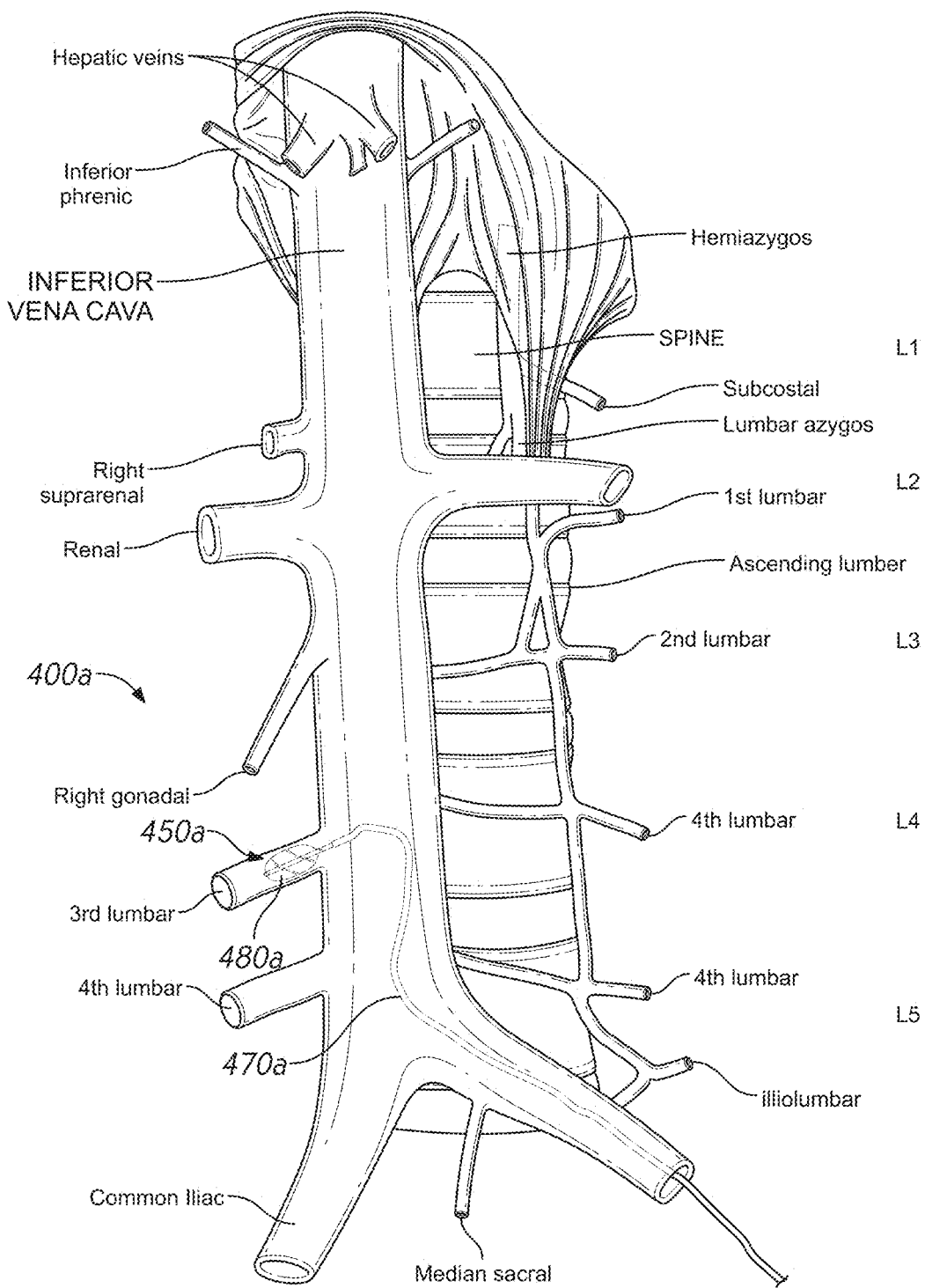
FIGS. 35A-35B illustrate a method of occluding an inferior vena cava of a patient in accordance with some aspects of this disclosure.
Figure 35B:
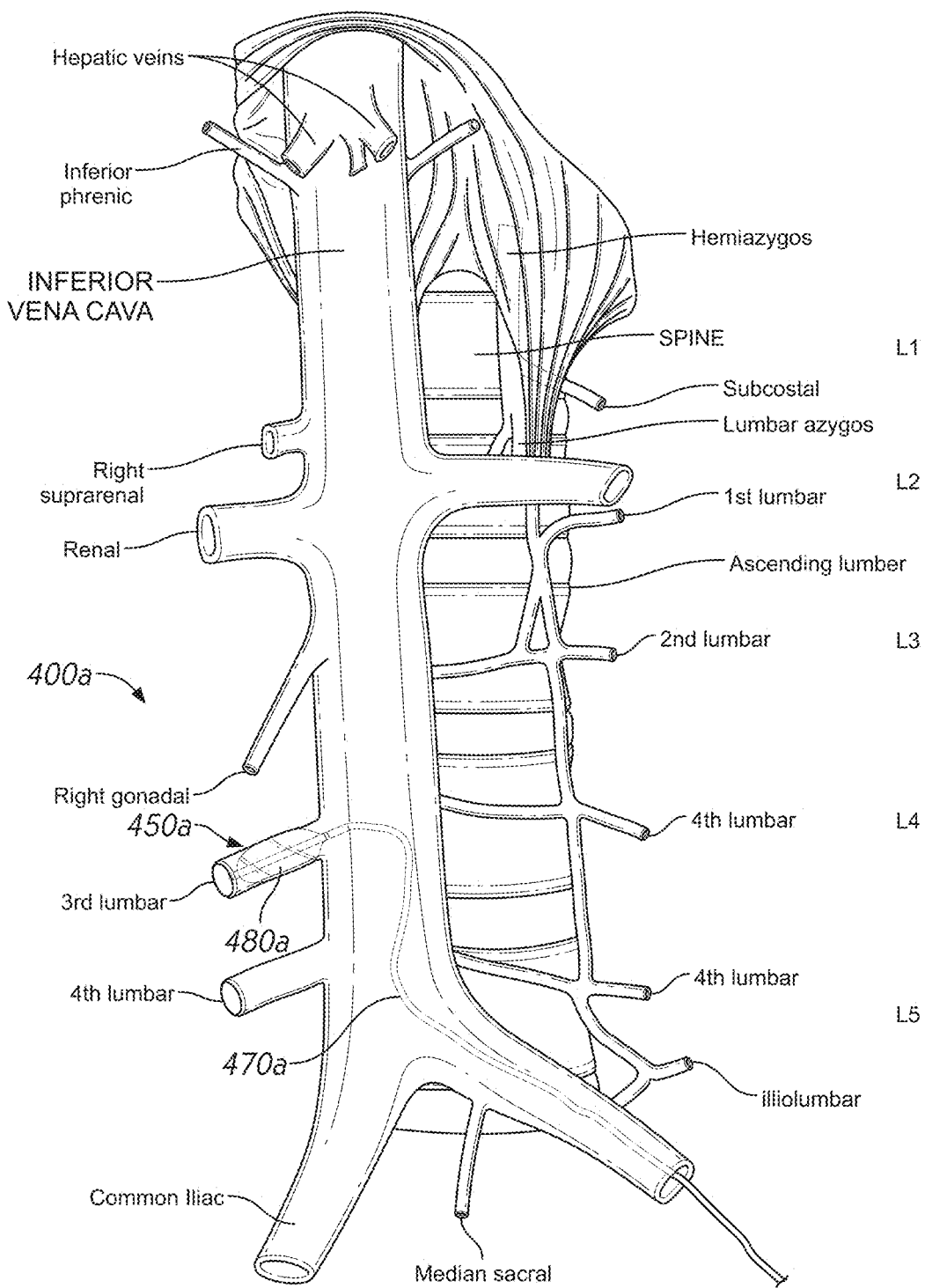

FIGS. 35A-36A illustrate a method of occluding the IVC of a patient using a fluidically actuated implant 400*a*. The implant 400*a* can be the same or similar and/or incorporate any of the features described with respect to the fluidically actuated implants described herein, with the exception that the implant 400*a* may not include an expandable body. The implant 400*a* can comprise a flow restrictor 450*a* including a balloon 480*a* fluidically connected to tubing 470*a* for expanding/collapsing the balloon (such as via a fluid reservoir as described herein or otherwise). The tubing 470*a* can also be used to advance and/or position the balloon 480*a* within the patient's body. As shown in FIG. 35A, the flow restrictor 450*a* can be advanced in the patient's vasculature to the IVC and into a lumbar vein (or other vein if desired) connected to the IVC. Shown in FIG. 35B, upon actuation of the flow restrictor 450*a*, the balloon 480*a* can expand and provide at least partial occlusion of the IVC.

Figure 36A:
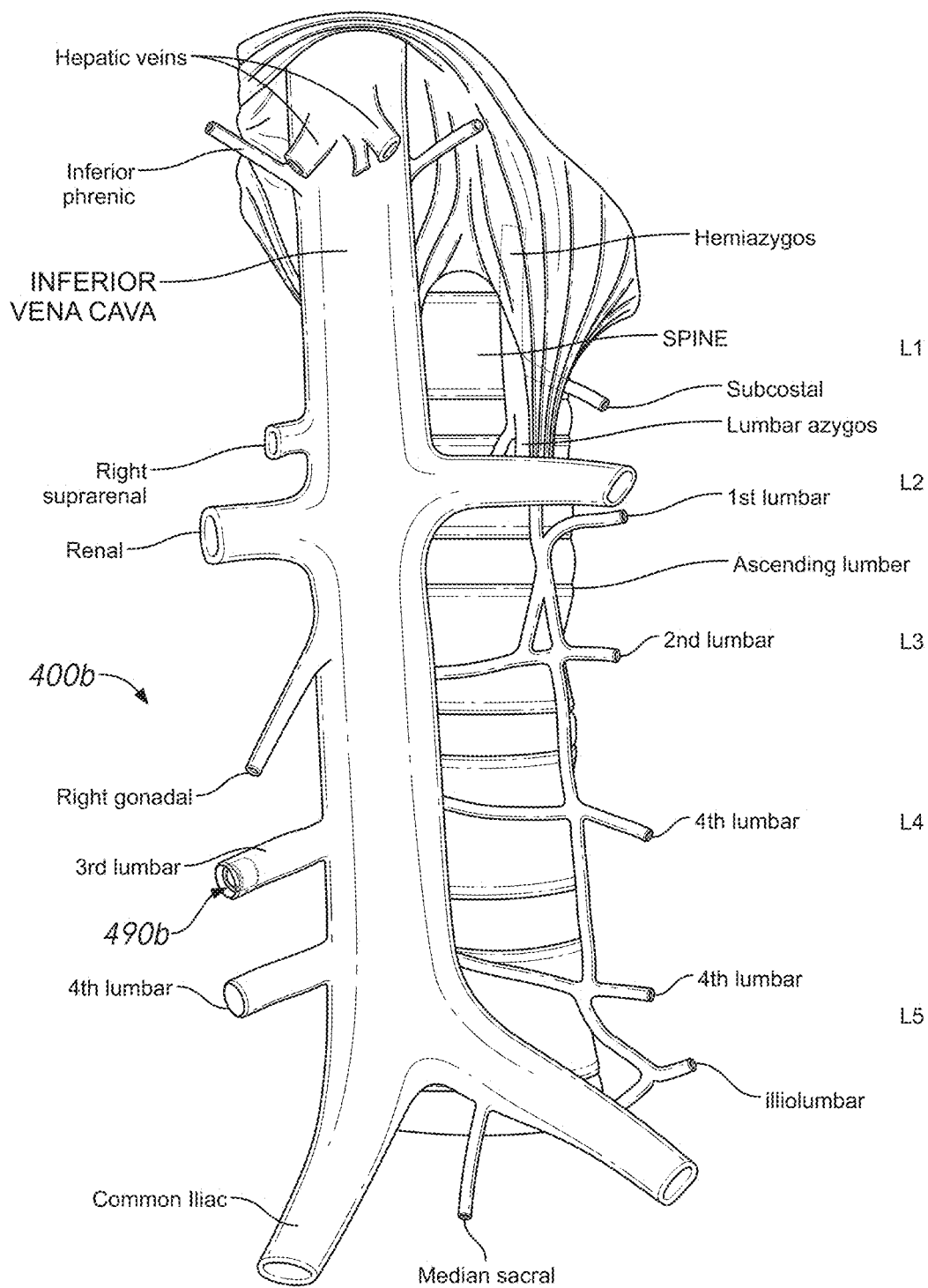
FIGS. 36A-36B illustrate another extravascular method of occluding an inferior vena cava of a patient in accordance with some aspects of this disclosure.
Figure 36B:
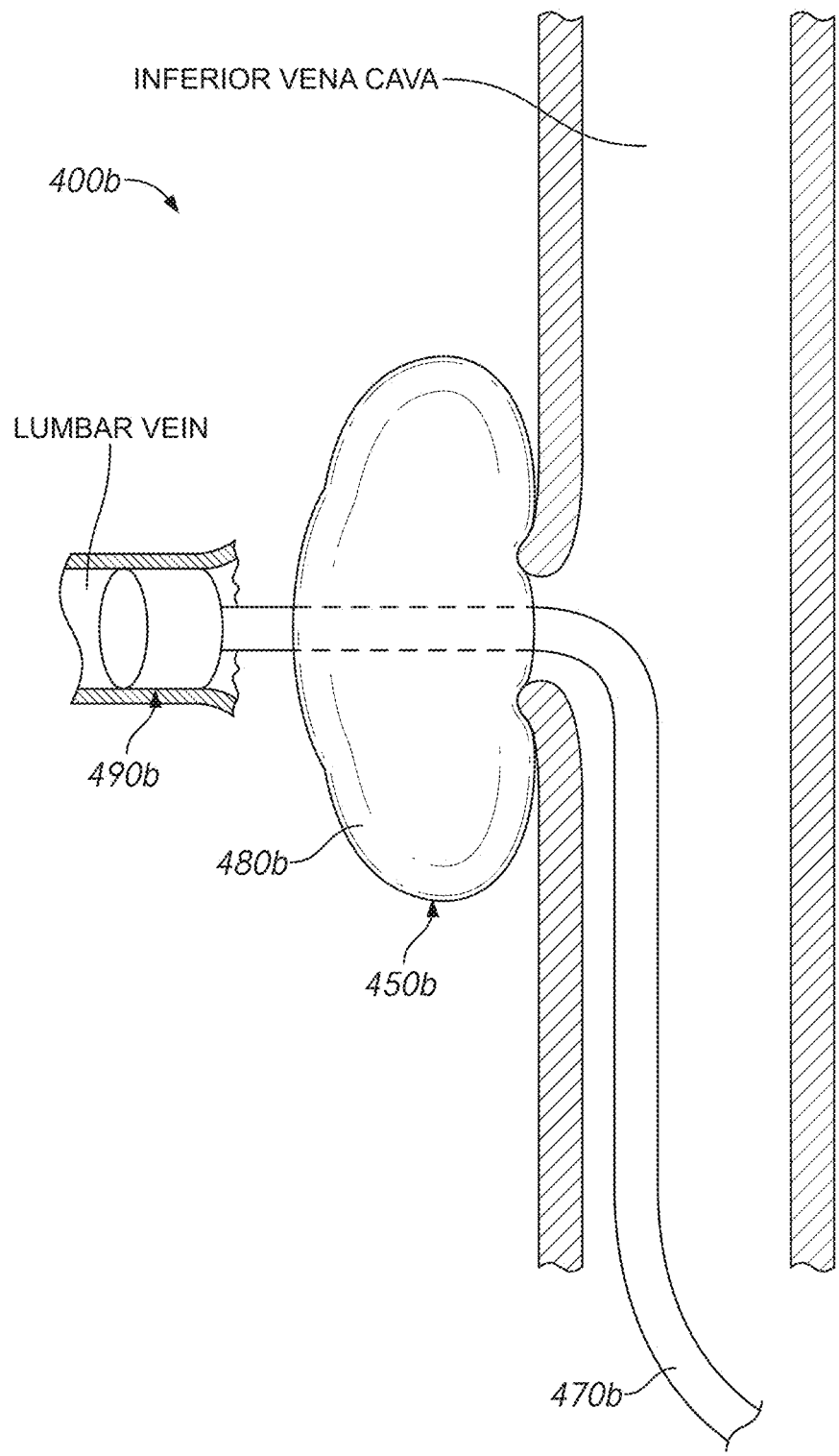

FIGS. 36A-36B illustrate an extravascular method of occluding the IVC of a patient using a fluidically actuated implant 400*b*. The implant 400*b* can be the same or similar and/or incorporate any of the features described with respect to the implant 400*a*. As shown in FIG. 36A, the implant 400*b* can comprise an occluder 490*b* placed in a lumbar vein (or other vein if desired) connected to the IVC. The occluder 490*b* can be configured to fully occlude blood flow of the lumbar vein. As shown in FIG. 36B, an implant 400*b* can further comprise a flow restrictor 450*b* comprising balloon 480*b* that can be advanced and positioned adjacent to the occluder 490*b* in the lumbar vein. In this position, the flow restrictor 450*b* can be actuated, causing the balloon 480*b* to expand and the lumbar vein to rupture as shown in FIG. 36B. Kept in this position, the balloon 480*b* of the flow restrictor can seal against the IVC in both its non-actuated and actuated state, preventing blood loss from the IVC. Upon actuation of the flow restrictor 450*b*, the balloon 480*b* can expand and provide at least partial occlusion of the IVC by compressing against an outer wall of the IVC and causing the IVC to buckle inward at that location. In some implementations and as shown in FIG. 36B, the occluder 490*b* can be connected to the implant 400*b* to aid in anchoring the implant 400*b* and maintaining it in the desired position.

Figure 37A:
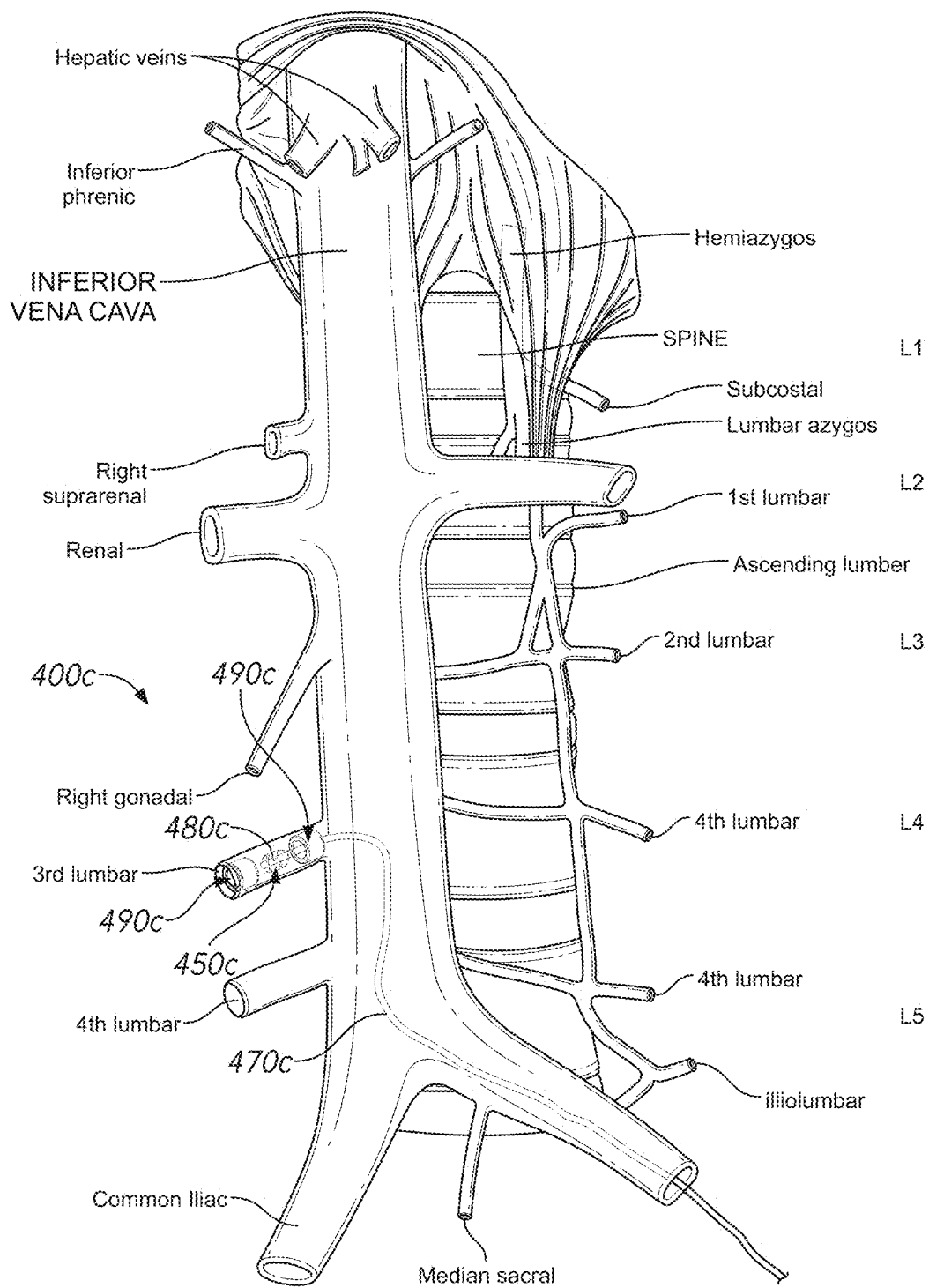
FIGS. 37A-37C illustrate another extravascular method of occluding an inferior vena cava of a patient in accordance with some aspects of this disclosure.
Figure 37B:
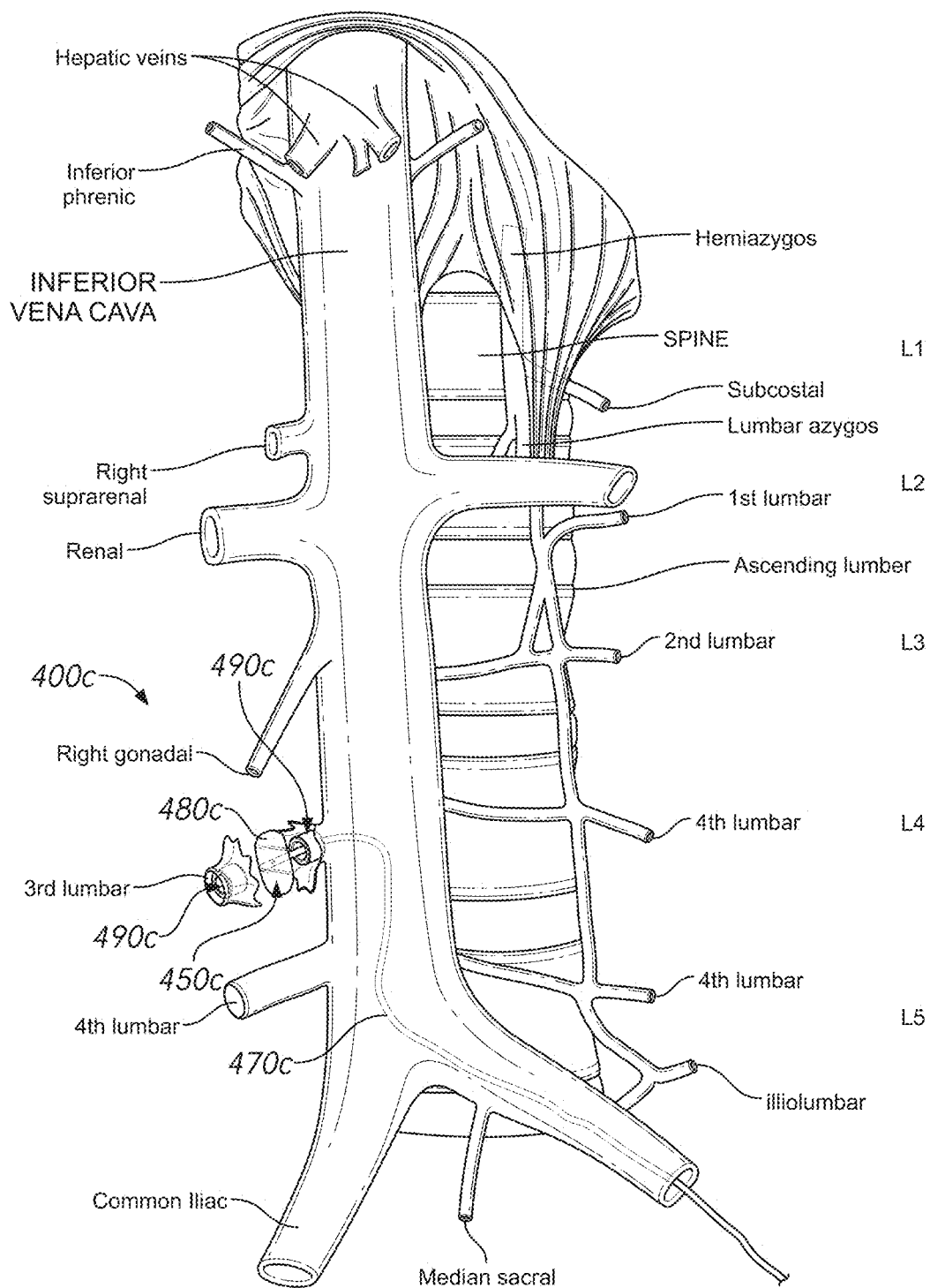
Figure 37C:
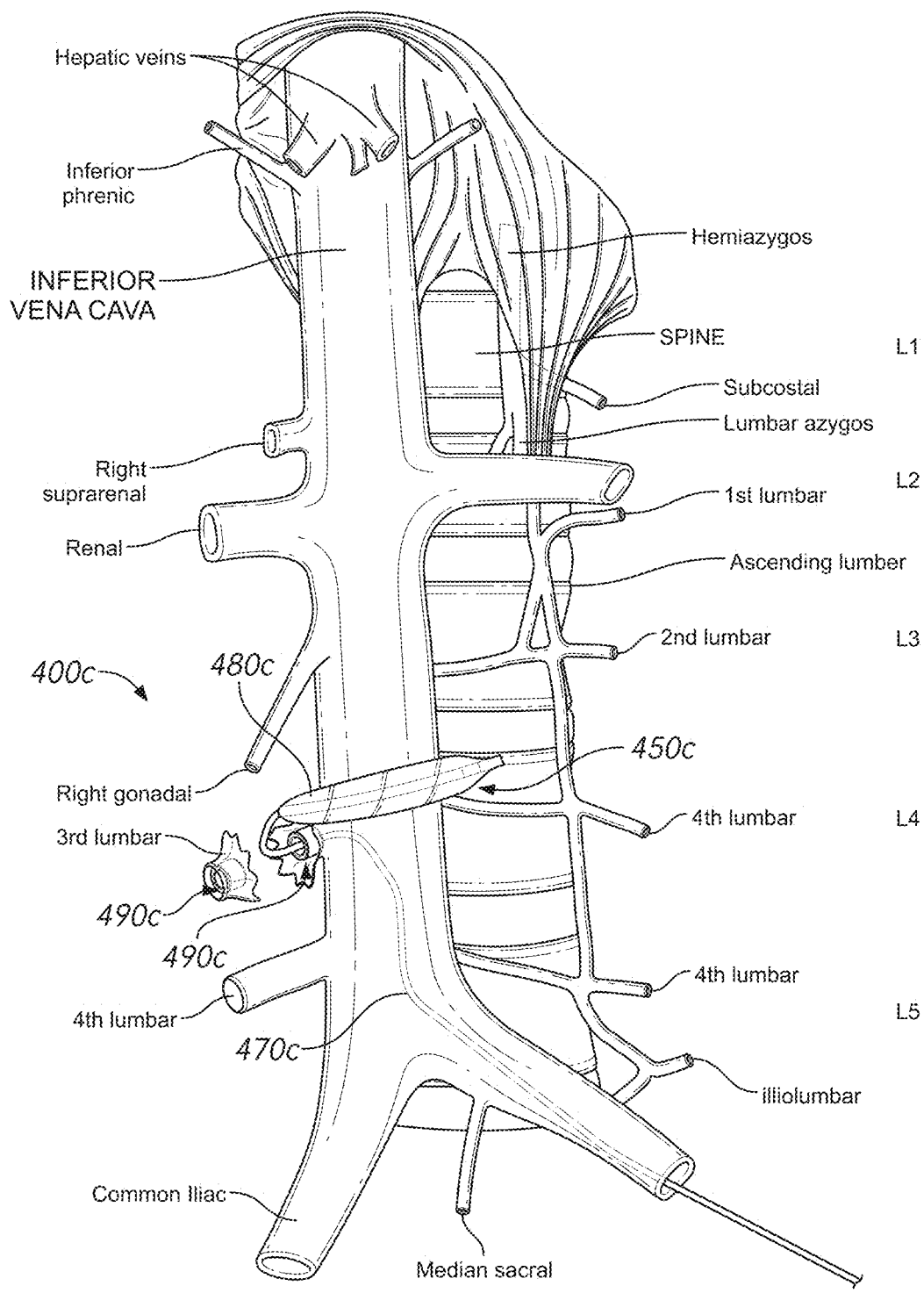

FIGS. 37A-37C illustrate another extravascular method of occluding the IVC of a patient using a fluidically actuated implant 400*c*. The implant 400*c* can be the same or similar and/or incorporate any of the features described with respect to the implants 400*a* and 400*b*. As shown in FIG. 37A, occluders 490*c* can be advanced and placed in a lumbar vein (or other vein if desired) connected to the IVC on both sides of the implant 400*b* which has also been advanced and placed in the lumbar vein. In this position, the flow restrictor 450*c* can be actuated, causing the balloon 480*c* to expand and the lumbar vein to rupture as shown in FIG. 37B. The implant 400*c* can then be advanced to a desired location external to the IVC as shown in FIG. 37C. Once the implant 400*c* is positioned and upon actuation of the flow restrictor 450*c*, the balloon 480*c* can expand and provide at least partial occlusion of the IVC by compressing against an outer wall of the IVC and causing the IVC to buckle inward at that location.

Figure 38:
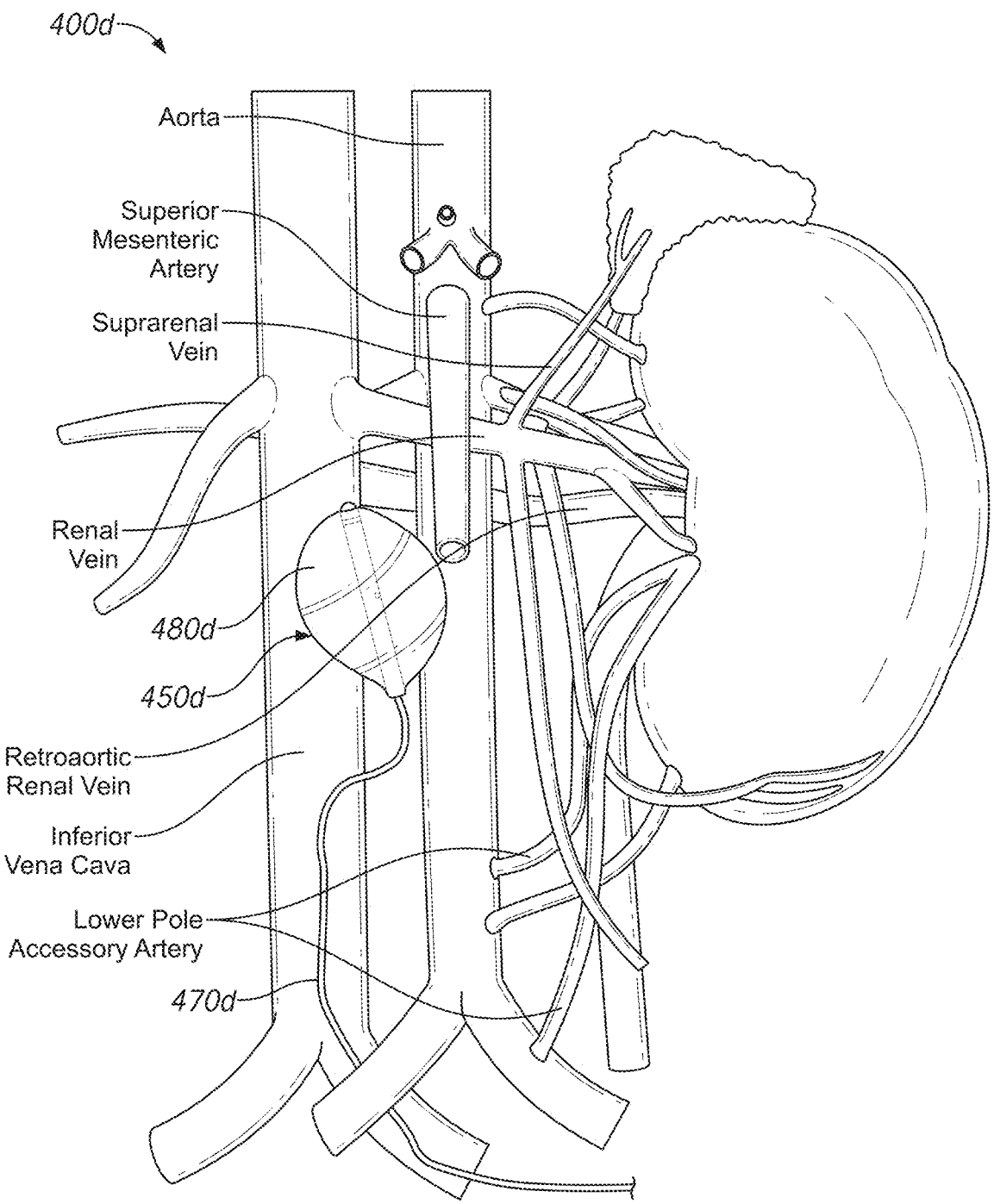
FIG. 38 illustrates another extravascular method of occluding an inferior vena cava of a patient in accordance with some aspects of this disclosure.

FIG. 38 illustrates another extravascular method of occluding the IVC of a patient using a fluidically actuated implant 400*d*. The implant 400*d* can be the same or similar and/or incorporate any of the features described with respect to the implants 400*a*, 400*b*, and 400*c*. As shown in FIG. 38, the implant 400*d* has been advanced through the IVC and externalized outside the IVC. The balloon 480*d* of the flow restrictor 450*d* can seal against the IVC in both its non-actuated and actuated state, preventing blood loss from the IVC. Upon actuation of the flow restrictor 450*d*, the balloon 480*d* can expand and provide at least partial occlusion of the IVC by compressing against an outer wall of the IVC and causing the IVC to buckle inward at that location. As mentioned above, the IVC is the most compliant structure in this space, so it will preferentially compress as opposed to the adjacent aorta.

Figures 39, 40:
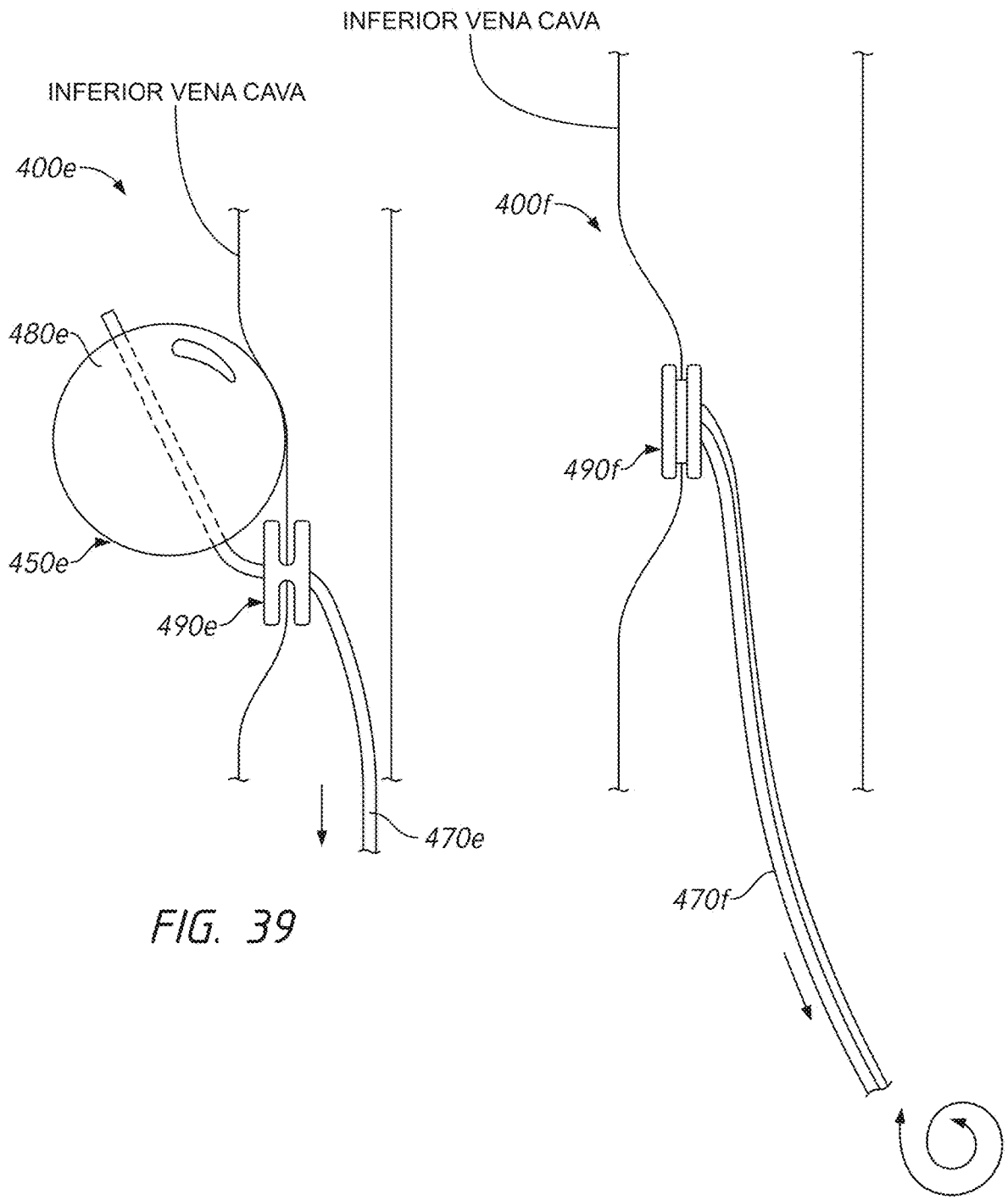
FIG. 39 illustrates another extravascular method of occluding an inferior vena cava of a patient in accordance with some aspects of this disclosure.
FIG. 40 illustrates another extravascular method of occluding an inferior vena cava of a patient in accordance with some aspects of this disclosure.

FIG. 39 illustrates another extravascular method of occluding the IVC of a patient using a fluidically actuated implant 400*e*. The method can be the same or similar to the extravascular method of occluding the IVC of a patient as described with respect to FIG. 38, with the addition of an occluder 490*e* being placed at the wall of the IVC to aid in sealing the penetration through the wall of the IVC. Upon actuation of the flow restrictor 450*e*, the balloon 480*e* can expand and provide at least partial occlusion of the IVC by compressing against an outer wall of the IVC and causing the IVC to buckle inward at that location.

FIG. 40 illustrates another extravascular method of occluding the IVC of a patient. The method can include placing an occluder/disk 490*f* attached to a wire 470*f* through the wall of the IVC. Upon pulling of the wire 470*f*, the occluder/disk 490*f* and thus the wall of the IVC can be pulled inward, providing at least partial occlusion of the IVC. While not shown, a variation of this method can include extending the wire 470*f* through the wall of the IVC at least twice such that a pull of the wire can cause compression of the IVC (e.g., similar to a purse-string suture).

Figure 41:
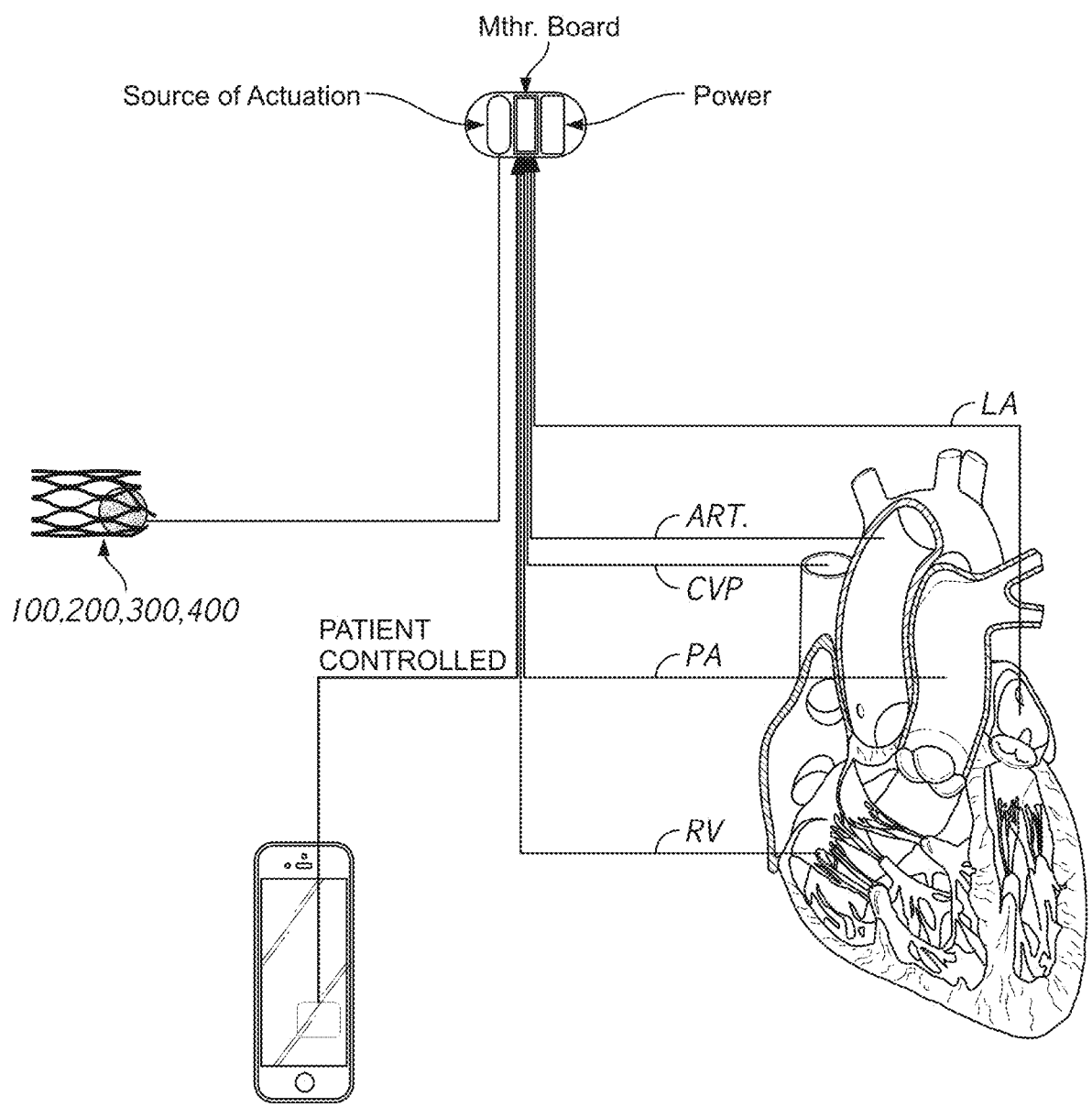
FIG. 41 illustrates a control system for a chronic, implantable flow restriction system in accordance with some aspects of this disclosure.

FIG. 41 illustrates a control unit (which can also be referred to as a "controller" herein) that can be used with any of the implants, such as implants 100, 200, 300, 400, and 500, described herein. The control unit can be patient-controlled and/or patient monitored, e.g., wirelessly through an app on a smart phone as shown. As shown, the control unit can be configured to be implantable within the patient and can including a source of implant actuation, a mother board comprising a processor, a memory, and in some implementations a communications module, and a source of power. The control unit can include circuitry configured to receive wireless or wired signals from pressure sensors (e.g., MEMS sensors) positioned in various locations within or around the heart or at other locations in the body, for example to measure pressure in the right ventricle, right atrial pressure, central venous pressure, aortic pressure, left atrial pressure, left ventricular pressure, aortic pressure, SVC pressure, IVC pressure, hepatic vein pressure, renal vein pressure, femoral vein pressure, and/or the pressure of any of the veins or portions thereof disclosed herein. Based on these readings, the control unit can appropriately actuate the implant to control the adjustable occlusion of the implant in order to control the amount of blood flowing through the implant. The control unit can provide for closed-loop, fully autonomous, and/or real-time adjustability and control of the implant. The control unit can implement a treatment protocol/algorithm prescribed by a physician and/or the control logic can be optimized to treat heart failure patients, for example by reducing cardiac preload, reducing central venous pressure and/or pressure of other veins disclosed herein, increasing cardiac output, reducing renal congestion (or promoting renal decongestion), enhancing renal circulation, and/or enhancing or controlling diuresis (e.g., to increase diuresis). In some implementations, the control unit can receive data from sensors connected to the implant as described herein for the control of actuation of the implant.

Figure 42:
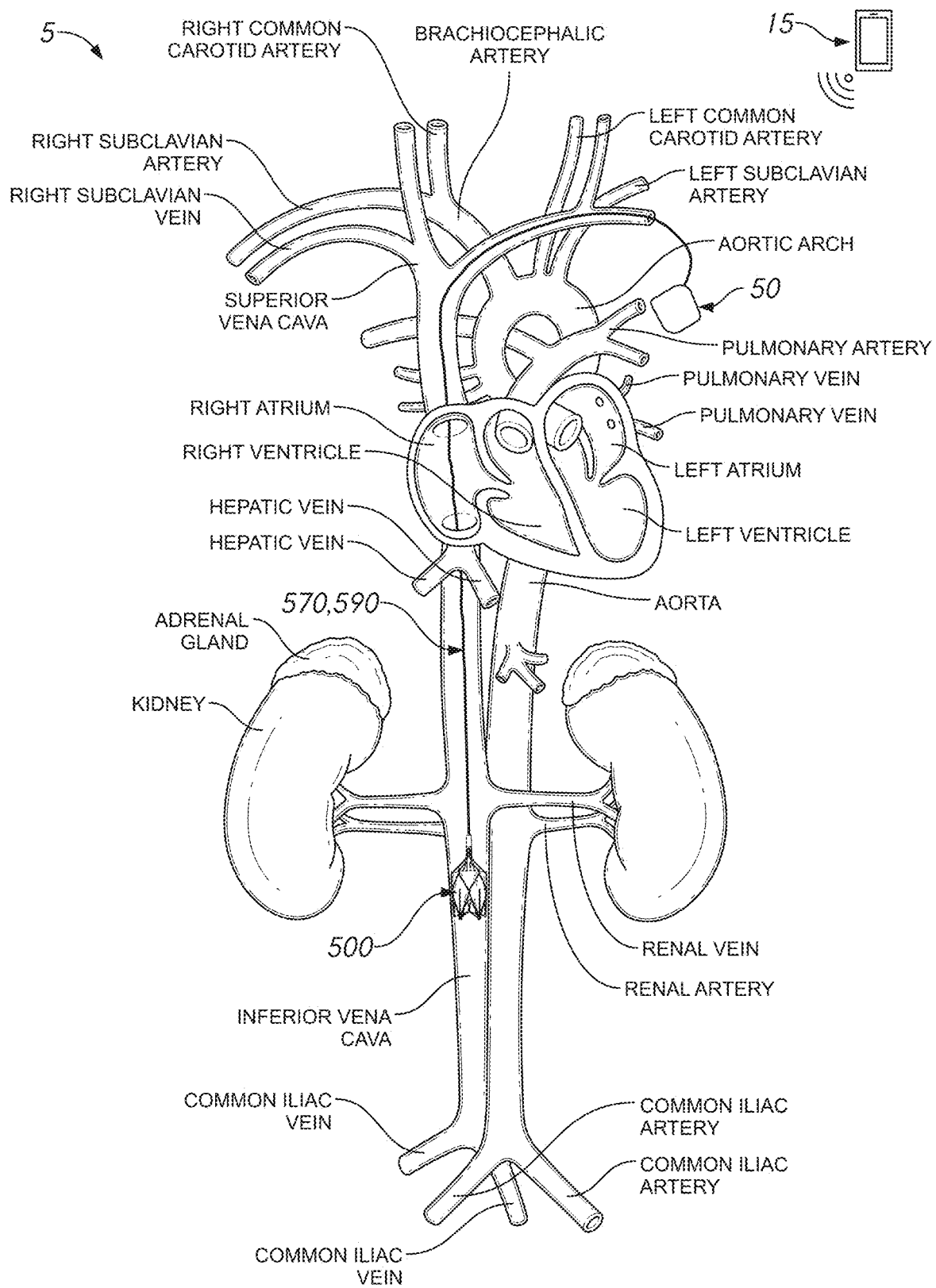
FIG. 42 illustrates a chronic, implantable flow restriction system that is implanted within the patient in accordance with some aspects of this disclosure.

FIG. 42 illustrates a potential location for implantation and placement of an implantable flow restriction system 5. The implantable flow restriction system 5 can be a mechanically-actuated, chronic implantable flow restriction system 5. While certain implementations of the implantable flow restriction system 5 may be described as a chronic system, components of the implantable flow restriction system could be used in an acute system. Moreover, certain implementations of the implant 500 of the implantable flow system 5 are described as being mechanically actuated. This may include electromechanically-actuated implants. Other actuation methods are also possible, for example a fluid or gas driven system.

An implantable flow restriction system 5 can include an implant 500 connected to a controller 50 (which can also be referred to herein as a "control unit"), for example via tubing 570 and shaft 590 (which can all be implanted), and an external device 15 for operating the system 5. In some implementations, the implantable flow restriction system 5 includes the implant 500, the controller 50, the tubing 570, and the shaft 590. Shown in FIG. 42 is one implant 500 implanted within the patient's IVC upstream of its connection to the renal veins (e.g., below the renal veins). An implant 500 placed in the IVC upstream of the renal veins can controllably and selectively occlude, restrict and/or divert flow within the patient's IVC and connected vasculature and/or organs, such as to reduce renal congestion (or promote renal decongestion), enhance renal circulation, and/or to control diuresis (e.g., to increase diuresis). For this, the implant 500 can have a flow restrictor portion 550 and/or a flow restrictor 560. Such flow restrictor portion 550 and/or flow restrictor 560 can be actuated by the controller 50 via shaft 590 and tubing 570 as described further herein.

The implant 500 can be implanted such that the flow restrictor portion 550 is upstream of the other portions of the implant 500 (e.g., the flow restrictor portion 550 is the first portion of the implant 500 to receive blood flow therethrough). In such position, the shaft 590 and tubing 570 can extend proximally from the implant 500 up the IVC, through the right atrium, into the superior vena cava (SVC), through a subclavian vein (left subclavian as shown), and out the subclavian vein to connect with the controller 50 that can be implanted in an infraclavicular subcutaneous pocket (e.g., similar to placement of a pacemaker). In some implementations, the implant 500 can be implanted in other positions, such as those shown and described with respect to implants 100, 200 and 300. Furthermore, in some implementations more than one implant 500 can be implanted within the patient, such as those shown and described with respect to implants 100, 200 and 300. In the case of multiple implants 500 being implanted within the patient, each can connect to a single controller 50 via separate tubing 570 and shaft 590, or each can connect to their own controller 50 via separate tubing 570 and shaft 590.

FIGS. 43A-43D illustrate various views of an implementation of an implant 500a, which can be the implant 500 in the implantable flow restriction system 5. FIGS. 43A and 43C show side views, FIG. 43B shows an end view of the implant 500a in a non-occluding (e.g., open, unactuated) state, and FIG. 43D shows a side view of the implant 500a in a fully occluding (e.g., closed, actuated) state. FIGS. 43A-43D also illustrate how the implant 500a can connect with the tubing 570a and the shaft 590a for operation thereof. The implant 500a can comprise an expandable body 510a having a proximal end 511a, a distal end 512a, and a lumen 513a for receiving blood flow therethrough. The implant 500a can connect to a distal end 572a of the tubing 570a and can include a filter portion 520a, a radial support portion 540a (which can also be referred to herein as a "sealing portion" or "sealing zone"), and a flow restrictor portion 550a.

As shown in FIGS. 43A-43D, the filter portion 520a can be positioned adjacent the proximal end 511a, the radial support portion 540a can connect to and be positioned distal of the filter portion 520a, and the flow restrictor portion 550a can connect to and be positioned distal of the radial support portion 540a. The filter portion 520a can be configured to capture thrombus that may pass through the lumen 513a of the implant 500a and can include a plurality of struts 527a that extend distally and radially outward from the connection between the tubing 570a and the implant 500a.

The radial support portion 540a can be configured to fluidically seal against the inner wall of the IVC and can include a ring 545a that extends along a circumference of the implant 500a in a chevron pattern. As shown, the ring 545a can include a plurality of ring struts 542a, wherein adjacent pairs of ring struts 542a join at a plurality of proximal apexes 543a and a plurality of distal apexes 544a. Further as shown, each of the plurality of proximal apexes 543a of the ring 545a of the radial support portion 540a can be connected to a strut 527a of the filter portion 520a.

The flow restrictor portion 550a can include a plurality of petals 560a configured to restrict/occlude flow through the lumen 513a of the implant 500a when actuated. As shown, each of the petals 560a can be formed by a pair of struts 562a that extend distally from adjacent pairs of distal apexes 544a of the ring 545a of the radial support portion 540a and that join at a distal apex 564a. Each of the plurality of petals 560a can also include a strut 566a that extends proximally from their respective distal apex 564a, which can aid in the ability of the petals to restrict flow when in use. Further as shown, the flow restrictor 550a can include a material 530a that spans each of the plurality of petals 560. The material 530a can comprise ePTFE, PTFE, PET cloth, polyurethane, and/or the like as described herein. Regions between the plurality of petals 560 can be free of the material 530a. In some implementations, the material 530a can span regions between the plurality of petals 560. The material 530a can also span the radial support portion 540a to aid in the ability of the implant 500a to fluidically seal against the inner wall of the IVC (or an inner wall of any other lumen/vessel in which it is placed) and restrict/block blood flow when in use. In some implementations and as shown, the implant 500a can include a plurality of anchors 525a configured to anchor the implant 500a within the IVC (or any other lumen/vessel in which it is placed). Such anchors 525a can extend in a generally proximal direction from each of the plurality of proximal apexes 543a of the ring 545a.

With continued reference to FIGS. 43A-43D, each of the petals 560a can connect to the shaft 590a by a connector. Various connectors are described herein, for example, a suture, wire, strut, or otherwise. For example, each of the distal apexes 564a of the petals 560a can connect to a suture or wire 595a at one end of the suture or wire 595a, and the other end of the suture or wire 595a can connect to a distal end 592a of the shaft 590a that extends generally centrally through the lumen 513a of the implant 500a. Further as shown, the distal end 592a of the shaft 590a can substantially longitudinally align with the distal apexes 564a of the petals 560a in the unactuated/open state of the implant 500a. With such relative position, the sutures or wires 595a can extend in a substantially radially outward direction from the distal end 592a of the shaft 590a to connect to the distal apexes 564a of the petals 560a. The shaft 590a can slidably move through a lumen of the tubing 570a and extend out the distal end 572a thereof as shown, and a collapsible and extendible coupling 580a can fluidically seal the lumen of the tubing 570a with the shaft 590a. A proximal end 571a of the tubing 570a (not shown) can connect with the controller 50a, and the shaft 590a can extend out such proximal end 571a and operably connect with an actuator of the controller 50a. To operate the flow restrictor portion 550a of the implant 500a and at least partially occlude/restrict flow therethrough, the actuator of the controller 50a can be actuated to cause the shaft 590a to move proximally relative to the tubing 570a and implant 500a, causing the distal apexes 564a of the plurality of petals 560a to move radially inward towards one another via the connection of the distal apexes 564a to the suture or wire 595a and to the distal end 592a of the shaft 590a. In other words, proximal movement of the shaft 590a can cause the petals 560a to come together and at least partially restrict flow through the lumen 513a of the implant 500a, such as shown in FIG. 43D. For example, the petals 560a can fold radially inward (e.g., hinge relative to the expandable body) with the distal apexes 564a of the petals 560a forming the distal-most tip of implant 500a. In use, blood flows toward and is occluded by exterior surfaces of the petals 560a. In some implementations, the flow restrictor portion 550a (e.g. the petals 560a) can be configured to attach or secure to a wall of the vessel in which the implant 500a is implanted, and when actuated can pull in the wall of the vessel to at least partially restrict flow through the vessel and/or lumen 513a. For this, and as described herein, the flow restrictor portion 550a (e.g., the petals 560a) can include one or more anchors and/or be configured to ingrow at least partially into the wall of the vessel.

Tubing 570a can comprise a unitary or a composite structure. For example, tubing 570a can include a tubing portion, a braided portion, and/or a liner. The tubing 570a can comprise, for example, PEBAX. A liner, if included, can comprise PTFE, HDPE, or a silicone blend and can facilitate sliding motion of the shaft 590a within the tubing 570a (e.g., the liner can reduce friction within the tubing 570a and force required to slide the shaft 590a within the tubing 570a). Connections between components of the system 5, such as the tubing 570a, implant 500a, collapsible and extendible coupling 580a, and shaft 590a, can be made via reflow (e.g., with PEBAX), heat shrink, or the like.

With reference to the end view of the implant 500a shown in FIG. 43B, the implant 500a can be configured such that the sutures or wires 595a substantially align with the struts 527a of the filter portion 520a. Such substantial alignment can advantageously allow other interventional devices to pass through the implant 500a if needed. For example, such substantial alignment can allow for a 28 French interventional device to pass through the implant 500a.

While the implant 500a of FIGS. 43A-43D is shown as having 6 petals 560a, 6 sutures or wires 595a connecting each of the 6 petals 560a to the shaft 590a, and a filter portion 520a having 6 struts 527a, the implant 500a can be configured to have less than or greater than these numbers of each.

FIGS. 44A-44C illustrate end views of the implant 500a of FIGS. 43A-43D in various states of actuation and restriction/occlusion of flow therethrough. FIG. 44A shows the implant 500a in its unactuated, non-restricting/non-occluding state, FIG. 44B shows the implant 500a in a partially actuated, partially restricting/occluding state, and FIG. 44C shows the implant 500a in a fully actuated, fully restricting/occluding state. As shown through FIGS. 44A-44C, the lumen 513a of the implant 500a (e.g., the lumen or opening of the flow restrictor portion 550a) can change from a generally circular shape (FIG. 44A) when unactuated, to a generally star/stellate shape when at least partially actuated (FIG. 44B), to a substantially blocked lumen when fully actuated (FIG. 44C). In some implementations, the lumen 513a of the implant 500a (e.g., the lumen or opening of the flow restrictor portion 550a) can have a generally circular shape when unactuated, a generally circular shape when partially actuated, and a substantially blocked lumen when fully actuated. When folded radially inward, an exterior surface of the each of the plurality of petals 560a can block blood flow via material 530a. In some implementations, such as shown in FIG. 44D, the implant 500a can be configured such that its lumen 513a can remain at least partially open even when the flow restrictor portion 550a is fully actuated, such as by the formation of elongate gaps 514a between each of or between at least some of the petals 560a.

FIG. 45 illustrates a flat pattern of view of the expandable body 510a of the implant 500a of FIGS. 43A-43D with aspects previously discussed identified.

FIGS. 46A-46B illustrate various views of components of the implantable flow restriction system 5a, which can be implanted as shown above with respect to FIG. 42. FIG. 46A shows the implant 500a connected to the shaft 590a and tubing 570a. The implant 500a, the shaft 590a, and the tubing 570a can be referred to herein as an implant assembly 501a. FIG. 46B shows the implant 500a connected to the shaft 590a and tubing 570a, which are in turn connected to the controller 50a. In other words, FIG. 46B shows the implant assembly 501a connected to the controller 50a.

FIGS. 47A-47D illustrate interaction of various components of the implant assembly 501a to actuate the implant 500a of FIGS. 43A-43D, with the material 530a of the implant 500a removed for clarity. As described with respect to FIGS. 43A-43D, each of the distal apexes 564a of the petals 560a can connect to the suture or wire 595a at one end of the suture or wire 595a, and the other end of the suture or wire 595a can connect to the distal end 592a of the shaft 590a. As an example, the sutures or wires 595a can connect to the distal apexes 564a via eyelets at the distal apexes 564a as shown. Further to this example, the sutures or wires 595a can connect to the distal end 592a of the shaft 590a via a crimp as shown, although other forms of connection are possible and are considered within the scope of this disclosure (e.g., via a set screw, press fit component, adhesive, and/or threaded end). In some implementations, the suture or wire 595a can extend from the distal end 592a of the shaft 590a, pass through an eyelet at the distal apex 564a of a petal 560a, and double back and connect to the distal end 592a of the shaft 590a. In some implementations, the suture or wire 595a can be integrally formed or a part of the shaft 590a. For example, in implementations in which the shaft 590a has a braided structure comprising a plurality of individual wires 593 as described with respect to FIGS. 64A-64B, the suture or wire 595a can be one or more of such individual wires 593.

With continued reference to FIGS. 47A-47D, with the material 530a removed from view, the collapsible and extendible coupling 580a configured to fluidically seal the tubing 580a with the shaft 590a can be seen. In some implementations and as shown, the collapsible and extendible coupling 580a can extend around the shaft 590a such that no portion of the shaft 590a is exposed except for where the shaft 590a is connected to the sutures or wires 595a. Alternatively, in some implementations the collapsible and extendible coupling 580a can extend around the shaft 590a such that no portion of the shaft 590a is exposed, which can include covering where the shaft 590a is connected to the sutures or wires 595a. As shown, the collapsible and extendible coupling 580a can connect at its proximal end to the distal end 572a of the tubing 570a, and it can connect at its distal end to the shaft 590a adjacent its distal end 592a, which can allow for sliding and/or rotational movement of the shaft 590a therewithin.

In some implementations and as shown in FIGS. 47A-47B, the implant 500a (e.g., the flow restrictor portion 550a) can be actuated by longitudinal movement (e.g., proximal and distal movement) of the shaft 590a relative to the implant 500a. Such longitudinal movement can include a sliding of the shaft 590a within the tubing 570a. In the unactuated, non-restricting/non-occluding state shown in FIG. 47A, the shaft 590a is in its distal-most position relative to the implant 500a and the collapsible and extendible coupling 580a is in its extended state. In its extended state, the collapsible and extendible coupling 580a can have a generally straight configuration as shown. Upon proximal movement of the shaft 590a within the tubing 570a as shown in FIG. 47B (e.g., upon proximal movement of the shaft 590a relative to the tubing 570a and implant 500a), the shaft 590a pulls the petals 560a radially inward towards one another via the sutures or wires 595a to occlude/restrict flow through the implant 500a. Such proximal movement of the shaft 590a also causes the collapsible and extendible coupling 580a to collapse into its collapsed state. Furthermore, and as shown in FIG. 47B, when the shaft 590a is in its proximal-most position relative to the implant 500a, the sutures or wires 595a can be oriented substantially longitudinally.

Figure 47D:
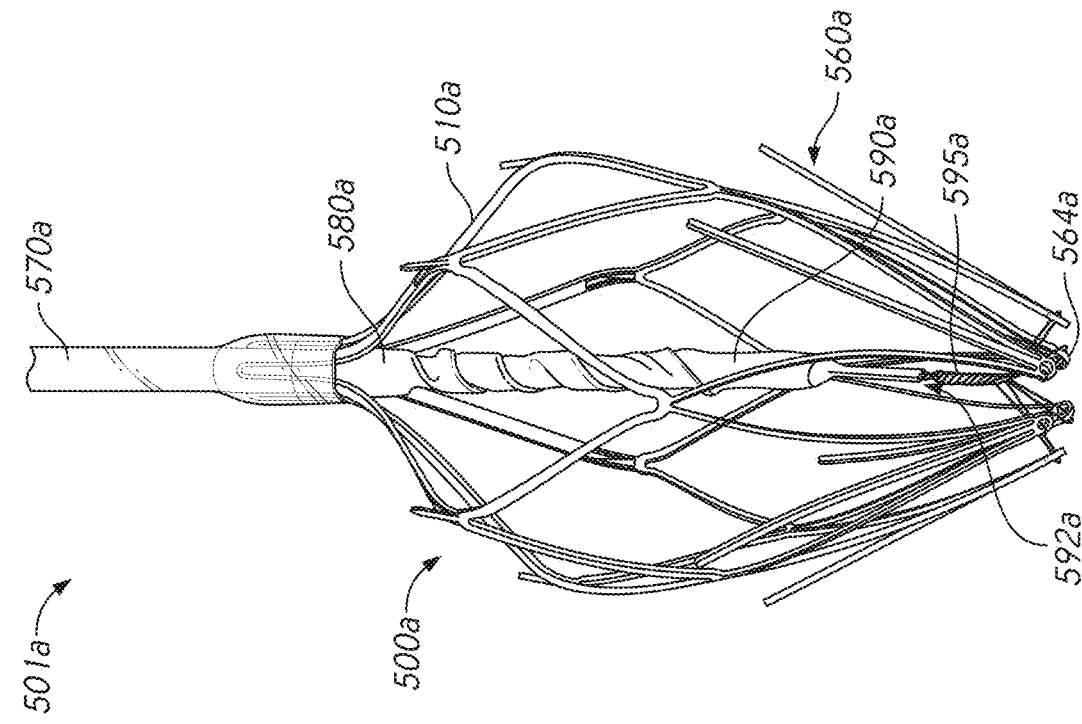
Figure 47C:
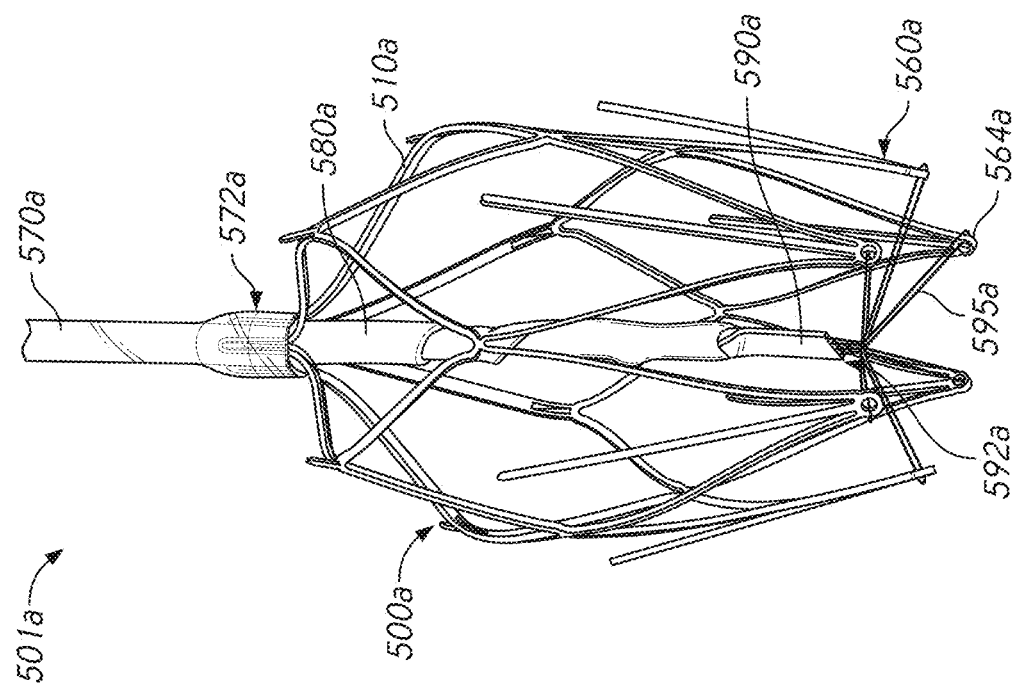

In some implementations and as shown in FIGS. 47C-47D, the implant 500a (e.g., the flow restrictor portion 550a) can be actuated by rotating the shaft 590a (e.g., clockwise or counterclockwise) relative to the implant 500a. Such rotation of the shaft 590a can cause the sutures or wires 595a to spool about the shaft 590a or twist and at least partially close the flow restrictor portion 550a. In other words, such rotation of the shaft 590a can cause the sutures or wires 595a to spool about the shaft 590a or twist and cause the petals 560a to at least partially fold radially inward. For this, the implantable controller 50a can be configured to rotate the shaft 590a. Furthermore, in such implementations the tubing 570a can be configured for rotational movement of the shaft 590a therewithin. Additionally, in such implementations the collapsible and extendable coupling 580a can be configured for such rotational movement. FIG. 47C-47D each show the petals 560a of the implant 500a pulled at least partially radially inward as a result of the shaft 590a being rotated, with FIG. 47D showing the shaft 590a in a more rotated state than as shown in FIG. 47C.

Referring back to FIG. 42, the implant 500a can be positioned within the IVC below the renal veins such that the distal apexes 564a of the petals 560a are aimed towards the incoming flow of blood. In other words, the implant 500a can be implanted such that the flow restrictor portion 550a is upstream of the other portions of the implant 500a (e.g., the flow restrictor portion 550a is the first portion of the implant 500a to receive blood flow therethrough). In such position, the shaft 590a and tubing 570a can extend proximally from the implant 500a up the IVC, through the right atrium, into the superior vena cava (SVC), through a subclavian vein (left subclavian as shown), and out the subclavian vein to connect with the controller 50a that can be implanted in an infraclavicular subcutaneous pocket (e.g., similar to placement of a pacemaker). Furthermore, such positioning of the flow restrictor portion 550a comprising the petals 560a can provide for a functional benefit of pushing any thrombi that may form or otherwise be gathered at the outer surface of the petals 560a when the implant 500a is actuated/closed towards the wall of the IVC upon opening of the petals 560a rather than allowing such thrombi to pass through the implant 500a upon opening of the petals 560a (such as may occur if the petals 560a were not aimed towards the incoming flow of blood). In this way, any thrombi are directed towards the sealing area around the implant 500a with the wall of the IVC and not through the implant 500a and towards the heart.

In some implementations, any of the flow restriction devices described herein (e.g., including at least implant 500a) may work with and/or be used in conjunction with sensors that are located remote from the flow restriction device that can provide physiological parameters of interest useful for control of the flow restriction device. Such physiological parameters of interest can include pressure, flow rate, heart rate, and/or the like. As an example, a flow restriction device can be used with a pressure sensor located within vessels and/or organs remote from the flow restriction device and provide a measure of the pressure at such locations for the control of the flow restriction device. One example of an implantable sensor is a MEMS pressure sensor. The MEMS or other implantable pressure sensor may be a remote component of the flow restriction device or may be an independent sensor with a separate control system. In one example, the MEMS pressure sensor may be located in the pulmonary artery and may measure the pressure of blood flowing through the pulmonary artery. The MEMS or other pressure sensor may include a separate electronics system that is configured to receive readings (e.g., data indicative of pressure) from the MEMS pressure sensor. These readings may be used by the patient, the patient's physician, etc. to determine when the patient should receive treatment via the flow restriction device. In one example, the MEMS pressure sensor may comprise a capacitive sensor. In another example, the MEMS pressure sensor may include a barometer and may be powered by an external antenna (e.g., in the form of radiofrequency signals). For example, the external antenna may be contained within an antenna device and a pressure reading may be taken and transmitted to the electronics system when the patient holds the antenna device against their body. Additionally or alternatively, the MEMS pressure sensor may include an inductor that can be used to create a circuit that creates a frequency, e.g., an LC circuit or LC tank circuit. The frequency may then be used to determine the pressure.

In some implementations, the MEMS pressure sensor described above may be coupled to a portion of the flow restriction devices described herein. As an example, a flow restriction device can have the MEMS pressure sensor attached to its proximal end, its distal end, both of its ends, its shaft, and/or the like. In the example of implant 500a, the MEMS pressure sensor may be coupled to the shaft 590a. The MEMS pressure sensor may be tied to/coupled to the flow restriction device with suture, reflow, and/or the like. In this example, the MEMS pressure sensor would be configured to measure the pressure at such location relative to the flow restriction device (e.g., upstream, downstream, both upstream and downstream, etc.). As noted above, the MEMS pressure sensor may transmit the pressure readings to a separate electronics system. Additionally or alternatively, the MEMS pressure sensor may transmit readings to a control system of the flow restriction device (e.g., the controller 50a).

Figure 48C:
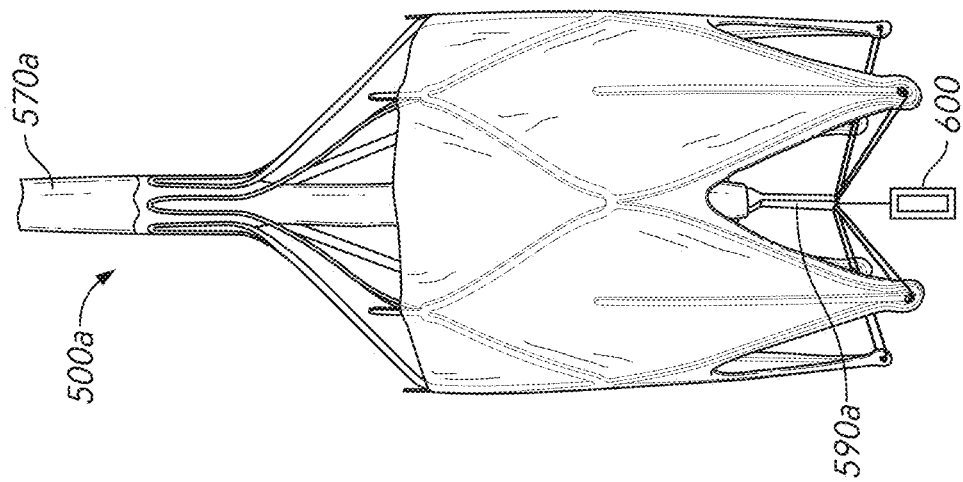
FIGS. 48A-48C illustrate various implementations of an implant of a flow restriction system with a sensor located in various positions relative to a flow restrictor portion of the implant in accordance with some aspects of this disclosure.
Figure 48B:
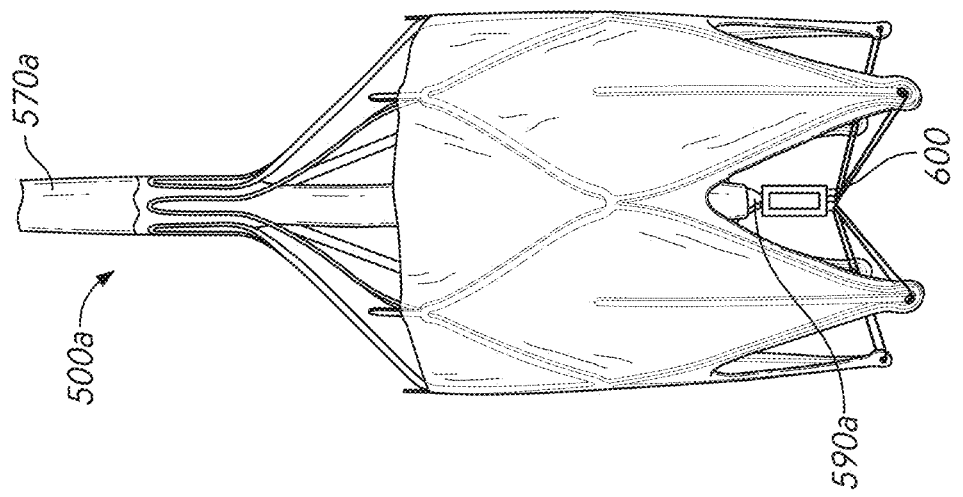
Figure 48A:
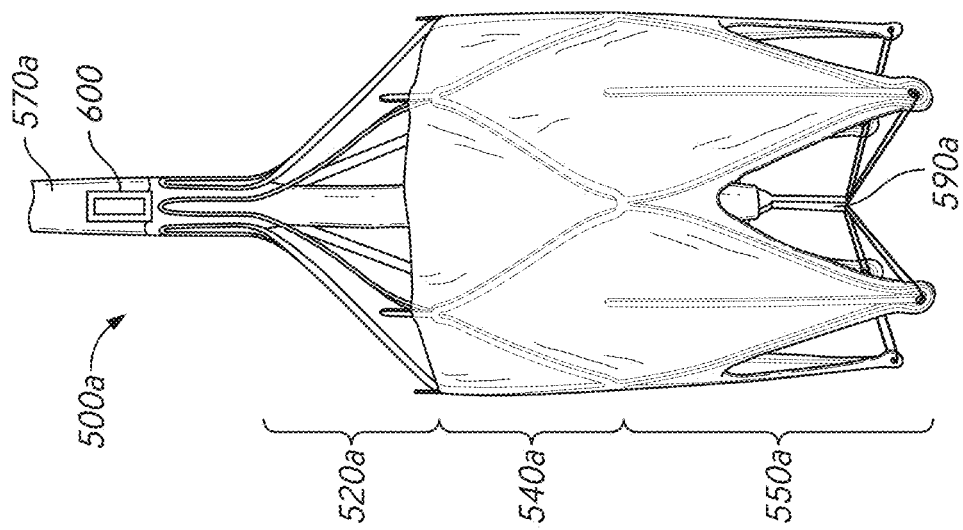

FIGS. 48A-48C show the implant 500a with a sensor 600 located in various positions relative to the flow restrictor portion 550a. The sensor 600 can be configured to measure the pressure within the vasculature at its location, and as such the placement of the sensor 600 relative to the flow restrictor portion 550a can determine which vascular pressure is being measured depending on the activation state of the flow restrictor portion 550a. The sensor 600 can be located adjacent the proximal end of the implant 500a (e.g., such as attached to the tubing 570a proximal to the implant 500a) and proximal of the flow restrictor portion 550a if it were to be actuated as shown in FIG. 48A, located adjacent the distal end of the shaft 590a and proximal of the flow restrictor portion 550a if it were to be actuated as shown in FIG. 48B, and/or located on an extension of the shaft 590a and distal of the flow restrictor portion 550a if it were to be actuated as shown in FIG. 48C. When the flow restrictor portion 550a of the implant 500a is unactuated (e.g., the implant is in a non-restricting/non-occluding state), the sensor 600 positioned as shown in any of FIGS. 48A-48C would measure substantially the same pressure. For example, when the flow restrictor portion 550a of the implant 500a is unactuated, the sensor 600 positioned as shown in any of FIGS. 48A-48C would measure substantially the same IVC pressure. When the flow restrictor portion 550a of the implant 500a is actuated, however, the sensor 600 positioned as shown in FIGS. 48A-48B would measure the renal venous pressure (e.g., since it can be positioned proximate the renal veins), whereas the sensor 600 positioned as shown in FIG. 48C would measure the femoral venous pressure. The implant 500a can include the sensor 600 in either of the positions as shown in FIGS. 48A-48B where it would measure the renal venous pressure. In some implementations, the implant 500a can include more than one sensor 600, with one located as shown in FIGS. 48A-48B to measure renal venous pressure, and one located as shown in FIG. 48C to measure femoral venous pressure. The sensor(s) 600 of the implant 500a can operably connect with the controller 50a, for example, via wire(s) that extend between the sensor(s) 600 and the controller 50a through the tubing 570a. In some implementations, the shaft 590a or a portion thereof can operably connect the sensor(s) 600 with the controller 50a. Pressures determined from signals generated by the sensor(s) 600 and/or differentials thereof (e.g., differentials between multiple sensors, and/or differentials between pressures determined through time) can be utilized in the control of the implant 500a.

Figure 49:
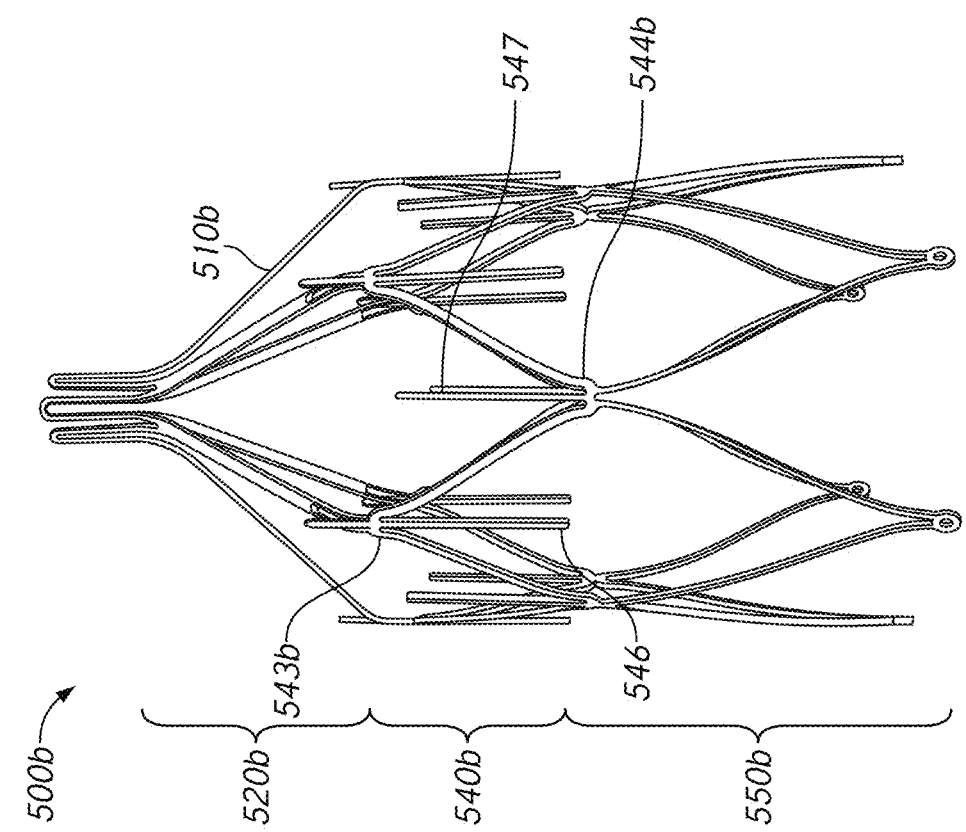
FIG. 49 illustrates an implementation of an implant of an implantable flow restriction system in accordance with some aspects of this disclosure.

FIG. 49 illustrates another implementation of an implant 500b that can be used in connection with implantable flow restriction system 5. The implant 500b can be the same or similar to and/or incorporate any of the features described with respect to the implant 500a. For example, the implant 500b can have an expandable body 510b having a filter portion 520b, a radial support portion 540b, and a flow restrictor portion 550b the same or similar to the expandable body 510a having the filter portion 520a, the radial support portion 540a, and the flow restrictor portion 550a of the implant 500a. FIG. 49 shows a side view of the expandable body 510a of the implant 500b without material covering the flow restrictor portion 550b. Different than the implant 500a, the expandable body 510b of the implant 500b can include distally extending struts 546 and/or proximally extending struts 547. The distally extending struts 546 can extend distally from the proximal apexes 543b of the radial support portion 540b in a generally longitudinal direction as shown. Furthermore, the distally extending struts 546 can be configured to enhance sealing of the implant 500b with a wall of the vessel (e.g., the wall of the IVC) in which the implant 500b is implanted. The proximally extending struts 547 can extend proximally from the distal apexes 544b of the radial support portion 540b in a generally longitudinal direction as shown. Furthermore, the proximally extending struts 547 can be configured to enhance sealing of the implant 500b with a wall of the vessel (e.g., the wall of the IVC) in which the implant 500b is implanted. In some implementations, the implant 500b includes only the distally extending struts 546. The implant 500a can include distally extending struts and/or proximally extending struts similar or the same as the distally extending struts 546 and proximally extending struts 547.

Figure 50:
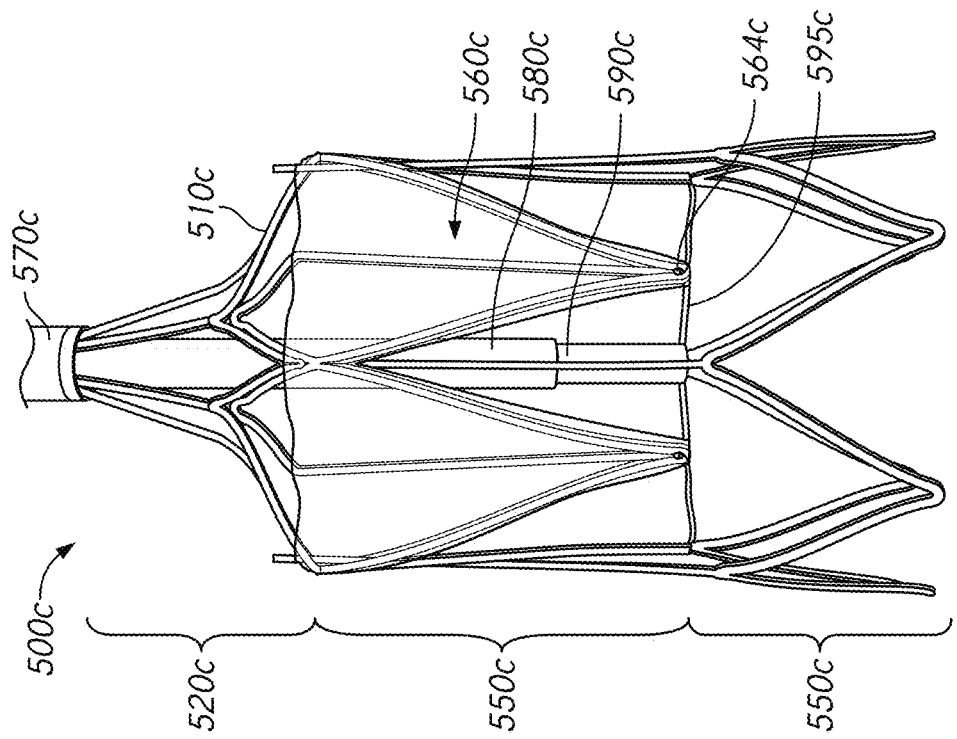
FIG. 50 illustrates an implementation of an implant of an implantable flow restriction system in accordance with some aspects of this disclosure.

FIG. 50 illustrates another implementation of an implant 500c that can be used in connection with implantable flow restriction system 5. The implant 500c can be similar to and/or incorporate any of the features described with respect to the other implants described herein, such as implants 500a and 500b. For example, the implant 500c can have an expandable body 510c having a filter portion 520c, a radial support portion 540c, and a flow restrictor portion 550c similar to the expandable body 510a having the filter portion 520a, the radial support portion 540a, and the flow restrictor portion 550a of the implant 500a. FIG. 49 shows a side view of the expandable body 510c of the implant 500c connected to shaft 590c and tubing 570c with collapsible and extendible coupling 580c that can be the same or similar to the shaft 590a, tubing 570a, and collapsible and extendible coupling 580a described with respect to implant 500a. Different than the implant 500a, the flow restrictor portion 550c can be connected to and located between the filter portion 520c and the radial support portion 540c as shown. In such arrangement, blood flowing through an implanted implant 500c would flow first through the radial support portion 540c rather than the flow restrictor portion as in implant 500a. Actuation of the flow restrictor portion 550c comprising petals 560c can be the same or similar to that described with respect to the flow restrictor portion 550a of implant 500a (e.g., via sutures or wires 595c connected between shaft 570c and distal apexes 564a of petals 560a). Furthermore, the implant 500c can similarly be positioned within the IVC below the renal veins such that the distal apexes 564c of the petals 560c are aimed towards the incoming flow of blood.

FIGS. 51A-51B illustrate another implementation of an implant 500d that can be used in connection with implantable flow restriction system 5. The implant 500d can be similar to and/or incorporate any of the features described with respect to the other implants described herein, such as implants 500a, 500b, and 500c. For example, the implant 500d can have an expandable body 510d having a filter portion 520d, a radial support portion 540d, and a flow restrictor portion 550d similar to the expandable body 510c having the filter portion 520c, the radial support portion 540c, and the flow restrictor portion 550c of the implant 500c. FIGS. 51A-51B show side views of the expandable body 510d of the implant 500d connected to shaft 590d and tubing 570d and can incorporate a collapsible and extendible coupling (not shown) that can be the same or similar to the shaft 590a, tubing 570a, and collapsible and extendible coupling 580a described with respect to implant 500a. Material spanning petals 560d of the flow restrictor portion 550d has been removed to show features of the implant 500d. Similar to the implant 500c, the flow restrictor portion 550d can be connected to and located between the filter portion 520d and the radial support portion 540d as shown. In such arrangement, blood flowing through an implanted implant 500d would flow first through the radial support portion 540d before encountering the flow restrictor portion 550d (similar to implant 500c). Different than the implants 500a and 500c, the implant 500d includes struts 595d rather than suture or wire 595a and 595c connecting apexes 564d of the petals 560d to the shaft 590d. Such struts 595d can be integrally formed with the expandable body 510d. With struts 595d, actuation of the flow restrictor portion 550d comprising petals 560d can be similar to that described with respect to the flow restrictor portion 550a of implant 500a. As shown, flow restrictor portion 550d can be oriented in an opposite direction than the flow restrictor portions 550a, 550b, and 550c such that apexes 564d are aimed away from the incoming flow of blood when in use. With such orientation, actuation of the flow restrictor portion 550d can occur via distal movement of the shaft 590d (e.g., pushing) rather than proximal movement of the shaft 590d (e.g., pulling). In some implementations, however, the flow restrictor portion can be oriented the same as the flow restrictor portions 550a, 550b, and 550c such that apexes 564d are aimed towards the incoming flow of blood when in use. FIG. 51A shows an unactuated implant 500d (e.g., the flow restrictor portion 550d is in a non-restricting/non-occluding state) and FIG. 51B shows a partially actuated implant 500d (e.g., the flow restrictor portion 550d is in a partially restricting/occluding state).

FIG. 52 illustrates another implementation of an implant 500e that can be used in connection with implantable flow restriction system 5. The implant 500e can be similar to and/or incorporate any of the features described with respect to the other implants described herein, such as implants 500a, 500b, 500c, and 500d. Different than the other implants described herein, the implant 500e can have an expandable body 510e having filter portions 520e and 520e' at proximal and distal ends of thereof with a combined radial support portion 540e and flow restrictor portion 550e connected thereto and in between such filter portions 520e, 520e'. FIG. 52 shows a side view of the expandable body 510e of the implant 500e connected to shaft 590e and tubing 570e and can incorporate a collapsible and extendible coupling (not shown) that can be the same or similar to the shaft 590a, tubing 570a, and collapsible and extendible coupling 580a described with respect to implant 500a. Material spanning petals 560e of the flow restrictor portion 550e has been removed to show features of the implant 500e. The flow restrictor portion 550e can include petals 560e as shown, which can be oriented such that proximal movement of the shaft 590e causes the petals 560e to collapse radially inward to occlude/restrict flow through the implant 500e (e.g., the petals 560e can be pulled inward to close via sutures or wires 595e connected between the ends of the petals and the distal end of the shaft 590e as described herein in related implementations). Arranged as such, blood flowing through an implanted implant 500e would flow first through the filter portion 520e', through the combined radial support portion 540e and flow restrictor portion 550e, and through the filter portion 520e. Furthermore, the implant 500e can similarly be positioned within the IVC below the renal veins such that the ends of the petals 560e are aimed towards the incoming flow of blood. Also shown, the implant 500e can include anchors 525e that extend generally proximally and anchors 525e' that extend generally distally where the combined radial support portion 540e and flow restrictor portion 550e meet the filter portions 520e and 520e'.

FIG. 53 illustrates another implementation of an implant 500f that can be used in connection with implantable flow restriction system 5. The implant 500f can be similar to and/or incorporate any of the features described with respect to the other implants described herein, such as implants 500a, 500b, 500c, 500d, and 500e. Similar to the implant 500e, the implant 500f can have an expandable body 510f having filter portions 520f and 520f' at proximal and distal ends of thereof with a combined radial support portion 540f and flow restrictor portion 550f connected thereto and in between such filter portions 520f, 520f'. FIG. 53 shows a side view of the expandable body 510f of the implant 500f connected to shaft 590f and tubing 570f and can incorporate a collapsible and extendible coupling (not shown) that can be the same or similar to the shaft 590a, tubing 570a, and collapsible and extendible coupling 580a described with respect to implant 500a. Furthermore, FIG. 53 shows the implant 500f in an unactuated state (e.g., non-restricting/non-occluding state). Material 530f is shown spanning petals 560f of the flow restrictor portion 550f, which can be the same or similar to the material 530a of implant 500a. As shown, flow restrictor portion 550f can be oriented in an opposite direction than the flow restrictor portions 550a, 550b, 550c, and 550e such that apexes 564f of the petals 560f are aimed away from the incoming flow of blood when in use. With such orientation, actuation of the flow restrictor portion 550f can occur via distal movement of the shaft 590f (e.g., pushing) rather than proximal movement of the shaft 590f (e.g., pulling). In some implementations, however, the flow restrictor portion can be oriented the same as the flow restrictor portions 550a, 550b, 550c, and 550e such that apexes 564f are aimed towards the incoming flow of blood when in use. Also shown, the implant 500f can include anchors 525f that extend generally proximally and anchors 525f' that extend generally distally where the combined radial support portion 540f and flow restrictor portion 550f meet the filter portions 520f and 520f'.

FIG. 54 illustrates another implementation of an implant 500g that can be used in connection with implantable flow restriction system 5. The implant 500g can be similar to and/or incorporate any of the features described with respect to the other implants described herein, such as implants 500*a*, 500*b*, 500*c*, 500*d*, 500*e*, and 500*f*. Similar to the implant 500*f*, the implant 500*g* can have an expandable body 510*g* having filter portions 520*g* and 520*g*' at proximal and distal ends of thereof with a radial support portion 540*g* connected thereto and in between such filter portions 520*g*, 520*g*'. Different than implants 500*a*-500*f*, the implant 500*g* can include a flow restrictor 560*g* that is not integrally formed with expandable body 510*g*. The flow restrictor 560*g* of implant 500*g* can be disposed within the lumen 513*g* of the implant 500*g* (e.g., substantially centered within lumen 513*g*) and be configured to attach to a distal end or distal portion of the tubing 570*g*. As shown, the flow restrictor 560*g* can comprise a balloon that can expand from a collapsed configuration to at least partially block flow through the lumen 513*g*. Actuation (e.g., expansion) of the balloon flow restrictor 560*g* can occur via distal movement of the shaft 590*g* relative to the implant 500*g*, wherein the shaft 590*g* enters the balloon flow restrictor 560*g* and causes it to expand (e.g., the shaft can assume a three dimensional shape to at least partially fill the balloon flow restrictor 560*g*, causing it to expand). The balloon flow restrictor 560*g* can collapse upon retraction of the shaft 590*g* (e.g., proximal movement of the shaft 590*g* relative to the implant 500*g*).

In some implementations, the implant 500*g* can be used in connection with other implantable flow restriction systems described herein, such as implantable flow restriction system 2. In such implementations, the implant 500*g* can be similar to and/or incorporate any of the features described with respect to implant 200*m*. For example, the implant 500*g* can be fluidically actuated (e.g., the balloon flow restrictor 560*g* can be fluidically actuated) to at least partially restrict flow through the lumen 513*g*.

Figures 55A, 55B, 55C:
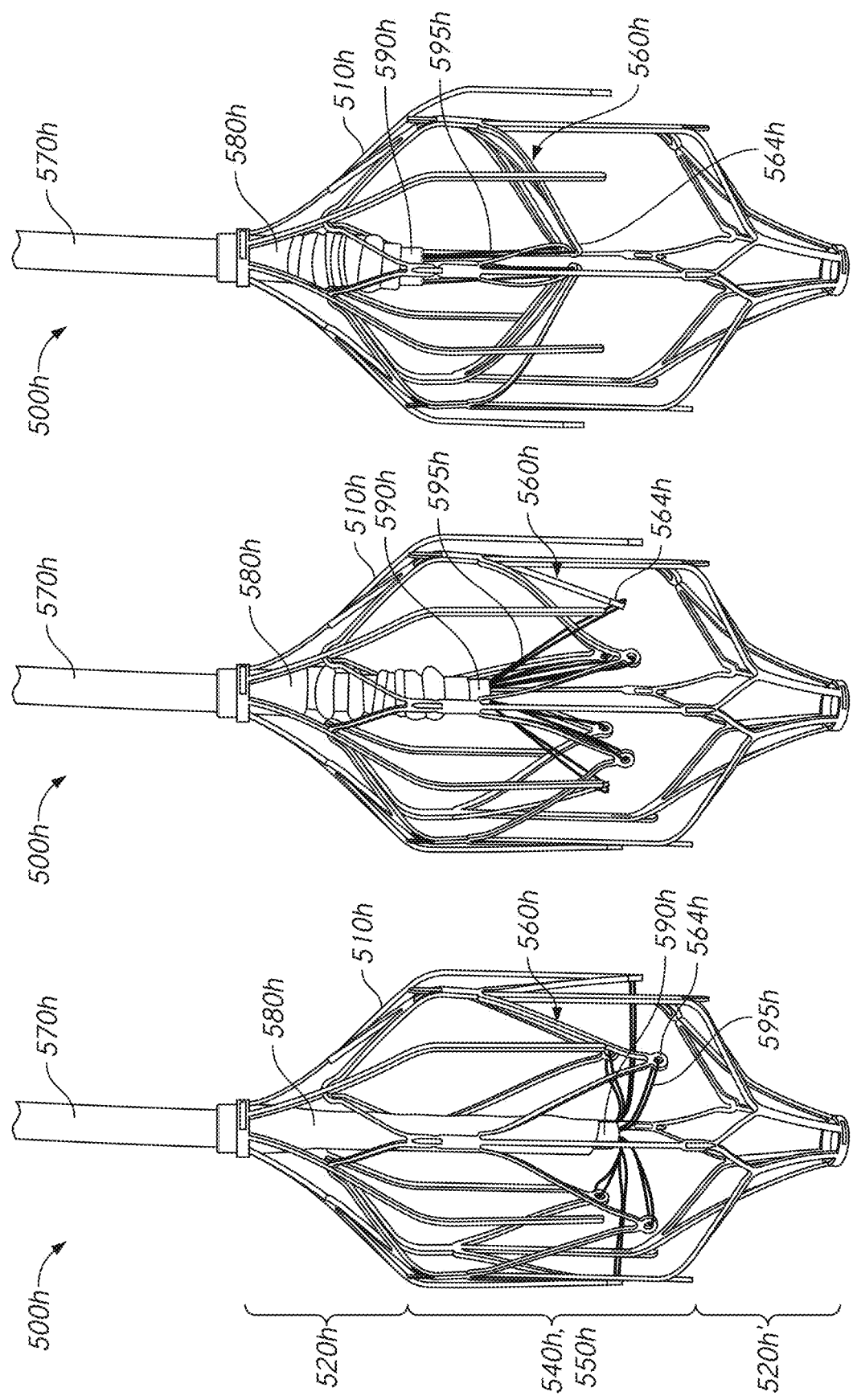
FIGS. 55A-55C illustrate interaction of various components of an implementation of a flow restriction system to actuate an implant thereof in accordance with some aspects of this disclosure.

FIGS. 55A-55C illustrate another implementation of an implant 500*h* that can be used in connection with implantable flow restriction system 5. The implant 500*h* can be similar to and/or incorporate any of the features described with respect to the other implants described herein, such as implants 500*a*, 500*b*, 500*c*, 500*d*, 500*e*, and 500*f*. Similar to the implant 500*e*, the implant 500*h* can have an expandable body 510*h* having filter portions 520*h* and 520*h*' at proximal and distal ends of thereof with a combined radial support portion 540*h* and flow restrictor portion 550*h* connected thereto and in between such filter portions 520*h*, 520*h*'. FIGS. 55A-55C show side views of the expandable body 510*h* of the implant 500*h* connected to shaft 590*h* and tubing 570*h* and can incorporate a collapsible and extendible coupling 580*h* that can be the same or similar to the shaft 590*a*, tubing 570*a*, and collapsible and extendible coupling 580*a* described with respect to implant 500*a*. FIG. 55A shows the implant 500*h* in an unactuated state (e.g., non-restricting/non-occluding state), FIG. 55B shows the implant 500*h* in a partially actuated state (e.g., partially restricting/occluding state), and FIG. 55C shows the implant 500*h* in a fully actuated state (e.g., restricting/occluding state). Material spanning petals 560*h* of the flow restrictor portion 550*h* has been removed to show features of the implant 500*h* and interaction between such features during actuation. Furthermore, and similar to implants 500*a*, 500*b*, 500*c*, and 500*e*, apexes 564*h* of petals 560*h* can point in the distal direction (e.g., when in the unactuated state). Similar to actuation of the flow restrictor portion 550*a* of implant 500*a*, FIGS. 55A-55C show that proximal movement of shaft 590*h* relative to tubing 570*h* and implant 500*h* can actuate the flow restrictor portion 550*h* to occlude/restrict flow through the implant 500*h*. Specifically, proximal movement of the shaft 590*h* can pull the apexes 564*h* of petals 560*h* of flow restrictor portion 550*h* radially inwards via sutures or wires 595*h* connected therebetween. FIGS. 55A-55C also show how the collapsible and extendible coupling 580*h* can extend and collapse during actuation of the implant 500*h* (e.g., the same or similar to that described with respect to collapsible and extendible coupling 580*a* of implant 500*a*).

Figure 56B:
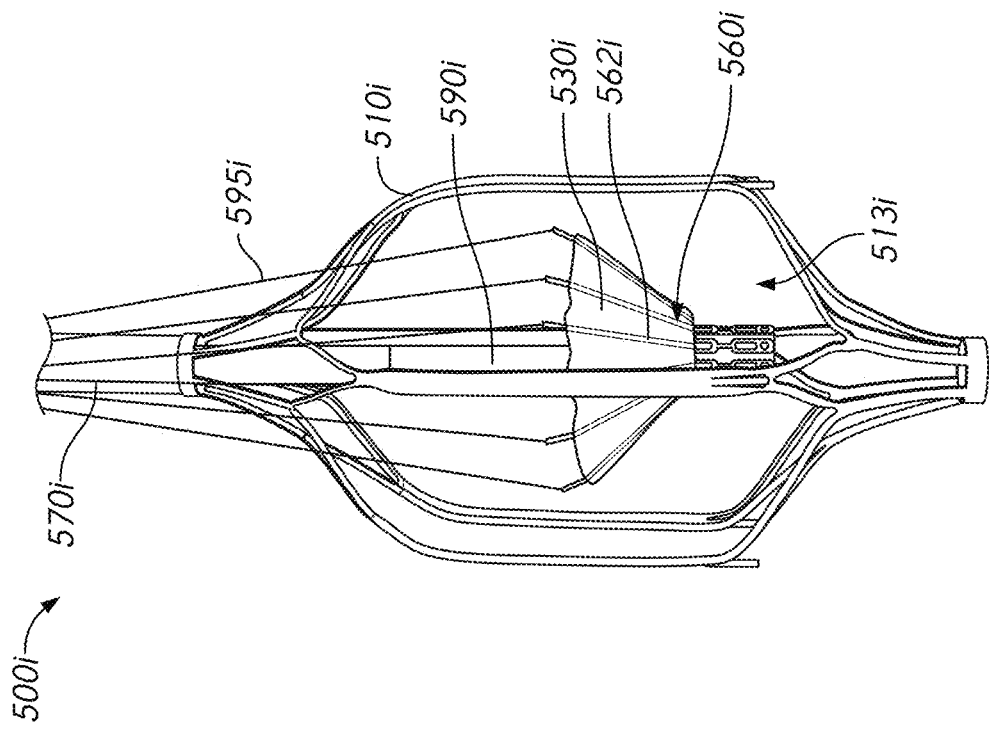
FIGS. 56A-56B illustrate an implementation of an implant of an implantable flow restriction system in accordance with some aspects of this disclosure.
Figure 56A:
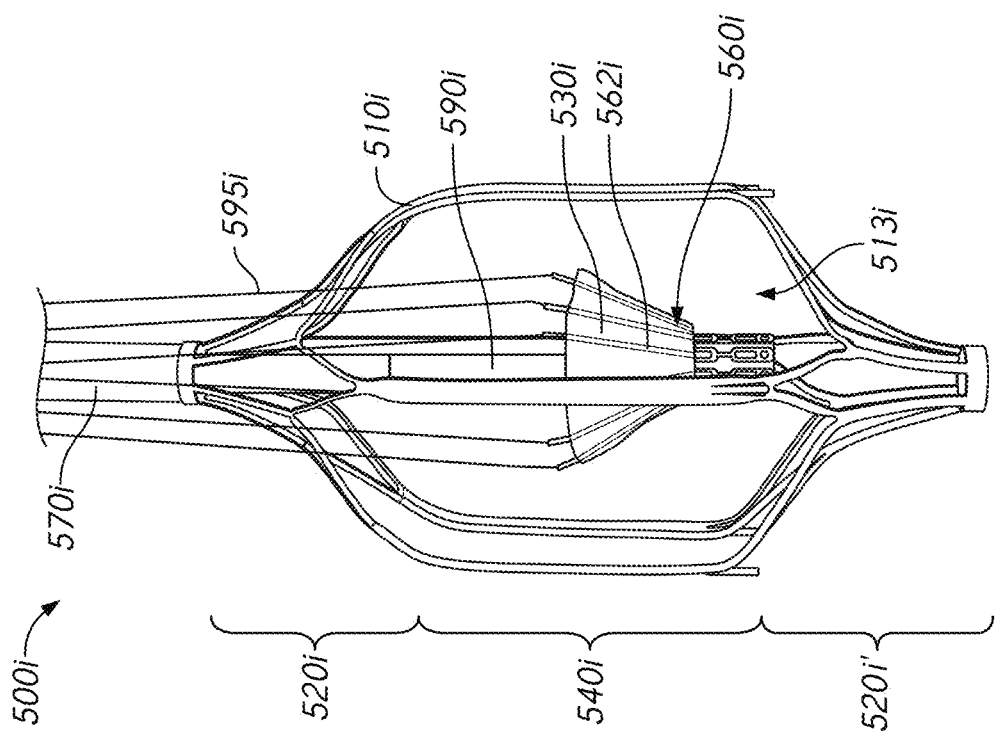

FIGS. 56A-56B illustrate another implementation of an implant 500*i* that can be used in connection with implantable flow restriction system 5. FIG. 56A shows the implant 500*i* in an unactuated state, and FIG. 56B shows the implant in an actuated state. The implant 500*i* can be similar to and/or incorporate any of the features described with respect to the other implants described herein, such as implants 500*a*, 500*b*, 500*c*, 500*d*, 500*e*, 500*f*, and 500*h*. Similar to the implant 500*e*, the implant 500*i* can have an expandable body 510*i* having filter portions 520*i* and 520*i*' at proximal and distal ends of thereof with a radial support portion 540*i* connected thereto and in between such filter portions 520*i*, 520'. Different than implants 500*a*-500*f* and 500*h*, the implant 500*i* can include a flow restrictor 560*i* that is not integrally formed with the expandable body 510*i*. The flow restrictor 560*i* of implant 500*i* can be disposed within the lumen 513*i* of the implant 500*i* and be configured to attach to a distal end of the shaft 590*i* and include struts 562*i* that extend radially outward from such connection to the distal end of the shaft 590*i*. Furthermore, the flow restrictor 560*i* can include material 530*i* spanning between struts 562*i* to form an umbrella-like flow restrictor 560*i*. Sutures or wires 595*i* can connect radially outward ends of the struts 562*i* to a fixed point adjacent the distal end of tubing 570*i*. To actuate the flow restrictor 560*i* and at least partially occlude/restrict flow through the implant 500*i*, the shaft 590*i* can be moved proximally relative to the tubing 570*i* and expandable frame 510*i*, allowing a biasing force of the radially outward oriented struts 562*i* to expand the flow restrictor 560*i* (e.g., opening the umbrella-like flow restrictor 560*i*). To return the flow restrictor 560*i* to its unactuated state, the shaft 590*i* can be moved distally relative to the tubing 570*i* and expandable frame 510*i*, causing the struts 562*i* to collapse radially inward (e.g., closing the umbrella-like flow restrictor 560*i*). While not shown, the implant 500*i* can also include a collapsible and extendible coupling 580*i* similar to the collapsible and extendible coupling 580*a* of implant 500*a* for fluidically sealing the shaft 590*i* with the tubing 570*i* and allowing longitudinal movement (e.g., distal and proximal movement) therebetween.

In a variant, the flow restrictor 560*i*''' can be fixed to a distal extension of tubing 570*i* and the radially outward ends of the struts 562*i* can connect via sutures or wires 595*i* to a distal end of a movable shaft 590*i* movingly disposed within the tubing 570*i*'''. In such arrangement, the flow restrictor 560*i* can be actuated by distal movement of such shaft 590*i* relative to the expandable body 510*i* and tubing 570*i*, allowing a biasing force of the radially outward oriented struts 562*i* to expand the flow restrictor 560' (e.g., opening the umbrella-like flow restrictor 560*i*). To return the flow restrictor 560*i* to its unactuated state, the shaft 590*i* can be moved proximally relative to the tubing 570*i* and expandable frame 510*i*, causing the struts 562*i* to collapse radially inward (e.g., closing the umbrella-like flow restrictor 560*i*).

Figure 57B:
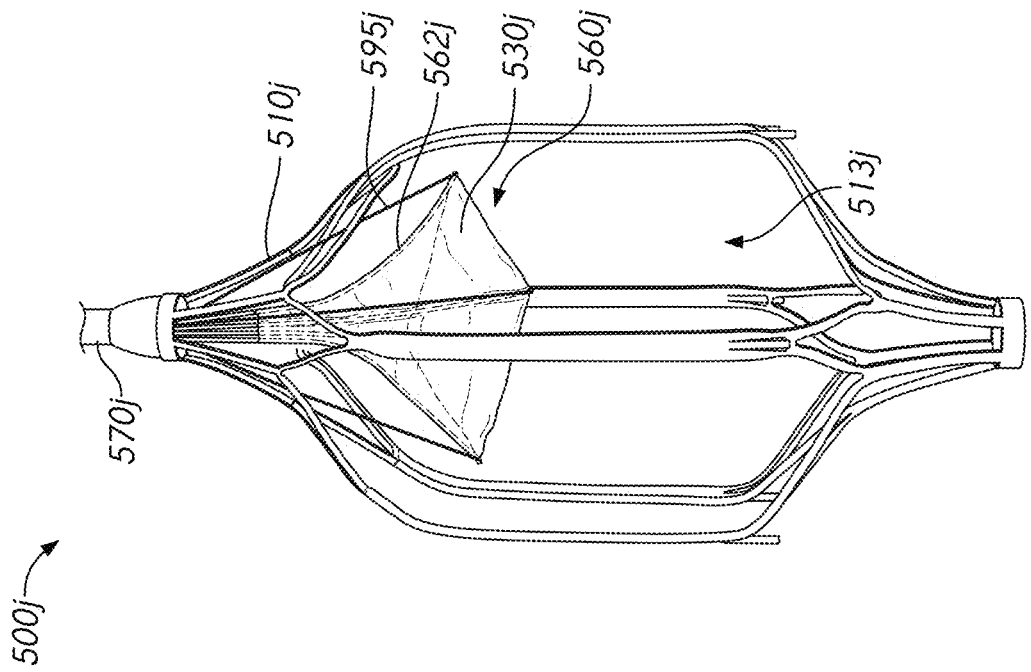
FIGS. 57A-57B illustrate an implementation of an implant of an implantable flow restriction system in accordance with some aspects of this disclosure.
Figure 57A:
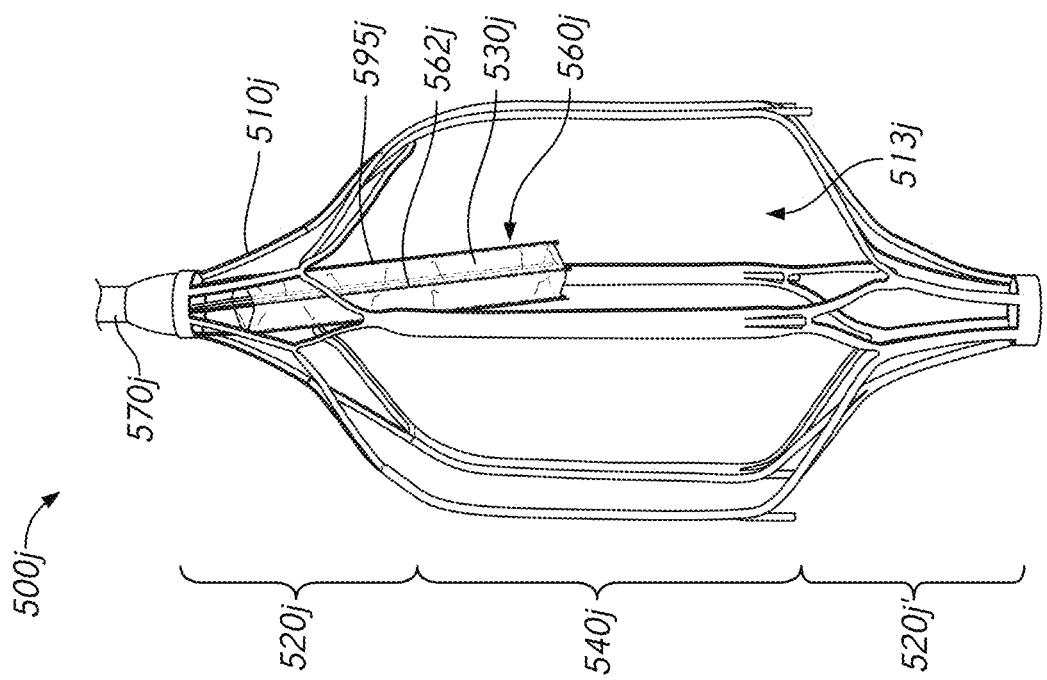

FIGS. 57A-57B illustrate another implementation of an implant 500*j* that can be used in connection with implantable flow restriction system 5. FIG. 57A shows the implant 500*j* in an unactuated state (e.g., non-occluding/non-restricting state), and FIG. 57B shows the implant 500*j* in an actuated state (e.g., at least partially occluding/restricting state). The implant 500*j* can be similar to and/or incorporate any of the features described with respect to the other implants described herein, such as implants 500a, 500b, 500c, 500d, 500e, 500f, 500h, and 500i. Similar to the implant 500i, the implant 500j can have an expandable body 510j having filter portions 520j and 520j' at proximal and distal ends of thereof with a radial support portion 540j connected thereto and in between such filter portions 520j, 520j'. The implant 500j can include a flow restrictor 560j that can be integrally formed with the expandable body 510j or connected thereto. The flow restrictor 560j of implant 500j can be disposed within the lumen 513j of the implant 500j and be configured to attach at its proximal end to the proximal end of the expandable frame 510j. Furthermore and as shown in FIG. 57A, the flow restrictor 560j can include struts 562j that extend generally longitudinally and distally from the proximal end of the expandable frame 510j in the unactuated state (e.g., non-occluding/non-restricting state) of the implant 500j. The flow restrictor 560j can include material 530j spanning between struts 562j to form an umbrella-like flow restrictor 560j. Sutures or wires 595j can connect distal ends of the struts 562j to a distal end of a shaft 590j configured to slidingly move within tubing 570j (shaft 590j is hidden from view within tubing 570j). To actuate the flow restrictor 560j and at least partially occlude/restrict flow through the implant 500j, the shaft 590j can be moved proximally relative to the tubing 570j and expandable frame 510j, pulling the distal ends of the struts 562j via sutures or wires 595j and causing them to bend radially outward. Such radially outward movement of the distal ends of the struts 562j can open the umbrella-like flow restrictor 560j as shown in FIG. 57B, which with material 530j can at least partially occlude/restrict flow through the implant 500j.

FIGS. 58A-58C illustrate another implementation of an implant 500k that can be used in connection with implantable flow restriction system 5. FIG. 58A shows the implant 500k in an unactuated state (e.g., non-occluding/non-restricting state), FIG. 58B shows the implant 500k in a partially actuated state, and FIG. 58C shows the implant 500k in an actuated state (e.g., at least partially occluding/restricting state). The implant 500k can be similar to and/or incorporate any of the features described with respect to the other implants described herein, such as implants 500a, 500b, 500c, 500d, 500e, 500f, 500h, 500i, and 500j. Similar to the implant 500j, the implant 500k can have an expandable body 510k having filter portions 520k and 520k' at proximal and distal ends of thereof with a radial support portion 540k connected thereto and in between such filter portions. Different than some of the implants described herein, the implant 500k can include a flow restrictor 560k that is not integrally formed with the expandable body 510k. The flow restrictor 560k of implant 500k can be disposed within the lumen 513k of the implant 500k and be configured to extend out of and retract within tubing 570k as shown. For this, the flow restrictor 560k can attach to a distal end of shaft 590k (not visible since it is inside tubing 570k) and comprise an expandable frame made of struts 562k having material 530k spanning such struts 562k to form a generally umbrella-like flow restrictor 560k. To actuate the flow restrictor 560k and at least partially occlude/restrict flow through the implant 500k, the shaft 590k can be moved distally relative to the tubing 570k and expandable frame 510k, allowing the flow restrictor 560k to extend distally out of tubing 570k and expand (e.g., opening the umbrella-like flow restrictor 560k). To return the flow restrictor 560k to its unactuated state, the shaft 590k can be moved proximally relative to the tubing 570k and expandable frame 510k, causing the expandable frame having struts 562k to collapse as it retracts within tubing 570k (e.g., closing the umbrella-like flow restrictor 560i).

Figure 59:
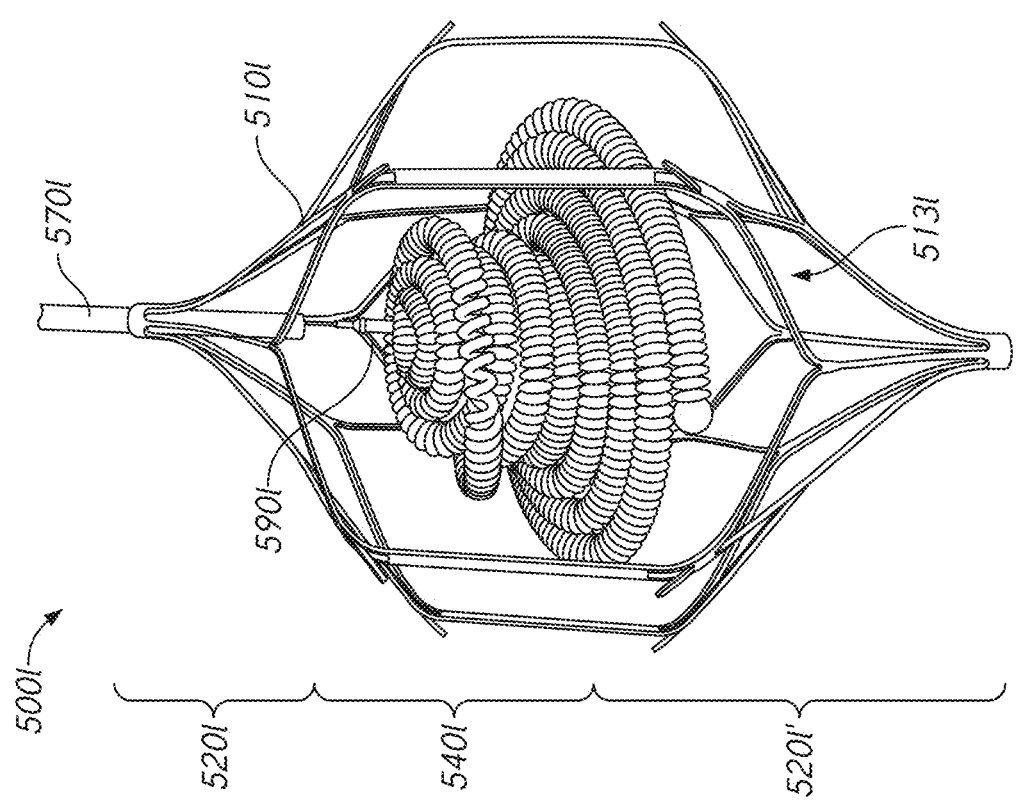
FIG. 59 illustrates an implementation of an implant of an implantable flow restriction system in accordance with some aspects of this disclosure.

FIG. 59 illustrates another implementation of an implant 500l that can be used in connection with implantable flow restriction system 5. FIG. 59 shows the implant 500l in an actuated state (e.g., at least partially occluding/restricting state). The implant 500l can be the same as the implant 500k except the flow restrictor 560l of implant 500l can comprise an expandable coil configured to attain a three dimensional shape upon expansion as shown. Actuation of the flow restrictor 560l is also the same as the that of flow restrictor 560k described herein. For example, to actuate the flow restrictor 560l and at least partially occlude/restrict flow through the implant 500l, the shaft 590l can be moved distally relative to the tubing 570l and expandable frame 510l, allowing the flow restrictor 560l to extend distally out of tubing 570l and expand (e.g., allowing the expandable coil to assume a three dimensional shape). To return the flow restrictor 560l to its unactuated state, the shaft 590l can be moved proximally relative to the tubing 570l and expandable frame 510l, causing the expandable coil to collapse as it retracts within tubing 570l.

Figure 60:
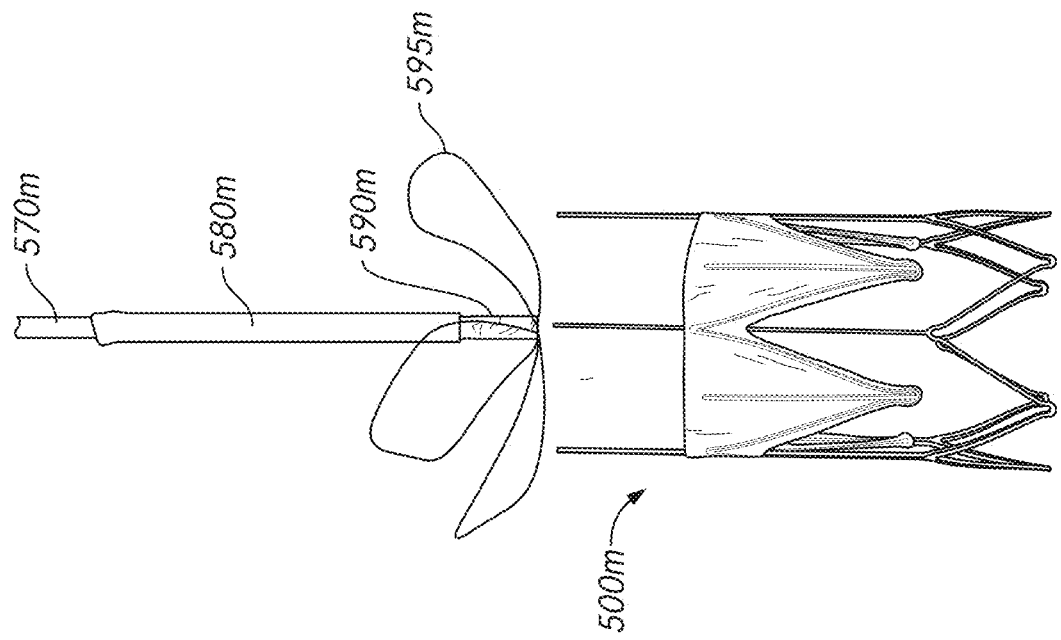
FIG. 60 illustrates an implementation of an implantable flow restriction system with a releasable implant in accordance with some aspects of this disclosure.

FIG. 60 illustrates an implementation of a releasable implant 500m that can be used in connection with implantable flow restriction system 5. The implant 500m shown can be similar to or the same as the implant 500c described with respect to FIG. 50, however it can be adapted to release from tubing 570m and shaft 590m. Any of the implants described herein can be adapted to be releasable. A releasable implant can allow removal of such implant from the patient if needed. Furthermore, a releasable implant can allow removal of the tubing, shaft, and/or controller of the system from the patient if needed. To release the implant 500m from the tubing 570m, the connection between the implant 500m and the tubing 570m can be severed as shown. In some implementations, severing the connection between the implant 500m and tubing 570m can include pulling the tubing 570m while maintaining the implant 500m in place, causing the implant 500m to break away from the tubing 570m. In some implementations, severing the connection between the implant 500m and tubing 570m can include peeling away or cutting an outer wrap or membrane that attaches the implant 500m to the tubing 570m. Such peeling away or cutting can be performed by another interventional device or via a pull string that can be contained within the tubing 570m and accessible at a proximal end of the tubing 570m. To release the implant 500m from the shaft 590m, the connection between the sutures or wires 595m and the implant 500m can be severed as shown. In some implementations, severing the connection between the sutures or wires 595m and the implant 500m can include cutting or heating the sutures or wires 595m via another interventional device. In some implementations, severing the connection between the sutures or wires 595m and the implant 500m can include pushing the shaft 590m distally past the implant 500m to cause the sutures or wires 595m to disconnect from the implant 500m (e.g., the connection between the sutures or wires 595m and the implant 500m can be configured to remain intact as long as the shaft 590m does not extend past the distal end of the implant 500m). In some implementations, to release the implant 500m from the tubing 570m and shaft 590m, the connection between the implant 500m and shaft 590m is severed first, followed by severing the connection between the implant 500m and tubing 570m.

Figures 61A, 61B, 61C:
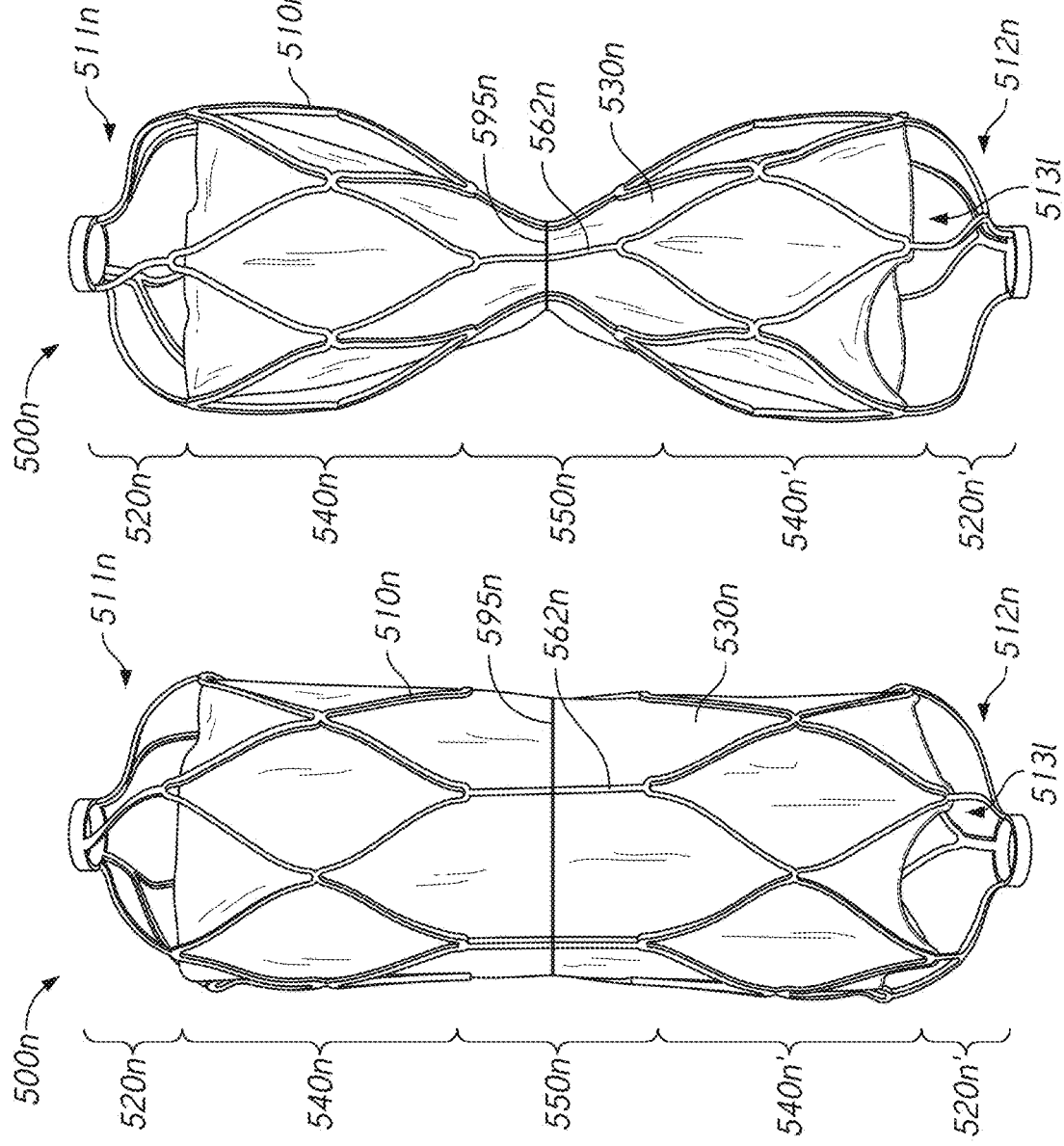
FIGS. 61A-61C illustrate an implementation of an implant of an implantable flow restriction system in accordance with some aspects of this disclosure.

FIGS. 61A-61C illustrate another implementation of an implant 500n. FIG. 61A shows a side view of the implant 500n in an unactuated state (e.g., non-occluding/non-restricting state), FIG. 61B shows a side view of the implant 500n in an actuated state (e.g., at least partially occluding/restricting state), and FIG. 61C shows an end view of the implant 500n in an unactuated state. The implant 500n can be similar to and/or incorporate any of the features described with respect to the other implants described herein. As shown, the implant 500n can comprise an expandable body 510n having a proximal end 511n, a distal end 512n, and a lumen 513n for receiving blood flow therethrough. The implant 500n can include a filter portion 520n, a radial support portion 540n, and a flow restrictor portion 550n, a radial support portion 540n', and a filter portion 520n'. Furthermore, the implant 500n can include a material 530n spanning at least the flow restrictor portion 550o (as shown, the material 530n spans the flow restrictor portion 550n and the radial support portions 540n, 540n'). The flow restrictor portion 550n can be configured to occlude/restrict flow by being cinched radially inward as shown in FIG. 61B via suture or wire 595n. Such suture or wire 595n can wrap around the flow restrictor portion 550n and/or pass through eyelets of struts 562n that make up the flow restrictor portion 550n. While not shown, the implant 500n can connect to tubing 570n at its proximal end 511n. Such tubing 570n can connect to the implant 500n at a position that is substantially central to the lumen 513n (as shown for at least some of the other implementations of implants 500 described herein). In some implementations, such tubing 570n can connect to implant 500n at a position along a circumference of the implant 500n (e.g., at a side of the implant 500n). The suture or wire 595n can extend from around the flow restrictor portion 550n and through the tubing 570n to connect to the actuator of the controller 50 for actuation of the implant 500n. In some implementations, the suture or wire 595n can connect to a shaft 590n that extends through the tubing 570n such as described herein for other implementations for actuation of the implant 500n. In such implementations, a collapsible and extendible coupling 580n similar to other collapsible and extendible couplings described herein can be used to fluidically seal the shaft 590n with the tubing 570n.

Figure 62:
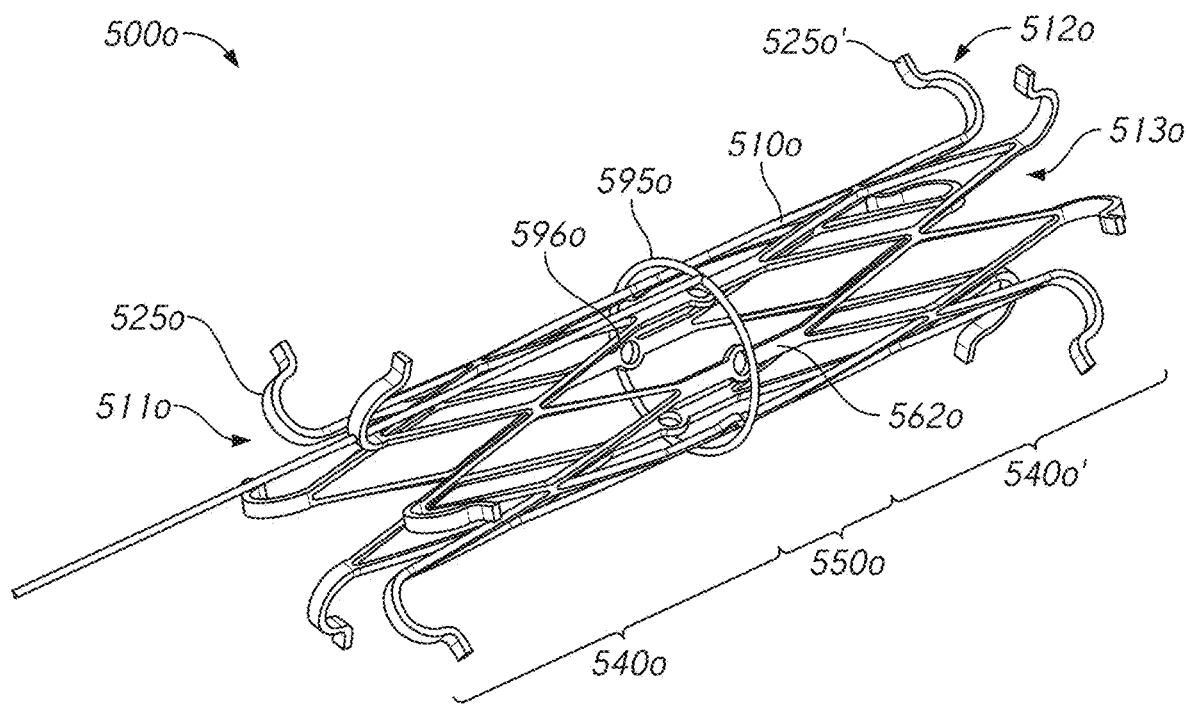
FIG. 62 illustrates an implementation of anchors of an implant of an implantable flow restriction system in accordance with some aspects of this disclosure.

FIG. 62 illustrates another implementation of an 500o. FIG. 62 shows a perspective view of the implant 500o in an unactuated state (e.g., non-occluding/non-restricting state). The implant 500o can be similar to and/or incorporate any of the features described with respect to implant 500n and the other implants described herein. As shown, the implant 500o can comprise an expandable body 510o having a proximal end 511o, a distal end 512o, and a lumen 513o for receiving blood flow therethrough. The implant 500o can include a radial support portion 540o, a flow restrictor portion 550o, and a radial support portion 540o'. Different than the implant 500n, the implant 500o can omit filter portion(s) adjacent its proximal and distal ends. While not shown, the implant 500o can include a material 530o spanning at least the flow restrictor portion 550o. In some implementations a material 530o can span the flow restrictor portion 550o and the radial support portions 540o, 540o'. Similar to the flow restrictor portion 550n of implant 500n, the flow restrictor portion 550o can be configured to occlude/restrict flow by being cinched radially inward via suture or wire 595o. Such suture or wire 595o can wrap around the flow restrictor portion 550o and/or pass through eyelets 596o of struts 562o that make up the flow restrictor portion 550o. While not shown, the implant 500o can connect to tubing 570o at its proximal end 511o. Such tubing 570o can connect to the implant 500o at a position along a circumference of the implant 500o (e.g., at a side of the implant 500o). The suture or wire 595o can extend from around the flow restrictor portion 550o and through the tubing 570o to connect to the actuator of the controller 50 for actuation of the implant 500o. In some implementations, the suture or wire 595o can connect to a shaft 590o that extends through the tubing 570o such as described herein for other implementations for actuation of the implant 500o. In such implementations, a collapsible and extendible coupling 580o similar to other collapsible and extendible couplings described herein can be used to fluidically seal the shaft 590o with the tubing 570o. As shown in FIG. 62, the implant 500o can include anchors 525o and 525o' at proximal and distal ends thereof, respectively. The anchors 525o and 525o' can have a hook-like configuration to facilitate anchoring the implant 500o in a vessel. In some implementations, the implant 500o or features thereof can be used as or incorporated into a shunt (e.g., a pulmonary artery to azygos vein shunt as described in U.S. Provisional Patent Application No. U.S. 63/331,496 incorporated by reference herein).

Figure 63:
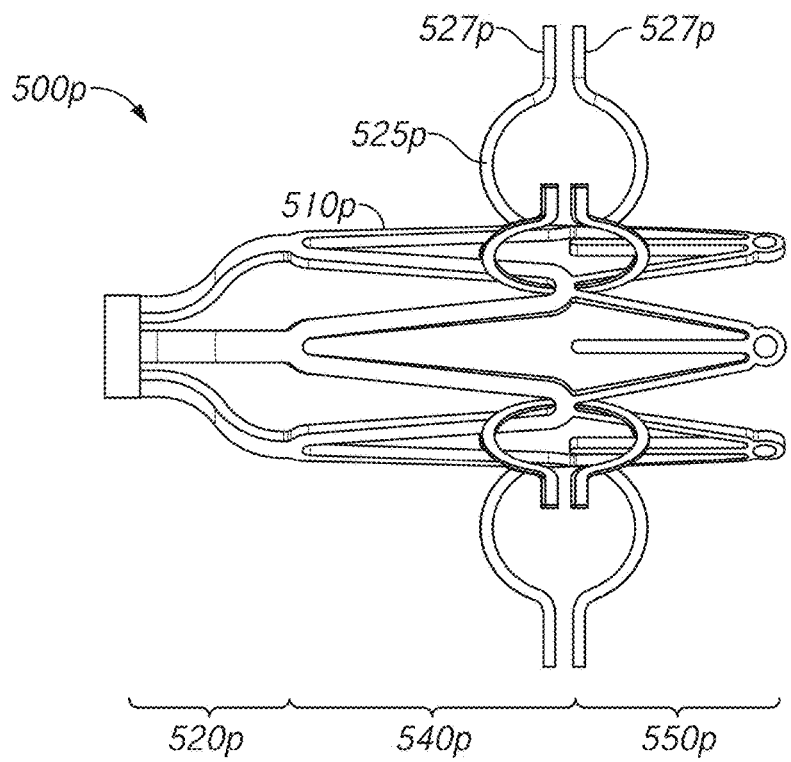
FIG. 63 illustrates an implementation of an implant of an implantable flow restriction system in accordance with some aspects of this disclosure.

FIG. 63 illustrates an implementation of anchors 525p of an implant 500p of an implantable flow restriction system 5. The implant 500p can be the same or similar to implant 500a described herein except for the configuration of the anchors 525p. As shown, the anchors 525p can have a circular configuration with a break in such circle to allow the anchors 525p to pass over and accept within such circle at least a portion of the expandable frame 510p of the implant 500p. For example, the anchors 525p are shown accepting a portion of the expandable frame 510p where the radial support portion 540p and the flow restrictor portion 550p meet, however the anchors 525p can be located along and/or accept any portion of the implant 500p. Also shown in FIG. 63, at the break in the circular configuration of the anchors 525p, the anchors 525p can have portions 527p that extend generally outward from such circle and substantially in the same plane as such circle. Such portions 527p can extend generally parallel with one another as shown, or they can extend at angles to one another. Such portions 527p can facilitate anchoring of the implant 500p in a vessel or shunt.

Figure 64A:
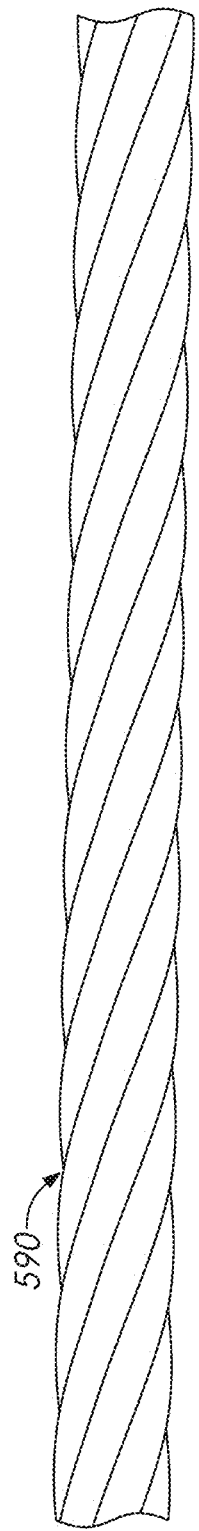
FIGS. 64A-64B illustrate an implementation of a shaft of an implantable flow restriction system in accordance with some aspects of this disclosure.
Figure 64B:
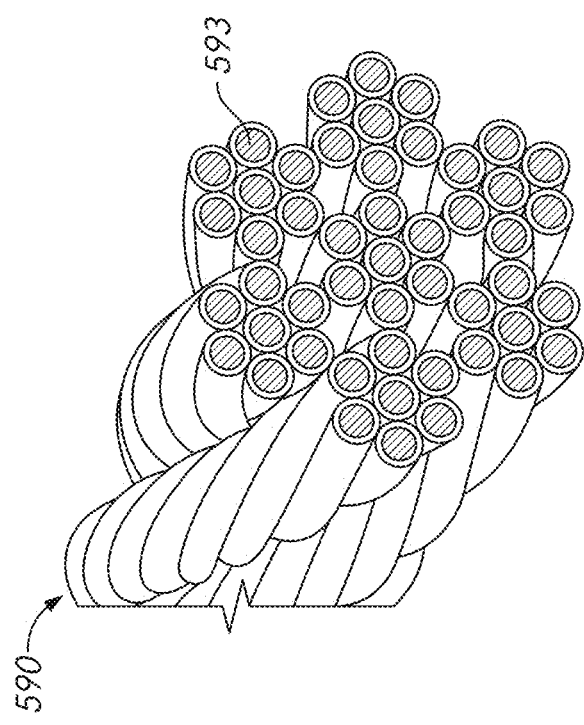

FIGS. 64A-64B illustrate an implementation of the shaft 590 of the implantable flow restriction systems 5 described herein. The shafts described below can be used in connection with any of the implants described herein. FIG. 64A shows a side view and FIG. 64B shows a perspective cross-sectional view of the shaft 590. As shown, the shaft 590 (which can also be referred to as a "wire" or "cable" herein) can have a braided structure comprising a plurality of individual wires 593. In some implementations, a plurality of individual wires 593 can be twisted upon one another to form a bundle, and the shaft 590 can be made of a plurality of such bundles twisted upon one another. In some implementations, the shaft 590 can be made of a single wire, a rod, a hypotube, or a laser cut hypotube depending on the application. For example, for flow restrictions systems that actuate via the shaft pulling on a portion of an implant to actuate a flow restrictor thereof, the shaft can be configured for tension and may have a form the same as or similar to that shown in FIGS. 64A-64B. As another example, for flow restrictions systems that actuate via the shaft pushing on a portion of an implant to actuate a flow restrictor thereof, the shaft can be configured for compression. In another example, for flow restriction systems that actuate via the shaft rotating, the shaft can be configured for rotation. In some implementations, one or more wires 593 of the shaft 590 can be configured to transmit power and/or signals to and/or from one more sensors 600 of a flow restriction system 5. The shaft 590 can be flexible and in some implementations have a lubricious coating or have a lubricious surface to facilitate sliding movement within tubing 570 as described herein. Furthermore, the shaft 590 can be made of biocompatible material (e.g., stainless steel).

Figure 65:
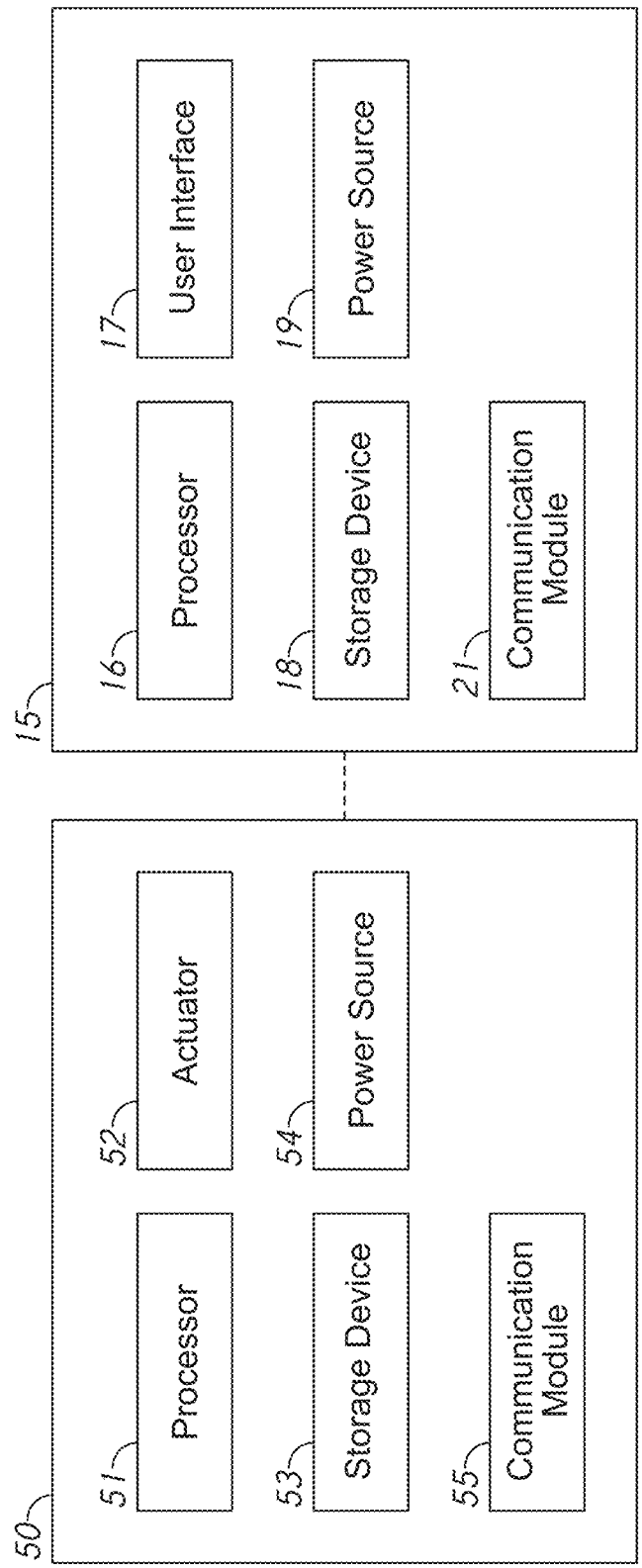
FIG. 65 illustrates a schematic diagram of certain features of an implantable controller and an external device of an implantable flow restriction system in accordance with some aspects of this disclosure.

FIG. 65 illustrates a schematic diagram of certain features which can be incorporated in the implantable flow restriction system 5 as well as any other implementations of the implantable flow restriction systems described herein. As shown, an implantable controller 50 of the implantable flow restriction system 5 can include a processor 51, an actuator 52, a storage device 53, a power source 54, and/or a communication module 55. Also shown, an external device 15 used to operate the implantable flow restriction system 5 can include a processor 16, a user interface 17, a storage device 18, a power source 19, and a communication module 21. In some implementations, the external device 15 can be a mobile phone, a tablet, a handheld or mobile device, or otherwise.

The processors 51 and 16 can be configured, among other things, to process data, execute instructions to perform one or more functions, and/or control the operation of the controller 50 and the external device 15, respectively. For example, the processor 51 can control operation of the actuator 52 and the sensor(s) 600 of the chronic, implantable flow restriction system 5. As another example, the processor 51 can process signals and/or data received and/or obtained from the sensor(s) 600 of the implantable flow restriction system 5. Further, the processor 51 can execute instructions to perform functions related to storing and/or transmitting such signals and/or data received and/or obtained from the sensor(s) 600 of the implantable flow restriction system 5 (e.g., such as transmitting such signals and/or data to external device 15). The processor 51 can execute instructions to perform functions related to storing and/or transmitting any or all of such received data.

The storage devices 53 and 18 can include one or more memory devices that store data, including without limitation, dynamic and/or static random access memory (RAM), programmable read-only memory (PROM), erasable programmable read-only memory (EPROM), electrically erasable programmable read-only memory (EEPROM), and the like. Such stored data can be processed and/or unprocessed data obtained from the implantable flow restriction system 5, for example.

The communication modules 55 and 21 can facilitate communication (e.g., via wireless connection) between the implantable flow restriction system 5 (and/or components thereof, such as controller 50) and external device 15 as well as other separate devices, such as separate monitoring, computing, electrical, and/or mobile devices. For example, the communication module 55 can be configured to allow the implantable flow restriction system 5 to wirelessly communicate with external device 15 and/or other devices, systems, and/or networks over any of a variety of communication protocols. The communication modules 55 and 21 can be configured to use any of a variety of wireless communication protocols, such as Wi-Fi (802.11x), Bluetooth®, ZigBee®, Z-Wave®, cellular telephony, infrared, near-field communications (NFC), RFID, satellite transmission, proprietary protocols, combinations of the same, and the like. The communication module 55 can allow data and/or instructions to be transmitted and/or received to and/or from the implantable flow restriction system 5 and separate computing devices, such as the external device 15. The communication module 55 can be configured to transmit (for example, wirelessly) processed and/or unprocessed data (e.g., data from sensor(s) 600) and/or other information to one or more separate computing devices, which can include, among others, external device 15, a patient monitor, a mobile device (for example, an iOS or Android enabled smartphone, tablet, laptop), a desktop computer, a server or other computing or processing device for display and/or further processing, among other things. Such separate computing devices can be configured to store and/or further process the received data and/or other information, to display information indicative of or derived from the received data and/or information, and/or to transmit information—including displays, alarms, alerts, and notifications—to various other types of computing devices and/or systems that can be associated with a hospital, a caregiver (for example, a primary care provider), and/or a user (for example, an employer, a school, friends, family) that have permission to access the patient's data. As another example, the communication module 55 of the controller 50 of the implantable flow restriction system 5 can be configured to wirelessly transmit processed and/or unprocessed obtained data, information and/or other information (for example, a status of actuation of an implant 500) to a mobile phone which can include one or more hardware processors configured to execute an application that generates a graphical user interface displaying information representative of the processed or unprocessed data, information and/or other information obtained from the implantable flow restriction system 5. The communication modules 55 and 21 can be and/or include a wireless transceiver.

The power sources 54 and 19 can provide power for hardware components of the implantable flow restriction system 5 and the external device 15, respectively, described herein. For example, the power source 54 of the controller 50 can provide power to the sensor(s) 600, the communication module 55, the processor 51, and the actuator 52. In some implementations, the power source 54 can comprise a battery, an induction receiver/rectifier, or both. The power source 19 can comprise a battery. In some implementations, the external device 15 can also include an induction transmitter to wirelessly transmit power to an induction receiver/rectifier of the implantable flow restriction system 5 (e.g., of the controller 50) if included. Any of such batteries can be rechargeable. For example, such batteries can be a lithium, a lithium polymer, a lithium-ion, a lithium-ion polymer, a lead-acid, a nickel-cadmium, or a nickel-metal hydride battery. In some implementations, such batteries can be non-rechargeable.

The actuator 52 of the controller 50 of the implantable flow restriction system 5 can be configured to move shaft 590 within tubing 570 for actuation of flow restrictor 560 and/or flow restrictor portion 550 of implant 500 (which can include any of the implants described herein). For example, the actuator 52 can be configured to slidingly move shaft 590 proximally and/or distally relative to the tubing 570 and implant 500. As another example, the actuator 52 can be configured to rotationally move shaft 590 relative to the tubing 570 and the implant 500. Furthermore, the actuator 52 can be configured to cause flow restrictor 560 and/or flow restrictor portion 550 of implant 500 to occlude/restrict flow through the implant 500 in a range of from and including about 0% to about 100%.

The user interface 17 of the external device 15 can be configured to allow a patient or their care provider to interact with the external device 15 for control of the implantable flow restriction system 5. The user interface can include button(s), a touch screen, and/or a microphone to accept physical touch and/or verbal input/commands.

FIGS. 66A-66C illustrate an implementation of a connector 700 between components of a flow restriction system 5. The connector 700 can be configured, for example, to releasably connect a proximal end 592 of the shaft 590 to the actuator 51 of the controller 50. As shown in FIG. 66A, the connector 700 can include a first component 710 and a second component 720 configured to releasably connect with one another via complementary features. Such first component 710 and second component 720 can be secured to the proximal end 592 of the shaft 590 and the actuator 51, respectively, or vice versa. The first component 710 be configured as a cylinder and can have a circular recess 712 at one of its ends and a protrusion extending radially inward into the recess 712 that is marked visually by point 714 located on an external surface of the first component 710. The second component 720 can be configured as a cylinder and can have a circular rod-like protrusion 722 extending from one of its ends sized to fit within the recess 712 of the first component 710. Furthermore, the protrusion 720 can have a slot 724 configured to receive the protrusion extending radially inward into the recess 712 of the first component 710. As shown in FIGS. 66A-66B, the slot 724 can extend in a longitudinal direction from the end of the protrusion 722 then turn about 90 degrees or more so that, upon alignment of the slot 724 with the point 714 and upon full insertion of the protrusion 722 into recess 712, the first component 710 and the second component 720 can be rotated in a first direction relative to one another to secure the first component 710 and the second component 720 together (e.g., the first and second components can stay connected via interaction between the protrusion of the first component 710 and the slot 724 of the second component 720). FIG. 66C shows how to release the first component 710 from the second component 720, which can include pressing the first component 710 and the second component 720 together, rotating the first component 710 and the second component 720 relative to one another in a second direction that is opposite the first direction, and then separating the first component 710 and the second component 720 from one another.

FIGS. 67A-67B illustrate a variant 700' of the connector 700. Like the connector 700, the connector 700' can be configured to releasably connect a proximal end 592 of the shaft 590 to the actuator 51 of the controller 50. As shown in FIG. 67A, the connector 700' can include a first component 710' and a second component 720' configured to releasably connect with one another via complementary features. The first component 710' can be configured as a cylinder and can have a circular recess 712' at one of its ends similar to the first component 710. Instead of a protrusion and point 714 marking the location of such protrusion, the first component 710' can include a slot 714' through a wall of the first component that extends longitudinally from the end of the first component 710' having the recess 712' then turns about 90 degrees or more. The second component 720' can be configured as a cylinder 722' sized to fit within the recess 712' of the first component 710' and can have a circular rod-like protrusion 724' extending radially outward from its external surface configured to fit within the slot 714'. To connect the first component 710' and the second component 720' to one another, the cylinder 722' can be inserted fully into the recess 712' with the protrusion 724' aligned with the slot 714' and the first component 710' and the second component 720' can be rotated in a first direction relative to one another (e.g., the first and second components can stay connected via interaction between the slot 714' of the first component 710' and the protrusion 724' of the second component 720'). To release the first component 710' from the second component 720', the first component 710' and the second component 720' can be pressed together and rotated relative to one another in a second direction that is opposite the first direction, then the first component 710 and the second component 720 can be separated from one another.

FIGS. 68A-68D illustrate an implementation of a connector 750 between components of an implantable flow restriction system 5. The connector 750 can be configured, for example, to releasably connect and fluidically seal a proximal end 572 of the tubing 570 to the controller 50 (e.g., to a housing of the controller 50). For this, the connector 750 can extend from the controller 50 (e.g., extend from the housing of the controller 50). FIG. 68A shows the tubing 570 separated from the connector 750 but in a position for connecting thereto, FIG. 68B shows a side view of a portion of the connector 750, FIG. 68C shows an end view of the connector 750, and FIG. 68D shows a cross-sectional side view of the connector 750. The connector 750 can have a main body 751 having a generally cylindrical shape with a lumen 753 extending therethrough. The connector 750 can include a first component 760 having a longitudinal through hole 762 configured to receive the proximal end 572 of tubing 570 and a second component 770 configured to receive the first component 760 (e.g., shown in FIG. 68D). Both the first and second components 760, 770 can be received by the main body 751. A proximal end of the second component 770 can include a plurality of radially inward extending arms 772 configured to bias the first component 760 in a direction distally away from the second component 770. Such arms 772 can also be configured to grab onto an external surface of the tubing 570 when the tubing 570 is inserted into the connector 750. To connect and fluidically seal the tubing 570 with the connector 750, the proximal end 572 of tubing 570 can be inserted fully into the connector 750 via the through hole 762 of the first component 760 until it cannot be inserted any further. A fluidic seal can be made between the tubing 570 and the connector 750 via a third component 780 configured as a circumferential ring within the main body 751 located proximal to the first and second components 760, 770. In such fully inserted position, the arms 772 of the second component 770 can grab onto the external surface of the tubing 570 and prevent it from releasing from the connector 750. To release the connection between the tubing 570 and the connector 750, the first component 760 can be pressed inward into the connector 750 (e.g., pressed proximally into the connector 750), causing a proximal end of the first component 760 to radially expand the arms 772 and release them from the tubing 570, while the tubing 570 is pulled out of the connector 750 (e.g., moved distally relative to the connector 750).

FIGS. 69A-69B illustrate an implementation of an implant assembly 501 comprising the implant 500, tubing 570, and shaft 590 having an extender 800 to aid in implantation of the implant assembly 501. The implant 500, tubing 570, and shaft 590 shown correspond to implant 500a, tubing 570a, and shaft 590a described herein, although in some implementations they can be any of the implants described herein. The extender 800 can comprise a flexible tube that attaches to the tubing 570 adjacent its proximal end 572 and extends proximally therefrom. For example, the extender 800 can comprise PEBAX that is reflowed on tubing 570. In some implementations, the extender 800 is a proximal continuation of the tubing 570. The extender 800 can advantageously provide the care provider that is implanting the implant assembly 501 a component that can be grasped outside the body to aid in positioning and handling of the implant assembly 501 during its implantation in the patient. As shown in the magnified view of FIG. 69B, the extender can be cut at cutline 803 and removed from the implant assembly 501 (e.g., by sliding it proximally) when no longer needed. In some implementations, the extender 800 is configured to peel away from the implant assembly 501 at cutline 803. Once the extender 800 is removed, the proximal end 572 of tubing 572 can coincide with the cutline 803. Also shown in FIGS. 69A-69B is a device 850 for testing function of the implant 500, which can extend proximally through the extender 800 and which will be described with respect to FIGS. 70A-70B, FIGS. 71A-71B, and FIG. 72.

FIGS. 70A-70B illustrate an implementation of a device 850 for testing function of the implant 500 during implantation thereof. As shown, the device 850 can releasably connect to the proximal end 591 of the shaft 590 for pulling and/or pushing the shaft 590 to actuate flow restrictor 560 and/or flow restrictor portion 550 of implant 500. For this, the device 850 can include one of the components of the connector 700 described herein, such as first component 710 as shown, to releasably connect with the other of the components of the connector 700, such as the second component 720 shown attached to the proximal end 592 of shaft 590. In some implementations, the device 850 can include the second component 720 of the connector 700 and the shaft 590 can have the first component 710 attached thereto. FIG. 70A shows the device 850 connected to the shaft 590, whereas FIG. 70B shows the device 850 disconnected from the shaft 590. To facilitate pulling and/or pushing the shaft 590 via device 850, the device 850 can include a proximal extension 855. As shown in FIGS. 70A-70B, the proximal extension 855 can comprise suture. In a variant 850' of the device 850 such as is shown in FIGS. 71A-71B, the proximal extension 855' can comprise a shaft. In some implementations, the proximal extension 855, 855' can comprise a wire, a rod, a hypotube, or a laser cut hypotube depending on the needs of the application (e.g., depending on the need to pull or push on the shaft 590 for testing actuation of the flow restrictor 560 and/or flow restrictor portion 550 of implant 500). Alternatively, or in addition, to testing function of the implant 500, the device 850, 850' can also be used to aid in removal of the implant 500 if needed. For example, to remove an implant 500 from a patient, the implantable controller 50 can be disconnected from the shaft 590 and tubing 570, the device 850, 850' can be connected to the shaft 590, a sheath can be slid over the device 850, 850' and distally over the shaft 590 and tubing 570 in the body, the sheath can be slid over the implant 500 and cause it to collapse within the sheath, and then the sheath with the implant 500, shaft 590, and tubing 570 therein can be retracted proximally from and out of the patient. The device 850, 850' can advantageously provide a working length to aid in removal of the implant assembly 501 out of the body.

Figure 72:
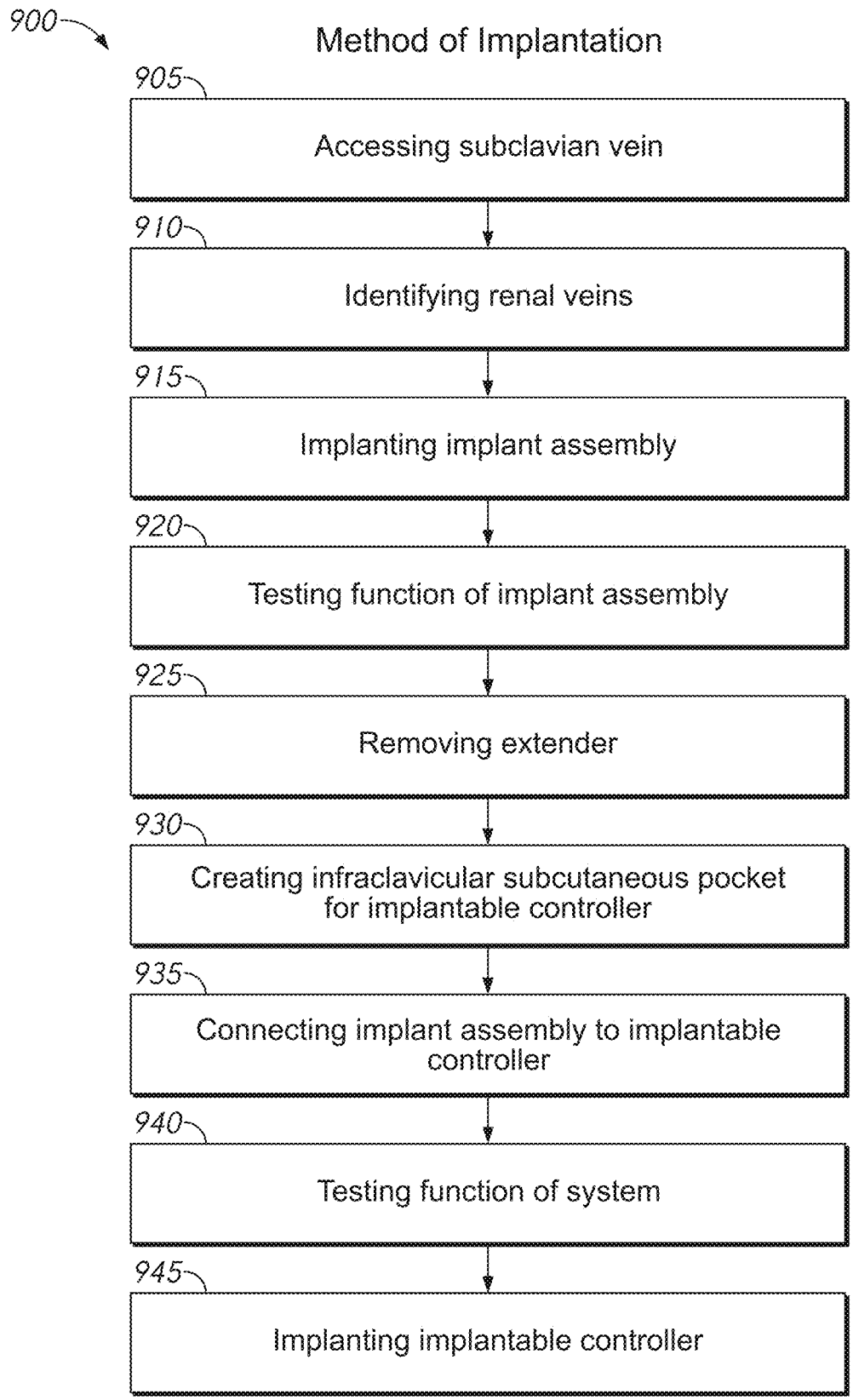
FIG. 72 illustrates a method of implanting an implantable flow restriction system in accordance with some aspects of this disclosure.

FIG. 72 illustrates a method 900 of implanting an implantable flow restriction system 5. The method 900 can be applied to any of the implementations of the implantable flow restriction systems 5 and components thereof described herein. Furthermore, the method 900 can include other steps and/or omit steps. The method 900 can be performed in a cardiac catheterization lab under local or general anesthesia and can be performed in a minimally invasive manner.

The method 900 can include the step 905 of accessing a subclavian vein of the patient. The access point to the subclavian vein, which can be the right or left subclavian vein, can be made at or near the junction of the middle and inner thirds, where the first rib and the clavicle are joined. The subclavian vein can be blindly punctured or under imaging guidance. Once access to the subclavian vein is made, a guide wire can be advanced through the subclavian vein, through the superior vena cava (SVC), through the right atrium, and into the inferior vena cava (IVC). A delivery sheath (which can also be referred to as a "delivery catheter herein") with dilator can be placed into the subclavian vein over the guide wire and into the IVC.

The method 900 can optionally include the step 910 of identifying the renal veins. Identifying the renal veins can be performed via fluoroscopy and intravascular dye via the delivery sheath during implantation, or it can be performed prior to implantation via CT imaging. With the renal veins identified, the distal end of the delivery sheath can be placed in the IVC below the renal veins (e.g., in the IVC upstream of its connection to the renal veins) and the dilator can be removed from the delivery sheath.

The method 900 can include the step 915 of implanting the implant assembly 501. In other words, the step 915 can include implanting the implant 500 connected to tubing 570 and shaft 590. For this, the implant assembly 501 can be inserted into the delivery sheath and delivered into the IVC with the implant 500 being positioned below the renal veins. To aid in delivery and handling of the implant assembly 501, the extender 800 can be optionally attached to the implant assembly 501 as described with respect to FIGS. 69A-69B. Repositioning of the implant 500 can be performed if needed.

Once the implant 500 has been deployed out the distal end of the delivery sheath, the method 900 can optionally include the step 920 of testing function of the implant assembly 501. For this, the device 850 for testing function of the implant 500 as described with respect to FIGS. 70A-70B and FIGS. 71A-71B can be utilized to actuate the implant 500 and test its function (e.g., the flow restrictor 560 and/or flow restrictor portion 550 of the implant 500 can be actuated via the device 850 to at least partially occlude flow through the implant 500). If the functional test is a success the delivery sheath can be removed proximally from the implant assembly 501 leaving the implant assembly 501 in place in the patient. If the functional test is not successful, the implant 500 can be resheathed within the delivery sheath (e.g., by distal movement of the delivery sheath over the implant 500 and/or pulling the implant 500 proximally relative to the delivery sheath) and the implant assembly 501 removed from the patient.

Where used, the method 900 can include the step 925 of removing the extender 800. This can be performed by either cutting the extender at cutline 803 or peeling it away at cutline 803 as described with respect to FIGS. 69A-69B. The device 850 for testing function of the implant 500 can also be removed.

The method 900 can include the step 930 of creating an infraclavicular subcutaneous pocket for the implantable controller 50 of the system 5.

The method 900 can include the step 935 of connecting the implant assembly 501 to the implantable controller 50. For this, the shaft 590 can be connected to the actuator 51 of the controller 50 as described with respect to FIGS. 66A-66C and FIGS. 67A-67B. Additionally, the tubing 570 can be connected to the controller 50 as described with respect to FIGS. 68A-68D.

The method 900 can include the step 940 of testing function of the implantable flow restriction system 5. For this, the external device 15 can be used to test operation of the implant 500.

With confirmation that the external device 15 can successfully operate the system 5, the method 900 can include the step of implanting the implantable controller 50. For this, the implantable controller 50 can be inserted into the subcutaneous pocket made in step 930. Closure can be performed and the implantation procedure concluded.

In some implementations, vascular access can be made via a femoral vein, a radial vein, or any of the veins shown in FIG. 42. Depending on the location of vascular access, the implantable controller 50 can be implanted in locations other than described in method 900. Furthermore, depending on the location of vascular access, the implant 500 can be configured as described with respect to implant 500a, or it can have a reverse configuration (e.g., with the flow restrictor 560 flipped and configured to be operated by push of shaft 590 rather than pull of shaft 590).

FIGS. 73A-73D illustrate deployment of implant 500 of an implantable flow restriction system 5 out a distal end 1002 of a delivery sheath 1000. The deployment of the implant 500 described with respect to FIGS. 73A-73D can be applicable to any of the implementations of the implants described herein.

Figure 73:
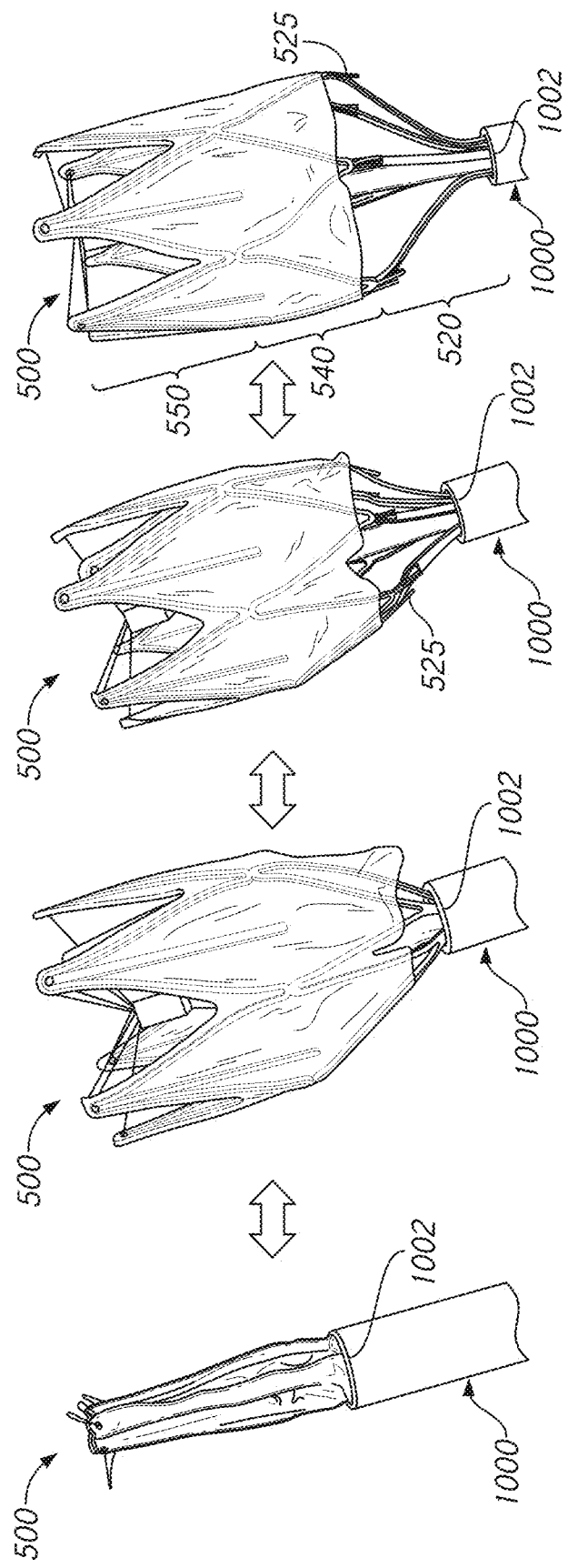
FIGS. 73A-73D illustrate deployment of an implant of an implantable flow restriction system in accordance with some aspects of this disclosure.

As shown in FIG. 73A, distal movement of the implant 500 relative to the distal end 1002 of the delivery sheath 1000 can lead to the implant 500 extending out the distal end 1002 of the delivery sheath 1000. Such relative movement can occur by maintain the position of the implant 500 and proximally retracting the delivery sheath 1000, by maintaining the position of the delivery sheath and distally extending the implant 500 therefrom, or both. Advantageously and as shown in FIG. 73A, the implant 500 can remain collapsed upon itself while extending distally past the distal end 1002 of the delivery sheath 1000 due to the configuration of the expandable frame 510 of the implant 500. Such configuration can facilitate implant repositioning if needed. For example, the implant 500 can remain collapsed upon itself while at least a portion of the radial support portion 540 remains inside the delivery sheath 1000.

FIGS. 73B-73C show progressive radial expansion of the implant 500 upon continued distal extension of the implant 500 past the distal end 1002 of the delivery sheath 1000. As shown, partial radial expansion of the implant 500 can occur once a majority of the filter portion 520 has extended distally past the distal end 1002 of the delivery sheath 1000. Advantageously and as shown in FIG. 73C, the anchors 525 can maintain a tucked position (e.g., extending at least partially radially inward) while the implant 500 is in a partially expanded state. Such configuration of the implant 500 can aid in repositioning of the implant 500 within a vessel if needed and/or retraction of the implant 500 back within the delivery sheath 1000 if needed.

FIG. 73D shows full deployment of the implant 500 out the distal end 1002 of the delivery sheath. Upon being fully deployed, the implant 500 can attain its fully expanded state as shown. In such state, the anchors 525 can assume their generally longitudinally oriented position to help anchor the implant 500 within a vessel. Advantageously, the implant 500 can be configured to be retrieved and retracted back within the delivery sheath 1000 even after full deployment therefrom due to the configuration of the filter portion 520 that can cause the proximal end of the implant 500 as well as the anchors 525 to tuck radially inward upon proximal retraction.

Figure 74:
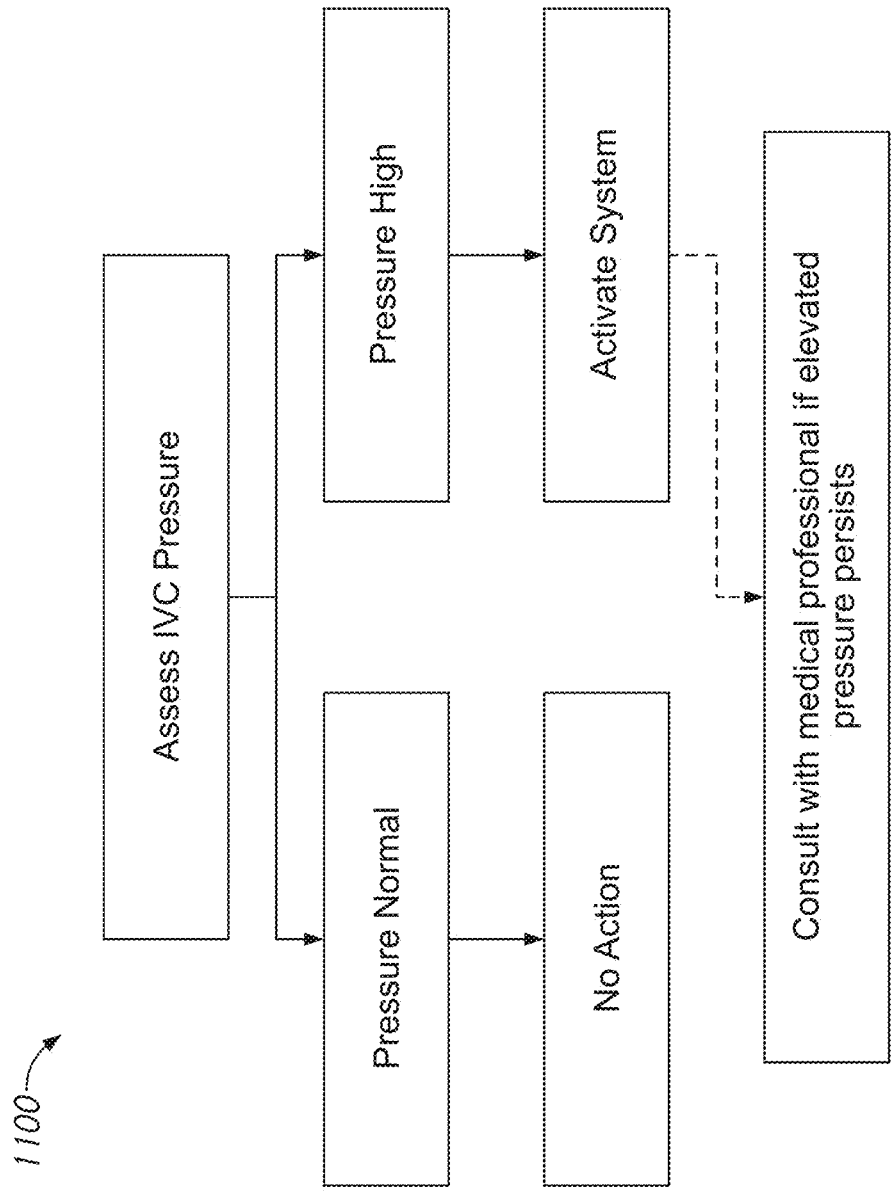
FIG. 74 illustrates a guideline for treatment of a patient using an implantable flow restriction system in accordance with some aspects of this disclosure.

FIG. 74 illustrates a guideline 1100 for treatment of a patient using the implantable flow restriction system 5 described herein. In some implementations, the guideline 1100 can apply to any of the flow restriction systems described herein. The guideline 1100 can include assessing the IVC pressure of the patient. If the IVC pressure is determined to be normal, no action may be required by the system 5 as shown. Normal IVC pressure can be a pressure of between about 0 mmHg and about 8 mmHg. If the IVC pressure is determined to be high, the system 5 can be activated as shown. High IVC pressure can be a pressure of greater than about 8 mmHg. The IVC pressure can be measured by the system 5 via sensor(s) 600. Furthermore, activation of the system can occur via the external device 15 as described herein (e.g., digital, wireless activation). If the IVC pressure remains high after activation of the system 5, a patient can be recommended to consult with their medical professional/care provider.

Figure 77:
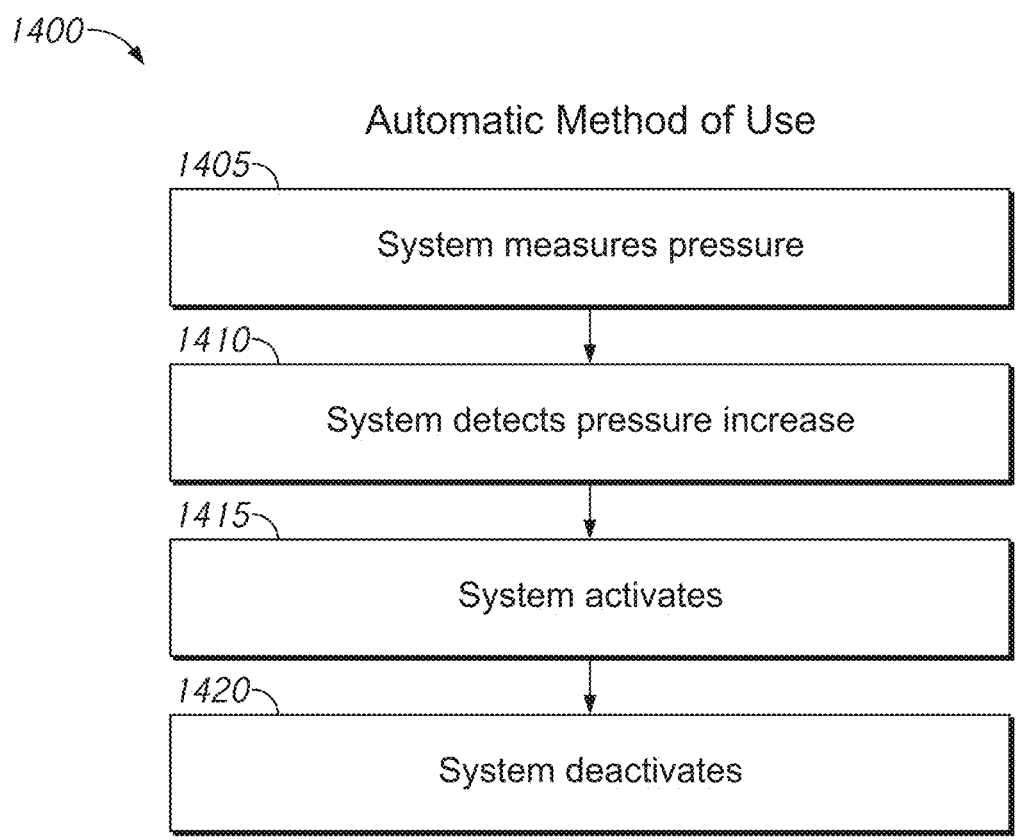
FIG. 77 illustrates an automatic method of using an implantable flow restriction system in accordance with some aspects of this disclosure.

FIGS. 75-77 illustrate various methods of using the implantable flow restriction system 5 described herein. The methods described with respect to FIGS. 75-77 can be adapted to any of the flow restriction systems described herein. Furthermore, while the methods described with respect to FIGS. 75-77 are described using sensor(s) 600 connected to the implant 500, the system 5 can include other sensors proximate the implant 500 and/or remote from the implant 500 for pressure determination(s) and control of the system 5 (e.g., such as sensors described with respect to FIG. 41 and elsewhere herein). Additionally, while the methods described with respect to FIGS. 75-77 have been described as being performed by a patient having the system 5 implanted, any steps of such methods can be performed by a medical professional/care provider of the patient or an authorized user.

FIG. 75 illustrates a manual method 1200 (which can also be referred to as a "patient driven method") of using an implantable flow restriction system 5. Furthermore, the method 1200 can include other steps and/or omit steps.

The manual method 1200 can include a step 1205 of requesting a pressure measurement (e.g., a renal venous pressure measurement or a femoral venous pressure measurement). Such a request can be made by the patient using the external device 15 or other separate electronic device as described herein (e.g., via wireless communication with the system 5).

The manual method 1200 can include a step 1210 of the system 5 measuring the pressure based on the request from step 1205. Such pressure measurement can be measured via the sensor(s) 600 of the system 5. For this, the processor 51 of controller 50 can be operably connected to the pressure sensor(s) 600 and configured to receive and process a signal from the pressure sensor(s) 600 to determine the pressure (e.g., of the patient's vasculature). For example, an implant 500 that is implanted in the IVC upstream of the renal veins having a sensor 600 connected thereto can be used to measure an IVC pressure, a renal venous pressure, and/or a femoral venous pressure (e.g., as described with respect to FIGS. 48A-48C). In other words, an IVC pressure, a renal venous pressure, and/or a femoral venous pressure can be measured from the implant 500.

The manual method 1200 can include a step 1215 of the system 5 detecting a pressure increase. For example, the system 5 can compare the pressure measured in step 1210 to a previously measured pressure and/or to a pressure value in memory (e.g., in storage device 53) to determine if the pressure has increased and/or is elevated/high. Determination of a high pressure can be performed according to the guideline 1100.

The manual method 1200 can include a step 1220 of the system 5 notifying the patient of a pressure increase if detected in step 1215. For this, the system 5 (e.g., the controller 50) can transmit to the external device 15 an indication that the pressure has increased. Such pressure can include the IVC pressure, the renal venous pressure, and/or the femoral venous pressure. Furthermore, the step 1220 can include notifying the patient, via external device 15, that the pressure has increased and/or is elevated/high. This can include receiving, from the external device 15, an instruction to activate the implant 500.

The manual method 1200 can include a step 1225 of activating the system 5, such as by the patient. For this, the patient can interact with the external device 15 (e.g., via user interface 17) to cause actuation of the implant 500. Actuation of the implant 500 can include actuation of flow restrictor 560 and/or flow restrictor portion 550 as described herein, which can at least partially occlude the lumen 513 of the implant 500. Furthermore, actuation of the implant 500 can at least partially occlude the flow of blood through a vessel in the patient's vasculature. For example, for an implant 500 implanted in the IVC below the renal veins of the patient, activating the implant 500 can cause the implant 500 to at least partially occlude blood flow through the IVC.

The manual method 1200 can include a step 1230 of deactivating the system 5. Deactivation of the system 5 can include returning the implant 500 to its unactivated, non-occluding/non-restricting state as described herein. Such deactivation can occur manually, semi-automatically, or automatically. For example, the system 5 can remain activated until deactivated by interaction with external device 15. As another example, the system 5 can notify the patient that therapy is complete and present a notification to deactivate the system 5. Such notification can occur similar to the notification of pressure increase described in step 1220. In another example, the system 5 can remain activated for a duration of time, and the system 5 can deactivate after such duration of time has passed. In yet another example, the system 5 can remain activated for as long as the pressure remains elevated/high, which can include periodic measurements of the pressure for such determination.

FIG. 76 illustrates a semi-automatic method 1300 (which can also be referred to as a "auto-sense with patient activation") of using an implantable flow restriction system 5. Furthermore, the method 1200 can include other steps and/or omit steps. The method 1300 can be similar to the method 1200 in many respects. For example, the method 1300 can include steps 1305, 1310, 1315, 1320, and 1325 that are the same as the steps 1210, 1215, 1220, 1225, and 1230 of method 1200, respectively. Different than the manual method 1200, the semi-automatic method 1300 can omit the step 1205 of requesting a pressure measurement. In the semi-automatic method 1300 without such a request for a pressure measurement, the system 5 can automatically measure pressure via the system 5. Such automatic pressure measurement can occur based on a predetermined schedule or time interval, which can be the same or different depending on the time of day, the patient, or other factors of the patient. The method 1300 can be referred to semi-automatic in that the system 5 must be activated in step 1320.

FIG. 77 illustrates an automatic method 1400 (which can also be referred to as a "closed loop" or "fully closed loop") of using an implantable flow restriction system 5. The method 1400 can be similar to the method 1300 in many respects. For example, the method 1400 can include steps 1405, 1410, 1415, and 1420 that are the same as the steps 1305, 1310, 1320, and 1325 of method 1300, respectively. Different than the semi-automatic method 1300, the automatic method 1400 can omit the step 1320 of the system being activated by the patient. In the automatic method 1400 without such a need to be activated by the patient, the system 5 can automatically activate to provide therapy.

FIGS. 78A-78C illustrate an implementation of delivering therapy using the implantable flow restriction system 5 described herein. The delivery of therapy using the system 5 described with respect to FIGS. 78A-78C can apply to any of the methods described with respect to FIGS. 75-77. FIGS. 78A-78C show the implant 500 of system 5 in the IVC of a patient below the renal veins. As indicated in FIG. 78A, the system 5 has detected an increased or elevated/high IVC pressure, renal venous pressure, and/or femoral venous pressure. Concomitant with the increased or elevated/high renal venous pressure, urine production may be reduced. Depending on the method of use, the system 5 can be activated manually, semi-automatically, or automatically. When activated, the implant 500 can at least partially occlude/restrict blood flow in the IVC as described herein and as shown in FIG. 78B (wherein the implant 500 is shown in an occluding/restricting state). By such placement of the implant 500 in the IVC, when activated the system 5 can reduce renal pressure (e.g., reduce renal venous pressure). Such a reduction in renal pressure can increase urine production of the patient (e.g., enhance/increase diuresis). Also, when activated the system 5 can increase femoral pressure (e.g., femoral venous pressure). The system 5 can be deactivated as shown in FIG. 78C. When deactivated, the implant 500 can assume its substantially non-occluding/non-restricting state and not substantially block/restrict blood flow therethrough. In other words, in the deactivated state the implant 500 may not substantially block/occlude/restrict blood flow in the IVC. Such deactivation can decrease femoral pressure while not substantially affecting renal pressure or urine production (e.g., renal pressure and urine production may normalize upon deactivation of the system 5).

Any portions of the implants described herein (e.g., filter portion(s) 520, radial support portion(s) 540, and flow restrictor portion(s) 550) can be omitted, duplicated, or connected to one another in different orders. Furthermore, while the flow restrictor portions 550 and/or flow restrictors 560 have been described as having certain orientations with regard to aspects of the implants 500 and/or the flow of blood traveling therethrough, such flow restrictor portions 550 and/or flow restrictors 560 can be oriented in a reverse manner or in other ways than shown. Furthermore, features of the implants described herein can be implemented in any of the implants described herein. Additionally, the while some implants described herein are shown and described as having components for their actuation that are substantially centrally located within their associated lumen (e.g., tubing 570, shaft 590), such implants can be adapted such that such components are located along a circumference or side of the implant to produce an implant having a lumen substantially free of such components.

Although systems, devices, and/or components thereof have been described as having particular orientations and/or locations when implanted within a patient, such orientations and/or locations are not intended to be limiting. For example, while systems, devices, and/or components thereof have been described as extending from the superior vena cava or veins branching therefrom to the inferior vena cava, such systems, devices, and/or components thereof can extend from a femoral vein to the inferior vena cava. For example, while the system 5 has been described as having an implantable controller 50 implanted in an infraclavicular subcutaneous pocket with other portions of the system extending through the superior vena cava and into the inferior vena cava, the implantable controller 50 of system 5 can be adapted for implantation in a subcutaneous pocket in or near the groin of the patient with other portions of the system extending through a femoral vein and into the inferior vena cava. In such implementations, venous access can be through a femoral vein of the patient. Furthermore, in such implementations, the flow restrictor of an implant of such system can be configured similar to or in a reverse manner to the flow restrictor of the implant 500 shown in FIG. 42.

Although systems, devices, and/or components thereof have been described and/or configured for chronic use, any of the systems, devices, and/or components thereof can be configured for acute use and/or used for acutely. For example, in some implementations an implantable controller or actuator as described herein can be positioned outside a patient's body while an implant operably connected thereto is implanted within the patient's vasculature as described herein. In such implementations, an external device may not be required to operate the system, for example, the patient or a user can operate the system via interaction with the controller that resides outside the patient.

Some of the features or advantages encompassed by one or more of the above implementations, or other aspects of the present application, include, but are not limited to, one or more of the following:

- an implant configured to controllably and selectively occlude, restrict and/or divert flow within a patient's vasculature
- a source of actuation configured to actuate the implant
- the implant can be configured to adjustably occlude blood flow in the vasculature in a range of 0 to 100 percent
- the implant can be configured for percutaneous delivery
- the implant can be configured for surgical implantation
- the implant can be positioned intravenously
  - the implant can be biased open and actuated to close
  - the implant can be biased closed and actuated to open
  - the implant can be biased partially closed and configured to open fully when positioned intravenously due to blood flow in the vasculature and actuated to close
  - the implant can comprise an expandable body and a flow restrictor, the expandable body configured to engage an interior wall of a vessel of the patient and position the flow restrictor in a blood flow path of the vessel
  - the implant can comprise an expandable body with a flow restrictor integrally formed therewith
  - the source of actuation can comprise a magnet and the implant can be magnetically actuated
    - the source of actuation can be configured to actuate the implant from outside the patient's body
  - the source of actuation can comprise an electromagnet and the implant can be magnetically actuated
    - the source of actuation can be implanted within the patient and/or located external to the patient
    - the source of actuation can be implanted within a vessel adjacent the vessel in which the occluding element is positioned
    - the source of actuation can be implanted in an interstitial space adjacent the vessel in which the occluding element is positioned
  - the source of actuation can comprise a fluid reservoir connected to the flow restrictor of the implant and the implant can be fluidically actuated
    - the fluid reservoir can connect to the flow restrictor of the implant via tubing
    - the fluid of the fluid reservoir can comprise air and/or a biologically compatible liquid including saline
    - the fluid reservoir can be implanted subcutaneously
      - the fluid reservoir can include a port configured to allow fluid to be removed and/or added to the fluid reservoir for controlling the actuation of the implant
    - compression of the fluid reservoir can actuate the implant
  - the source of actuation can comprise a source of energy configured to actuate the implant via heat
    - the source of energy can comprise ultrasound, microwaves, and/or a magnetic field generator (such as an electromagnet)
    - the implant can include an inductive coil configured to interact with the source of actuation for controlling the occlusion of the implant
  - the source of actuation can comprise an actuator configured to actuate the implant mechanically
  - the implant can be configured to be positioned in an IVC of a patient upstream of the renal veins
    - the implant can be configured to adjustably enhance renal circulation and/or improve diuresis
  - the implant can be configured to be positioned in an IVC of a patient upstream of the hepatic veins
    - the implant can be configured to adjustably enhance hepatic circulation and/or improve liver function
  - the implant can be configured to be positioned in an SVC of a patient upstream of the right atrium
    - the implant can be configured to adjustably decrease cardiac preload, decrease central venous pressure and/or pressure of other veins disclosed herein, and/or increase cardiac output
- the implant can be configured to be positioned extravenously
  - the source of actuation can include a fluid reservoir connected to a flow restrictor of the implant and the implant can be fluidically actuated
    - the fluid reservoir can be fluidically connected to the flow restrictor of the implant via tubing
    - the fluid of the fluid reservoir can comprise air and/or a biologically compatible liquid including saline
    - the fluid reservoir can be implanted subcutaneously
      - the fluid reservoir can include a port configured to allow fluid to be removed and/or added to the fluid reservoir for controlling the actuation of the implant
  - the implant can be configured to be positioned adjacent an outer wall of the IVC of the patient
  - the implant can adjustably compress a portion of an outer wall of the IVC to adjustably occlude blood flow within the IVC Additional Embodiments 1. A chronic, implantable flow restriction system for controllably and selectively occluding, restricting and/ or diverting flow within a patient's vasculature to reduce renal congestion and/or to reduce cardiac preload.
2. The system of any one of the preceding Embodiments, wherein the system is adapted to controllably and selectively reduce central venous pressure or other venous pressure.
3. The system of any one of the preceding Embodiments, wherein the system is adapted to enhance renal circulation.
4. The system of any one of the preceding Embodiments, wherein the system is adapted to enhance or to control diuresis.
5. The system of any one of the preceding Embodiments, wherein the system is adapted to improve cardiac output.
6. The system of any one of the preceding Embodiments, wherein the system is adapted to controllably and selectively occlude or divert flow from the superior vena cava.
7. The system of any one of the preceding Embodiments, wherein the system is adapted to controllably and selectively occlude or divert flow from the inferior vena cava.
8. The system of any one of Embodiments 1-7, wherein the system comprises a magnetically actuated implantable device.
9. The system of any one of Embodiments 1-7, wherein the system comprises a fluidically actuated implantable device.
10. The system of any one of Embodiments 1-7, wherein the system comprises a heat actuated implantable device.
11. The system of any one of Embodiments 1-7, wherein the system comprises a mechanically actuated implantable device.
12. The system of any one of Embodiments 1-7, wherein the system comprises an implantable device configured to be delivered extravenously to at least partially surround or be positioned adjacent to a patient's vein.
13. The system of any one of Embodiments 1-7, wherein the system comprises a mechanical cinching mechanism on an implantable stent.
14. The system of any one of the preceding Embodiments, further comprising a control unit configured to control occluding, restricting and/or diverting flow within the patient's vasculature.
15. The system of Embodiment 14, wherein the control unit is configured to receive readings from one or more pressure sensors positioned within the patient, and wherein the control unit is configured to control occluding, restricting and/or diverting flow within the patient's vasculature based on the readings.
16. The system of any of Embodiments 14-15, wherein therapy delivered by the system is digitally actuated.
17. The system of any one of the preceding Embodiments, wherein therapy delivered by the system is scheduled based on a time of a day and/or on an amount of time per day.
18. A chronic, implantable flow restriction system for controllably and selectively occluding, restricting and/or diverting flow of a patient's vasculature, the system comprising:
an implant comprising:
an expandable body comprising a proximal end and a distal end and a lumen extending from the proximal end to the distal end, wherein the expandable body is configured to collapse to a collapsed configuration for delivery into a patient and to expand from the collapsed configuration to an expanded configuration for implantation within the patient; and
a flow restrictor connected to the expandable body, the flow restrictor configured to adjustably occlude the lumen when the expandable body is in the expanded configuration.
19. The system of Embodiment 18, wherein the expandable body comprises an expandable metallic frame comprising a plurality of struts and defining a plurality of collapsible cells.
20. The system of Embodiments 19, wherein one or more of the plurality of struts of the expandable body are aligned diagonally relative to a longitudinal axis of the implant.
21. The system of any one of Embodiments 18-20, wherein the expandable body is configured to collapse sideways and/or via elongation.
22. The system of any one of Embodiments 18-19, wherein the expandable body is configured to collapse radially.
23. The system of any one of Embodiments 19-22, wherein one or more of the plurality of struts of the expandable body coalesce at an end of the implant that is offset relative to a central longitudinal axis of the implant.
24. The system of any one of Embodiments 18-23, wherein the flow restrictor comprises a magnet and the implant is magnetically actuated.
25. The system of Embodiment 24, wherein the flow restrictor is configured to move between a first, non-occluding position and a second, at least partially occluding position that at least partially blocks the lumen.
26. The system of any one of Embodiments 24-25, wherein the flow restrictor comprises one or more struts connecting the magnet to the expandable body and a material spanning the one or more struts.
27. The system of any one of Embodiments 24-26, further comprising a magnetic field source configured to actuate the implant.
28. The system of Embodiment 27, wherein the magnetic field source is configured to be implanted within an interstitial space and/or a vessel adjacent the implant.
29. The system of Embodiment 27, wherein the magnetic field source is configured to be positioned outside the patient's body.
30. The system of any one of Embodiments 18-23, wherein the flow restrictor comprises a balloon and the implant is fluidically actuated.
31. The system of Embodiment 30, wherein the balloon is configured to expand from a non-actuated state to an actuated state that at least partially blocks the lumen.
32. The system of any one of Embodiments 30-31, wherein the balloon is configured as a prolate or oblate spheroid.
33. The system of any one of Embodiments 30-31, wherein the balloon is configured as an elongate partial circle that is adhered to an interior of the expandable body and/or to a mounting portion of the expandable body.
34. The system of any one of Embodiments 30-31, wherein the balloon is configured as a cylinder with a through opening that is adhered to an interior of the expandable body and/or to a mounting portion of the expandable body.

35. The system of any one of Embodiments 30-34, wherein the expandable body comprises an inner body and an outer body, and the balloon is disposed in between the inner body and the outer body.

36. The system of Embodiment 35, wherein the inner body is configured to be more compliant than the outer body.

37. The system of any one of Embodiments 35-36, wherein the inner body is configured to encapsulate the balloon and hide it from flow going through the lumen.

38. The system of any one of Embodiments 35-37, wherein the inner body is configured to have a smooth inner surface.

39. The system of any one of Embodiments 35-38, wherein the inner body is configured to deflect inwards and at least partially occlude the lumen when the balloon is actuated.

40. The system of any one of Embodiments 30-39, further comprising tubing and a fluid reservoir fluidically connected to the balloon.

41. The system of Embodiment 40, wherein the fluid reservoir is configured to be implanted subcutaneously.

42. The system of any one of Embodiments 40-41, wherein the tubing is connected coaxial with the balloon.

43. The system of any one of Embodiments 40-41, wherein the tubing is connected off-center and/or tangent to the balloon.

44. The system of any one of Embodiments 30-43, wherein the expandable body further comprises a plurality of struts and/or a membrane positioned downstream of the balloon in relation to a direction of flow within the implant and located within a flow path of the lumen, the plurality of struts and/or membrane configured to filter and/or capture thrombus.

45. The system of any one of Embodiments 31-44, wherein the flow restrictor further comprises a shaft configured to cover the balloon when the balloon is in its non-actuated state.

46. The system of Embodiment 45, wherein the shaft is configured to hide the balloon from flow through the lumen when the balloon is in its non-actuated state.

47. The system of any one of Embodiments 18-23, wherein the flow restrictor comprises a material, a balloon, and/or a wire configured to change shape upon heating and the implant is heat actuated.

48. The system of any one of Embodiments 18-23, wherein the flow restrictor comprises a material, a balloon, and/or a wire configured to change shape upon movement and the implant is mechanically actuated.

49. The system of any one of Embodiments 18-23, wherein the flow restrictor comprises a shape memory material configured to at least partially occlude the lumen when mechanically actuated.

50. A method of treating heart failure of a patient, the method comprising occluding, restricting and/or diverting flow using the system of any one of the preceding Embodiments.

51. A system comprising one or more features of the foregoing description.

52. An implantable flow restriction device comprising one or more features of the foregoing description.

53. A method of occluding, restricting and/or diverting blood within a patient's vasculature comprising one or more features of the foregoing description.

54. A chronic, implantable flow restriction system comprising:
an implant configured to be implanted in an inferior vena cava of a patient upstream of renal veins of the patient and adjustably occlude the inferior vena cava; and
an implantable control unit operably connectable to the implant via a tubing, the implantable control unit comprising:
an actuator, wherein actuation of the actuator causes the implant to adjustably occlude the inferior vena cava;
a processor configured to receive an instruction to actuate the actuator; and
a communication module operably connected to the processor and configured to wirelessly communicate with an external device.

55. The system of Embodiment 54, wherein the implant comprises:
an expandable body having a proximal end and a distal end and a lumen extending longitudinally therethrough; and
a flow restrictor configured to hinge relative to the expandable body to at least partially restrict flow through the lumen.

56. The system of Embodiment 55, wherein the flow restrictor comprises struts and a material spanning the struts, the material configured to block blood flow.

57. The system of any one of Embodiments 55-56, wherein the flow restrictor is positioned adjacent the distal end of the expandable body such that, when implanted in the inferior vena cava, the flow restrictor is upstream of the expandable body with respect to blood flow.

58. The system of any one of Embodiments 55-57, wherein the implant further comprises a filter portion disposed adjacent the proximal end of the expandable body, the filter portion configured to capture thrombus.

59. The system of any one of Embodiments 54-58, wherein the implant comprises a pressure sensor operably connectable to the processor of the implantable control unit.

60. The system of Embodiment 59, wherein the implantable control unit is configured to wirelessly transmit pressure readings from the pressure sensor to the external device.

61. The system of any one of Embodiments 54-60, further comprising the external device.

62. The system of any one of Embodiments 54-61, wherein the external device comprises a handheld or mobile device.

63. The system of any one of Embodiments 54-62, wherein actuation of the actuator to cause the implant to adjustably occlude the inferior vena cava is controlled via the external device.

64. The system of Embodiment 63, wherein said actuation via the external device is controlled by the patient or a user.

65. The system of any one of Embodiments 55-64, wherein the flow restrictor has a non-circular opening when at least partially restricting flow through the lumen.

66. The system of any one of Embodiments 54-65, wherein the system does not include an assist device or a pump.
67. The system of any one of Embodiments 54-66, wherein the implantable control unit is configured to be removably connectable to the implant.
68. The system of any one of Embodiments 54-67, wherein the implant is configured to be actuated mechanically by a wire.
69. A chronic, implantable flow restriction system comprising:
    an implantable control unit comprising a housing and an actuator disposed within the housing;
    an implant comprising an expandable body having a proximal end and a distal end and a lumen extending longitudinally therethrough, and a flow restrictor configured to adjustably occlude the lumen when the expandable body is in an expanded configuration;
    a tubing configured to connect the proximal end of the expandable body of the implant to the housing of the implantable control unit; and
    a shaft movingly disposed within the tubing configured to connect the actuator of the implantable control unit to the flow restrictor of the implant;
    wherein actuation of the actuator of the implantable control unit moves the shaft within the tubing to cause the flow restrictor of the implant to adjustably occlude the lumen.
70. The system of Embodiment 69, wherein the expandable body of the implant further comprises:
    a filter portion disposed adjacent the proximal end configured to capture thrombus, the filter portion comprising a plurality of struts that extend radially outward and distally from the connection between the proximal end of the expandable body and the tubing; and
    a radial support portion connected to and disposed distal of the filter portion, the radial support portion configured to fluidically seal against an inner wall of the patient's vasculature.
71. The system of Embodiment 70, wherein the flow restrictor is connected to and extends distally from the radial support portion.
72. The system of any one of Embodiments 69-71, wherein the flow restrictor is integrally formed with the expandable body.
73. The system of any one of Embodiments 70-72, wherein the flow restrictor comprises:
    a plurality of petals each formed by a pair of struts that extend distally from the radial support portion and that join at a distal apex; and
    a material spanning each of the plurality of petals.
74. The system of Embodiment 73, wherein the flow restrictor comprises three petals or more.
75. The system of any one of Embodiments 73-74, wherein the material further spans at least a portion of the radial support portion.
76. The system of any one of Embodiments 73-75, wherein a distal end of each of the petals of the flow restrictor connect to a distal end of the shaft via a suture or a wire, and wherein proximal sliding or rotation of the shaft within the tubing causes the suture or the wire to pull the distal end of each of the petals of the flow restrictor towards one another to at least partially occlude the lumen.
77. The system of any one of Embodiments 69-76, wherein a distal end of the tubing is fluidically sealed with the shaft by a collapsible and extendible flexible coupling.
78. The system of any one of Embodiments 69-77, wherein the implant is configured to be implanted in an inferior vena cava of the patient below renal veins of the patient and a distal end of the flow restrictor positioned to first receive blood flow therethrough.
79. The system of any one of Embodiments 69-78, further comprising one or more pressure sensors configured to measure a pressure of the patient's vasculature and output at least one signal responsive to the measured pressure.
80. The system of Embodiment 79, wherein the one or more pressure sensors comprise a pressure sensor configured to measure a renal pressure of the patient.
81. The system of Embodiment 80, wherein the pressure sensor configured to measure the renal pressure of the patient is disposed proximal of the flow restrictor.
82. The system of any one of Embodiments 80-81, wherein the pressure sensor configured to measure the renal pressure of the patient is disposed adjacent the proximal end of the expandable body or the distal end of the tubing.
83. The system of Embodiments 79, wherein the one or more pressure sensors comprise a pressure sensor configured to measure an inferior vena cava pressure of the patient.
84. The system of Embodiment 83, wherein the pressure sensor configured to measure the inferior vena cava pressure of the patient is disposed proximal or distal of the flow restrictor.
85. The system of any one of Embodiments 83-84, wherein the pressure sensor configured to measure the inferior vena cava pressure of the patient is disposed adjacent the distal end of the expandable body.
86. The system of any one of Embodiments 79-85, wherein the implantable control unit further comprises a processor, wherein the processor is operably connectable to the one or more pressure sensors and configured to receive and process the at least one signal to determine the pressure of the patient's vasculature.
87. The system of Embodiment 86, wherein the implantable control unit further comprises a communication module operably connected to the processor and configured to wirelessly communicate with an external device.
88. The system of Embodiment 87, wherein the communication module transmits the determined pressure of the patient's vasculature to the external device.
89. The system of Embodiment 88, wherein the processor is operably connected to the actuator of the implantable control unit, and based on the determined pressure, the patient or a user can digitally actuate the actuator via the external device and thereby cause the flow restrictor of the implant to adjustably occlude the lumen.
90. The system of any one of Embodiments 87-89, further comprising the external device.
91. The system of any one of Embodiments 69-89, wherein the expandable body further comprises one or more anchors configured to anchor the implant within the patient's vasculature.
92. The system of any one of Embodiments 69-91, wherein the implantable control unit is configured to be powered by a battery disposed within the housing.

93. The system of Embodiment 92, wherein the battery is configured to be charged by induction charging.
94. The system of any one of Embodiments 68-91, wherein the implantable control unit is configured to be powered by induction.
95. An implantable flow restriction system comprising:
an implant comprising:
an expandable body comprising a metallic frame having a proximal end and a distal end and a lumen extending longitudinally therethrough; and
a flow restrictor comprising:
a plurality of petals each formed by struts; and
a material spanning each of the plurality of petals;
wherein the flow restrictor is configured to hinge relative to the expandable body to at least partially restrict flow through the lumen; and
an implantable control unit comprising:
an actuator configured to operably connect with the flow restrictor of the implant;
a processor configured to receive an instruction to actuate the actuator; and
a communication module operably connected to the processor and configured to wirelessly communicate with an external device;
wherein actuation of the actuator causes the flow restrictor to at least partially restrict flow through the lumen.
96. The system of Embodiment 95, further comprising:
a tubing configured to connect the proximal end of the expandable body of the implant to the implantable control unit; and
a shaft movingly disposed within the tubing configured to connect the actuator of the implantable control unit to the flow restrictor of the implant;
wherein actuation of the actuator of the implantable control unit moves the shaft within the tubing to cause the flow restrictor of the implant to at least partially restrict flow through the lumen.
97. The system of any one of Embodiments 95-96, wherein the implant further comprises a filter portion disposed adjacent the proximal end of the expandable body, the filter portion configured to capture thrombus.
98. The system of any one of Embodiments 95-97, wherein the struts that form each of the plurality of petals comprise a pair of struts that extend distally from the expandable body and join at a distal apex.
99. The system of any one of Embodiments 95-98, wherein the implant comprises a pressure sensor operably connectable to the processor of the implantable control unit.
100. The system of Embodiment 99, wherein the implantable control unit is configured to wirelessly transmit pressure readings from the pressure sensor to the external device.
101. The system of any one of Embodiments 95-100, further comprising the external device.
102. The system of any one of Embodiments 95-101, wherein the external device comprises a handheld or mobile device.
103. The system of any one of Embodiments 95-102, wherein actuation of the actuator to cause the flow restrictor to at least partially restrict flow through the lumen is controlled via the external device.
104. The system of any one of Embodiments 95-103, wherein the implant is configured to be implanted in an inferior vena cava of a patient upstream of renal veins of the patient and adjustably occlude blood flow in the inferior vena cava when the flow restrictor at least partially restricts flow through the lumen of the implant.
105. The system of any one of Embodiments 95-104, wherein, when implanted in a patient, the flow restrictor of the implant is configured to be positioned upstream of the expandable body with respect to flow through the lumen.
106. The system of any one of Embodiments 95-105, wherein when hinged relative to the expandable body, an exterior surface of the plurality of petals is configured to occlude blood flow.
107. An implantable flow restriction system comprising:
an implant comprising:
an expandable body having a proximal end and a distal end and a lumen extending longitudinally therethrough; and
a flow restrictor configured to be secured within a vessel of a patient's vasculature; and
an implantable control unit comprising:
an actuator configured to operably connect with the flow restrictor of the implant;
a processor configured to receive an instruction to actuate the actuator; and
a communication module operably connected to the processor and configured to wirelessly communicate with an external device;
wherein actuation of the actuator causes the flow restrictor to pull in a wall of the vessel to at least partially restrict flow through the lumen.
108. The system of Embodiment 107, further comprising:
a tubing configured to connect the proximal end of the expandable body of the implant to the implantable control unit; and
a shaft movingly disposed within the tubing configured to connect the actuator of the implantable control unit to the flow restrictor of the implant;
wherein actuation of the actuator of the implantable control unit moves the shaft within the tubing to cause the flow restrictor of the implant to pull in the wall of the vessel to at least partially restrict flow through the lumen.
109. The system of any one of Embodiments 107-108, wherein the flow restrictor comprises a plurality of petals each formed by struts and configured to hinge relative to the expandable body.
110. The system of any one of Embodiments 107-109, wherein the struts that form each of the plurality of petals comprise a pair of struts that extend distally from the expandable body and join at a distal apex.
111. The system of any one of Embodiments 109-110, wherein the flow restrictor further comprises a material spanning each of the plurality of petals.
112. The system of any one of Embodiments 107-111, wherein the flow restrictor is configured to ingrow at least partially into the vessel wall.
113. The system of any one of Embodiments 107-112, wherein the flow restrictor further comprises one or more anchors configured to secure the flow restrictor to the vessel wall.
114. The system of any one of Embodiments 107-113, wherein the implant comprises a pressure sensor operably connectable to the processor of the implantable control unit.

115. The system of Embodiment 114, wherein the implantable control unit is configured to wirelessly transmit pressure readings from the pressure sensor to the external device.
116. The system of any one of Embodiments 107-115, further comprising the external device.
117. The system of any one of Embodiments 107-116, wherein the external device comprises a handheld or mobile device.
118. The system of any one of Embodiments 107-117, wherein actuation of the actuator to cause the flow restrictor to pull in the wall of the vessel to at least partially restrict flow through the lumen is controlled via the external device.
119. The system of any one of Embodiments 107-118, wherein the implant is configured to be implanted in an inferior vena cava of the patient upstream of renal veins of the patient and adjustably occlude blood flow in the inferior vena cava when the flow restrictor pulls in a wall of the inferior vena cava to at least partially restrict flow through the lumen of the implant.
120. The system of any one of Embodiments 107-119, wherein, when implanted in the patient, the flow restrictor of the implant is configured to be positioned upstream of the expandable body with respect to flow through the lumen.
121. The system of any one of Embodiments 107-120, wherein the system does not include an assist device or a pump.
122. A method for implanting a chronic, implantable flow restriction system in a patient, the method comprising:
    implanting an implant in an inferior vena cava of the patient below renal veins of the patient, the implant configured to at least partially occlude the inferior vena cava upon actuation;
    implanting an implantable controller subcutaneously; and
    operably connecting the implant to the implantable controller, the implantable controller comprising an actuator configured to actuate the implant for at least partially occluding the inferior vena cava and a processor configured to receive an instruction to actuate the actuator.
123. The method of Embodiment 122, wherein the implant is operably connected to the implantable controller prior to implanting the implantable controller.
124. The method of any one of Embodiments 122-123, further comprising accessing a subclavian vein of the patient.
125. The method of any one of Embodiments 122-124, further comprising testing actuation of the implant after its implantation in the inferior vena cava and before operably connecting the implant to the implantable controller.
126. The method of any one of Embodiments 122-125, wherein implanting the implantable controller comprises implanting the implantable controller subcutaneously adjacent a collarbone of the patient.
127. The method of any one of Embodiments 122-126, wherein the implantable controller further comprises a communication module operably connected to the processor and configured to wirelessly communicate with an external device.
128. The method of any one of Embodiments 122-127, further comprising actuating the implant to at least partially occlude the inferior vena cava.
129. The method of any one of Embodiments 122-128, wherein actuating the implant comprises receiving an instruction from an external device.
130. The method of any one of Embodiments 122-129, wherein the implant comprises:
    an expandable body having a proximal end and a distal end and a lumen extending longitudinally therethrough; and
    a flow restrictor configured to hinge relative to the expandable body to at least partially restrict flow through the lumen.
131. The method of Embodiment 130, wherein the flow restrictor is positioned adjacent the distal end of the expandable body, and wherein implanting the implant in the inferior vena cava includes positioning the distal end to first receive blood flow therethrough.
132. The method of any one of Embodiments 129-131, wherein the implantable flow restriction system further comprises:
    a tubing extending from the implant configured to releasably connect with the implantable controller; and
    a shaft movingly disposed within the tubing configured to releasably connect the actuator of the implantable controller with the flow restrictor of the implant;
    wherein operably connecting the implant to the implantable controller comprises:
        connecting the tubing to the implantable controller; and
        connecting the shaft to the actuator of the implantable controller.
133. The method of Embodiment 132, further comprising implanting the tubing and the shaft such that they extend from the implant through the inferior vena cava, through a right atrium, through at least a portion of a superior vena cava, and through at least a portion of the subclavian vein of the patient.
134. The method of any one of Embodiments 130-133, wherein the implant further comprises a pressure sensor disposed downstream of the flow restrictor in regard to a direction of blood flow in the inferior vena cava, the pressure sensor configured to measure pressure.
135. The method of Embodiment 134, wherein the pressure sensor is positioned adjacent the renal veins of the patient when the implant is implanted in the inferior vena cava below the renal veins.
136. The method of any one of Embodiments 122-135, further comprising removing the implant and the implantable controller from the patient.
137. A method of controllably and selectively occluding, restricting and/or diverting flow of a patient's vasculature, the method comprising:
    measuring an inferior vena cava pressure from an implant implanted in the inferior vena cava of the patient upstream of renal veins of the patient;
    transmitting the inferior vena cava pressure from an implantable controller positioned within the patient to an external device;
    receiving, by the implantable controller from the external device, an instruction to activate the implant; and
    activating the implant;
    wherein activating the implant causes the implant to at least partially occlude blood flow through the inferior vena cava.

138. The method of Embodiment 137, wherein activating the implant to at least partially occlude blood flow through the inferior vena cava enhances renal circulation.

139. The method of any one of Embodiments 137-138, wherein activating the implant to at least partially occlude blood flow through the inferior vena cava enhances diuresis.

140. The method of any one of Embodiments 137-139, wherein activating the implant to at least partially occlude blood flow through the inferior vena cava reduces renal venous pressure.

141. The method of any one of Embodiments 137-140, wherein activating the implant to at least partially occlude blood flow through the inferior vena cava reduces cardiac preload.

142. The method of any one of Embodiments 137-141, further comprising measuring a renal venous pressure from the implant when blood flow through the inferior vena cava is at least partially occluded by the implant.

143. The method of any one of Embodiments 137-142, further comprising:
detecting an increase in the inferior vena cava pressure; and
transmitting, to the external device, an indication the inferior vena cava pressure has increased.

144. The method of any one of Embodiments 137-142, further comprising:
detecting the inferior vena cava pressure has reached a threshold value; and
transmitting, to the external device, an indication the inferior vena cava pressure has reached the threshold value.

145. The method of any one of Embodiments 137-144, wherein the implant comprises:
a flow restrictor configured to at least partially occlude blood flow through the inferior vena cava when the implant is activated; and
a pressure sensor disposed downstream of the flow restrictor in regard to a direction of blood flow in the inferior vena cava, the pressure sensor configured to measure said pressure.

146. The method of any one of Embodiments 137-144, wherein the implant comprises:
a flow restrictor configured to at least partially occlude blood flow through the inferior vena cava when the implant is activated; and
a pressure sensor disposed upstream of the flow restrictor in regard to a direction of blood flow in the inferior vena cava, the pressure sensor configured to measure said pressure.

147. The method of any one of Embodiments 137-144, wherein the implant comprises:
a flow restrictor configured to at least partially occlude blood flow through the inferior vena cava when the implant is activated; and
a pressure sensor disposed downstream of the flow restrictor in regard to a direction of blood flow in the inferior vena cava, and
a pressure sensor disposed upstream of the flow restrictor in regard to a direction of blood flow in the inferior vena cava.

148. The method of any one of Embodiments 137-147, wherein activation of the implant is controlled via the external device.

149. The method of any one of Embodiments 137-148, wherein the instruction to activate the implant is wirelessly received from the external device.

150. The method of any one of Embodiments 137-149, further comprising receiving, from the external device, an instruction to deactivate the implant, wherein deactivating the implant causes the implant to not occlude blood flow through the inferior vena cava.

151. The method of any one of Embodiments 137-150, further comprising deactivating the implant after a duration of time.

152. The method of any one of Embodiments 137-150, further comprising deactivating the implant after the pressure measured from the implant reaches a threshold value.

153. The method of any one of Embodiments 137-152, further comprising deactivating the implant after a duration of time after the pressure measured from the implant reaches a threshold value.

154. The method of any one of Embodiments 137-153, wherein the implantable controller comprises:
a communication module configured to wirelessly communicate with the external device;
a processor operably connected to the communication module, the processor configured to receive the instruction to activate the implant; and
an actuator operably connected to the processor, the actuator configured to activate the implant.

155. The method of any one of Embodiments 145-154, wherein activating the implant comprises causing the flow restrictor to hinge relative to an expandable body of the implant to at least partially occlude blood flow through the inferior vena cava.

156. The method of any one of Embodiments 137-155, wherein activating the implant comprises mechanically activating the implant by a wire.

157. A method of controllably and selectively occluding, restricting and/or diverting flow of a patient's vasculature, the method comprising:
activating a flow restrictor implanted in a vessel of the patient's vasculature,
wherein activating the flow restrictor causes the flow restrictor to pull in a wall of the vessel to at least partially restrict flow through the vessel.

158. The method of Embodiment 157, wherein the flow restrictor is implanted in an inferior vena cava of the patient upstream of renal veins of the patient, and wherein activating the flow restrictor causes the flow restrictor to pull in a wall of the inferior vena cava to at least partially restrict flow through the inferior vena cava.

159. The method of Embodiment 158, wherein activating the flow restrictor to cause the flow restrictor to pull in the wall of the inferior vena cava to at least partially restrict flow through the inferior vena cava enhances renal circulation.

160. The method of any one of Embodiments 158-159, wherein activating the flow restrictor to cause the flow restrictor to pull in the wall of the inferior vena cava to at least partially restrict flow through the inferior vena cava enhances diuresis.

161. The method of any one of Embodiments 158-160, wherein activating the flow restrictor to cause the flow restrictor to pull in the wall of the inferior vena cava to at least partially restrict flow through the inferior vena cava reduces renal venous pressure.

162. The method of any one of Embodiments 158-161, wherein activating the flow restrictor to cause the flow restrictor to pull in the wall of the inferior vena cava to at least partially restrict flow through the inferior vena cava reduces cardiac preload.
163. The method of any one of Embodiments 158-162, further comprising measuring an inferior venous pressure from an implant comprising the flow restrictor.
164. The method of Embodiment 163, further comprising transmitting the inferior venous pressure from an implantable controller positioned within the patient to an external device.
165. The method of Embodiment 164, further comprising receiving, by the implantable controller from the external device, an instruction to activate the flow restrictor.
166. The method of any one of Embodiments 163-165, further comprising measuring a renal venous pressure from the implant comprising the flow restrictor when flow through the inferior vena cava is at least partially restricted.
167. The method of any one of Embodiments 164-166, further comprising:
    detecting an increase in the inferior vena cava pressure; and
    transmitting, to the external device, an indication the inferior vena cava pressure has increased.
168. The method of any one of Embodiments 164-166, further comprising:
    detecting the inferior vena cava pressure has reached a threshold value; and
    transmitting, to the external device, an indication the inferior vena cava pressure has reached the threshold value.
169. The method of any one of Embodiments 164-168, wherein activation of the flow restrictor is controlled via the external device.
170. The method of any one of Embodiments 165-169, wherein the instruction to activate the flow restrictor is wirelessly received from the external device.
171. The method of any one of Embodiments 165-170, further comprising receiving, from the external device, an instruction to deactivate the flow restrictor, wherein deactivating the flow restrictor causes the wall of the inferior vena cava to not occlude flow through the inferior vena cava.
172. The method of any one of Embodiments 157-171, further comprising deactivating the flow restrictor after a duration of time.
173. The method of any one of Embodiments 163-172, further comprising deactivating the flow restrictor after the pressure measured from the implant reaches a threshold value.
174. The method of any one of Embodiments 163-173, further comprising deactivating the implant after a duration of time after the pressure measured from the implant reaches a threshold value.
175. The method of any one of Embodiments 164-174, wherein the implantable controller comprises:
    a communication module configured to wirelessly communicate with the external device;
    a processor operably connected to the communication module, the processor configured to receive the instruction to activate the flow restrictor; and
    an actuator operably connected to the processor, the actuator configured to activate the flow restrictor.
176. The method of any one of Embodiments 157-175, wherein activating the flow restrictor comprises causing the flow restrictor to hinge relative to an expandable body of an implant comprising the flow restrictor.
177. The method of any one of Embodiments 157-176, wherein activating the flow restrictor comprises mechanically activating the flow restrictor by a wire.
178. An implant configured to be implanted in a patient for controllably and selectively occluding, restricting and/or diverting flow of the patient's vasculature, the implant comprising:
    an expandable body having a proximal end and a distal end and a lumen extending longitudinally therethrough, and a filter portion disposed adjacent the proximal end configured to capture thrombus; and
    a flow restrictor extending from the distal end of the expandable body, the flow restrictor configured to adjustably occlude the lumen when the expandable body is in an expanded configuration;
    wherein when implanted, the flow restrictor is configured to be positioned upstream of the expandable body with respect to blood flow.
179. The implant of Embodiment 178, wherein the filter portion comprises a plurality of struts that extend proximally and radially inward.
180. The implant of Embodiment 179, wherein the expandable body of the implant further comprises a radial support portion connected to and disposed distal of the filter portion, the radial support portion configured to fluidically seal against an inner wall of the patient's vasculature.
181. The implant of Embodiment 180, wherein the flow restrictor is connected to and extends distally from the radial support portion.
182. The implant of any one of Embodiments 178-181, wherein the flow restrictor is integrally formed with the expandable body.
183. The implant of any one of Embodiments 178-182, wherein the flow restrictor comprises a plurality of petals configured to fold radially inward to adjustable occlude the lumen, wherein when folded radially inward, an exterior surface of the plurality of petals is configured to occlude blood flow.
184. The implant of Embodiment 183, wherein each of the plurality of petals is formed by a pair of struts that extend from the expandable body and join at a distal apex.
185. The implant of any one of Embodiments 183-184, wherein the flow restrictor comprises three petals or more.
186. The implant of any one of Embodiments 183-185, wherein the flow restrictor carries an occlusive material, and wherein regions between the plurality of petals are free of the occlusive material.
187. The implant of any one of Embodiments 183-185, wherein the flow restrictor carries an occlusive material, and wherein the occlusive material spans the plurality of petals and regions between the plurality of petals.
188. The implant of any one of Embodiments 186-187, wherein the occlusive material further spans at least a portion of the expandable body.
189. The implant of any one of Embodiments 178-188, wherein the flow restrictor has a non-circular opening when at least partially occluding the lumen.
190. The implant of any one of Embodiments 178-189, wherein the flow restrictor has a stellate shaped opening when at least partially occluding the lumen.

191. The implant of any one of Embodiments 178-190, wherein the implant further comprises a pressure sensor.
192. The implant of Embodiment 191, wherein the pressure sensor is disposed proximal of the flow restrictor.
193. The implant of any one of Embodiments 180-192, further comprising an anchor that extends proximally from the radial support portion, the anchor configured to anchor the implant within the patient's vasculature.
194. The implant of any one of Embodiments 178-193, wherein the implant is configured to be implanted in an inferior vena cava of the patient.
195. A system comprising the implant of any one of Embodiments 180-194 and a delivery sheath configured to implant the implant.
196. The system of Embodiment 195, wherein the implant is configured to remain in a collapsed configuration when extending out of the delivery sheath while at least a portion of the radial support portion remains inside the delivery sheath.
197. An implant configured to be implanted in a patient for occluding, restricting and/or diverting flow of the patient's vasculature, the implant comprising:
an expandable body comprising a metallic frame having a proximal end and a distal end and a lumen extending longitudinally therethrough; and
a flow restrictor comprising:
a plurality of petals each formed by a pair of struts that extend distally from the expandable body and join at a distal apex; and
a material spanning each of the plurality of petals;
wherein the flow restrictor is configured to fold radially inward to at least partially restrict flow through the lumen.
198. The implant of Embodiment 197, wherein the expandable body of the implant further comprises a filter portion disposed adjacent the proximal end configured to capture thrombus.
199. The implant of Embodiment 198, wherein the expandable body of the implant further comprises a radial support portion connected to and disposed distal of the filter portion, the radial support portion configured to fluidically seal against an inner wall of the patient's vasculature.
200. The implant of any one of Embodiments 197-199, wherein the flow restrictor is integrally formed with the expandable body.
201. The implant of any one of Embodiments 197-200, wherein when folded radially inward, an exterior surface of the plurality of petals of the flow restrictor is configured to occlude blood flow.
202. The implant of any one of Embodiments 197-201, wherein the flow restrictor comprises three petals or more.
203. The implant of any one of Embodiments 197-202, wherein regions between the plurality of petals are free of the material.
204. The implant of any one of Embodiments 197-202, wherein the material further spans regions between the plurality of petals.
205. The implant of any one of Embodiments 197-204, wherein the material further spans at least a portion of the expandable body.
206. The implant of any one of Embodiments 197-205, wherein the flow restrictor has a non-circular opening when at least partially occluding the lumen.
207. The implant of any one of Embodiments 197-206, wherein the flow restrictor has a stellate shaped opening when at least partially occluding the lumen.
208. The implant of any one of Embodiments 197-207, wherein the implant further comprises a pressure sensor.
209. The implant of Embodiment 208, wherein the pressure sensor is disposed proximal of the flow restrictor.
210. The implant of any one of Embodiments 199-209, further comprising an anchor that extends proximally from the radial support portion, the anchor configured to anchor the implant within the patient's vasculature.
211. The implant of any one of Embodiments 197-210, wherein the implant is configured to be implanted in an inferior vena cava of the patient.
212. The implant of any one of Embodiments 197-211, wherein when implanted, the flow restrictor is configured to be positioned upstream of the expandable body with respect to blood flow.
213. A system comprising the implant of any one of Embodiments 199-212 and a delivery sheath configured to implant the implant.
214. The system of Embodiment 213, wherein the implant is configured to remain in a collapsed configuration when extending out of the delivery sheath while at least a portion of the radial support portion remains inside the delivery sheath.
215. An implant configured to be implanted in a patient for occluding, restricting and/or diverting flow of the patient's vasculature, the implant comprising:
an expandable body having a proximal end and a distal end and a lumen extending longitudinally therethrough; and
a flow restrictor configured to be secured within a vessel of the patient's vasculature;
wherein activation of the flow restrictor causes the flow restrictor to pull in a wall of the vessel to at least partially restrict flow through the lumen.
216. The implant of Embodiment 215, wherein the flow restrictor comprises a plurality of petals each formed by struts and configured to hinge relative to the expandable body.
217. The implant of Embodiment 216, wherein the struts that form each of the plurality of petals comprise a pair of struts that extend distally from the expandable body and join at a distal apex.
218. The implant of any one of Embodiments 216-217, wherein the flow restrictor further comprises a material spanning each of the plurality of petals.
219. The implant of any one of Embodiments 215-218, wherein the flow restrictor is configured to ingrow at least partially into the vessel wall.
220. The implant of any one of Embodiments 215-219, wherein the flow restrictor further comprises one or more anchors configured to secure the flow restrictor to the vessel wall.
221. The implant of any one of Embodiments 215-220, wherein the flow restrictor is integrally formed with the expandable body.
222. The implant of any one of Embodiments 215-221, wherein the implant comprises a pressure sensor configured to measure pressure.
223. The implant of Embodiment 222, wherein the pressure sensor is disposed proximal of the flow restrictor.
224. The implant of any one of Embodiments 215-223, wherein the expandable body of the implant further comprises a filter portion disposed adjacent the proximal end of the expandable body, the filter portion configured to capture thrombus.
225. The implant of Embodiment 224, wherein the filter portion comprises a plurality of struts that extend proximally and radially inward.
226. The implant of any one of Embodiments 215-225, wherein the implant is configured to be implanted in an inferior vena cava of the patient.
227. The implant of any one of Embodiments 215-226, wherein when implanted, the flow restrictor is configured to be positioned upstream of the expandable body with respect to flow through the lumen of the implant.
228. A method of controllably and selectively occluding, restricting and/or diverting flow of a patient's vasculature, the method comprising:
receiving, by an implantable controller positioned within the patient from an external device, an instruction to activate an implant implanted in an inferior vena cava of the patient upstream of renal veins of the patient; and
activating the implant;
wherein activating the implant causes the implant to at least partially occlude blood flow through the inferior vena cava.
229. The method of Embodiment 228, wherein activating the implant to at least partially occlude blood flow through the inferior vena cava enhances renal circulation.
230. The method of any one of Embodiments 228-229, wherein activating the implant to at least partially occlude blood flow through the inferior vena cava enhances diuresis.
231. The method of any one of Embodiments 228-230, wherein activating the implant to at least partially occlude blood flow through the inferior vena cava reduces renal venous pressure.
232. The method of any one of Embodiments 228-231, wherein activating the implant to at least partially occlude blood flow through the inferior vena cava reduces cardiac preload.
233. The method of any one of Embodiments 228-232, wherein the implant comprises:
a flow restrictor configured to at least partially occlude blood flow through the inferior vena cava when the implant is activated; and
a pressure sensor disposed downstream of the flow restrictor in regard to a direction of blood flow in the inferior vena cava.
234. The method of any one of Embodiments 228-232, wherein the implant comprises:
a flow restrictor configured to at least partially occlude blood flow through the inferior vena cava when the implant is activated; and
a pressure sensor disposed upstream of the flow restrictor in regard to a direction of blood flow in the inferior vena cava.
235. The method of any one of Embodiments 228-232, wherein the implant comprises:
a flow restrictor configured to at least partially occlude blood flow through the inferior vena cava when the implant is activated;
a pressure sensor disposed downstream of the flow restrictor in regard to a direction of blood flow in the inferior vena cava; and
a pressure sensor disposed upstream of the flow restrictor in regard to a direction of blood flow in the inferior vena cava.
236. The method of any one of Embodiments 228-235, further comprising:
measuring an inferior vena cava pressure from the implant; and
transmitting the inferior vena cava pressure from the implantable controller to the external device.
237. The method of any one of Embodiments 228-236, further comprising:
measuring a renal venous pressure from the implant when blood flow through the inferior vena cava is at least partially occluded by the implant; and
transmitting the renal venous pressure from the implantable controller to the external device.
238. The method of any one of Embodiments 236-237, further comprising:
detecting an increase in the inferior vena cava pressure; and
transmitting, to the external device, an indication the inferior vena cava pressure has increased.
239. The method of any one of Embodiments 236-238, further comprising:
detecting the inferior vena cava pressure has reached a threshold value; and
transmitting, to the external device, an indication the inferior vena cava pressure has reached the threshold value.
240. The method of any one of Embodiments 228-239, wherein activation of the implant is controlled via the external device.
241. The method of any one of Embodiments 228-240, wherein the instruction to activate the implant is wirelessly received from the external device.
242. The method of any one of Embodiments 228-241, further comprising receiving, from the external device, an instruction to deactivate the implant, wherein deactivating the implant causes the implant to not occlude blood flow through the inferior vena cava.
243. The method of any one of Embodiments 228-242, further comprising deactivating the implant after a duration of time.
244. The method of any one of Embodiments 236-243, further comprising deactivating the implant after the pressure measured from the implant reaches a threshold value.
245. The method of any one of Embodiments 236-243, further comprising deactivating the implant after a duration of time after the pressure measured from the implant reaches a threshold value.
246. The method of any one of Embodiments 236-245, wherein the implantable controller comprises:
a communication module configured to wirelessly communicate with the external device;
a processor operably connected to the communication module, the processor configured to receive the instruction to activate the implant; and
an actuator operably connected to the processor, the actuator configured to activate the implant.
247. The method of any one of Embodiments 233-246, wherein activating the implant comprises causing the flow restrictor to hinge relative to an expandable body of the implant to at least partially occlude blood flow through the inferior vena cava.
248. The method of any one of Embodiments 228-247, wherein activating the implant comprises mechanically activating the implant by a wire.
249. A chronic, implantable flow restriction system comprising:

an implant configured to be implanted in a vessel, lumen, or orifice of a patient and adjustably occlude the vessel, lumen, or orifice; and an implantable control unit operably connectable to the implant via a tubing, the implantable control unit comprising:
  an actuator, wherein actuation of the actuator causes the implant to adjustably occlude the vessel, lumen, or orifice;
  a processor configured to receive an instruction to actuate the actuator; and
  a communication module operably connected to the processor and configured to wirelessly communicate with an external device.

250. The system of any one of Embodiments 54-58, further comprising a pressure sensor operably connectable to the processor of the implantable control unit and/or operably coupled to a separate device to provide pressure readings useful in operating the implantable control unit.

Additional Considerations and Terminology

Features, materials, characteristics, or groups described in conjunction with a particular aspect, implementation, or example are to be understood to be applicable to any other aspect, implementation or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some implementations, the actual steps taken in the processes illustrated or disclosed may differ from those shown in the figures. Depending on the implementation, certain of the steps described above may be removed, others may be added. For example, the actual steps or order of steps taken in the disclosed processes may differ from those shown in the figure. Depending on the implementation, certain of the steps described above may be removed, others may be added. Furthermore, the features and attributes of the specific implementations disclosed above may be combined in different ways to form additional implementations, all of which fall within the scope of the present disclosure.

Although the present disclosure includes certain implementations, examples and applications, it will be understood by those skilled in the art that the present disclosure extends beyond the specifically disclosed implementations to other alternative implementations or uses and obvious modifications and equivalents thereof, including implementations which do not provide all of the features and advantages set forth herein. Accordingly, the scope of the present disclosure is not intended to be limited by the described implementations, and may be defined by claims as presented herein or as presented in the future.

Conditional language, such as "can," "could," "might," or "may," unless specifically stated otherwise, or otherwise understood within the context as used, is generally intended to convey that certain implementations include, while other implementations do not include, certain features, elements, or steps. Thus, such conditional language is not generally intended to imply that features, elements, or steps are in any way required for one or more implementations or that one or more implementations necessarily include logic for deciding, with or without user input or prompting, whether these features, elements, or steps are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

What is claimed is:

1. An implantable flow restriction system comprising:
  an implant comprising:
    an expandable body comprising a metallic frame having a proximal end and a distal end and a lumen extending longitudinally therethrough; and
    a flow restrictor comprising:
      a plurality of petals each formed by struts; and
      a material spanning each of the plurality of petals;
      wherein the flow restrictor is configured to hinge relative to the expandable body to at least partially restrict flow through the lumen;
  an implantable control unit comprising:

an actuator configured to operably connect with the flow restrictor of the implant;

a processor configured to receive an instruction to actuate the actuator; and a communication module operably connected to the processor and configured to wirelessly communicate with an external device;

wherein actuation of the actuator causes the flow restrictor to at least partially restrict flow through the lumen;

a tubing configured to connect the proximal end of the expandable body of the implant to the implantable control unit; and a shaft movingly disposed with the tubing configured to connect the actuator of the implantable control unit to the flow restrictor of the implant;

wherein actuation of the actuator of the implantable control unit moves the shaft within the tubing to cause the flow restrictor of the implant to at least partially restrict flow through the lumen.

2. The system of claim 1, wherein the implant further comprises a filter portion disposed adjacent the proximal end of the expandable body, the filter portion configured to capture thrombus.

3. The system of claim 1, wherein the struts that form each of the plurality of petals comprise a pair of struts that extend distally from the expandable body and join at a distal apex.

4. The system of claim 1, wherein the implant comprises a pressure sensor operably connectable to the processor of the implantable control unit.

5. The system of claim 4, wherein the implantable control unit is configured to wirelessly transmit pressure readings from the pressure sensor to the external device.

6. The system of claim 1, further comprising the external device.

7. The system of claim 1, wherein the external device comprises a handheld or mobile device.

8. The system of claim 1, wherein actuation of the actuator to cause the flow restrictor to at least partially restrict flow through the lumen is controlled via the external device.

9. The system of claim 1, wherein the implant is configured to be implanted in an inferior vena cava of a patient upstream of renal veins of the patient and adjustably occlude blood flow in the inferior vena cava when the flow restrictor at least partially restricts flow through the lumen of the implant.

10. The system of claim 1, wherein, when implanted in a patient, the flow restrictor of the implant is configured to be positioned upstream of the expandable body with respect to flow through the lumen.

11. The system of claim 1, wherein when hinged relative to the expandable body, an exterior surface of the plurality of petals is configured to occlude blood flow.

* * * * *

UNITED STATES PATENT AND TRADEMARK OFFICE
CERTIFICATE OF CORRECTION

PATENT NO. : 11,883,030 B2
APPLICATION NO. : 18/300076
DATED : January 30, 2024
INVENTOR(S) : Arshad Quadri et al.

It is certified that error appears in the above-identified patent and that said Letters Patent is hereby corrected as shown below:

In the Specification

In Column 19, Line 1, delete "FIG." and insert --FIGS.--.

In Column 36, Line 65, delete "270g" and insert --217g--.

In Column 37, Line 25, delete "217g" and insert --217h--.

In Column 37, Line 27, delete "217g" and insert --217h--.

In Column 37, Line 43, delete "270h" and insert --217h--.

In Column 41, Line 45, delete "290n" and insert --280n--.

In Column 42, Line 20, delete "and or" and insert --and/or--.

In Column 44, Line 12, delete "FIG." and insert --FIGS.--.

In Column 45, Line 56, delete "wire 380c" and insert --wire 370c--.

In Column 50, Line 63, delete "560" and insert --560a--.

In Column 50, Line 66, delete "560" and insert --560a--.

In Column 51, Line 1, delete "560" and insert --560a--.

In Column 53, Line 21, delete "580a" and insert --570a--.

In Column 54, Line 8, delete "FIG." and insert --FIGS.--.

Signed and Sealed this
Fourth Day of June, 2024

Katherine Kelly Vidal
*Director of the United States Patent and Trademark Office*

CERTIFICATE OF CORRECTION (continued)
U.S. Pat. No. 11,883,030 B2

In Column 57, Line 1, delete "570c" and insert --590c--.

In Column 60, Line 46, delete "560i'" and insert --560i--.

In Column 60, Line 50, delete "570i'" and insert --570i--.

In Column 60, Line 54, delete "560'" and insert --560i--.

In Column 67, Line 19, delete "720" and insert --722--.

In Column 69, Line 9, delete "tubing 572" and insert --tubing 570--.